(12) United States Patent
Schwartz

(10) Patent No.: US 11,045,246 B1
(45) Date of Patent: Jun. 29, 2021

(54) APPARATUS FOR EFFECTING FEEDBACK OF VAGINAL CAVITY PHYSIOLOGY

(71) Applicant: Alan N. Schwartz, Edmonds, WA (US)

(72) Inventor: Alan N. Schwartz, Edmonds, WA (US)

( * ) Notice: Subject to any disclaimer, the term of this patent is extended or adjusted under 35 U.S.C. 154(b) by 266 days.

(21) Appl. No.: 16/219,876

(22) Filed: Dec. 13, 2018

Related U.S. Application Data

(63) Continuation of application No. 15/974,652, filed on May 8, 2018, now abandoned, which is a (Continued)

(51) Int. Cl.
*A61B 18/06* (2006.01)
*A61N 1/00* (2006.01)
(Continued)

(52) U.S. Cl.
CPC ............. *A61B 18/06* (2013.01); *A61B 18/02* (2013.01); *A61B 18/1477* (2013.01); *A61N 1/00* (2013.01); *A61N 2/004* (2013.01); *A61N 5/00* (2013.01); *A61N 5/1027* (2013.01); *A61B 2017/00743* (2013.01); *A61B 2018/00017* (2013.01); *A61B 2018/0022* (2013.01); *A61B 2018/00196* (2013.01); *A61B 2018/00279* (2013.01); *A61B 2018/00428* (2013.01); *A61B 2018/00577* (2013.01); *A61B 2018/00613* (2013.01); *A61B 2018/00642* (2013.01); *A61B 2018/00702* (2013.01); *A61B 2018/00708* (2013.01);
(Continued)

(58) Field of Classification Search
CPC ..... A61B 18/14; A61B 5/4437; A61B 5/1076; A61B 8/08; A61B 2018/523; A61B 8/12; A61B 2018/0022; A61B 5/6875; A61B 1/303; A61B 5/4337; A61B 5/4368; A61K 9/0034; A61H 2201/5071; A61H 19/44

See application file for complete search history.

(56) References Cited

U.S. PATENT DOCUMENTS 3,563,235 A   2/1971   Zipper
3,779,241 A   12/1973  Vennard et al.
(Continued)

FOREIGN PATENT DOCUMENTS

DE   10241071   1/2010
JP   4716119    7/2011
(Continued)

OTHER PUBLICATIONS

Ganguly, Rumpa, "Accuracy of linear measurement in Galileos cone beam CT under simulated clinical condition," MS (Master of Science) thesis, Universtiy of Iowa, (2009).
(Continued)

*Primary Examiner* — Patrick Fernandes
(74) *Attorney, Agent, or Firm* — Patrick J. S. Inouye

(57) ABSTRACT

The subject matter described herein is designed to facilitate and overcome the limitations of rehabilitation of body changes and to improve, retrain, and facilitate body functions micturition, defecation, sexual pleasure, anatomic prolapse, and their related bodily dysfunctions. The devices can include sensor, optics, send and receive transmitters, local positioning system (LPS) or sensors, computing devices and display elements and devices, which can be powered by bio-generating machines and devices.

20 Claims, 19 Drawing Sheets

Related U.S. Application Data continuation-in-part of application No. 15/842,815, filed on Dec. 14, 2017, now abandoned, and a continuation-in-part of application No. 15/785,278, filed on Oct. 16, 2017, now abandoned, which is a continuation of application No. 14/639,991, filed on Mar. 5, 2015, now Pat. No. 9,820,798, which is a continuation of application No. 13/624,841, filed on Sep. 21, 2012, now abandoned, said application No. 15/974,652 is a continuation-in-part of application No. 15/808,833, filed on Nov. 9, 2017, now Pat. No. 10,342,476, which is a continuation of application No. 15/345,458, filed on Nov. 7, 2016, now Pat. No. 9,931,071, which is a continuation of application No. 13/897,322, filed on May 17, 2013, now Pat. No. 9,521,966, said application No. 15/974,652 is a continuation-in-part of application No. 14/663,348, filed on Mar. 19, 2015, now abandoned, which is a continuation of application No. 13/343,626, filed on Jan. 4, 2012, now abandoned.

(60) Provisional application No. 62/504,463, filed on May 10, 2017, provisional application No. 62/435,016, filed on Dec. 15, 2016, provisional application No. 61/648,425, filed on May 17, 2012, provisional application No. 61/538,708, filed on Sep. 23, 2011, provisional application No. 61/475,469, filed on Apr. 14, 2011, provisional application No. 61/475,489, filed on Apr. 14, 2011, provisional application No. 61/475,530, filed on Apr. 14, 2011, provisional application No. 61/429,693, filed on Jan. 4, 2011, provisional application No. 61/429,687, filed on Jan. 4, 2011.

(51) Int. Cl.

| | |
|---|---|
| *A61B 18/14* | (2006.01) |
| *A61B 18/02* | (2006.01) |
| *A61N 5/10* | (2006.01) |
| *A61N 5/00* | (2006.01) |
| *A61N 2/00* | (2006.01) |
| *A61B 18/00* | (2006.01) |
| *A61N 7/02* | (2006.01) |
| *A61B 18/04* | (2006.01) |
| *A61B 90/00* | (2016.01) |
| *A61M 25/00* | (2006.01) |
| *A61N 1/40* | (2006.01) |
| *A61B 17/00* | (2006.01) |

(52) U.S. Cl.
CPC .............. *A61B 2018/00791* (2013.01); *A61B 2018/00839* (2013.01); *A61B 2018/00863* (2013.01); *A61B 2018/00875* (2013.01); *A61B 2018/00994* (2013.01); *A61B 2018/0262* (2013.01); *A61B 2018/0293* (2013.01); *A61B 2018/044* (2013.01); *A61B 2018/1472* (2013.01); *A61B 2090/378* (2016.02); *A61B 2090/3908* (2016.02); *A61B 2090/3966* (2016.02); *A61B 2218/002* (2013.01); *A61M 25/0068* (2013.01); *A61M 2025/0046* (2013.01); *A61N 1/406* (2013.01); *A61N 7/02* (2013.01); *A61N 2007/025* (2013.01)

(56) References Cited

U.S. PATENT DOCUMENTS

| | | |
|---|---|---|
| 3,822,702 A | 7/1974 | Bolduc et al. |
| 3,918,443 A | 11/1975 | Vennard et al. |
| 3,933,153 A | 1/1976 | Csatary et al. |
| 4,509,504 A | 4/1985 | Brundin |
| 4,537,186 A | 8/1985 | Verschoof et al. |
| 4,769,215 A | 9/1988 | Ehrenkranz |
| 4,858,613 A | 8/1989 | Fry et al. |
| 4,922,917 A | 5/1990 | Dory |
| 5,150,711 A | 9/1992 | Dory |
| 5,354,258 A | 10/1994 | Dory |
| 5,377,678 A | 1/1995 | Dumoulin et al. |
| 5,409,473 A | 4/1995 | Rosenshein |
| 5,897,552 A | 4/1999 | Edwards et al. |
| 5,935,137 A | 8/1999 | Saadat et al. |
| 5,995,875 A | 11/1999 | Blewett et al. |
| 6,016,452 A | 1/2000 | Kasevich |
| 6,098,205 A | 8/2000 | Schwartz et al. |
| 6,152,137 A | 11/2000 | Schwartz et al. |
| 6,217,530 B1 | 4/2001 | Martin et al. |
| 6,231,496 B1 | 5/2001 | Wilk |
| 6,263,232 B1 | 7/2001 | Norman |
| 6,285,902 B1 | 9/2001 | Kienzle et al. |
| 6,425,867 B1 | 7/2002 | Vaezy et al. |
| 6,494,886 B1 | 12/2002 | Wilk et al. |
| 6,508,774 B1 | 1/2003 | Acker et al. |
| 6,656,136 B1 | 12/2003 | Weng et al. |
| 6,666,835 B2 | 12/2003 | Martin et al. |
| 6,685,639 B1 | 2/2004 | Wang et al. |
| 6,726,627 B1 | 4/2004 | Lizzi et al. |
| 6,738,656 B1 | 5/2004 | Ferre et al. |
| 6,741,895 B1 * | 5/2004 | Gafni .................. A61B 5/4337 600/38 |
| 6,960,204 B2 | 11/2005 | Eggerse et al. |
| 6,989,129 B2 | 1/2006 | Mak et al. |
| 7,015,859 B2 | 3/2006 | Anderson |
| 7,699,056 B2 | 4/2010 | Tran et al. |
| 7,739,907 B2 | 6/2010 | Boiarski |
| 7,909,836 B2 | 3/2011 | McLean et al. |
| 8,042,548 B2 | 10/2011 | Neuwirth et al. |
| 8,366,719 B2 | 2/2013 | Markey |
| 8,408,212 B2 | 4/2013 | O'Brien et al. |
| 8,434,489 B2 | 5/2013 | Gopal et al. |
| 8,880,149 B2 | 11/2014 | Barbot et al. |
| 9,521,966 B2 | 12/2016 | Schwartz |
| 9,636,188 B2 | 5/2017 | Gattani |
| 2001/0037098 A1 | 11/2001 | Snyder |
| 2003/0018251 A1 | 1/2003 | Solomon |
| 2003/0029457 A1 | 2/2003 | Callister et al. |
| 2003/0032995 A1 | 2/2003 | Handy |
| 2003/0060702 A1 | 3/2003 | Kuth et al. |
| 2003/0163177 A1 | 8/2003 | Eggers |
| 2003/0208195 A1 | 11/2003 | Thompson et al. |
| 2004/0097806 A1 | 5/2004 | Hunter et al. |
| 2004/0171924 A1 | 9/2004 | Mire et al. |
| 2005/0240170 A1 | 10/2005 | Zhang et al. |
| 2006/0052820 A1 | 3/2006 | Haig |
| 2006/0184003 A1 | 8/2006 | Lewin et al. |
| 2007/0299464 A1 | 6/2007 | Cruise et al. |
| 2007/0163601 A1 | 7/2007 | Pollock |
| 2007/0225550 A1 | 9/2007 | Gattani |
| 2007/0250139 A1 | 10/2007 | Kanzius |
| 2007/0293458 A1 | 12/2007 | Shamsuddin |
| 2008/0017201 A1 | 1/2008 | Sawhney |
| 2008/0051776 A1 | 2/2008 | Bliweis et al. |
| 2008/0097468 A1 | 4/2008 | Adams et al. |
| 2008/0097469 A1 | 4/2008 | Gruber et al. |
| 2008/0178890 A1 | 7/2008 | Townsend |
| 2008/0215042 A1 | 9/2008 | Swanson |
| 2008/0300571 A1 | 12/2008 | LePivert |
| 2009/0131959 A1 | 5/2009 | Rolland |
| 2009/0171241 A1 | 7/2009 | Garcia et al. |
| 2009/0277455 A1 | 11/2009 | Lee-Sepsick et al. |
| 2010/0006105 A1 | 1/2010 | Carter et al. |
| 2010/0043802 A1 | 2/2010 | O'Brien et al. |
| 2010/0152687 A1 | 6/2010 | Carlozzi |
| 2010/0186750 A1 | 7/2010 | Tran et al. |
| 2010/0192959 A1 | 8/2010 | Shandas et al. |
| 2010/0241129 A1 | 9/2010 | Markey |

(56) References Cited

U.S. PATENT DOCUMENTS

| | | |
|---|---|---|
| 2010/0256620 A1 | 10/2010 | Maytal |
| 2011/0094519 A1 | 4/2011 | Gopal et al. |
| 2011/0106021 A1 | 5/2011 | Ruegg et al. |
| 2011/0220120 A1 | 9/2011 | Frigstad et al. |
| 2013/0060116 A1 | 3/2013 | Messerly |
| 2014/0163300 A1 | 6/2014 | Rigney et al. |
| 2015/0032233 A1 | 1/2015 | Cheng et al. |
| 2017/0164885 A1 | 6/2017 | Schwartz |

FOREIGN PATENT DOCUMENTS

| | | |
|---|---|---|
| RU | 2342172 | 12/2008 |
| RU | 2381525 | 2/2010 |
| RU | 2410136 | 1/2011 |
| RU | 2434600 | 11/2011 |
| WO | 200218967 | 3/2002 |
| WO | 2011141829 | 11/2011 |

OTHER PUBLICATIONS

Khati et al., AJR "Multimodality Imaging of the Essure Permanent Birth Control Device: Emphasis on Commonly Overlooked Abnormalities," vol. 196, pp. 648-658 (2011).

Goel et al. "Endometrial Thickness," URL <http://radiopaedia.org/articles/endometrial-thickness>.

Peckham et al. The Histology Guide: Female: Oviduct <http://www.histology.leeds.ac.uk/female/oviduct.php>, University of Leeds.

Formerly Chapel Hill Tubal Reversal Center <https://www.tubal-reversal.net/blog/migrating-essure-coils-is-it-possible-can-essure-coils-move/> (2005).

Woolridge et al., "In Vitro Effects of Oxytocin, acepromazine, detomidine, xylazine, butorphanol, terbulatine, isoproterenol, and dantrolene on smooth smooth muscles of the equine esophagus," Am. Journal Vet. Res., vol. 63 (12), pp. 1732-1737 (Dec. 2002).

Encyclopedia Britannica, <http://www.britannica.com/EBchecked/topic/200908/fellopian-tube.com> (2009).

Clemente et al., Wiliams & Wilkins, "Anatomy, A Regional Atlas of the Human Body," Plate 263, (1997).

Ades et al., Lippincott Williams & Wilkins "Stedman's Medical Dictionary", 28th Edition, pp. 641, 1274, 1459, 1670, 1401, 2078, (2006).

* cited by examiner

Female Urinary Collecting Device
Vulvar Contour
Vaginal-Urethral-Clitoral Relationship Urethral Orifice At Vaginal Orifice Urethra Outside Of Vaginal Orifice Urethra Inside Of Vaginal Orifice FUCD With Visualizing Optics And Camera FUCD With Periscope And Periscope-Like Devices FUCD To Perineum Anus With Flexible Components 8 Skin
25 Perineum 26 Flexible Component of
UCD/6, 9 FUCD/7 Seal FUCD Computerized Alignment Mechanism And System For Placement And Female Anatomy FUCD With Computerized and Display Devices For Placement MUCD With Conduit And Reservoir And Sensors Menstrual Containment Unit And Contraception Menstruation Flow Unit Fecal Collection Unit Breast and Oral Units for Breastfeeding, Pleasure, and Nipple Shaping and Production Sexual and Sensual and Bio-Functional Stimulation and Biofeedback Device with Computerized and Display Units Incontince - Prolapse Device Bladder, Uretha, Vaginal Uterine Changes with Incontince and/or Prolapse Female Pelvic Floor Devices and Detail of Device Separate Vaginal/Anal     Fused Vaginal/Anal 82 Fused Element Anal/Vaginal Device 86 Mechanical, Hydraulic
39, 40, 41, 70, 71
87 Substance
88 Energy
85
89 Battery Change Shape 85 Shape Change Device
39, 40, 41

Devices to Improve Pelvis, Genitourinary, Reproduction, Sexual, and Alimentary Function Penile Covering and Sensors and Devices Activation of LPS and LPS On-Off Energy Generator Related to Blood Flow Induced emf $$e = \int_0^{L_1} u \times B \cdot dL$$

B = Magnetic Flux Density

L = Length Between Electrodes

U = Instantaneous Velocity of Blood Flow, m/s

Inducing Energy with Injectable Substance

Substance with Binding Properties to Tissue

Ferro Magnetic and Magnetic Particles That Can Return to a Magnetic Device

APPARATUS FOR EFFECTING FEEDBACK OF VAGINAL CAVITY PHYSIOLOGY

CROSS-REFERENCE TO RELATED APPLICATIONS

This non-provisional patent application is a continuation of U.S. patent application Ser. No. 15/974,652, filed May 8, 2018, which is a continuation-in-part of U.S. patent application Ser. No. 15/842,815, filed Dec. 14, 2017, which claims the benefit of U.S. Provisional Patent Application Ser. No. 62/435,016, filed on Dec. 15, 2016;
   is a continuation of U.S. patent application Ser. No. 15/974,652, filed May 8, 2018, which is a continuation-in-part of U.S. patent application Ser. No. 15/785,278, filed Oct. 16, 2017, which is a continuation of U.S. Pat. No. 9,820,798, issued Nov. 21, 2017, which is a continuation of U.S. patent application Ser. No. 13/624,841, filed Sep. 21, 2012, which claims the benefit of U.S. Provisional application Ser. No. 61/538,708, filed on Sep. 23, 2011;
   is a continuation of U.S. patent application Ser. No. 15/974,652, filed May 8, 2018, which is a continuation-in-part of U.S. Pat. No. 10,342,476, issued Jul. 9, 2019, which is a continuation of U.S. Pat. No. 9,931,071, issued Apr. 3, 2018, which is a continuation of U.S. Pat. No. 9,521,966, issued Dec. 20, 2016, which claims the benefit of U.S. Provisional Patent application Ser. No. 61/648,425 filed on May 17, 2012;
   is a continuation of U.S. patent application Ser. No. 15/974,652, filed May 8, 2018, which is a continuation-in-part of U.S. patent application Ser. No. 14/663,348, filed Mar. 19, 2015, which is a continuation of U.S. patent application Ser. No. 13/343,626, filed Jan. 4, 2012, which claims priority under 35 U.S.C. § 119(e) to U.S. Provisional Patent Application No. 61/429,687, filed Jan. 4, 2011, U.S. Provisional Patent Application No. 61/429,693, filed Jan. 4, 2011, U.S. Provisional Patent Application No. 61/475,469, filed Apr. 14, 2011, U.S. Provisional Patent Application No. 61/475,489, filed Apr. 14, 2011, and U.S. Provisional Patent Application No. 61/475,530, filed Apr. 14, 2011; and
   is a continuation of U.S. patent application Ser. No. 15/974,652, filed May 8, 2018, which claims the benefit of U.S. Provisional Patent application Ser. No. 62/504,463, filed May 10, 2017, the disclosures of which are incorporated herein by reference in their entireties.

FIELD

This application relates in general to medical urological devices and, in particular, to an apparatus for facilitating sterile collection of urinary fluids in females.

BACKGROUND

The challenge with the collection of a urine sample for diagnostic urine analysis and culture and, specifically, sterile samples is a significant problem in medical care. The challenge of collecting a clean urine sample, sterile urine sample, or both is particularly difficult in females because of difficulty of contamination of the urine sample from fluids and organisms in the periurethral region and specifically from vaginal contaminants that confuses the accuracy of the urine culture and or the urine analysis.

The challenge of urinary incontinence and prolapse, especially in women, is that with aging, after childbirth, and post-hysterectomy, the pelvic floor weakens, which includes weakened muscle and supportive structures. Many rehabilitation strategies fail because of the lack of support for the structures during retraining and rehab and urinary and defecation functions, causing dysfunction of micturition, sexual function and defecation as well as resulting in prolapse of urinary and genital and reproductive structures.

To overcome these and related challenges and limitations, collecting and bodily function devices and improved methods and devices to treat, cure, and rehabilitate bodily functions are described.

SUMMARY

In one embodiment, a urine collection device (UCD) is used in patients who require a more than one urine collection use and this can also include but is not restricted to a UCD that is used in incontinent individuals, or bedridden individuals or individuals with chronic or acute needs for urine collection for either multiple urine collections that can include but are not restricted to long-term urine collections that can include but is not restricted to a 24-hour urine collection sample or a urine collection system that could replace an indwelling urethral catheter or is used in an incontinent or a bedridden, post prostatectomy, incontinence and prolapse or neurologically impaired individual.

In another embodiment of the UCD the sterile urine sample is a one-time urine collection device or method to include but not restricted to be used for urinary laboratory analysis. The UCD for the one-time urine collection use can include but is not restricted to having overlapping designs, similar designs, or both and methods as well as different designs and methods when compare to a UCD that is intended for multiple uses. In the case of the one-time urine collection use UCD the importance of the design and method for acquiring a sterile or clean sample is usually more important than the multi-urination UCD 6 and if such a sterile or clean sample cannot be acquired then this can alter the urine laboratory results and can include but is not restricted to creating a false positive diagnoses because of contamination including but not restricted to infection, renal and bladder dysfunction diagnoses.

In one embodiment, a device which can include but is not restricted to an insert that can be inserted into the vagina 3 or anus 4, can contain to include but not restricted to electrodes 106, sensors 39, magnets 38 and measuring devices that can assess to include but not restricted to pressure, force, magnetic forces 38, transmitters and receivers 40, camera 12, fiber optics 13 and LPS 41 which can communicate with a computing device 18, computer 18, digital computing communication device or phone 18, and can include a display 17 and can anticipate and respond to body 8 movements to include female anatomy 11 including but not restricted to pelvic floor muscles and ligaments 74, muscles and muscle changes 65, Uterus 75, bladder 76, urethral sling 78, prolapsing anatomy 79 changes including prolapsing anatomy 79, 80, 81, to include but not restricted to into the vagina 3 or anal 4 or urethral 2 regions and for which to include but not restricted to the computing devices feedback 70 and response and stimulation 71, EMG, or magnetic forces 38, sensors and sensory changes 39, 66 can be perceived and which can be exerted by the anatomic changes to include but not restricted to prolapse and incontinence and sexual pleasure or sexual dysfunction and for which adaptive responses of the shape and size changing 85, and continuous or intermittent sensory stimulation 71 and feedback 70 can alter the device with adaptive responsive changes to the device 85 which can be generated by mechanical 86 or substance 87 or energy changing mechanisms 88 and which can be generated by to include but not restricted to a battery 84, energy 43 or a substance 44 or a wire 13 or fiber optic 13 energy 43 source or a generator 109, 110 including but not restricted to a standard or biogenerator that, can be exert forces or changes to include but not restricted to pressure, heat, light, electrical 43 or substance 44 discharge or delivery systems 42 can act to include but not restricted to neuro-muscle innervation or blood flow 104 or movement or repositioning of organs of the body to include but not restricted to train or retrain the body to improve or cure or correct or facilitate normal positioning or functional positioning or adequate or improved bodily and sexual functions.

The subject matter described herein is designed to facilitate and overcome the limitations of rehabilitation of body changes and to improve, retrain, and facilitate body functions to include but not restricted to micturition, defecation, sexual pleasure, anatomic prolapse, and their related bodily dysfunctions. The devices can include sensor, optics, send and receive transmitters, local positioning system (LPS) or sensors, computing devices and display elements and devices, which can be powered by bio-generating machines and devices.

In one embodiment, an apparatus for facilitating sterile collection of urinary fluids in females is provided. A conduit is shaped to operatively cover an external ureteral orifice. A receptacle defines a reservoir open along a proximal aspect along which a contoured concave lip is formed and into which the conduit is molded. A flexible watertight seal is provided along the contoured concave lip at an interface to the labia minor.

Many of the elements that are desired for the embodiments herein are discussed in U.S. Provisional Patent application, entitled "Female Urine Collection Device," Ser. No. 62/435,016, filed Dec. 15, 2016; U.S. Patent application, entitled "Gel-Based Seals And Fixation Devices And Associated System And Methods," Ser. No. 14/663,348, filed Mar. 19, 2015; U.S. Pat. No. 9,820,798, issued Nov. 21, 2017; U.S. Pat. No. 9,931,071, issued Apr. 3, 2018; and U.S. Pat. No. 9,521,966, entitled "Localization Of The Parathyroid," issued Dec. 20, 2016, the disclosures of which are incorporated herein by reference.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

In FIG. 1A the urethral 2 orifice is at the vaginal 3 orifice. In FIG. 1B the urethral 2 orifice is superior and outside of the vaginal 3 orifice. In FIG. 1C the urethral 2 orifice is inside of the vagina 3 and posterior to the vaginal 3 orifice.

FIGS. 24A1-A2 are renderings of a conduit 5 with holes 133 with a cover over the holes 133, which when the covers are exposed to a substance 44 or an energy 43 change in size.

DETAILED DESCRIPTION

Figure 1A:
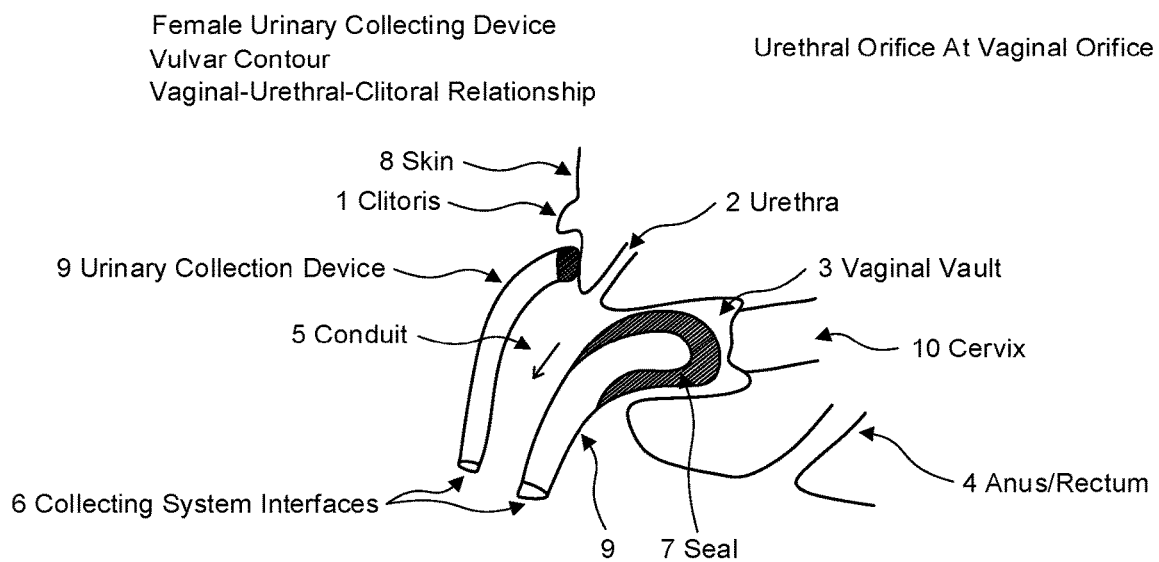
FIGS. 1A-C are sagittal renderings of a Female Urinary Collection Device fitted to fit the contours of the female anatomy.

The term waterproof and watertight can be used interchangeably.

This application relates in general to collection of a Urine Sample for Diagnostic Urine Analysis and Culture using Sterile/Clean Urinary Collection Device (UCD 6) as well as a Fecal/Stool 51 Collection Device (FCD), Breast 57 Collection and Stimulation 71 Device (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices.

This application also relates to energy 43 generation and storage devices and methods that would be utilized to turn-on or operate or activate or control or maneuver or cause a device to function and this can also be applied to the local positioning system/signal 14 device (LPS 41), alone or in concert with these and other devices and how it can assist with localization, and sensing, treating, detection and integration of the LPS 41 with these and with other devices to include but not restricted to the devices and methods and applications herein and as cited by this patent application and as discussed herein this patent application and where applicable to include but not restricted to other sensor 39 or localization or treatment or diagnostic devices or any combination of these. The energy 43 generator 99 and storage units focus on but are not restricted to miniaturizing said units and to use, utilize, apply, exploit, employ, operate, capture or develop biological and non-biological sources of energy 43 and energy 43 capture and transmission and storage to cause these and other devices to function.

The application also relates to activated and not yet activated treatment substance 44 and treatment energy 43 devices for the use of cytotoxic 127 ablation of target hyperfunctioning tissue to include but not restricted to parathyroid 121 glands and adenoma 122, non-parathyroid, adenoma 122, and hyperfunctioning tissue and benign and malignant cells and tissue.

Figure 1B:
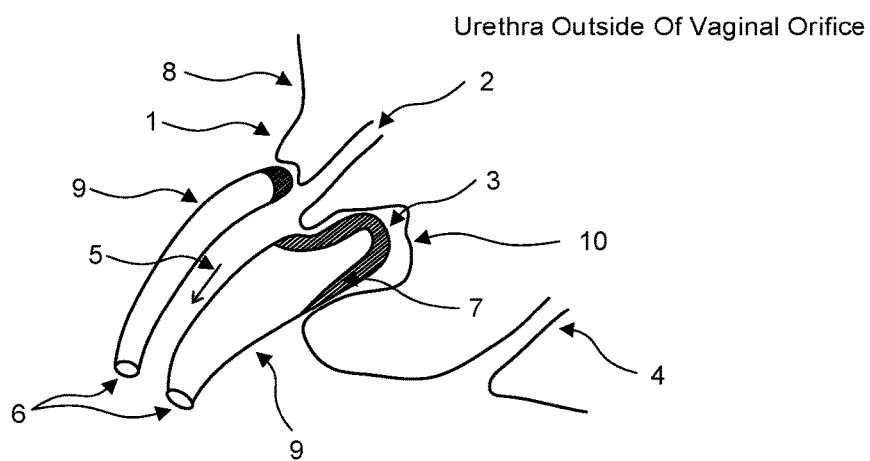
Figure 1C:
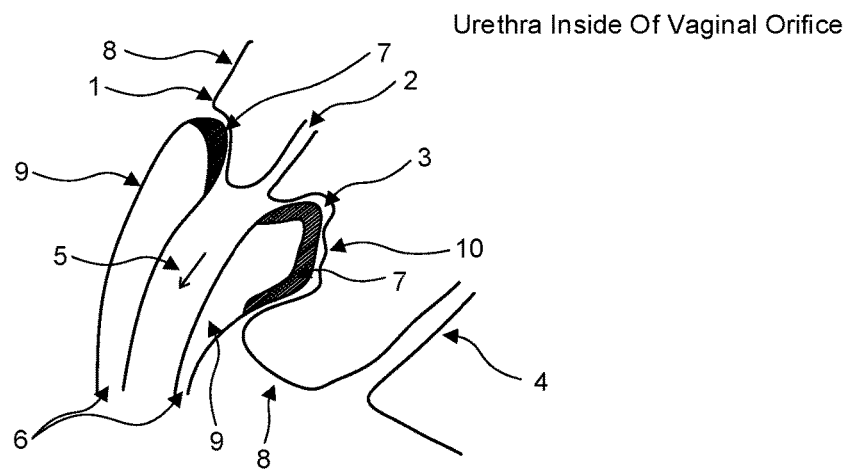

FIGS. 1A-C are sagittal renderings of a Female Urinary Collection Device 6, 9 fitted to fit the contours of the female anatomy 11. In FIG. 1A the urethral 2 orifice is at the vaginal 3 orifice. In FIG. 1B the urethral 2 orifice is superior and outside of the vaginal 3 orifice. In FIG. 1C the urethral 2 orifice is inside of the vagina 3 and posterior to the vaginal 3 orifice. Demands for the device can include but are not restricted to, guiding the placement of the Female Urine collection device 9, sterile or non-sterile collection and facilitation, near watertight or watertight seal 7 (in some designs), does not make a mess at some critical regions, little or no contamination from the vagina, specifically if a sterile collection, conform and take into account the unique vulva 11 and urethral 2 and vaginal anatomy, and guide the urine to its reservoir 43 or collecting system. In some cases, the device can be separated to collect urine during the early stages of urination from late- and midstream urine. In some cases, the device can be used to create a collecting system that is one piece or a minimum number of components, and can also be structured to take into account lab processing and handling, cost, and other considerations.

For sterile/clean urine collection, vaginal 3 fluids are hypothesized to be the leading cause of urine sample contamination. A method and/or device that are used for sterile/clean urine collection can include but is not restricted to a device and/or method to minimize or eliminate contaminates to include but not restricted to vaginal 3 contaminates. One device and/or method to eliminate vaginal 3 contaminants is to place a cover the vaginal 3 orifice. Another method or device is to create a division or wall or barrier separating to include but not restricted to the urine from the urethra 2 from any other non-urethral 2 tissue or contaminants which can include but is not restricted to partially or fully dividing one or more regions of the vulva 11 and vagina 3 from other vulva 11 and vaginal 3 structures from the urethra 2 and the periurethral 2 mucosa but also to separate the urethra 2 and urine from the clitoris 1, the mucosa, redundant mucosa, the skin 8, the mons pubis, the pubic bone 77, the urethral sling 78, the local skin 8 and hair and mucosa or any combination of these. Divisions can also separate and isolate and restrict anal 4 and perianal and perineal 25 region contaminates from the urethra 2 and urine. On one embodiment the vagina 3 cover or cap can include but is not restricted to be constructed with a bump, knob or protrusion that can include but is not restricted to cap, plug, constrain or prevent vaginal 3 contaminates from escaping the vaginal 3 vault and preventing these contaminates from exiting the vaginal 3 vault and preventing urine from entering the vaginal 3 vault. In one embodiment, the vaginal 3 cover or cap can be near to fully airtight or watertight with the vaginal 3 and perivaginal 3 mucosa. In another embodiment the vaginal 3 bump, knob or protrusion can have a near to fully airtight or watertight seal. In another embodiment the bump, knob or protrusion can be elongated to fill a portion or all-of or nearly all-of-the vaginal 3 vault. This elongation of the vaginal 3 protrusion can include but is not restricted to being composed of a solid or gel or a gas or liquid that is enveloped or contained and this elongation can include but is not restricted to form an airtight or near airtight or watertight seal 7 with to include but not restricted to the vaginal 3 vault and can include the vaginal 3 orifice. In another embodiment the urethra 2 and immediate periurethral 2 region and the urinary cavity or reservoir 43 or site of urine flow can be separated from the other living body structures to include but not restricted to the perineal 25 region, the regions of the living body away from and peripheral to the urethra 2 and immediate periurethral 2 region using by divisional means herein described utilizing to include but not restricted to a solid or a gel or a fluid or liquid that is encapsulated. In another embodiment the vaginal 3 component can insert fully or partially into the vagina.

To adhere or attach the divisions or walls or covering 36 material to the human body including but not restricted to the skin 8 or hair or mucosa the attaching component can be used to include but not restricted to adhesives, tackifying materials and glues and magnets 38 or magnetic materials.

Visualizing Anatomy:

Females have difficulty with positioning clean/sterile urine collection devices 6 because of limitations in viewing the vaginal 3 region. Surveys indicate that up to 50% of women do not fully understand or have not fully viewed their own or other women's vaginal 3 anatomy. A method and/or device that is used for sterile urine collection can include but is not restricted to a device and/or method to visualize the female periurethral 2 female anatomy, urethra, vulva 11, labia, vagina, perineal 25 and anal anatomy.

Figure 2:
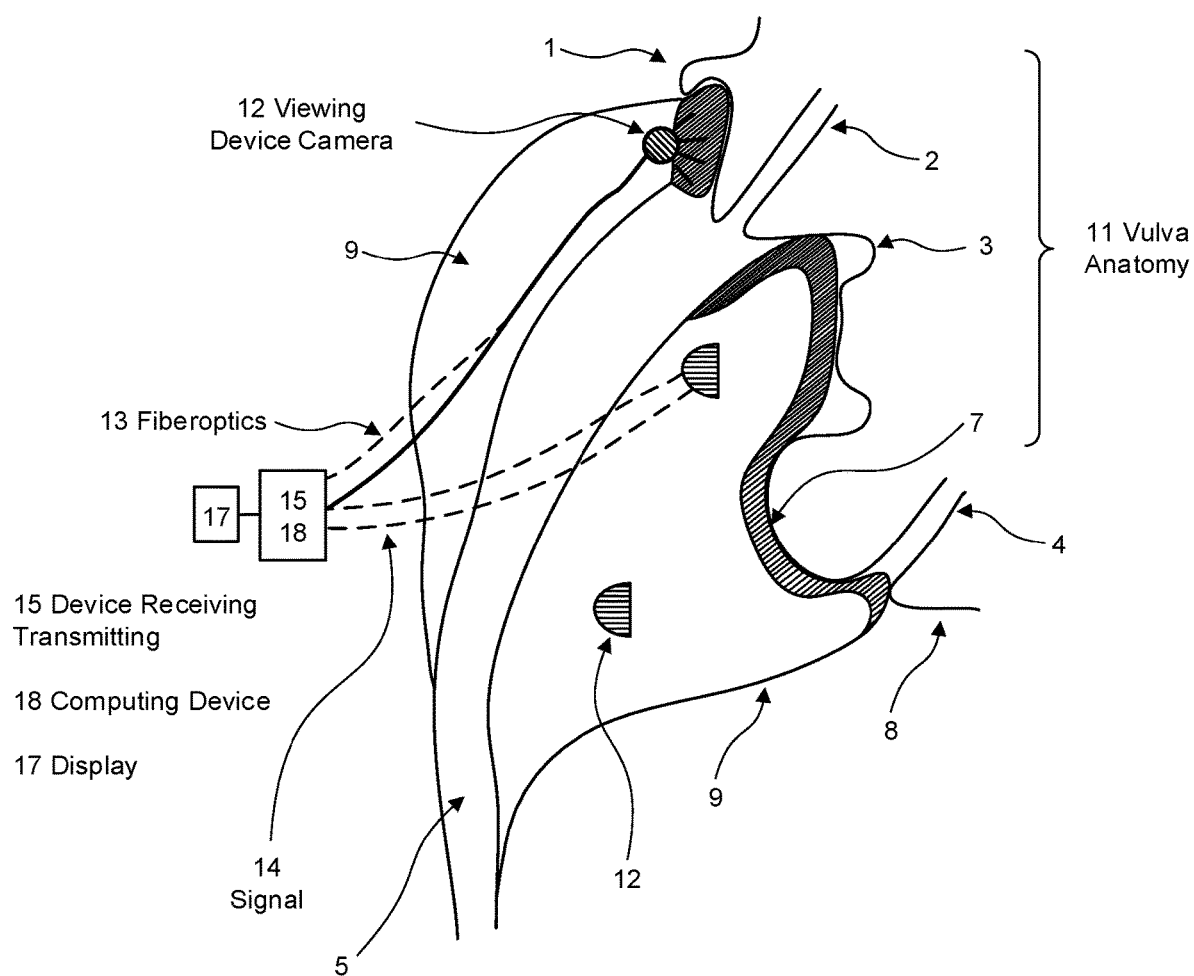
FIG. 2 is a sagittal rendering of a Female Urinary Collection Device with cameras and optical 12 viewing devices for accurate placement to fit the contours of the vulva 11 and female anatomy.

FIG. 2 is a sagittal rendering of a Female Urinary Collection Device 6. 9 with cameras 12 and optical 12 viewing devices for accurate placement to fit the contours of the vulva 11 and female anatomy 11. The placement of the UCD 6 can include a visualization means to include a method and device that can include but not restricted to embedding optical 12 devices, optics and fiber optics 13 and cameras 12 12. The term optics or optical 12 devices can include but is not restricted to optical 12 elements standardly known, optics and fiber optics 13 and cameras 12 or all varieties and variations of optics and fiber optics 13 and cameras 12 and the terms can be used interchangeably. Optics can include but are not restricted to at least one of optics and fiber optics 13 and cameras 12 to include but not restricted to lenses 24 and optics that can include but is not restricted to curve of one or multiple geometric shapes. Optics and fiber optics 13 and cameras 12 can include but is not restricted to having the ability to magnify, minify, give true appearance, angulate and reverse and inversion correct and provide the user with the true directional or orientation anatomic appearance that would enable the user to include but not restricted to position, adjust perform functions required for the UCD 6 or other devices.

Figure 3:
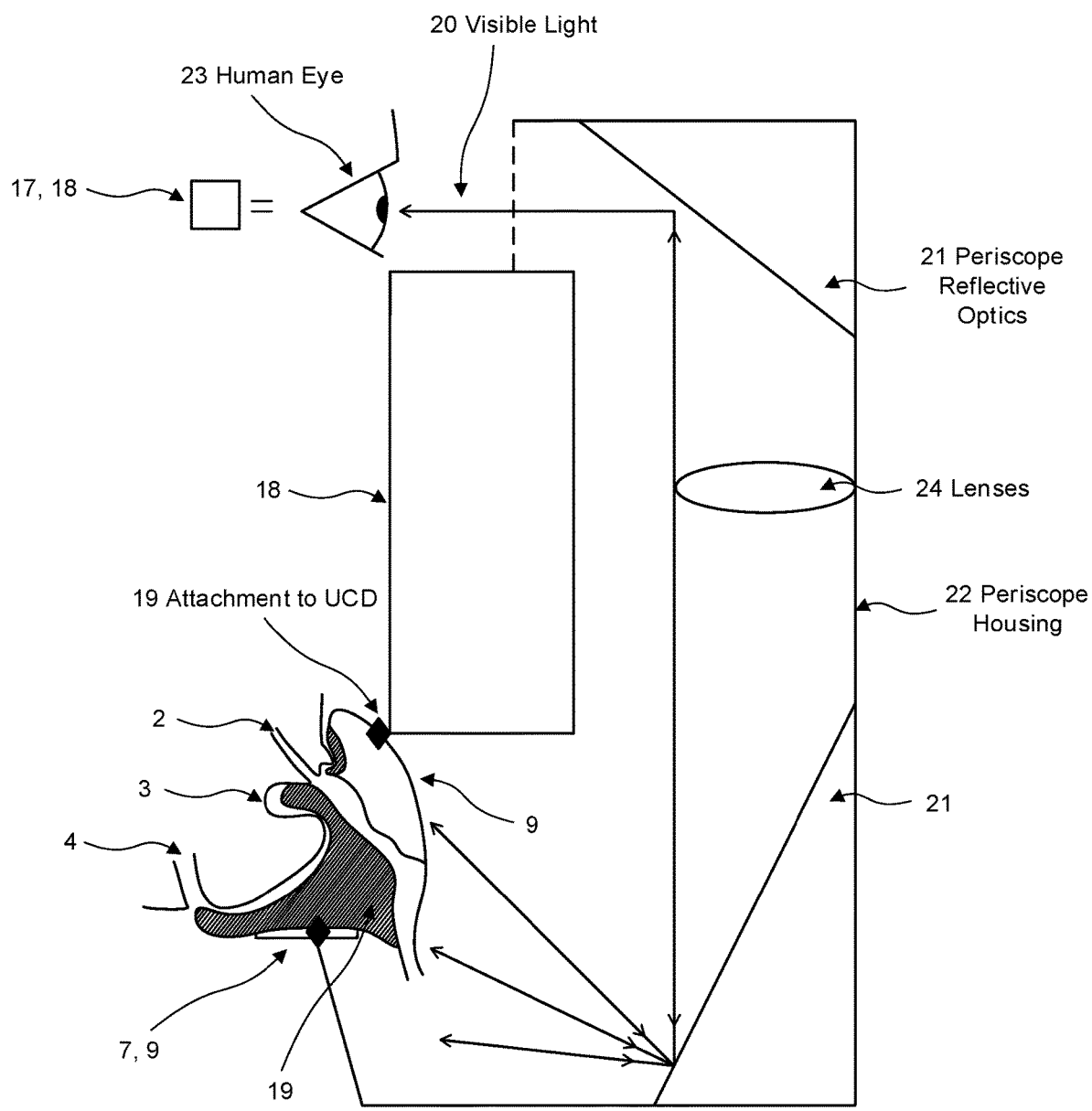
FIG. 3 is a sagittal rendering of a Periscope and Periscope-like device that can incorporate the Female Urinary Collection Device for accurate placement to fit the contours of the vulva 11 and female anatomy.

FIG. 3 is a sagittal rendering of a Periscope 21 and Periscope-like 21 device that can incorporate the Female Urinary Collection Device 6. 9 for accurate placement to fit the contours of the vulva 11 and female anatomy 11. The optics and fiber optics 13 and camera 12 and camera-like devices can incorporate other optic devices and other optic correction devices that can include but is not restricted lenses 24 and prisms 21 and that can include but is not restricted to be used in multiplicity (more than one), alone or in combination and to include but not restricted to be used in multiple formats, shapes, sizes to include but not restricted to a periscope 21,22 or periscope 21,22-like device, and a non-reversing optics and fiber optics 13 and cameras 12. Optical 12 methods can also include but are not restricted to fiber optics 13, transmitting 16 wire 13, transmitting 16 cables 13, cameras 12, cellular devices and phones 18 and computers 18 that can include but are not restricted to sending 16 and receiving 16 and communicating and projecting, displaying 17, transmitting 16 signals 14 and sending 16 and receiving 16 and communicating and displaying analog and digital information and data and images 29 to include but is not restricted to a living body or a machine or computer 18 or digital or computing 18 or projecting analog or digital device. The said video device and behave similar to a video game aligning the individual anatomy with the optimal positioning of the device with the anatomy. In one embodiment is to include but not restricted to the image of the UCD 6 can be maneuvered such that to the real anatomy of the vulva 11 and urethra 2 and adjusted until the misaligned 31 UCD image is aligned with the true aligned 30 anatomic image. In this embodiment to include but not restricted to sensor 39 and optics 12 and camera 12 and computing devices 18 and the displays 17 can assist the human in aligning the components of the UCD 6 and the real anatomy 11. This can be applied to other parts of the human body and skin 8.

In one embodiment, these optics and optical 12 and optical 12-like devices can include but are not restricted to be used in combination or alone and can that can include but is not restricted to devices and methods the visualize and project and reflect and produce images 29 of the vulva 11 and urethral 2 region and its surrounding and bordering tissue and parts and that can include but is not restricted to creating the optimal orientation and magnification to include but not restricted to the true directional or orientation anatomic appearance.

The optics and fiber optics 13 and cameras 12, periscope 21,22 or periscope 21,22-like, or visualization methods can be one or multiple in number and can be located on the inner or outer surfaces or can be incorporated into the UCD 6 or can be a combination of these and can reside at one or multiple locations.

In one embodiment, the optics and fiber optics 13 and cameras 12 or periscope 21,22 or periscope 21,22-like or visualization methods can be one or multiple in number and can be located on the inner or outer surfaces or can be incorporated into the Collecting Reservoir 43 or cup that can be used but is not restricted to be used by the laboratory to collect and transmit the specimen from the patient to the laboratory or for medical or other analytic uses or for culture or for medical or environmental or industrial or personal uses or any combination of these and said optics and fiber optics 13 and cameras 12 or periscope 21,22 or periscope 21,22-like or visualization devices can reside at one or multiple locations. In one embodiment, the optics and fiber optics 13 and cameras 12 or periscope 21,22 or periscope 21,22-like or visualization methods can be in the lid of a container that can include but is not restricted to a cup, ajar, a reservoir 43, a flask or beaker or pouch or test tube or cylinder or other holder or container of the urine or liquid collected and that that container can have a periscope 21,22 or periscope 21,22-like or optics and fiber optics 13 and cameras 12 or visualization system that can be incorporated into the lid of the container or on the bottom of the container or on any portion of that container and said container can be formed with shapes that can include but is not restricted to having the ability to magnify, minify, give true appearance, angulate and reverse and inversion correct. The optics and fiber optics 13 and cameras 12 device can incorporate other optic devices and other optic correction devices that can include but is not restricted lenses 24 and prisms 21 and optics and fiber optics 13 and cameras 12 and that can include but is not restricted to be used in multiplicity (more than one), alone or in combination and to include but not restricted to be used in multiple formats, shapes, sizes to include but not restricted to a periscope 21,22 or periscope 21,22-like reflecting device, and a non-reversing optics and fiber optics 13 and cameras 12. The collecting container can be to include but not restricted to the optics and fiber optics 13 and cameras 12, the periscope 21,22 or periscope 21,22-like, or contain any of the optics needed for visualization of the urethral 2 regions including but not restricted to visible 20, 43 light.

In another embodiment the periscope 21,22 21,22 and the UCD 6 can be to include but not restricted to attached 19 mechanically connected 19 or incorporated to each other 19.

In another embodiment the optics and fiber optics 13 and cameras 12 or periscope 21, 22 or periscope 21, 22-like or visualization method can be included but not restricted to the inner surface or outer surface or within the substance 44 or structure of the UCD 6 or collection container or any combination of these surfaces or structures.

In another embodiment the optics and fiber optics 13 and cameras 12 or periscope 21, 22 or periscope 21,22-like can be placed onto or peeled off of the UCD 6 or Container and can have all of the optical 12 variations described for the UCD 6 and Container optics and fiber optics 13 and cameras 12 and periscope 21,22 or periscope 21,22-likes and visualization methods and devices.

Morphologic Vulva 11, Vaginal 3 and Periurethral 2: Fit Taking into Account variability:

Vulva 11 and vaginal 3 shape vary widely amongst females. The size of the labia and clitoris 1 has been studied and vary widely. The length of the clitoral to urethral 2 distance is in the medical literature with a range of 1.5 to 4.5 cm with a mean of approximately 2.5 cm. The vaginal 3 urethral 2 relationship is variable. The description and the length between the urethral 2 position and distance relative to the vagina 3 have not been studied and the urethral 2 position can vary from the anterior vagina 3 with a position adjacent to the vaginal 3 orifice which can include but is not restricted to within, in, at, on, or superior to the vaginal 3 orifice. Therefore, a collecting device optimally can include but is not restricted to a method to position said device to be positioned in a manner to include but is not restricted to be able to that take into account the periurethral 2 female anatomy, urethra, vulva 11, labial vaginal 3, perineal 25 and anal 4 variability. Urethral 2 Variation and position relative to the vaginal 3 orifice affects the shape vaginal 3 component of the urinary collection device 9 and the efficacy of sterile and clean urine collection.

The medical literature is inconsistent and sparse in defining the folds including but not restricted to the labia and other as well as other divisions of the vulva 11 other. The medical literature generalizes the folds of the vaginal 3 region as labia minor and majora. Observations of the variability of the vulva 11 and the secondary folds need to be taken into account if a targeted periurethral 2 tight seal 7 is to be formed. In additional the urethra 2 can have multiple embryologic and anatomic variations and adjacent folds and redundant tissue surrounding its location. If a tightly targeted and fitting female urinary collecting device is to be created then these variations need to be taken into account and manual sensing or directional placement elements or visualization of this region or any combination of these during engagement of the collecting device and living body may prove useful if not necessary.

Although it can be possible that a guiding system utilizing the anatomy may suffice in some individuals, for other individuals a visualization system may helpful or even be required. There are considerations in these variations in the shape of the vulva 11 and vagina 3 and urethra 2 that are provided herein this patent application to improve urine collection that can include but is not restricted to refer to all vulva 11 and vaginal 3 and periurethral 2 structures and folds to include but not restricted to the labia minora, the labia majora, adjacent and overlying skin 8, hair, glands, the secondary folds, the urethra, the periurethral 2 region, the clitoris 1, the mucosa, redundant mucosa, the skin 8, the mons pubis, the vagina, the local skin 8 and mucosa and the adjacent perineum 25 and perineal 25 region near and including the anus 4 in some cases. And creating to include but not restricted to a watertight, urine tight or airtight seal, or proper placement of the device for optimal urine collection that is clean, or sterile or does not make a mess are all taken into account.

Because of the variability or the urethral 2 opening position relative to the vagina, the device near the urethra 2 and covering 36 the vagina 3 and its contaminants, can include but is not restricted to have an unobstructed pathway about the urethra 2 such that the urine and urine stream when released does not mix with the vaginal 3 contaminants, allows the urine to flow relatively or fully freely, and the device does not block the urine stream, such that the urine can flow into any reservoir 43 or collecting device if one is present, can flow away from the human body without obstruction, does not cause discomfort, is easily positioned or repositioned and/or guided into place so that the urine is maximally and effectively captured, and does not leak and create a mess that the device at or near the urethra 2 and periurethral 2 region is relatively or fully watertight, guides the urine to its target collecting device.

Because the urethra 2 and vaginal 3 junction is variable in shape and size and location this morphologic variation can be considered when constructing a device and creating a method to capture clean or sterile urine in an efficient manner. In one embodiment the vaginal 3 opening is covered and the site nearest the vaginal 3 and urethral 2 and periurethral 2 junction is fashioned in a manner that can include but is not restricted to creating a contour that can include but is not restricted to a groove or indentation or protuberance or concave or convex shapes or semi-circular or geometric and non-geometric shapes or uniform or non-uniform shapes and linear shapes or have conduits 5 or any combination of the above that allows for the urine and urine stream leaving the urethra 2 to and not restricted to being obstructed or encroached upon fully or partially or to being sprayed or disseminated or being directed into or toward the vaginal 3 region or vagina 3 or being directed toward contaminated regions. The contoured shape at the site of the cover near the vaginal 3 or vaginal 3 region and near or nearest the urethra 2 and periurethral 2 region can be constructed in a manner that can include but is not restricted to allow the urine to flow freely to include but not restricted to away from contaminated regions, the vagina 3 and vaginal 3 regions, the anus 4 and perianal 4 and perineal 25 regions or to regions that do not optimally serve to collect the urine in an efficient manner. Contours and seals 7 and designs should take into account structures that can include but is not restricted to contaminated areas of the skin 8 and tissue and body parts.

Contours and seals 7 and designs should allow urine to flow away from the urethra 2 and avoid a creating a leak or mess that is undesired but it can be intended to allow the urine to flow to include toward the desired direction and that said desired direction can include but is not restricted toward devices to collect the urine which can include but not restricted to one or more collecting receptacles, vessels or cups or containers or reservoirs 43.

In one preferred embodiment the UCD 6 can include but is not restricted to have a concave contour on the vaginal 3 covering 36 with said contour being concave and forming a valley or valley like configuration and the said concave component facing the direction of the urethra 2 and allowing the urine stream to pass unabated as it leaves the urethra 2 and travels away from the living body. Other embodiments can include but are not restricted to can include but is not restricted to a groove or indentation or protuberance or concave or convex shapes 85, 86, 87, 88 or semi-circular or geometric and non-geometric shapes 85, 86, 87, 88 or uniform or non-uniform shapes 85, 86, 87, 88 and linear shapes or have conduits 5 or any combination.

Acceptability of Using a Device that Requires Self-Manipulation or Touching of the Vaginal 3 Region Some women may not choose to use a urinary collection device 9 because of the need to manipulate the vaginal 3 region. This will likely be a small percentage given that is estimated that over 92% of women have masturbated in their lifetime and that 40-60 percent of women use a tampon at any given time in the US but still acceptability is an area of 'cultural sensitivity' that must be honored. Therefore, if a UCD 6 is instituted it would be expected to be acceptable based on these statistics. In order to enhance usage and minimize objections to usage the UCD 6 can be constructed in a manner that minimizes the need for a user to perform multiple manipulations of the device. Methods to reduce manipulations include but are not restricted to a conforming and well-fitting UCD 6 that can include but is not restricted to fit inside or under or outside the folds of the vulva 11, clitoral, the labia majora, the labia minora and the vagina 3 or vaginal 3 region or any combination or these structures. The butt or gluteal cheeks and anus 4 can be used to position the UCD 6 and the UCD 6 can lay both inside, on, and outside or around the vulva 11 and clitoral, the labia majora, the labia minora and the vagina 3 or vaginal 3 region or any combination or these structures.

Guiding Urinary Device Placement:

Guiding the Urinary collection system into place is currently performed without visualization and without a guidance system.

Guidance systems can be but are not restricted to non-visual guidance systems. Guidance systems can include but are not restricted to using the contours of the vulva 11 and vagina, labia, surrounding skin 8, and periurethral 2 and urethral 2 regions. The UCD 6 can include but is not restricted to lie inside or on or in or outside or any combination of these locations. The clitoral region is shaped like a U or V-shape and a device that can include but is not restricted to lie inside of that a U or V-shape and that shape can be used to guide or sense the proper fit of the device; the groove of the labia minora and labia majora and their folds such that that shape can be used place the device; the vaginal 3 opening has a shape that can serve as a guide for placement of the device; the vaginal 3 hole 133 has a hole 133 that can be used to guide the device although limitations of the vaginal 3 hole/cylinder can include angle and depth that must be compensated for as opposed to the opening; the vaginal 3 orifice can be felt and can serve as a guidance point specifically as relates to the vaginal 3 rim and vaginal 3 opening and the vaginal 3 hole/cylinder; the accessory folds and contours of the vulva 11 can assist in guidance, the perineum 25 and butt cheeks and anus 4 can serve as points of guidance.

The UCD 6 that can include but is not restricted to a guidance system that can include but is not restricted to a computer 18 or computer-assisted device that that can include but is not restricted to a device that identifies the vulva 11 structures to include but not restricted to the urethra 2 and periurethral 2 and clitoral and all vulva 11 and vulva 11 related structure to include but not restricted to all vaginal 3 and periurethral structures and folds to include but not restricted to the labia minora, the labia majora, adjacent and overlying skin 8, hair, glands, the secondary folds, the urethra, the periurethral 2 region, the clitoris 1, the mucosa, redundant mucosa, the skin 8, the mons pubis, the vagina, the local skin 8 and mucosa and the adjacent perineum 25 and perineal 25 region near and including the anus 4 in some cases. The guidance system that can include but is not restricted to using electromagnetic, visual, optical 12, kinetic, ultrasound, radioactive, thermal, sensory 39, 66, or topographic systems. And the guidance system can give feedback 70 to the user as the UCD 6 is positioned and feedback 70 can include but is not restricted to feedbacks 70 of computers 18 to include but not restricted to voice commands, a directional map of the users vaginal 3 and vulva 11 region and can show the effectiveness of placement that can include but is not restricted to showing a pictorial overlay of the UCD 6 and the users vagina 3 and directional adjustments can be made from this and can include but are not restricted to auditory, visual, tactile and other sensor 39 or sensory 39, 66 inputs or any combination of these. The inputs can be in combination with a computer-assisted device or can involve no computer-assisted device.

The UCD 6 and these devices and their interfaces can be to include but not restricted to be near or fully air-tight or watertight and can be made to include but not restricted to a gel or a material that is compressed against the body or fits the contours of the body or has one or multiple walls or flanges to prevent leakage outside or away from the desired direction of urine flow or a combination of these.

One of the objectives is to have the user not make a mess or have to even touch or come in contact with the urine of the user or the receiver of the urine.

One acknowledgement is that the user of the UCD 6 or these devices may not be the receiver of the urine or stool 51 or blood and also that the individual positioning the device may or may not be the user of the UCD 6 or devices because of to include but not restricted to handicaps, age, comfort, injury or other limitations.

Construction

The UCD 6 can include but is not restricted to be continuous without openings or pores or fenestrations 133 or it can be discontinuous and with openings or pores or fenestrations 133 and either UCD 6 formation can include none or one or more than on conduits 5 for urine flow egress or collection or windows or openings or pores or fenestrations 133 for visualization. In one embodiment the UCD 6 will cover the outer aspect of the labia majora and interface with the skin 8 with a conforming gel that is urine tight and will have a conduit 5 allowing the urine to be directed toward and collected into a urine receptacle. In another embodiment the UCD 6 will fit inside of the labia minor and under the folds of the labia minora and the clitoris 1 and will have a vaginal 3 cover with a valley-like contour facing the urethra 2 and a urethral 2 opening surrounding the urethra 2 and leading to include but not restricted to a urine containing cavity or a continuous urinary tube or channel or conduit 5 leading to a receptacle that can collect said urine and that receptacle can be separated from the UCD 6 for laboratory processing and this embodiment can include the UCD 6 being composed of a optics and fiber optics 13 and cameras 12 or periscope 21, 22 or periscope 21, 22-like on the outer to guide the placement of the UCD 6 into its proper position with a computer-assisted device that is a handheld device, such as a cellular phone.

A continuous covering 36 of a UCD 6 can include but is not restricted to pores or fenestrations 133 or openings for and for a window for visualization of the anatomy including but not restricted to the urethral 2 urinary flow and for vulva 11 and urethral 2 and periurethral 2 cleansing, and for positioning of the UCD 6 and for urinary collection which can include but not restricted to a receptacle or urinary cup or a series of urinary channels or tubes.

A discontinuous covering 36 of the UCD 6 can include but is not restricted to fenestrations 133 or openings or pores for visualization of the anatomy including but not restricted to the urethral 2 urinary flow and for vulva 11 and urethral 2 and periurethral 2 cleansing and for window, and for positioning of the UCD 6 and for urinary collection including but not restricted to a receptacle or urinary cup or a series of urinary channels or tubes.

The UCD 6 or its covering 36, its material and components can include but is not restricted to be composed of a solid or a gel, a gel slurry or a gel, or an encapsulated gel, gel slurry, fluid/liquid, solid or gas encapsulated or can be a combination of these and that can include but is not restricted to a silicon, cloth or rubber, or a waterproof or water resistant material, plastic, metallic organic or inorganic material, carbon fiber, a hydrophobic or hydrophilic gel, or neutral gel, or nano 63 particle or any combination of these. The UCD 6 can be composed of one or multiple layers 98.

The interface with the living body can include a solid or a gel, gel slurry, or an encapsulated gel, gel slurry, liquid/fluid, solid or gas or a combination of these and that can include but is not restricted to a silicon, cloth or rubber, or a waterproof or water resistant material, plastic, metallic organic or inorganic material, carbon fiber, a hydrophobic or hydrophilic gel, or neutral gel or a nano 63 particle or any combination of these. The interface can be composed of one or multiple layers 98.

The Interface of the UCD 6 with the living body can include but are not restricted to none, one or more than one flaps and wedges and divided components of the interfaces and these interfaces can include but are not restricted to having these interfaces have divisions, brackets, walls and anatomic structures dividing structures. In one embodiment the interfaces can bracket the labia minora with one or more brackets lying inside and one or more brackets lying outside the labia minora. In another embodiment the bracketed interface can be a wedge shape that lies under the clitoris 1 and a flat bracket lying over the clitoris 1. In one embodiment a soft gel flap can lay above the labia minor and a thin and firmer gel flap or thin soft silicone-gel-like can lie beneath the labia minora. These individual flaps and interfaces can include but are not restricted to be constructed of the same or different materials, and of the same or different elasticity or hardness or softness or durometers, or stretchiness and that varies between the living body and the UCD 6 components The covers and interfaces can be constructed to include but not restricted to be such that the elasticity or hardness or softness or durometers, or stretchiness varies between the living body and the covering 36. In one embodiment the covering 36 can be softer near the vulva 11 and the living body relative to away from the vulva 11 and the living body. In another embodiment the covering 36 can be harder near the vulva 11 and the living body relative to away from the vulva 11 and the living body.

The UCD 6 can be composed of a moldable or a non-moldable material. The moldable material of the UCD 6 can conform to the living body. The moldable nature can be created to include but not restricted to it being moldable as the result of thermal change, pressure, dampness, a soft gel or gel-slurry, foam, encapsulated liquid or gas, a meniscus effect, an adhesive-like or glue-like material, a poly-phase 94, 96 or change phase 94, 96 material that can include but is not restricted to having the material conform to the living body or the UCD 6 by means to include but not restricted to thermal, hot or cold, electromagnetic, UV 43, Infrared, visible 20, 43 light, electrical, chemical, aqueous and non-aqueous chemicals, fat-like and oil, protein-like and amino acid and nucleotide, and carbohydrate, Kinetic, Ultrasound, pressure and their effects and processes and reactions and any combination of these means methods or materials.

The covering 36 can be constructed such that there is variable elasticity and hardness and softness and durometers and stretchiness exists about and around and relative to and within and involving the variable aspects of the cover and relative to the interfaces and relative to the discontinuous or opening components and relative to the living body. In one embodiment the covering 36 can be softer near the vulva 11 and the living body and harder away from the vulva 11 and the living body. In one embodiment the interface can be a gel that is firm near the UCD 6 cover allowing the gel to bond firmly to the cover and the gel that lies near the living body can be soft or softer to allow the gel to for a seal 7 that that can include but is not restricted to forming a near or complete airtight or watertight seal 7 and the interface with the mucosa or skin 8 or hair of the living body and can create a comfortable bond between the interface cover and the living body.

In one embodiment the covering 36 can include openings with gaskets that can be softer to allow but not restricted to transmitting 16 object to include but not restricted to tubes, instruments, wires 13, sensor 39 or fiber optics 13 or cables 13 pass through the UCD 6 including but not restricted to its materials and covering 36 and create an airtight or watertight seal. In one embodiment the gaskets can include but are not restricted to be self-sealing or self-closing and be watertight.

The UCD 6 can include one or more tubes or channels or conduits 5. In one embodiment the tube can be continuous from the urethral 2 opening to a location to include but not restricted to the collecting receptacle, collecting device or urine analysis tubes. In another embodiment the tube can arise from a region that is not the urethra 2 and the tube can drain the urine to include but not restricted to from within the UCD 6, a cavity of the UCD 6 or a reservoir 43 of the UCD 6 to the urine collection receptacle.

Figure 4:
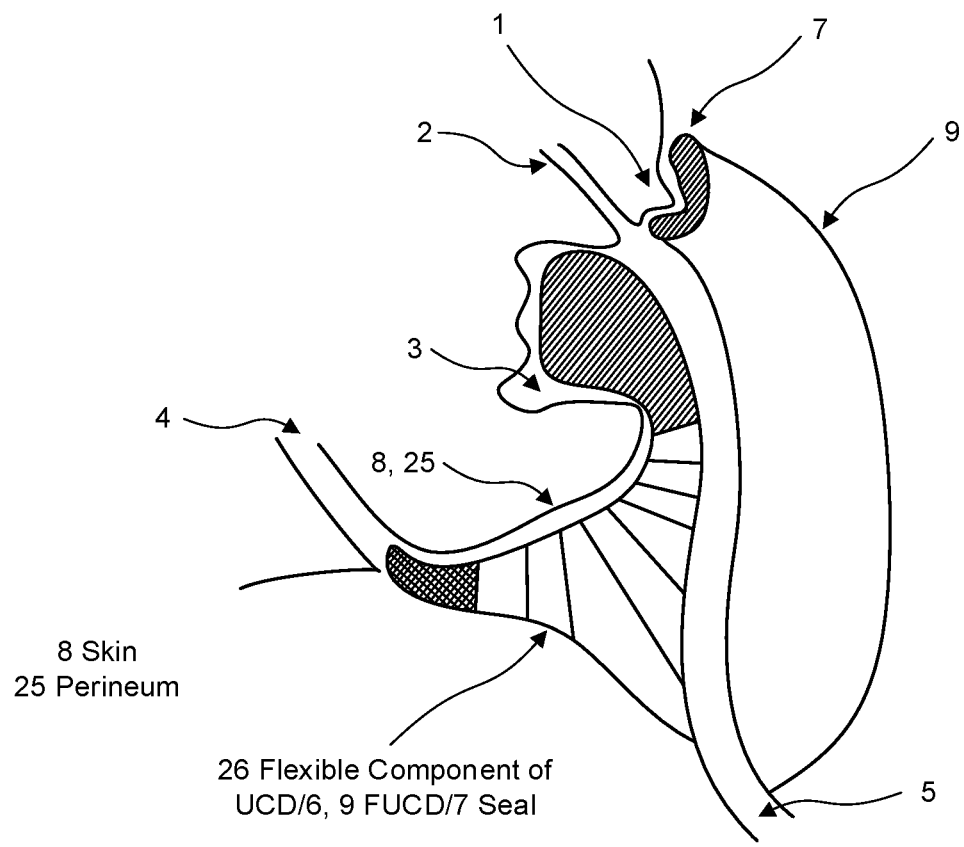
FIG. 4 is a sagittal rendering of a Female Urinary Collection Device fitted to fit the contours of the female anatomy extending along the perineum 25 and anal region with flexible 26 components.

FIG. 4 is a sagittal rendering of a Female Urinary Collection Device 6, 9 fitted to fit the contours of the female anatomy 11 extending along the perineum 25 and anal region with flexible 26 components. The UCD 6 can include but is not restricted to having a thin shape. The thin UCD 6 can include but is not restricted to being a combination of flexible 26 or hard in varying regions and curved and thin and conforming to the contours of the vulva 11 which can include but is not restricted to the UCD 6 lying within the folds, beneath the folds or between the folds or on the labia minor or labia major and clitoris 1. In one embodiment the UCD 6 is thin and conforms to the mucosa of the precise or general vulva 11 and mucosal contour and lies within the biologic cavity or confines created by the labia minora and clitoris 1 and can have openings or pores or fenestrations 133 or an opening for the urethra 2 for allowing urine to flow away from the living body and said UCD 6 can also have a vaginal 3 cover overlying the vagina 3 and said vaginal 3 cover can include but is not restricted to have a portion of said vaginal 3 cover of the UCD 6 to insinuate itself into or around or above or about the vaginal 3 orifice or its opening or circumference. The urethral 2 opening in the UCD 6 is open in a manner to allow flow of urine to egress freely out from the urethra. The urine can then egress into to include but not restricted no separate components or can spate into one or more components of the UCD 6 or a cavity or cavities created by the UCD 6 or by a cavity created by any combination of the UCD 6 and the living body and/or any component of a conduit 5 or tube or channel. The conduit 5 or tube or channel can be separate from or can be a component of the UCD 6 or a combination of these. The conduit 5 or tube or channel can include but is not restricted to arise from the urethral 2 opening of the UCD 6, from the outer borders or circumference of the UCD 6 or any component of the UCD 6 or its material or covering 36. In one embodiment the thin UCD 6 conforms to the living body mucosa between the labia minora and the clitoral folds with a wall at the cephalad (toward the living beings head) end of the vagina 3 and the vaginal 3 cover and with a urethral 2 opening in the UCD 6 and with a conduit 5 emerging from the UCD 6 at the perimeter of the urethral 2 opening of the UCD 6 and said conduit 5 attaching to a urinary receptacle and the urinary receptacle can have but is not restricted to having at least one optics and fiber optics 13 and cameras 12 that allows for viewing of the vulva 11 and urethral 2 region for initial positioning, maintenance of position and placement of the UCD 6 relative to the vulva 11 and urethral 2 region.

The UCD 6 can have elbows or flex-points that allow the UCD 6 or its components to move or flex to changes in anatomy or changes in body position or changes to the anatomic or functional needs of the UCD 6.

The UCD 6 can contain none or one or more than one handle to facilitate the gripping, stabilization and conduct and handling of the UCD 6. The handle can have none or one or multiple optics and fiber optics 13 and cameras 12.

The UCD 6 can be composed of one or multiple layers 98.

The UCD 6 can include the urine collecting device or reservoir 43 that is used for the Urine being collected for laboratory analysis laboratory analysis. The UCD 6 and its components can be separate or any of the components or units can be merged and one unit or component.

The UCD 6 can be separate from the urine collecting device or reservoir 43 that is used for the Urine being collected for laboratory analysis.

The UCD 6 can be composed of one or more than one piece

Figure 5:
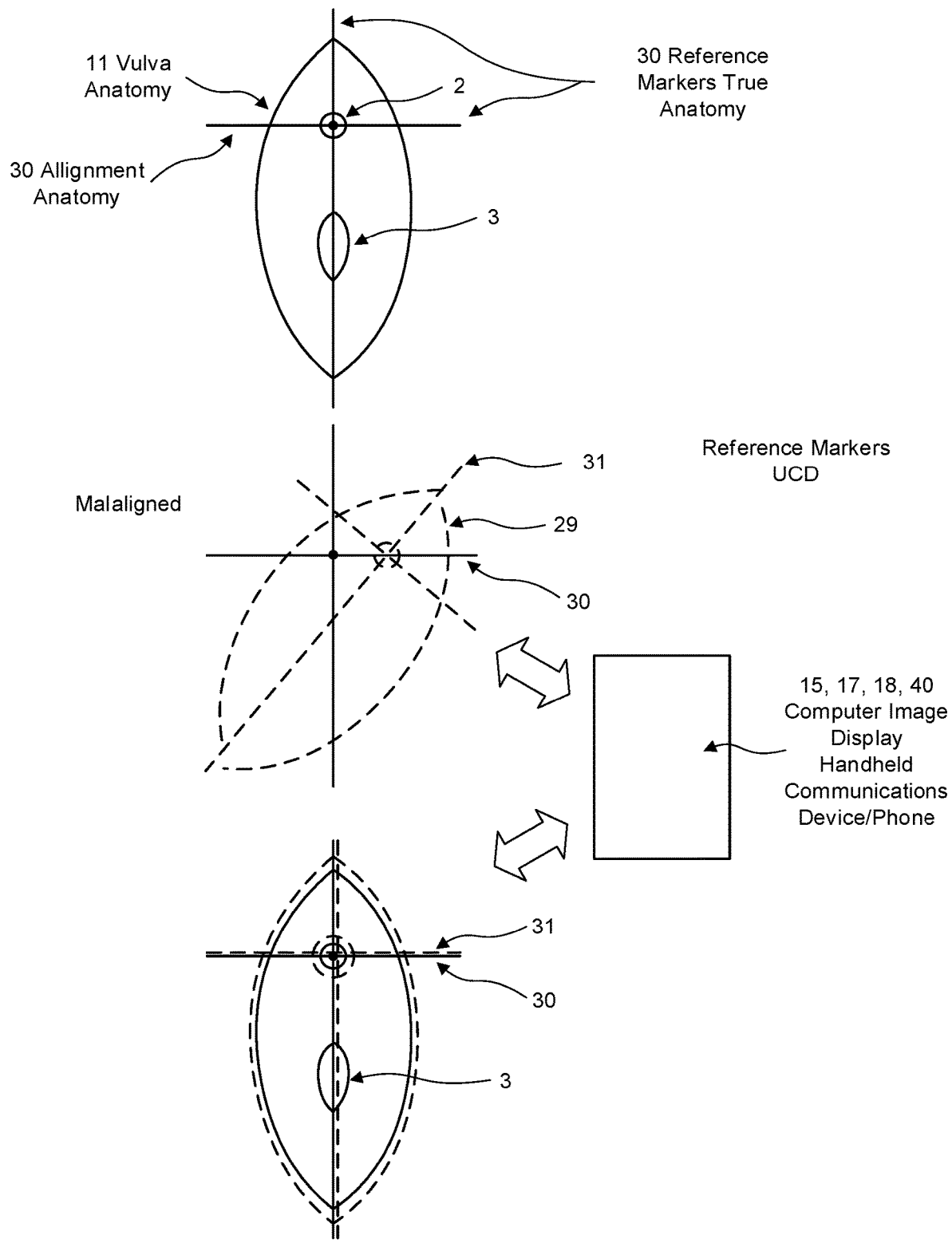
FIG. 5 is a frontal rendering of a Female Urinary Collection Device with a computerized alignment system and device for placement onto the female anatomy.

FIG. 5 is a frontal rendering of a Female Urinary Collection Device 6, 9 with a computerized alignment system and device for placement onto the female anatomy 11.

Figure 6:
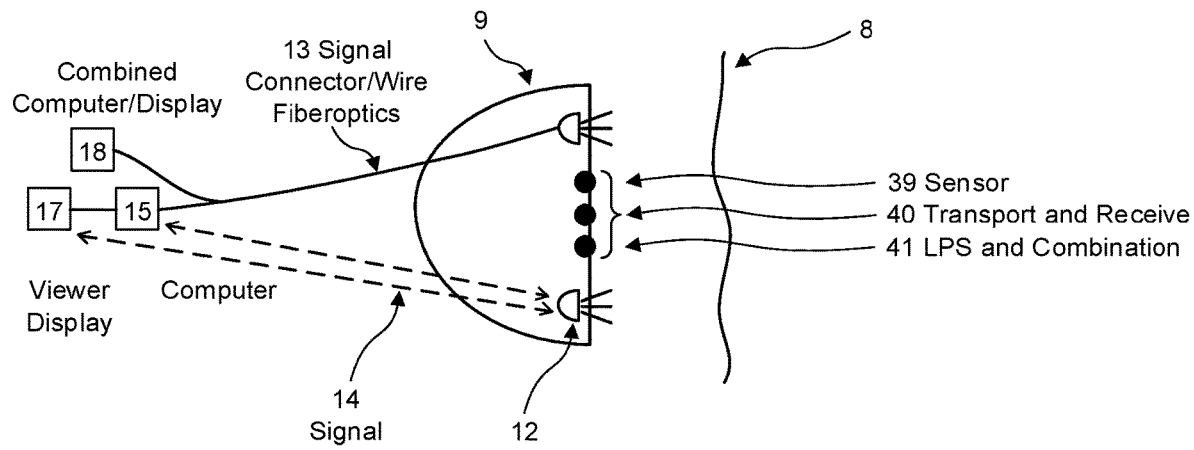
FIG. 6 is a sagittal depiction of a Female Urinary Collection Device with separate or combined Sensor 39, Transmit and receive units, optical 12 and LPS 41 systems with computerized and display 17 devices for placement onto the female anatomy.

FIG. 6 is a sagittal depiction of a Female Urinary Collection Device 6, 9 with separate or combined sensors 39, Transmit and receive units, optical 12 and LPS 41 systems with computerized and display 17 devices for placement onto the female anatomy 11.

The UCD 6, 9 alignment device and behave similar to a video game aligning the individual anatomy with the optimal positioning of the device with the anatomy. In one embodiment is to include but not restricted to the image of the UCD 6 can be maneuvered such that to the real anatomy of the vulva 11 and urethra 2 and adjusted until the misaligned 31 UCD image is aligned with the true aligned 30 anatomic image. In this embodiment to include but not restricted to sensor 39 and optics 12 and camera 12 and computing devices 18 and the displays 17 can assist the human in aligning the components of the UCD 6 and the real anatomy 11. This can be applied to other parts of the human body and skin 8.

Cleansing Methods for the UCD 6

To obtain a clean or a sterile urine collection the biological tissue should first be cleansed and for a urinary sample this can include but is not restricted to the vulva 11, minora, the labia majora, adjacent and overlying skin 8, hair, glands, the secondary folds, the urethra, the periurethral 2 region, the clitoris 1, the mucosa, redundant mucosa, the skin 8, the mons pubis, the pubic bone 77, the vagina, the local skin 8 and mucosa around the vulva 11 and the adjacent perineum 25 and perianal 4 region near and including the anus 4 in some cases. The cleansing can take place before or after the UCD 6 is in position. Optimally this cleansing can occur both before and before the placement of the UCD 6. This cleansing can be done by manual guidance or with a optics and fiber optics 13 and cameras 12. In one embodiment the cleansing material can be incorporated into the UCD 6 and the cleansing material can include but is not restricted to a solid or liquid or gel or gas which can include but are not restricted to disinfectants or cleaning or sterilizing materials to include but not restricted to iodine compounds, ozone, aerosol suspensions of disinfectants, glycols such as but not restricted to propylene and triethylene glycols and alcohols and alcohol compounds, aldehydes and aldehyde compounds, chlorine and its compounds, ammonia and ammonium and its compounds, metallic elements and its compounds to include but not metals and metallic compounds, such as borax, copper, silver, iron, brass, aluminum acetate, antimony, arsenic, barium, bismuth, boron, gold, lead, mercury, nickel silver, thallium, tin and zinc, as well as giving oligodynamic and biocidal effects, oxidizing agents to include but not restricted to hydrogen peroxide peracetic acid, potassium permanganate sodium hypochlorite, electrolyzed water, chlorine dioxide chloramine-T, Potassium peroxymonosulfate, phenolics to include but not restricted to Thymol, hexachlorophene, Amylmetacresol, Chloroxylenol, and alpha-phenyl phenol; and quaternary ammonium compounds. Energy 43 can be used with cleansing and sterilizing either alone or in combination with other cleansing materials and the energies can include but are not restricted to vibrational, mechanical, ultrasound, electromagnetic, thermal, radiation, hydraulic and magnetic. These compounds can be separate or a component of the UCD 6 and as a component can include but are not restricted to being in an envelope or pouch that can be compressed to release above said disinfectants and cleansing and sterilizing agents, can be sprayed on, can be blown on, can be washed on, or can be imbedded into components of the UCD 6 that come in contact with the vulva 11, urethra, periurethral 2 and vaginal 3 and living body regions and components that needed to be cleansed and this can include but is not restricted to having a layer 98 of material that is embedded with one or more disinfectants and cleansing and sterilizing agents such that when the embedded material contacts or comes or in close contact with the skin 8 and mucosa and living body tissue said tissue becomes cleansed, sterilized or disinfected. One embodiment can include a thin UCD 6 that has a layer 98 of material that is imbued and impregnated with iodine and the periurethral and urethral 2 components can be peeled away cleaning these regions and at the same time forming an opening or fenestration 133 that allows the urine to flow out of the urethra 2 and pass through the UCD 6 and into the collecting reservoir 43. After the imbued and impregnated layer 98 with cleaning, disinfecting and sterilizing or a combination of these is removed from the urethral 2 opening the exposed living tissue can be washed or rinsed or sprayed or blown-upon with additional materials to be further disinfected or can be left as is and not washed or rinsed or sprayed or blown-upon with additional materials to be further disinfected. In another embodiment the urethral 2 opening can be composed of a gel imbued and impregnated cleaning, disinfecting and sterilizing or a combination of these, that can include but is not restricted to being removed manually or dissolved by thermal energy 43 such as heat of the body or infrared or heating elements or UV 43 light, washing or rinsing with a dissolving agent or can be dissolved by the urine as it flows and contacts the gel.

Collecting Mid and Late Stream Urine:

Women may have more difficulty with aiming and collecting mid-stream samples of their urine stream than do men because of differences in anatomy and sphincter control.

A sterile urine collection device 9 optimally can be incorporated into the UCD 6 include but is not restricted to a device and a method to assist in collecting mid or late stream urine and discarding or minimizing early stream urine.

In one embodiment regions of the UCD 6 and the catheters can be replaceable and can be used one or multiple times and for one use short or long use or for multiple short or long periods ranging to include but not restricted to seconds to days and months.

The UCD 6 can include but not restricted to one or more conduits 5 or urine cavities that fills a container that can include but is not restricted to a cup, a jar, a reservoir 43, a flask or beaker or pouch or test tube or cylinder and that container can be made of materials that are currently standard in medicine and can include but are not restricted to plastics and glass, and polyethylene and other porous and non-porous bags.

In one embodiment the container can be constructed to sequestrate the initial grouping or portion of the urine sample and can include but is not restricted to a volume of less than one or to twenty or more cc's (cubic centimeters) of urine. After the initial sample other urine grouping can be obtained and can include no additional, one additional or more than one additional grouping of urine collected.

One embodiment the UCD 6 or the collecting container can include but is not restricted to have a device that can be a component of regulates, or directs or controls the flow of the urine of another liquids, or a gas or a fluidized solids, or slurries and this can include methods and devices to include but is not restricted to be accomplished by a means of opening, closing, or partially obstructing various passages or passageways and these methods and devices can include but are not restricted to hydraulic, pneumatic, manual, motorized or mechanical and solenoid valves and these valves can include standard valve components that can include but are not restricted to the body, bonnet, ports, discs, seat, stem, gaskets, trim, handles or actuators, and forms of valves can include but are not restricted to a valve member, ball valves, hinge valves, check valves, poppet valves, two and multiple port valves.

In one embodiment the valve can differ from the standard valves. The urine can enter at least one of a conduit, chamber, grouping or reservoir 43 or collecting component of the UCD 6 or container and this conduit, grouping or reservoir 43 or collecting component can have an absorbent material that serves as a valve or cover that can include but is not restricted to when dry allows urine or fluids or gas to enter to include but not restricted to a conduit, chamber, grouping or reservoir 43 or collecting component but as the material becomes wet or hydrates the material can to include swell, enlarge, expands or increases in a manner that closes off the opening and causes urine flow to include but not restricted to be directed away from the initial conduit 5 grouping or reservoir 43 or collecting component and redirected toward another conduit 5 grouping or reservoir 43 or collecting component and this can be used to include but not restricted to separate the early urine from the mid and later urine flow. This urine separation technique can be located and used once or more than once or not at all within the UCD 6 or Urine Collecting Container depending on the needs of the urine sample.

The container, the UCD 6, the conduit 5 or the tubing the catheter, or the pipe or the chamber and any individual component or components or any combination of these can include but is not restricted to have zero, one or more than one connection 82 or connectors 82 that can include but are not restricted to nozzles, a spouts, or valve that can include but is not restricted to be at an end or a portion or section of said conduit 5 or pipe, hose, or tube, or chamber used to control the stream of the urine or a liquid or a gas and said conduit 5 or tubing or catheter, pipe or chamber's nozzles, a spouts, or valve can have a locking or not locking or locking into place and unlocking mechanism, or releasing mechanism that can include but is not restricted to a screw-like, gasket, a snap-like, a magnetic element, a luer-lock that can be a slip on or screw and can contain a hub, a spring fitting, a gasket that can move in place like when moved into position and prevents the flow of fluids or gases similar to the mechanism of the temporal mandibular joint, a lock that expand and contracts to lock the male or female portion of the nozzle or spout or valve in place and said locking or releasing mechanisms can be sensitive to the pull or force placed on said mechanisms to include but not restricted to release when there is a force generated that may prove uncomfortable or damaging or undesirable to the UCD 6 or collection container or the user.

In one embodiment the conduit 5 or tubing catheter, or pipe or chamber can contain but is not restricted to have connectors or connection 82 that can be regulated and adjusted manually or digitally or by analog means and said regulator can be adjusted to be responsive to include but not restricted to pressure, mechanical forces, time, hydration and the presence or absence of liquids or gas.

In one embodiment the UCD 6 and the Collection container can be one or more than one pieces.

In one embodiment, the Urine collection device 9 or container or UCD 6 can include but is not restricted to having absorbent materials that can include but is not restricted to transforming the liquid or urine or bodily material that is secreted or excreted or expelled and convert the liquid to include but not restricted to a solid, a gel, a gel-slurry or a liquid of altered properties that can include the liquid being thicker or more viscous. In another embodiment the urine or bodily materials can be converted to a gas or change in the liquid or urine by means that can include but is not restricted to thermal, chemical, kinetic, or electromagnetic 102 energy 43 or reactions.

In one embodiment the Collection container or the UCD 6 can contain an absorbent material that can be fixed in place or removable and replaceable. In one embodiment this absorbent material can be placed into a layer 98 of the UCD 6 and removed and replaced as needed. In one embodiment this layer 98 could be separated from the skin 8 and in another embodiment it can be adjacent to the skin 8 and in either embodiment it can be accessible for easy replacement.

In one embodiment the collecting container or UCD 6 can have zero divisions and can have but is not restricted to having one chamber and can include but is not restricted to a cup or reservoirs 43 and in a component of the cup to include but not restricted to the bottom of the cup there can be an absorbent material and the first or early urine flow can be absorbed by this absorbent material and can communicate with or can be separated from the remaining urine flow by a material that can include but is not restricted to a material that flows in only one direction and in this embodiment the urine would flow into the absorbent material but cannot flow out these can include but is not restricted contain no membrane or one way water membranes to include but not restricted to stretched polytetrafluoroethylene (PTFE) or Gore-Tex and in one embodiment these can include but are not restricted to the absorbent materials being titrated to absorb a given amount and in the case of the early urine flow that can include but is not restricted to a volume of less than one or to twenty or more cc's (cubic centimeters) of urine.

In another embodiment the urine collection container or UCD 6 can include but is not restricted to direct the urine via a conduit 5 or tube toward the collection container and the first chamber can fill with the first early urine sample and using a valve system to include but not restricted to a check valve, clack valve, non-return valve or one-way valve the first early urine can flow into that first chamber but cannot flow out of the chamber and this would allow the first urine to be discarded and/or separate from the remaining urine sample. The remaining urine can be collected in separate chamber that can subsequently fill and can include but are not restricted to containing zero, one or multiple valves that can include but is not restricted to having the same or a combination of valves or separating mechanisms. The valve or separating mechanisms can be used with the absorbent separating methods discussed.

In another embodiment the valve can be the absorbent material, which can include but is not restricted to in the early urine stream the urine is directed or funneled to the early sieve absorbent material and that material is titrated to expand after a given volume of fluid has passed through the material and that expansion prevents further urine from passing into the chamber containing the urine and this separating the urine into separate chambers and this method can be used one or more than one time in one or more than one chamber as needed. In this embodiment this initially sieve material becomes a valve and restricts the flow of water or urine out from its designated confine space. The chambers can be constructed in geometric shapes to include but not restricted to areas that narrow or widen to facilitate this separation process.

In another embodiment, the UCD 6 and Collection chambers can use a flap valves in which the valve is configured to allow flow in one direction but restricts flow in the other direction and allows inflow and prevents back flow. There can be one or more than one flap. These backflow flaps of the flap valve can include but are not restricted to being concave, convex, or flat and can include but is not restricted to be partially or fully or not overlapping or any combination of these. And these flap valves can be used alone or in combination with other valves to include but not restricted to ball or hinge valves.

In another embodiment, the UCD 6 and Collection chambers can use ball valves in which the valve is configured to allow flow in one direction but restricts flow in the other direction and allows inflow and prevents back flow. There can be one or more than one flap. These backflow flaps of the flap valve can include but are not restricted to being concave, convex, or flat and can include but is not restricted to be partially or fully or not overlapping or any combination of these. In one embodiment what the flap is concave away from the direction of inflow and directed toward the chamber the chamber will fill up and the pressure of the urine or liquid will get trapped in the concave flap and close the flaps and seal 7 off the chamber and direct flow of liquids and urine away from that chamber. This can be used in any component of the UCD 6 and the collection container or conduits 5 and can be one or multiple or none in number or usage for any given site. One of the advantages of this valve is that it can include but is not restricted to directing the urine away from the users body and maintaining a dry environment and in the male and female this can be used near the urethra 2 to keep the mucosa and skin 8 and periurethral 2 tissue dryer and allow flow to be sequestered away from the penis 35, in the tubing it can prevent backflow to the penis 35 and in the collecting container it can allow for sequestration of the various temporal elements of flow to be sequestered to include but not restricted to early mid and late urine sampling chambers and groupings. In one embodiment the valve close to the urethra 2 can include to be composed or have surfaces, or be lined by different materials. In on embodiment the valve side closest to the living being can be designed to cause the environment to be safe and healthy in a manner to include but not restricted to keeping the region between the valve/UCD 6 components and body components such as the skin 8, periurethral 2 region, urethra, user's body, or mucosa to be to include but not restricted to be dry, or preserve natural body oils, or prevent over or under hydration of the skin 8, or to prevent infection or damage to the living body. In one embodiment the side of the valve/UCD 6 closest to the environment between the living body and the valve/UCD 6 can include but is not restricted to be composed of or can release a wax, a breathable material, an oil, an emollient, a cream, a medication, an anhydrous 45 material, a material that can absorb and wick materials away from the more hydrated environment, or a material that when it combines with liquids or urine can create a dry or clean or sterile environment.

In another embodiment, the ball valve or ball valve-like mechanism can include but is not restricted to contain a substance 44 to include but not restricted to a material that floats that can include but is not restricted to a gas or liquid or a solid and this material that floats can be encapsulated or not encapsulated. In another embodiment the ball valve or ball valve like mechanism can absorb liquid or urine and can transition from a ball valve that floats to a ball valve or ball valve mechanism that can sink and this can include but is not restricted to changing the specific gravity of the material once imbued and absorbed with a liquid.

In another embodiment, the chambers or UCD 6 and Collection container or tubes can be oriented to include but not restricted to vertically or off vertical axis or sideways and the valves can work in any direction and this can be accomplished to include but not restricted to using one or multiple valve systems.

The UCD 6 and tubing and Collection container systems can be used in combination with other sealing or connection 82 mechanisms that can respond to include but is not restricted to mechanical, pressure, digital, analog, electromagnetic, magnetic and visible 20, 43 or color 95 changing units.

The term UCD 6 can refer to all elements of the UCD 6 including but not restricted to the UCD 6 covering 36, valves, tubing, collecting containers, connection 82 mechanisms and anchoring or fitting mechanisms.

In one embodiment the UCD 6 and tubes and Collection Container can include but are not restricted to containing sensor 39. Sensor 39 can include but are not restricted to being digital with send and receive and master send and receive units and can communicate with each other; can be analog or can be mechanical, thermal or electromagnetic/electric/light/UV 43/RF/Infrared or hydration or air or water indicating sensor 39 that can include but are not restricted to be used to inform the user of the status of the UCD 6 and its components and the Collection container as to its readiness or fullness or capacity; can be used to indicate the initiation and state and termination of flow; can be used to indicate the humidity or wetness of the living body and UCD 6 environment and moisture.

The sensor 39 can include analytic and visual elements that can include but is not restricted to analyze the volume, chemical analysis and composition of the urine, assessment of protein and peptides and amino acids, fats and carbohydrates and or environment, humidity or dryness, the presence or absence of contaminants, the presence or absence of infection or infectious organisms that can include but are not restricted to viruses, fungus, yeast and bacteria or bacteria and infectious-like organisms, such as described in U.S. Provisional Patent application Ser. No. 62/435,016 and U.S. patent application Ser. No. 14/663,348, cited supra.

Positioning and Motion

The UCD 6 and the Collecting container can include a device or method to allow for positional changes and movement of the living body relative to the UCD 6 and the collecting container.

In one embodiment the movement can be allowed or provided or created by a gel or gel-slurry and said gel or gel-slurry can be one or multiple layers 98 of similar or differing softness or hardness that allow for variable motion. In one embodiment the movement can be created by a combination of materials that allow for motion that can include but are not restricted to gels, and gel-slurries, clothes, and rubbers and plastics and other solids or liquids or gases that can be incorporated or annealed or attached to said materials that together or alone can encourage freedom and motion and comfort to the user and the living body and maintain when necessary the water or airtight seal 7 or water-resistant seal. In another embodiment the devices including the UCD 6 and components can have elbows or flex-points that allow the UCD 6 or its components to move or flex to changes in anatomy or changes in body position or changes to the anatomic or functional needs of the UCD 6.

In one embodiment any component to include but not restricted to the UCD 6 and tubes and Collection Container can be incorporated into clothing or water protective gear or a material and design that can include but is not restricted to being comfortable and allow movement or fixation of the UCD 6 and tubes and Collection Container, such as described in U.S. Provisional Patent application Ser. No. 62/435,016 and U.S. patent application Ser. No. 14/663,348, cited supra.

Skin 8 Protection

In one embodiment the UCD 6 or its components can dispense oils or emollients or skin 8 or hair protecting material that can include but is not restricted to water protective creams or lotions or oils or emollients to protect the skin 8 and the dispensing can include but is not restricted to release from a reservoir 43, from a time-release material that can include to be worn. Other methods can include but are not restricted to being sprayed or applied on and said materials can arise from the UCD 6 or Collection container or a separate container or reservoir 43. In another embodiment the device or UCD 6 and its components can include In another embodiment the hair can be present and can have an airtight or watertight seal 7 created by using materials that are conforming and can include but are not restricted to gels, gel-slurries, foams, phase 94, 96-change materials, silicon, or soft plastics.

In another embodiment the skin 8 protective materials can include but are not restricted to a medicated gel, a breathable material, an oil, an emollient, a cream, a medication, an anhydrous 45 material, a material that can absorb and wick materials away from the more hydrated environment, or a solid or liquid or gel that can include but is not restricted to ozone and a material that when it combines with liquids or urine and which can create a dry or clean or sterile environment.

In another embodiment the urine can fill a cavity within the UCD 6 and that cavity keeps the urine separate or nearly completely separate from the living body except such areas that can include but is not restricted to include the urethra 2 and this can include one or more cavities.

Male UCD 6

Figure 7:
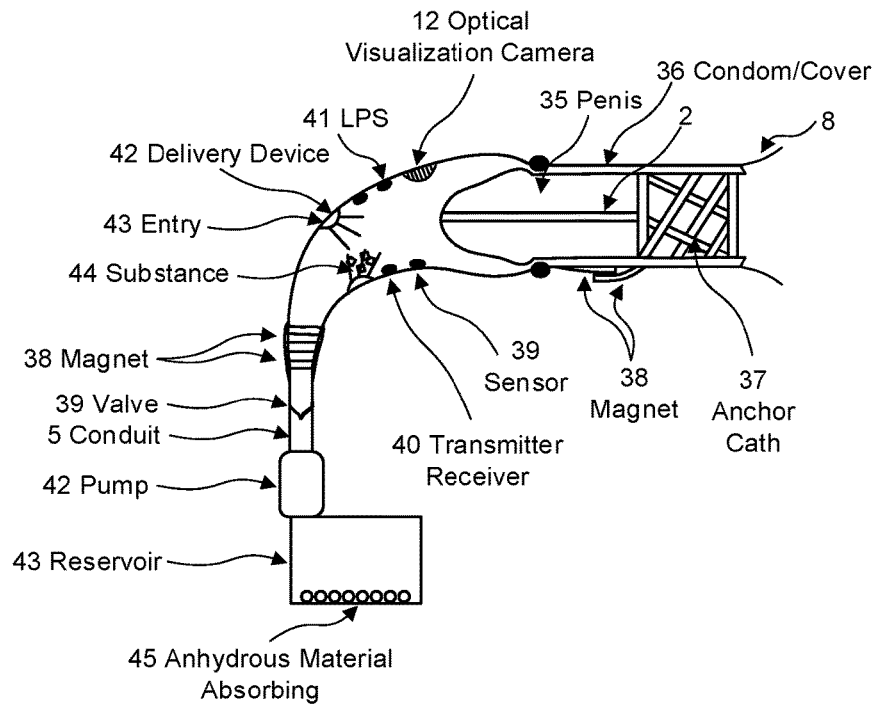
FIG. 7 is a sagittal rendering of a Male Urinary Collection Device with separate or combined Sensor 39, Transmit and receive units, optical 12 and LPS 41 systems with conduit 5 and reservoir 43.

FIG. 7 is a sagittal rendering of a Male Urinary Collection Device 6,9 with separate or combined Sensors 39, Transmit and receive units, optical 12 and LPS 41 systems with conduit 5 and reservoir 43 43.

Although the subject matter discussed herein concentrates heavily on female anatomy and a female UCD 6, the subject matter also applies to a male UCD 6 and includes but is not restricted to many of these same design and composition and covering 36 and interface and fenestration 133 and cleansing, skin 8 protection, drying, flexibility construction, collecting, eliminating contaminants and other elements described for the female UCD 6 and components can also be used in males and the male UCD 6 and its components or designs can also be used interchangeably in the female MFPD and MFP device and elements of the male UCD 6 and the female MFPD and MFP, UCD 6 device can be used interchangeably.

Many of the principles are similar if not identical for both male and female devices despite the differences in the male and female anatomy. Although visualization is not a major issue for placing a simple condom 36 catheter it may be important if the condom catheter is more complex and/or has valves or attachments for egress of urine away from the penile component. In these cases the visualization methods can utilize the visualization methods described herein and as described in U.S. Provisional Patent application Ser. No. 62/435,016 and U.S. patent application Ser. No. 14/663,348, cited supra.

In another embodiment the male UCD 6 can include but is not restricted to similar elements of design of the condom catheter but said catheter is housed within a structure or covering 36 that can include but is not restricted to surrounding a portion or all of the condom catheter and all or a portion of the penis 35 or it can surround the penis 35 and not have a condom catheter and in this second situation the urine can fill a cavity within the UCD 6 covering 36 that is separate from the living body or can contact a portion of the living body including a portion or all of the penis 35 or the tissue of the living body near the penis 35. The same elements of design that are used for the female UCD 6 and the general concepts of the UCD 6 described above can be used for the male UCD 6.

In one embodiment the male UCD 6 covering 36 can be made of silicon or firmer gel with a transition to a soft silicon or gel interface that can create an airtight and watertight seal 7 with the skin 8 and hair surrounding the penis 35 and the UCD 6 can have a conduit 5 exiting said UCD 6. In this embodiment there can be a condom catheter that is attached to this UCD 6 cover or housing. The attachment of the UCD 6 covering 36 or housing and the condom catheter can include but is not restricted to being loosely attached so that the penis 35 can have normal movement or can be firmly attached such that the penis 35 is more fixed in position and the attachment can be created such that the condom does not migrate away from or off the penis 35. The condom catheter in this embodiment can have a mooring or anchored 37 region that can include but is not restricted to be moored or tethered or affixed or compressed or combination of these is moored or anchored 37 in which a portion of the condom catheter complex mooring region is pressed or constricted or influenced to remain in place and this can include but is not restricted in this embodiment to include a gel or gel-like or silicon or an inelastic or elastic material that can include but is not restricted to partially or fully circumnavigate the penis 35 to include but not restricted to a design that is non-annular or annular or continuous or discontinuous or overlapping or on-overlapping and can include but is not restricted to have loose gel or a mixture of gel and non-gel material that can be tightened to acquire the right fit of the gel and or the condom or a combination of both around the penis 35 without excess penis 35 compression. The gel or the condom or condom-like or tightening-like or any combination of these can be in contact with the penis 35 or skin 8 or mucosa of the living body. In one embodiment the penile mooring region can be at one or multiple sites and these sites can include but are not restricted to the corona or shaft or base of the penis 35. A sensor 39 can be placed at the site of the penile mooring region to access the compression of the device relative to the penis 35. These sensor 39 can include measuring penile blood flow 104, thermal measurements, oxygenation, color 95 and pressure, kinetics and exerted on the penis 35. The housing or UCD 6 covering 36 can be worn and the material that is worn can include being worn to surround the scrotum, the abdomen, the buttocks and buttocks crease or any combination of these and can extend around portions of the living body. The urine can egress to include but not restricted to from the UCD 6 covering 36 or housing or the condom catheter through a conduit 5 or catheter or tube or can be captured by a material that absorbs the urine, such as described in U.S. Provisional Patent application Ser. No. 62/435,016 and U.S. patent application Ser. No. 14/663,348, cited supra.

In another embodiment the UCD 6 covering 36 can be constructed such that there is a layer 98 of the UCD 6 covering 36 that is anterior and posterior and lateral to the penis 35. In this embodiment the UCD 6 is bag-like structure that fits loosely around the penis 35 and forms a cavity rather than a relatively tight condom-like structure that is designed to fit around the penis 35 more tightly. This embodiment can include but not restricted to where the entire penis 35 can lie freely within the bag-like cavity or can include where just the tip of the penis 35 at and distal to the corona is capped and surrounded to collect the urine directly from the urethra 2 and penis 35 a mooring or tightening region.

In another embodiment the bag-like cavity can be formed of a watertight or breathable material or construction.

In another embodiment the region surrounding the corona or tip region/glans and shaft junction region can be made of a watertight or breathable material or construction.

In another embodiment the flap or valve that prevents the backflow of urine can include but not restricted to be adjacent to, on or touching or near or very close to (1-5 mm) to include but not restricted to keep the penis 35 and glands dry and prevent the backflow of urine from the conduit 5 or catheter back to the living body and the backflow valve can include but is not restricted to being a component of the condom catheter or a component of the conduit 5 or a component of the gel interface or the anchoring device at or near the corona and glans-penile shaft junction or any combination of these.

In another embodiment a connection 82 between the penile covering 36 or the condom catheter can include no multiple or one magnet that can include but is not restricted to having the north and south poles of the magnet facing each other and adjacent to create a fixation or seal 7 or connection 82 that can be surrounded by to include but not restricted to liquid or solid or gas or gel or gel or other form of slurry particles and these can include membranes or envelopes and said magnets 38 can also include interfaces with but not restricted to other non-magnets 38 to include materials to include but not restricted to magnetic attractive materials, ferromagnetic metals, and ceramic and combinations of these materials and these magnets 38 and materials can be used in combination and can be other material embedded or impregnated into other materials that can include but are not restricted to be components of the UCD 6.

In another embodiment the UCD 6 and collecting component can have a optics and fiber optics 13 and cameras 12 or a periscope 21,22 or periscope 21,22-like to insure that the UCD 6 and its structure to include but not restricted to its conduits 5, valves, and UCD 6 or condom catheter positioning.

General Applications

Keeping the Skin 8 as Dry as Possible

In another embodiment the UCD 6 can contain drying elements. Drying Agents can include but are not restricted to fans that can include but is not restricted to nano 63 fans, and piezoelectric motors and fans, micro-mechanical fans and macro-mechanical fans. Drying elements can include dehumidifying and desiccant or hygroscopic agents to include but not restricted to inert materials such as silica, activated charcoal, calcium sulfate and calcium chloride and molecular sieves (zeolites) and they can also include color 95 saturation indicators that can include but is not restricted to cobalt chloride, which is blue when anhydrous 45 and purple when mildly hydrated and pink when more markedly hydrated; and anhydrous 45 gels and solvents, and nano 63 particles, other anhydrous 45 materials that absorb water. These desiccants can line all or portions of the UCD 6 and can include to be positioned in enveloped packets that have a layer 98 that can communicate with the urinary or wet cavity, or openings or pores or fenestrations 133 that alone for air drying between urination. These openings or pores or fenestrations 133 that can include but is not restricted to having openings or pores or fenestrations 133 and openings and covers that open and close based on sensor 39 that can control these coverings 36 by materials that swell and close the opening when wet and open when dry these can include but are not restricted to gels and phase change 94. 96 materials and other methods and devices can include small motors and hatches that can on the macro, micro or nano 63 scale. In one embodiment the UCD 6 can have multiple covering 36 layers 98 and can include but is not restricted to the outer layer 98 being airtight and watertight or just watertight and the inner layer 98 can have openings and between the inner and outer layer 98 can reside to include but not restricted to fans, desiccants, dehumidifying, hygroscopic and anhydrous 45 agents or any combination of these. Because this is a separate layer 98 it can include the separate layer 98 to be self-contained and changed as needed to maintain a dry inner cavity.

In one embodiment of the UCD 6 the inner cavity is dry or near-fully dry in that the tip of the penis 35 is attached to a cap that is airtight and watertight and only the glans and portions near the corona are damp as there is a conduit, channel, catheter or tube that exits from this cap and passes through this dry layer 98 of the UCD 6 which is constricted with a material that can absorb fluid if needed. Also this catheter can be tethered or embedded or pass through this layer.

In another embodiment of the UCD 6, there a first inner layer 98 that is adjacent to the skin 8 and in one embodiment can include but is not restricted to be composed of a cloth that might be worn as an undergarment; a second watertight thin layer 98 that can include but is not restricted to watertight or waterproof or water resistant material; a third middle layer 98 that is waterproof and in which resides but is not restricted to the penis 35, the urine conduit 5 or catheter, the penile junction cap that collects the urine and a condom or condom catheter. This third layer 98 can contain hydrous or urine or water absorbent materials; the fourth layer 98 is a watertight or waterproof or water resistant material. The fifth or outer layer 98 can include but is not restricted to be composed of a cloth that might be worn as an undergarment. Layer 98 one is the inner or closest layer 98 to the skin 8 and the fifth or outer layer 98 is the furthest layer 98 from the skin 8.

In one embodiment the UCD 6 can be incorporated into and fit and wear 50 and that can include but is not restricted to feel and wear similar to underwear, shorts, pants, a thong or jock-strap 50 and can have a structure and materials that can include clothes and natural and synthetic materials and can include the feel and look of lace and cottons for comfort and as found in standard clothing wear. These said materials can also be water absorbent and act like a diaper or tampon and can be composed to include but not restricted to an inner layer 98 that is absorbent, and outer layer 98 that is similar to the standard clothing and a middle layer 98 that is watertight.

Absorbent materials can include but are not restricted to superabsorbent polymers, hydrogels, and gel polymers, cloth, cellulosic or fiber-based products, cotton, sponges, foam, fluff pulp or paper, silica, and other desiccants and anhydrous 45 materials, drying elements can include dehumidifying and desiccant or hygroscopic agents to include but not restricted to inert materials such as silica, activated charcoal, calcium sulfate and calcium chloride and molecular sieves (zeolites).

Water resistant differs from Waterproof and watertight. In place of Waterproof and watertight materials water resistant materials and breathable near watertight materials can be used and substituted but may not function as efficiently but still may accomplish the goal of the material or layer.

Assistance and Propagation of Flow of Solids or Liquids or Gases

In one embodiment the UCD 6 and tubing and collection chamber can incorporate pumps and these pumps can include but are not restricted to peristaltic pumps, pulsatile, positive displacement pumps, impulse, velocity, gravity, steam, valve-less, hose and tube and centrifugal and centripetal, and rotatory, gear, screw, rotatory vane, scroll, reciprocating and linear, hand and mechanical pumps, Rotary lobe pump, Progressive cavity pump, Rotary gear pump, Piston pump, Diaphragm pump, Screw pump, Gear pump, Hydraulic pump, Rotary vane pump, Peristaltic pump, Rope pump, Flexible 26 impeller pump, and Gravity pumps and any combination of these and said pumps can be micro, macro, and nano 63 particle pumps and any combination of these. These pumps can utilize energy 43 sources that can include standard energy 43 sources to include but not restricted to batteries, solar, electromagnetic, magnetic, kinetic and mechanical and piezoelectric energy 43.

In one embodiment, the pump can include but is not restricted to a circular and circular-like pump or a linear peristaltic pump and can include but are not restricted to variations on the types of pulsatile pumps used in heart-lung, bypass, and dialysis and can be used to move or cause the flow of urine or a liquid or a gas or a slurry that can include gel or solid materials from one location to another.

In one embodiment, a new pump or device that can move liquid or solid or gas or gel or slurry in any given direction can be created that can include but is not restricted to being used in a standard gravity or pressure or altered gravity or differential pressure or force environment that can include but is not restricted to outer space or spacesuit or vacuum or partial vacuum or differential pressure or force environments environment and the said pump or device for creating movement of a liquid or solid or gas or gel or gel or other form of slurry particles in any given direction and which can include but is not restricted to using differences in these standard gravity or pressure or altered gravity or differential pressure and gravity and force environment the above pump elements or diaphragms or membranes as a device and method to drive or motivate or institute or continue the motion or flow of these particles in a manner that can include but is not restricted to using the difference in the environments as a pump or pump-like driving force device that can include but is not restricted to enforcing this pressure onto but not restricted to tubing or diaphragms or pumps or any combination of these in a manner that gravity or vacuum, altered or differential pressure environment fully or partially or by exposing a membrane or opening and closing of a valve or valve-like or cover or cover-like device or membrane to include but not restricted to a vacillating or alternating periodicity of differential gravity, pressure or vacuum and partial-vacuum.

In one embodiment a spacesuit worn by a living being that contains a greater pressure relative to the suit than does outer space or the space ship can open and close to include but not restricted to a valve or opening and cover, or flap. When the flap is open the vacuum is this sequestered region of the spacesuit can exert a force on the tubing filled with urine and when the valve is closed the pressure of the suit exerts a pressure on the tubing. This tubing which can include but is not restricted to having facilitating membranes designed to include but not restricted to facilitate or modulate or amplify the differential forces, and said tubing can include but is not restricted to having zero or one or multiple valves, can have one-way valves that allow the urine to flow in one direction away from the human body and toward the urine-collecting container. In another embodiment a similar or the same device can be used to allow materials to flow toward the body. In others embodiments, the material moving can be a liquid, a gas, a solid, a gel or a solid or slurry and can include but are not restricted to Urine or fecal matter or blood which can include but is not restricted to menstrual 46 blood. There can be one of more of these devices and of each of the components or regions for these devices or components.

In one embodiment, a pulsatile pump can be used to move material or particles that can include but is not restricted to moving urine, blood, menstrual 46 blood, fecal material, a liquid, a gas, a solid, a gel or a solid or slurry and can include but are not restricted to Urine or fecal matter or blood which can include but is not restricted to menstrual 46 blood.

In one embodiment a spacesuit worn by a living being that contains a pulsatile pump that can include but is not restricted to being composed of tubing that can include but is not restricted to having zero or one or multiple valves, that can include but are not restricted to one-way valves that allow the urine to flow in one direction away from the human body and toward the urine-collecting container. In another embodiment a similar or the same device can be used to allow materials to flow toward the body. In others embodiments, the material moving can be, a liquid, a gas, a solid, a gel or a solid or slurry and can include but are not restricted to urine or fecal matter or blood which can include but is not restricted to menstrual 46 blood. There can be one of more of these devices and of each of the components or regions for these devices or components.

The device can be used in exposing a solid or liquid or gas or gel or piezoelectric crystal to this to include but not restricted to vacillating or alternating periodicity of differential gravity, pressure or vacuum and partial-vacuum can be used to store or create a battery 84 or create or store energy 43 to include but not restricted to similar to a generator 99 that can include but is not restricted to a hydraulic, or mechanical or movement generator 99 and the moving particles can include but are not restricted to liquid or solid or gas or gel or slurry particles.

In one embodiment a spacesuit worn by a living being that contains a pump that can include to be activated or motivated or driven by the body or a biological structure or body functions that can include but is not restricted to muscular movements that can include but is not restricted to flexion and extension and can be performed by a muscle 65 of the body that can include but is not restricted to a body movement or function walking, tapping the foot, flexing and extending the arm or repeatedly opening and closing and making and relaxing the fist and said UCD 6 or tubing and collection device 9 can be but is not restricted to having tubing that can include but is not restricted to having zero or one or multiple valves, that can include but are not restricted to one-way valves that allow the urine to flow in one direction away from the human body and toward the urine-collecting container. In another embodiment a similar or the same device can be used to allow materials to flow toward the body. In others embodiments, the material moving can be, a liquid, a gas, a solid, a gel or a solid or slurry and can include but are not restricted to urine or fecal matter or blood which can include but is not restricted to menstrual 46 blood.

In one embodiment the UCD 6, tubing or Collection system can contain a pulsatile pump that can include to be activated or motivated or driven by the body or a biological structure or body functions that can include but is not restricted to muscular movements that can include but is not restricted to flexion and extension and can be performed by a muscle 65 of the body that can include but is not restricted to a body movement or function walking, tapping the foot, flexing and extending the arm or repeatedly opening and closing and making and relaxing the fist and said UCD 6 or tubing and collection device 9 can be but is not restricted to having tubing that can include but is not restricted to having zero or one or multiple valves, that can include but are not restricted to one-way valves that allow the urine to flow in one direction away from the human body and toward the urine-collecting container. In another embodiment a similar or the same device can be used to allow materials to flow toward the body. In others embodiments, the material moving can be, a liquid, a gas, a solid, a gel or a solid or slurry and can include but are not restricted to urine or fecal matter or blood which can include but is not restricted to menstrual 46 blood that can include but is not restricted to being composed of tubing that can include but is not restricted to having zero or one or multiple valves, that can include but are not restricted to one-way valves that allow the urine to flow in one direction away from the human body and toward the urine-collecting container. In another embodiment a similar or the same device can be used to allow materials to flow toward the body. In others embodiments, the material moving can be, a liquid, a gas, a solid, a gel or a solid or slurry and can include but are not restricted to urine or fecal matter or blood which can include but is not restricted to menstrual 46 blood.

The device can be used in exposing a solid or liquid or gas or gel or piezoelectric crystal to this to include but not restricted to vacillating or alternating periodicity of differential gravity, pressure or vacuum and partial-vacuum can be used to store or create a battery 84 or create or store energy 43 to include but not restricted to similar to a generator 99 that can include but is not restricted to a hydraulic, or mechanical or movement generator 99 and the moving particles can include but are not restricted to liquid or solid or gas or gel or slurry particles.

The UCD 6 can have a vaginal 3 insert that can include materials that are solids, liquids or gases, gel or gel slurries and said materials can include but not restricted to be enveloped fully, partially or not at all. The vaginal 3 insert of the UCD 6 can include but is not restricted to be conforming to the structures at or in or about the vagina 3 and cervix 10 and vulva 11 and can include areas that can include but is not restricted to being fully or partially solid or hollow or a combination of these but the vaginal 3 insert for the UCD 6 is solid and airtight and watertight at the vaginal 3 orifice such that the vaginal 3 and urethral 2 tissue and there contaminant to include but not restricted to urine and vaginal 3 contaminants to include but not restricted to menstrual 46 blood and bacteria and yeast and fungi and biologic and organisms and non-biologic contaminants do not mix together so that the urine flow that is collected is urine that is as free of non-urine elements is as reasonable or feasible or biologically or humanly needed or attainable or possible for the function being performed. In one embodiment of this vaginal 3 insert application the vaginal 3 insert is fashioned from a gel that can include but is not restricted to be pre-formed and then conforms to the vaginal 3 space and can to include but not restricted to being resiliently or non-resiliently deformable such that the gel takes on the contours and maintains the contours to include but not restricted to the vagina 3 and the vaginal 3 orifice and the vaginal 3 and cervical junction.

Menstrual 46 Collection Device (MCD)

Figure 8:
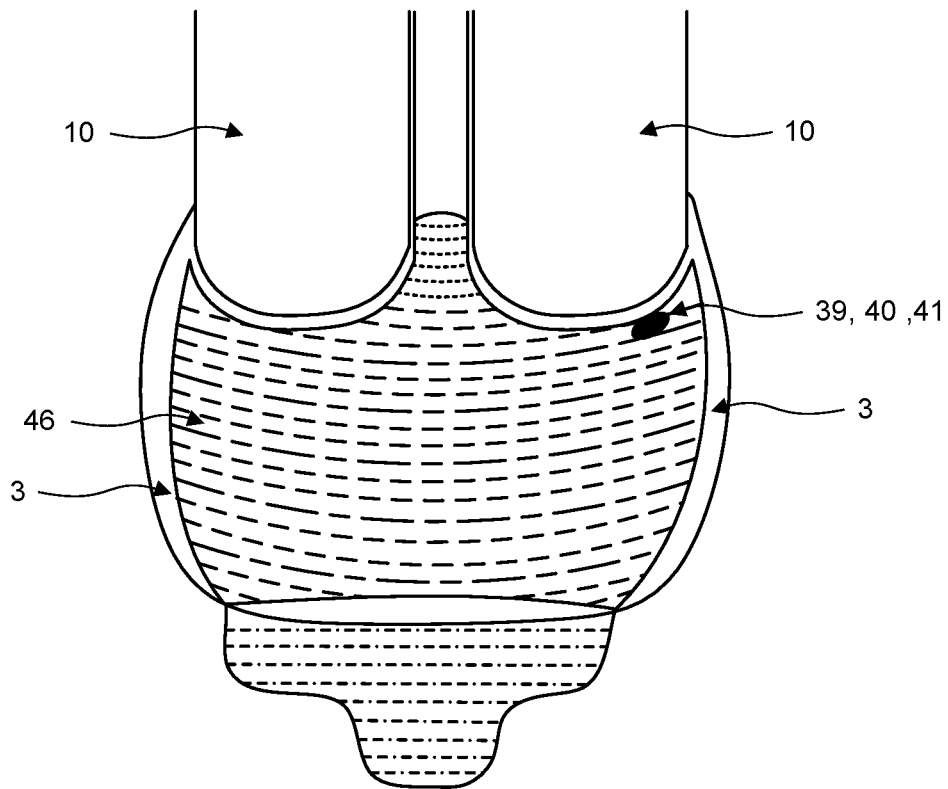
FIG. 8 is a frontal rendering of a female menstruation containment and contraception device.
Figure 9:
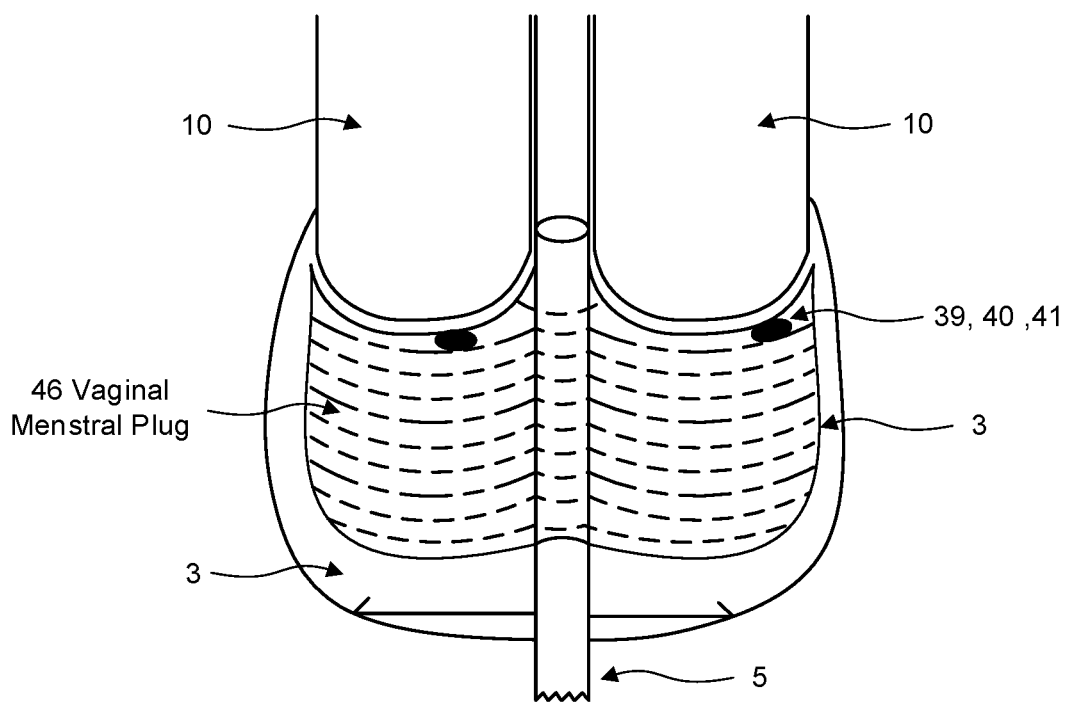
FIG. 9 is a frontal rendering of a female menstruation flow collection device.

FIG. 8 is a frontal rendering of a female menstruation containment and contraception device. FIG. 9 is a frontal rendering of a female menstruation flow collection device. In a manner similar to how urine exits through the urethra, menstrual 46 blood that is derived from the uterus 75 is expelled and exits from the cervical os or cervical opening into the vagina 3 and if the blood can be captured at the cervical os and is not allowed to spill into the vagina 3 then a more efficient and clean and orderly collection of menstrual 46 blood can be achieved and attained. Although the cervix 10 and vaginal 3 junction manifests variation, in most females the cervix 10 is like a cap and protrudes into the vaginal 3 vault. This configuration results in a configuration where there is a region where there is cervix 10 and then a space and then vaginal 3 tissue of non-vaginal 3 tissue that can include but is not restricted to form a suction or suction-like cup configuration if the vaginal 3 insert is molded to and conforms to the shape of this cervical and vaginal 3 junction. In one embodiment a gel can be molded to conform to the cervical and vaginal 3 junction and can include to be created as pre-fabricated vagina 3 insert general shape that can include but is not restricted to be conforming or non-conforming. It is believed that the more conforming the vaginal 3 insert the better the seal 7 and the more effective the MCD will likely be in a large population of females and this can be constructed to include but not restricted to be pre-formed based on preconceived geometric models or based on a mold from a user other than the female user, using the given MCD. These pre-fabricated vaginal 3 inserts can include but are not restricted to once inserted can conform to the specific female user by the insert conforming to the specific user to include but not restricted to conforming by molding to that specific user by inserting a larger size than that users vagina 3 and having compression create conformation, or by inserting a vaginal 3 insert that can include but is not restricted to undergo transformation and molding that can include but are not restricted to pressure, compression, thermal, chemical, electromagnetic, or other magnetic or kinetic, ultrasound or a combination of methods and techniques.

In another embodiment, the vaginal 3 insert can be fabricated by a Direct method to precisely conform to a single individual living female vaginal 3 who will be the user of the MCD and this vaginal 3 insert can include but is not restricted to being molded to the user female by direct or indirect molding techniques which can include blow molding, powder molding, compression molding, extrusion molding, injection molding, matrix molding, rotational molding, spin casting, transfer molding, thermoforming molding and vacuum forming molding or laminating and reaction injection molding.

In another embodiment the vaginal 3 insert can be created by an Indirect method or device that can include but is not restricted to imaging that can be used to include but not restricted to create a construct or model or image or structure or device or topographic representation that is conforming that can include but is not restricted to the vulva 11, urethra 2 and vagina 3 and uterus 75 and anus 4 and living body structures in the region of interest that can include but is not restricted to the region of interest and surrounding regions, for the MCD embodiment of the vulva 11 and vagina 3 and vaginal 3 vault and its insert and the uterus 75 and the vaginal 3 and cervical cap region and in one embodiment the region of the vaginal 3 vault and its wall or lining and the cervical cap can be an area of specific attention such that the vaginal 3 structure created not only fills and is intimate with the vagina 3 and the vulva 11 and periurethral 2 regions but also can include but is not restricted to be structure to create suction or a suction-like structure that will create a near or a full airtight or watertight or blood tight or menstrual 46 blood tight seal. The imaging to create this include but not restricted to this construct or model or image or structure or device or topographic representation that is used to create the MCD device can be performed by imaging that is standard in the field 103 or imaging and radiology and forensics and can include 2-D and 3-D which includes temporal changes which in imaging is often referred to as 4-D and can be performed by Ultrasound, CT (Computer 18 Tomography), MRI, Electromagnetic 102 methods and RF 43 and LPS 41 (Local positioning system/signal 14 Device), MRI (Magnetic Resonance Imaging, NM (Nuclear Medicine) and PET (Positron Emission Imaging), X-ray, Thermography, Topography Imaging and Scanners, Visible 20, 43 and non-visible 43 light photography, Endoscopy, Fiber optics 13, Angiography and future imaging techniques to be developed or any combination of these.

To create the MCD the Direct and indirect methods can be used alone or in combination.

To create the MCD a 3-D scanner/printer 59 of any variety that creates physical objects can be used to create the MCD using the techniques discussed above and other know techniques present in the art of 3-D scanning/printing.

The MCD vaginal 3 insert can have a hole 133 or an opening at the junction of the vaginal 3 insert and the cervical os and said opening in the vaginal 3 insert can include but is not restricted to be designed to allow the menstrual 46 blood to exit from the Uterus 75 through the cervical os and pass through the vaginal 3 insert's opening. The opening that can include but is not restricted to be shaped as a geometric shape that can include but is not restricted to a geometric shape to include but not restricted to a circle, a cylinder, a cone shape, a rectangle, pentagon, hexagon etc. or a shape that can include but is not restricted to a non-geometric to include but not restricted to biologic shape that mirrors or matches or contours or abuts, or conforms to include but not restricted to the cervix 10, or cervical os or vaginal 3 vault or the vaginal 3 vault and cervical junction or a shape that involves or envelopes or opens to or abuts or conforms or contours to one or more than one of these biologic structures.

In one embodiment the portion of the vaginal 3 insert that interfaces at the cervix 10 can include one or more channels or conduits 5 or tubes or areas that are hollow and these one or more channels of conduits 5 or tubes or areas that are hollow can pass through the vaginal 3 insert and take have the opening be continuous from one end of the vaginal 3 insert and can include but is not restricted to having a continuous conduit 5 from the opening of the cervical os through and to the opening at the end opposite to the cervical os opening and which can be located but not restricted to an opening at the vaginal 3 orifice and the menstrual 46 blood can include but is not restricted to flow through the vaginal 3 insert through the cervical os opening through the body of the vaginal 3 insert and out the end opposite of the cervical os opening which can include but is not restricted to an opening at the vaginal 3 orifice such that the menstrual 46 blood can flow out of the uterus 75 and can in an orderly and structured manner can exit the vagina 3 and vaginal 3 vault and by design the menstrual 46 blood can exit the body and be captured by the MCD and its covers and tubes and a menstrual 46 blood connecting container.

For these one or more channels or conduits 5 or tubes or areas that are hollow to not collapse they may require a structure to enable, an Enabling Structure, and that said structure can include but not restricted to maintain integrity, orientation, structural cohesiveness, function, job, purpose or task of a device or method or component and that the enabling structure can include but is not restricted to a matrix or architecture design or housing or envelope or layer 98 or exoskeleton or endoskeleton, skeleton or cover at, in or around or integrated into or any combination of these and that the enabling structure can include to consist of a variability and/or a difference in materials that can include but is not restricted to a difference or variability of hardness or softness or durometers or elasticity or stretchability or physical properties of materials. The enabling structure can include being a component of the channel or conduit 5 or tube or hollow or a component of the substance 44 that is not the channel or conduit 5 or tube or hollow or a combination or surrounding or enveloping these and this can be applied to the but is not restricted to being applied or incorporated into the MCD, UCD 6 or Fecal Collector and contraceptive device and that can include but is not restricted to a vaginal 3 insert with or without a conduit, tubing, covering 36 materials, and collecting containers.

In one embodiment there can be zero or one or more than one enabling structures and these enabling structures can include to be but not restricted to be separate or confluent or connected or tangential or touching or unified.

The enabling structures uses and purposes can also include and facilitate the ability to include but not restricted to movement, flexibility, changes in hydration, changes in environment and changes in gravity and pressure and vacuum, and active and passive and inactive periods of usage of the devices that can include but are not restricted to the MCD, UCD 6 or Fecal Collector and contraceptive device. The enabling structure can be variable in its qualities such that they are greater near the living being and their skin 8 or mucosa than away from the living being or can be lesser near the living being and their skin 8 or mucosa than away from the living being or can be a combination of both of these. The enabling structure can be variable in its qualities such that they are greater at or near the conduit 5 or channel or hollow than away from the living being or can be lesser at or near than away from the conduit 5 or channel or hollow or can be a combination of both of these.

The MCD and enabling device can include Sensor 39 that can include but are not restricted to include assessing physical properties of the devices and their components and their substances 44 and conduits 5 and that said sensor 39 can include send and receive components that can include but is not restricted to RF, electromagnetic, thermal, kinetic, pressure, gravity, vacuum or mechanical or flow or degree of hydration signals 14 that can then Induce a function or an Event that can include but is not restricted to altering the device or method to include but not restricted to changing its shape or function or design or airtight or watertight or blood-tight nature, or flexibility or operation. In one embodiment the Sensor 39 and its Signal 14 or message and Induction of an event that can include but is not restricted to improve or decrease or maintain the status quo of the effectiveness or effectiveness or function or role of the device or method of the MCD, UCD 6 or Fecal Collector and MFPD, contraceptive device.

The MCD and its tubing and Collecting container can include but are not restricted to having medications and materials and cleansing materials that can include but is not restricted to fluids liquids or gases or gels or slurries.

In one embodiment materials can include bit are not restricted to fluids liquids or gases or gels or slurries, medications or materials that can flow toward or away from the uterus 75 and cervix 10 and the flow of materials or medications or cleansing materials. In one embodiment the medications and materials and cleansing material that can medications and materials and cleansing materials hydrogen peroxide, ozone, contraceptives, anti-infectious agents.

In one embodiment, the vaginal 3 insert at the cervical os is conical and the cone which is hollow inside and which can be a conduit 5 is a conduit 5 which is open at both the wider and narrower ends of the cone/conical conduit 5 and through which, the menstrual 46 blood can flow. In one embodiment this conical cervical-vaginal 3 insert is composed of a gel or gel-like material conforms to the vaginal 3 vault, cervical cap and creates a suction or suction-like connection 82 with this component of the vaginal 3 insertion and this portion of the female anatomy.

In one embodiment there is a Cervical Os Centering device that can protrude from MCD into the Cervical Os orifice or can protrude or insert deeper than the Cervical Os orifice and extend partially or fully through the cervical os and can enter the uterus 75. The protruding element that arises from the MCD can include but not restricted to arise from the hollow or conduit 5 of the vaginal 3 insert, the matrix or supportive structure of the vaginal 3 insert or the MCD, or from the non-conduit 5 substance 44 and body of the MCD vaginal 3 insert or any combination of these. The protrusion can be composed of to include but not restricted to a solid or liquid or gel or gel slurry and it can be enveloped or covered or laminated or layer. In one embodiment the protrusion arises from the matrix or architectural form of a combination of the matrix of the vaginal 3 insert that can include but is not restricted to arise from zero, one or more than one the channels or hollows or conduit 5 of said vaginal 3 insert and the insert or protrusion can include but is not restricted to being confluent and/or being covered by a gel that can include but is not restricted to arise from the substance 44 of the body of the vaginal 3 insert located at or near the cervical os and protrudes into the orifice of the cervical os and can include but is not restricted to insert or protrude into the os between 1 to 10 mm, but can in some individuals protrude or insert into the os to a lesser or greater distance and degree. In the preferred embodiment the cervical os centering device would not obstruct menstrual 46 flow out of the uterus 75 but would allow menstrual 46 blood to freely flow from the uterus 75 into the one or more hollows or channels or conduits 5 of the components of the vaginal 3 insert of the MCD.

Menstrual 46 Flow Prevention Device (MFPD)

There can be a Menstrual 46 Flow Prevention Device (MFPD) a protruding or inserting component into the cervical os can include but is not restricted to occlude and fill the cervical os and all or a portion of the and most specifically the uterus 75 and all or a portion of the vaginal 3 vault or any combination of these. The MFPD can include but is not restricted to filling, obstructing and blocking the cervical os for a period of time temporarily preventing the egress of menstrual 46 fluid. The MFPD can include but is not restricted to prevent the egress of the menstrual 46 blood out of the uterus 75 on a temporary basis. In one embodiment the shape and configuration of the MFPD could include an hour-glass or hour-glass like shape and the hour-glass shape of hour-glass like shape can be symmetric or asymmetric can include but is not restricted to be made partially or fully of a gel or gel-like insert that can be composed of the same materials as the MFD and can even be hollow inside so long are there is no conduit 5 that communicate between the uterus 75 and the cervical or and vaginal 3 vault in a manner that would allow blood to egress out of the uterus 75 and into the vaginal 3 vault or out of the living body.

The MFPD can include but is not restricted to be composed of a solid or liquid or a gel or a gel-slurry or gas or any combination of these and all or none of these can be enveloped or covered or surrounded by a membrane. In one embodiment the use of this MFPD can include but not restricted to space travel or underwater exploration or long-travel or car racing. In each of these applications the changes and demands of the environment must be considered when designing or utilizing or inserting or using this device.

The MFPD can be 3-D printed or molded by direct and indirect methods described within this patent application for other devices and can include but is not restricted to being pre-formed by imaging methods discussed herein this patent application.

Contraceptive Device

The design of the MFPD can include but is not restricted to be used for temporary contraception for the prevention of the mixing of sperm and egg.

In one embodiment the design of a Fallopian tube and or uterine junction occluding device that can be used for contraception can include but is not restricted to being imaged by methods discussed herein this patent application and can be 3-D printed or molded by direct and indirect by methods described within this patent application.

In one embodiment the design of a Fallopian tube and or uterine junction occluding device that can be used for contraception can include but is not restricted to having the components of said contraceptive device be held in place, be connected, be assembled to include by magnetic forces and magnets and said magnets 38 can be within the lumen of the fallopian tube, or uterine os or uterus 75 or can lie within the fallopian tube, or uterine os or uterus 75 or lie external to the fallopian tube, or uterine-fallopian tube junction or uterus 75.

Fecal Collection Device (FCD)

Figure 10:
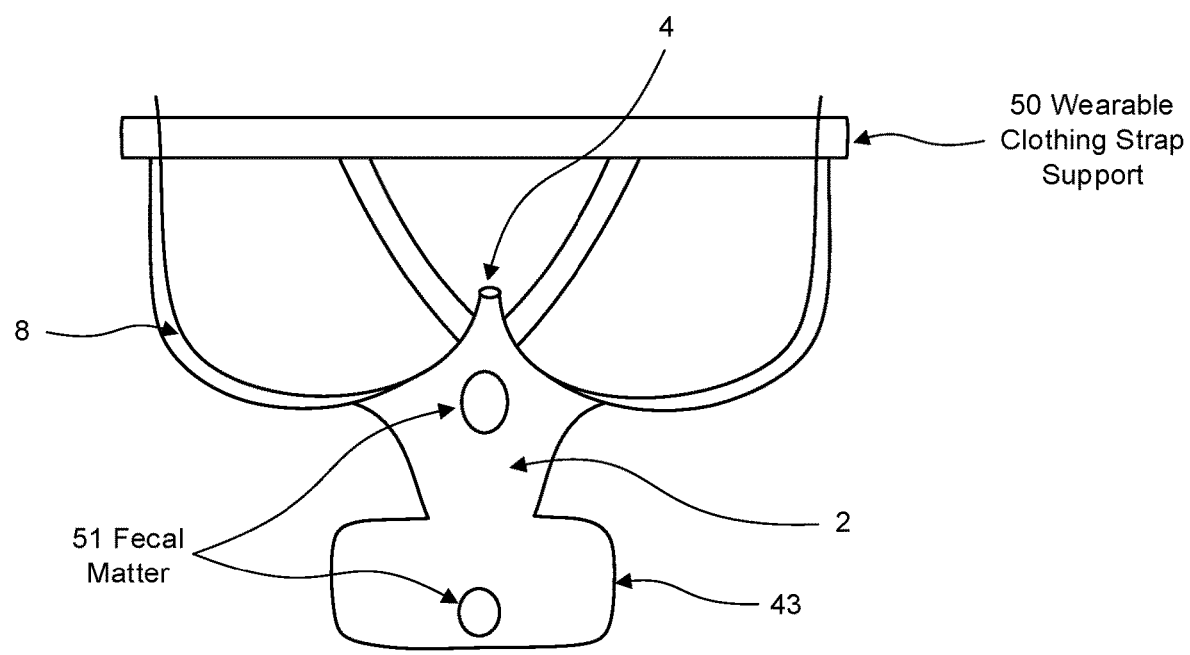
FIG. 10 is a posterior rendering of a fecal collection unit.

FIG. 10 is a posterior rendering of a fecal collection unit. A feces 51/stool 51 collection (FCD) device can include but is not restricted to have elements of the menstrual 46 and UCD 6 collection devices 6 wherein the feces 51 and/or stool 51 (which are term to be used interchangeably) is the element that is caused to move away from the living body and the goal is to prevent mixing of the contaminants arising from the urethra 2 and or from the vagina 3 and anal 4 regions. In the stool 51 collection device 9 the goal is the egress and flow of fecal material away from the living body and away from the urethra 2 and vulva 11 mucosa and anal 4 region such that the fecal material does not contaminate or intermix with to include but not restricted the urethra, anus 4, vulva 11 and mucosa of vulva 11 region and causes contaminants to move away from the living body such that contaminants do not collect in the urethral 2 or vagina 3 or vulva 11, anal 4 regions and that contaminants do not remain stationary and do not cause to include but not restricted to infection, contamination, putrification, or toxicity to urethra, vulva 11, vagina, skin 8 or internal organs to include but not restricted to the bladder 76 and kidneys and fallopian tubes and uterus 75 and abdomen as well as the remainder of the living body A feces 51/stool 51 collection (FCD) device can include but is not restricted to have a grinding mechanism to include but not restricted to a wet grinder or a dry grinder or a combination of these. In one embodiment the grinder can be but is not restricted to be a cutting blade, or a set of gears that are located within a housing in which the blades are not exposed to the FCD and its components and the living body in order to protect these from damage. In another embodiment the fecal material can include but is not restricted to be crushed or mashed by methods to include but not restricted to gears and compression between two or more objects or materials.

In another embodiment the stool 51 can be sequestered in compartments that can include but is not restricted to having valves that can be opened and closed to include mechanical, electric, electromagnetic, magnetic, hydraulic, kinetic, ultrasound, pressure, air pockets and cavitation and thermal energy 43 methods. Once sequestered in the fecal material can be exposed to include other solids or liquids or fluids or gels or slurries or energy 43 that can include but is not restricted to mechanical, electronic, electromagnetic, magnetic, hydraulic, kinetic, ultrasound, pressure, air pockets and cavitation and thermal energy 43 methods to alter the state of the fecal material from solid or semi-solid to a state that can include but is not restricted to semi-solid, a slurry, a gel, a liquid or a gas.

In one embodiment, the FCD can include but is not restricted to utilize a vacuum or a vacuum pack-like device that includes a bag to trap and compress the fecal matter and this can be utilized from the anal opening and throughout the FCD.

Breast 57 Collection and Stimulation 71 Devices (BCSD)

Figure 11:
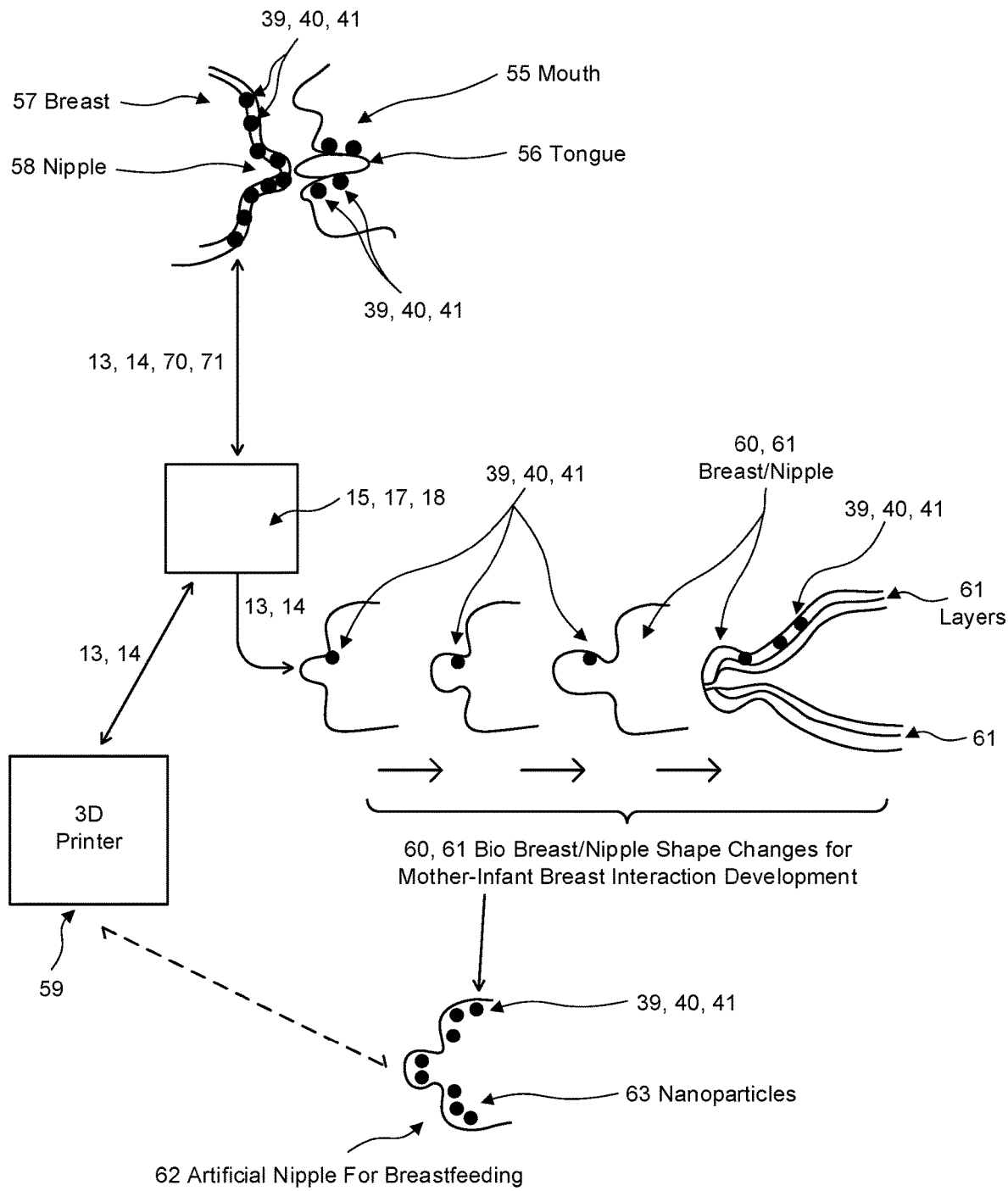
FIG. 11 is sagittal depiction of a feedback 70 and stimulation 71 breast 57 unit with oral component that can be used for breast 57 feeding-collection, pleasure, and infant feeding nipple 58 shaping and production.

FIG. 11 is sagittal depiction of a feedback 70 and stimulation 71 breast 57 unit with oral component that can be used for breast 57 feeding-collection, pleasure, and infant feeding nipple 58 shaping and production.

U.S. patent application Ser. No. 14/663,348, cited supra, contains multiple descriptions of a breast 57 collection device 9 with feedback 70 sensor 39 and interactive mechanisms. Some of these embodiments are repeated in this provisional and some elaboration for clarity are described herein.

A breast 57 collection device 9 that is designed to improve comfort to the mother by utilizing a gel based interface between the suction device and/or its cover and the women's breast 57. Currently pumps are plastic and are hard and can be painful.

The Breast 57 Collection and Stimulation 71 Devices (BCSD) can be used to include mother and the infant/child as well as the father, other family members, the general population and caregivers, lovers and males and female living-beings both human and not-human.

In one embodiment the gel seal 7 can include but is not restricted to being washable, soft, conformable, and can include but is not restricted to being fully or partially airtight, watertight and breast 57-milk tight, and the interface can include but is not restricted to being can include but is not restricted to be composed of a solid or a gel, a gel slurry or a gel, or an encapsulated gel, gel slurry, fluid/liquid, solid or gas encapsulated or can be a combination of these and that can include but is not restricted to a silicon, cloth or rubber, or a waterproof or water resistant material, plastic, metallic organic or inorganic material, carbon fiber, a hydrophobic or hydrophilic gel, or neutral gel, or nano 63 particles or any combination of these and the interface can be of variable elasticity and durometers, and hardness and softness between the living body and the skin 8 cover or frame or pump receptacle that can include but is not restricted to collecting the breast 57 milk as it leaves the mother's nipple 58. The breast 57 can include but is not restricted to the orifice or meatus of the nipple 58 out of which the milk egresses, secretes, excretes or exits. The pump receptacle can include but is not restricted to include the conduit 5 or the interface with the breast 57, or the frame or the pump or any combination of these.

In another embodiment the pump or suction device interface with the breast 57 and the living body cam be composed of multiple layers 98 and one embodiment that can include but is not restricted to at least one portion of one layer 98 having a structure that simulates the mouth 55 or lips or a tongue 56 or a combination of these and these structures can be activated by the pump or suction mechanism to simulation or movement of periodicity or suction of a living beings use of the mouth 55 or lips or tongue 56.

An embodiment of the BCSD can include but is not restricted to having an interface that can include but is not restricted to having sensor 39 that can include but is not restricted to the ability to sense, monitor, and feedback 70 with both input and output of data and information. The sensing and monitoring and feedback 70 information and data can include but is not restricted to communication with the mother and the infant/child as well as the father, other family members, the general population and caregivers, lovers and males and female beings. The sensor 39 can include but is not restricted to macro, micro and nano 63 sensor 39 and particles. And this said information and feedback 70 gathered and stored and distributed and used for operation and feedback 70 can include but is not restricted to be referred to as data or information. This data can be used to create algorithms to include but not restricted to optimizing the mother and infant experience of breast 57 feeding to include but not restricted to improving breast 57 milk flow, the let-down reflex and sensation and experience, the mother-infant bond and the said data can be updated and can help control the breast 57 mechanism that can include but is not restricted to assist the mother's breast 57 experience which can include but is not restricted to pumping, suction, let-down, flow, enjoyment, bonding, promoting psychological and biologic function and sensation as well as control, assist the baby or infant or toddler and child's mechanism of intake of milk, sucking, movement, and coordination and reproducibility and lips and mouth 55 and face and intake muscle 65 function of the child and mother to assist and promote the child's intake of milk and nourishment as well as the joy and pleasure and enjoyment of the mother and child to include but not restricted to the suckling experience which can include but is not restricted to which can include but is not restricted to pumping, suction, let-down, flow, enjoyment, bonding, promoting psychological and biologic function and sensation as well as control, assist the baby or infant or toddler and child's mechanism of intake of milk, sucking, movement, and coordination and reproducibility and lips and mouth 55 and face and intake muscle 65 function of the child and mother to assist and promote the child's intake of milk and nourishment as well as the joy and pleasure and enjoyment of the mother-child experience.

In one embodiment, the mother's breast 57 experience and the baby's suckling can also include and be augmented by devices and methods to include but are not restricted having the data be input into a computer 18 that can include but is not restricted to storing and modulating to include but not restricted to modifying and controlling and enhancing and correcting data of breast 57 feeding and suckling experiences to include but not restricted to the mother and the infant as well as the father, other family members, the general population and caregivers. This data can include but is not restricted to be used or stored or managed on a hand-held device, the cloud, servers or a personal computer. One embodiment can include but is not restricted to include a feedback 70 loop and an updating system.

In one embodiment, the data from the breast 57 and suckling experience can include a temporal component that can include but is not restricted to the initial, early, mid and late breast 57 and suckling experience and can be modulated by the feedback 70 algorithm and this can be fully or partially controlled by the computer, the living being to include but not restricted to a human and non-human being or any combination of these.

In one embodiment, the data from the breast 57 and suckling experience can include when the child is transitioned away from the breast 57 to an artificial nipple 58 and can be modulated by the feedback 70 algorithm and this can be fully or partially controlled by the computer, the living being to include but not restricted to a human and non-human being or any combination of these.

The artificial nipple 58 can include but is not restricted to be fashioned, molded, and/or created or reproduced to include but not restricted to have the shape and configuration and feel of the mother's breast 57 and/or an optimal or functional shape that can include but is not restricted to promote the child's ability to nourish itself. In one embodiment a reproduction to include but not restricted to the mother's breast 57 or the child's lips and mouth 55 or a combination of these can be created and one embodiment can include but is not restricted to can be created with a 3-D printer 59 or a moldable material. In another embodiment the nipple 58 can be fashioned with element of both the mother's breast 57 and the child's lips and mouth 55 or any combination of these to include but not restricted to one side being the mother and breast 57 side and one side being the child's side or a combination of elements on either or both sides and an element of these configurations can be restricted to one or both sides.

In one embodiment the breast 57 covering 36 or interface of the mother, the breast 57 nipple 58 or the child nipple 58 or the artificial nipple 58 of the mother or child nipple 58 can include but are not restricted to be dynamic to include but not restricted to being able to change shape 85, 86 or configuration to fit the needs of the mother or the child depending on the stage of breast 57 feeding and suckling.

In one embodiment, the artificial nipple 58, 60 can be transitioned to include but not restricted to initially be a nipple 58, 60 that closely resembles the mother's breast 57 but over time can transition to be less like the mothers breast 57.

In one embodiment the artificial or transitioning nipple 58 can have a nourishment assist device that can pump milk or nourishment to the child/infant nipple 58, 60. In another embodiment this artificial nipple 58,60 can include but is not restricted to utilize the data and information collected on the infants suckling and breast 57 feeding to assist the infant in transiting from the breast 57 to the artificial nipple 58, 60. And the pumping and suction can include the input and output data and modification of the data and information to assist the child from transitioning from the breast 57 to the artificial nipple 58, 60 in a similar or reverse or modified manner in comparison to the child learning to suckle/breast 57 feed.

Filtering and Safety

In one embodiment, the breast 57 pump can include but is not restricted to filter out materials harmful to the child to include but not restricted to medications used by topically or arising from the breast 57 milk, pathogens to include but not restricted to living and inert and non-living organisms or their by-products or chemical or biological components or reactions to their components; and toxins to include but not restricted to heavy metals, metals and metallic compounds, petrochemicals and chemical compounds that are toxic to living beings and said filtering systems can include solids and liquids and gels and gases to include but not restricted to chelating agents such as ozone, peroxide, CaNa2EDTA, carbon filters, HEPA filters, filter paper, coalescing agents, electrostatic, mechanical, kinetic, ultrasonic and electromagnetic 102 filters such as but not restricted to UV 43 and activating and deactivating agents that can be activated or deactivated but adding additional agents to include but not restricted to chemical, mechanical, ultrasonic visible 20, 43 and non-visible 43 electromagnetic 102 energy 43 including but not restricted to electrical, magnetic and UV 43 energies. In addition the breast 57 pump and its components can include organo-cidal and bacteria-cidal and viral-cidal properties as can be found in metals and metal compounds and metal polymers to include but not restricted to copper and silver and zinc and borax and iodine and gold and to include but not restricted to nano 63 particles and these pathogen-cidal (killing) materials would be used in a manner that can include but is not restricted to being safe for both the mother and the child and to include but not restricted to the pathogen-cidal (killing) material being in low quantities, being bonded to a polymer such that the material such as copper comes in contact with the milk but is not released into the milk and in one embodiment this can include copper that can include but is not restricted to be in the milk reservoir 43 or tubing or pump or collecting receptacle or skin 8 covering 36 such that the milk is exposed to the copper and one embodiment can include but is not restricted to having a method and device to stir or agitate or swirl the milk in a manner to include but not restricted to increase the milk to copper surface area ratio, or the milk to chelating agent area ratio to sterilize or purify or cleanse or remove toxins from the milk.

Sensor 39 and Sensation Monitoring, and Data Collection and Feedback 70

Figure 12:
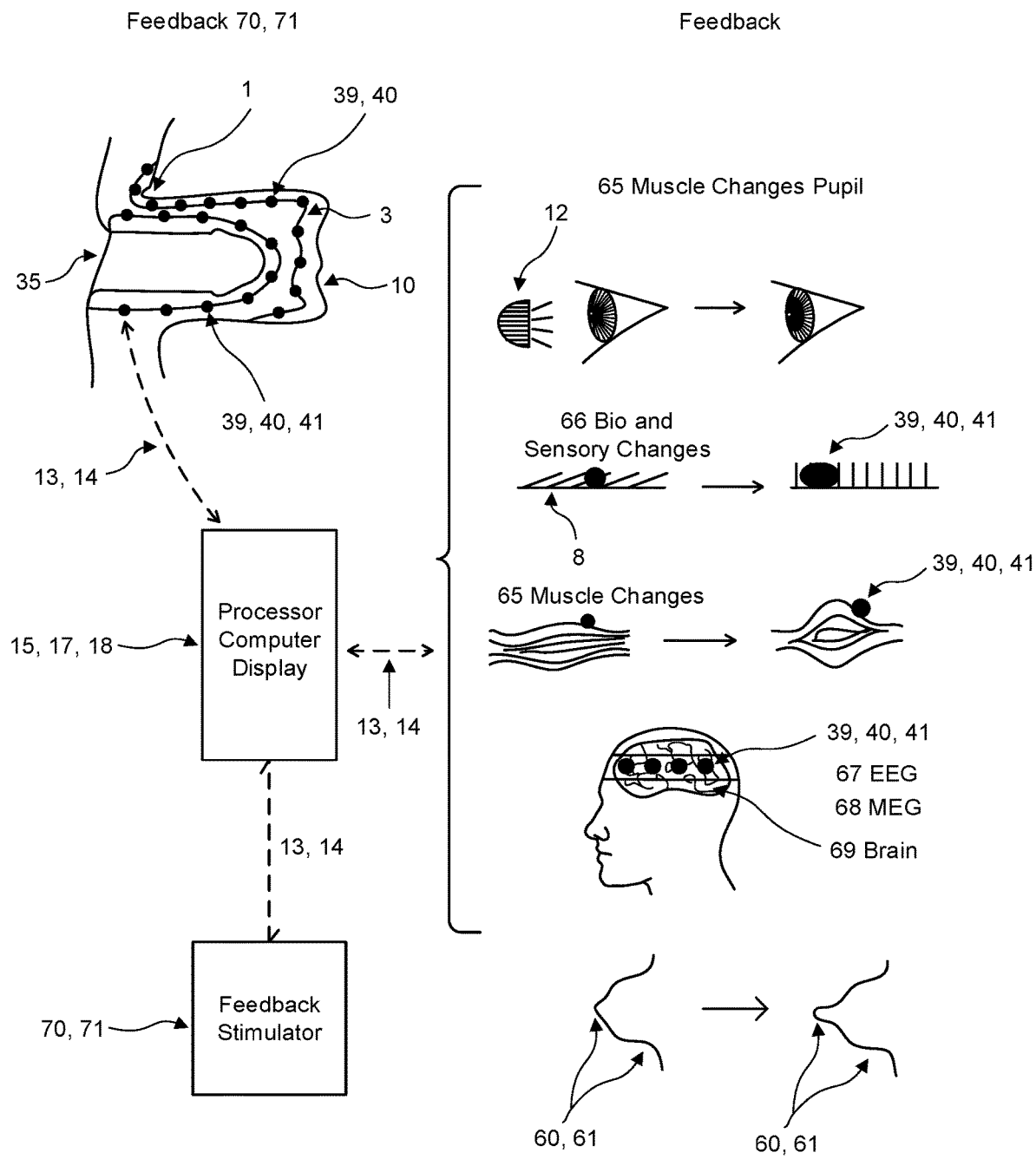
FIG. 12 is sagittal schematic depiction a bio-function, sexual, and sensual device for biofeedback 70 and biostimulation 71 with computerized and display 17 units.

FIG. 12 is sagittal schematic depiction a bio-function, sexual, and sensual device for biofeedback 70 and bio-stimulation 71 with computerized and display 17 units. In another embodiment, the sensor 39 can acquire/assess/gather and transfer and send and receive and provide feedback 70 and modify and activate or deactivate components of the vulva 11, penis, 35, anus 4, perineum 25, breast 57 pump mechanisms and apparatus and functions to include all known human and animal senses to include but not restricted to be used to collect data and information and process and interpret and transmit or modify said data and information and facilitate the lactation or pleasure or effectiveness of the experience and provide a feedback 70 that can include but is not restricted to facilitate or augment the lactation or suckling or pleasure or arousal or reflexes such as but not restricted to let-down and flow of breast 57 milk and improved suckling of the infant to include but not restricted to through natural biological functions or facilitated or mechanical or augmented psychological or physiological or biological functions to include but not restricted to alteration or facilitation of senses artificially or naturally and such augmentations or senses can include but are not restricted to:

olfactory sensations to include but not restricted to the one or more of the male or female or adult or child or a location or substance 44 or other creature's scents or other fragrances living and non-living to include but not restricted to the baby's, the children's, the father's, the lover's, the mother's, the family's scents or perfumes, herbs, foods, flowers, lavender, vanilla or chocolate or coffee scents or a desired or favorite smell;

visual sensations to include but not restricted to pictures or images 29 to include but not restricted to one or more of the male or female or adult or child or a location or substance 44 or other creature's likeness or other visualizations living and non-living likeness, image or representation or 3-D representation or hologram to include but not restricted to the baby's, the children's, the father's, the lover's, the mother's, the family's representation or a favorite living or non-living object or location or vacation sunset or representational or a desired or favorite image;

auditory or vibrational or sensations to include but not restricted to one or more of the male or female or adult or child or a location or substance 44 or other creature's likeness or other auditory sensation living and non-living image to include but not restricted to a women's, a child's, man's or other living creatures voice, sound, crying, cooing, sucking, sounds of pleasure or non-pleasure, singing, a heartbeat or biological sound, or music or musical sounds, or non-human animal sounds;

taste or gustatory sensations to include but not restricted to one or more of the male or female or adult or child or a location or substance 44 or other creature's likeness or other living and non-living auditory sensations or a desired or favorite auditory sensation or sound;

taste or gustatory sensations to include but not restricted to one or more of the male or female or adult or child or a location or substance 44 or other creature's taste or gustatory sensations living and non-living image to include but not restricted to a woman's, a child's, man's or other creatures taste or gustatory sensations living and non-living image to include but not restricted to a women's, a child's, man's or other living creatures to include but not restricted to the baby's, the children's, the father's, the lover's, the mother's, the family's tastes or gustatory sensations living and non-living including but not restricted to basic taste sensations of sweetness, sourness saltiness, bitterness and umami, foods, herbs, foods, flowers, flavors, lavender, vanilla or chocolate or coffee scents or a desired or favorite smell;

kinesthetic or tactile and tactile-like sensations to include but not restricted to one or more of the male or female or adult or child or a location or substance 44 or other creature's kinesthetic or tactile and tactile-like sensations living and non-living image to include but not restricted to stretch, stretch reflexes, neural reflexes neural signals 14, muscle 65 tone, proprioception, stereognosis, pain, pleasure, heat, cold, vibration or vibration-like or ultrasonic, thermal and temperature, pressure touch that can include but is not restricted to light touch and light pressure, tickling, tactile location, tactile discrimination, pressure, spatial location perception of size and shape, wetness and dryness, slipperiness, hardness and softness as well as the composite sensation referred to as feel and/or the lack or removal or loss of these tactile and tactile like sensations. And can include some examples to include but are not restricted to simulation of movement of the tongue 56, softness and pliability of the breast 57, the warmth and wetness and movement of the lips, and simulation of suckling;

observed and subliminal signals 14 and sensations and reflexes and biological responses can include but are not restricted to one or more of the male or female or adult or child or a location or substance 44 or other creature's subliminal signals 14 and sensations living and non-living image to include but not restricted to a woman's, a child's, man's or other creatures taste or gustatory sensations living and non-living image to include but not restricted to facial movements, muscular movements, licking and sucking and brushing or light pressure across the cheek of a baby such as the rooting reflex or other reflexes such as the sucking reflex, or sensations, autonomic and non-autonomic reflexes and functions and triggers that can include but is not restricted to releasing hormones or peptides in the mother or child to include but not restricted to Oxytocin, Prolactin, Endorphins, Pheromones, FSH, LH, and their likenesses or simulators and sex hormones to include but not restricted to Estrogen and Estrogen-like, Progesterone and Progesterone-like or Testosterone and Testosterone-like compounds as well as priming and facilitating muscle 65 and gland and breast 57 and digestive and eating functions and pleasures.

In one embodiment, the breast 57 pump can be composed of functional and sensory 39, 66 outputs units that can be a component of but not restricted to be a component of the interface or the skin 8 covering 36 or the pump or suction device and to include but not restricted to be associated with the breast 57 or the lips or mouth 55 or another component of the living body. In one embodiment the output unit can be a component of or a separate interchangeable or add-on unit from the interface or skin 8 covering 36 or pump or suction device. The output unit can include but is not restricted to contain a sensor 39 and these sensor 39 can be or can communicate or be coupled with output or transmitter devices and activators 97 that can include but are not restricted to input and output and transfer data and information and perform a function or task that can include but is not restricted to modify the environment and that can include but is not restricted to treat a biological living being to include but not restricted to delivering medication or energy 43 or solids or liquids or gasses or gels and which can interface with a computer 18 and modify and feedback 70 data and information in a continuous or a non-continuous or intermittent basis or in a feed-back loop or continuous or discontinuous-loop and that data and information can include but is not restricted to have the ability to activate output devices that can be used to deliver olfactory, visual, auditory, taste or gustatory, kinesthetic or tactile and tactile-like sensations and observed and subliminal signals 14 and sensations and reflexes and biological responses to include but not restricted to stimulate lactation, suckling and bonding and pleasure or pleasurable events or experiences.

In one embodiment olfactory output devices can include but are not restricted to be delivered through a nasal cannula or a nasal plug, which can be fully or partially airtight. Olfactory output devices can include but are not restricted to be utilized such that the olfactory sensation can arise and be delivered from sites distant to the nose that can include but is not restricted to a fragrance, perfume, essential oil, pheromone, hormone or chemical that can include but is not restricted to stimulate lactation, suckling and bonds and pleasure or pleasurable events or experiences. In one embodiment the breast 57 device can be associated with a reservoir 43 of scent or fragrance or smell that can be released at designated time to be promote a function to include but not restricted to stimulate lactation, suckling and bonding and pleasure or pleasurable events or experiences. The scent or fragrance or smell can be acquired or released by a means to include thermal, chemical, electromagnetic, mechanical, light, UV 43, Infrared, electric, magnetic, kinetic, vibrational or ultrasound to distribute or release of disseminate or deliver said scent.

In one embodiment visual output devices can include but are not restricted to be delivered through a screen or projection device retinal projection, hologram, or 3-D device, goggle or glasses, which can be viewed to include but is not restricted to the male, father, female mother, child, or infant, lover or intimate individual, family member or another living body both human and non-human. Visual output devices can include but are not restricted to be utilized such that the visual sensation can arise and be delivered from sites distant or adjacent to the eye and iris 23, 6423 and which can have the same or different images 29 for different users and can consist of cameras 12 that can include but are not restricted to imaging the mother and infant bond and suckling or can image sites and images 29 other than the mother and infant bonding and suckling and that can include but is not restricted to stimulate lactation, suckling and bonding and pleasure or pleasurable events or experiences. The visualization or image can be acquired or released by a means to include thermal, chemical, electromagnetic, mechanical, visible 20, 43 light, UV 43, Infrared, electric, magnetic, kinetic, vibrational or ultrasound to distribute or release of disseminate or deliver said visualization or image.

In one embodiment auditory output devices can include but are not restricted to be delivered through a cochlear implant, Bluetooth or wireless devices, speakers, ear bud, or any audio production device, which can be heard or listened to and can include but is not restricted to the male, father, female mother, child, or infant, lover or intimate individual, family member or another living body both human and non-human. Auditory output devices can include but are not restricted to be utilized such that the auditory sensation can arise and be delivered from sites distant or adjacent to the ear and which can have the same or different sounds for different users and can consist of microphones 18 and speakers that can include but are not restricted to include auditory input or output from or to the mother and infant bond and suckling or can record or play sounds other than the mother and infant bonding and suckling and that can include but is not restricted to stimulate lactation, suckling and bonding and pleasure or pleasurable events or experiences. The sound or auditory sensation can be acquired or released by a means to include thermal, chemical, electromagnetic, mechanical, visible 20, 43 light, UV 43, Infrared, electric, magnetic, kinetic, vibrational or ultrasound to distribute or release of disseminate or deliver said sound or auditory sensation.

In one embodiment taste or gustatory output devices can include but are not restricted to be delivered through a solid or liquid or gel or gas and which can be delivered via tubes or pellets or food or granules or masks, or droppers or electromagnetic, mechanical, or chemical or kinetic stimulation 71 or any taste or gustatory stimulation 71 or production device, which can be tasted or listened to and can include but is not restricted to the male, father, female mother, child, or infant, lover or intimate individual, family member or another living body both human and non-human. Taste or gustatory output devices can include but are not restricted to be utilized such that the taste or gustatory sensation can arise and be delivered from sites distant or adjacent to the mouth 55 and which can have the same or different tastes or gustatory sensations for different users and can consist of delivery 42 devices that can include but are not restricted to include taste or gustatory input or output from or to the mother and infant bond and suckling or can provide taste or gustatory sensations other than the mother and infant bonding and suckling and that can include but is not restricted to stimulate lactation, suckling and bonding and pleasure or pleasurable events or experiences. The taste or gustatory sensation can be acquired or released by a means to include thermal, chemical, electromagnetic, mechanical, visible 20, 43 light, UV 43, Infrared, electric, magnetic, kinetic, vibrational or ultrasound to distribute or release of disseminate or deliver said taste or gustatory sensation.

In one embodiment kinesthetic or tactile and tactile-like sensations output devices can include but are not restricted to be delivered through a solid or liquid or gel or gas and which can be delivered via devices to include but not restricted to motors, vibrators, compression, and pulley devices to include but not restricted to devices that can stretch, tap, cause stretch muscle 65 and neural reflexes neural signals 14, neural stimulation 71, muscle 65 signals 14 and tone, proprioception and stereognostic sensations, can pierce or inject or stroke, and which can produce pain, pleasure, heat, cold, vibration or vibration-like sensations, wetness and dryness, fanning and blowing sensations, ultrasonic stimulation 71, and signals 14 and sensations that create thermal and temperature, pressure and touch that can include but is not restricted to light touch and light pressure, tickling, tactile location, tactile discrimination, pressure, spatial location perception of size and shape, wetness and dryness, slipperiness, friction, rubbing, sensations that simulate the tongue 56 and breast 57, hardness and softness as well as the composite sensation referred to as feel and/or the lack of feeling, anesthesia or overstimulation 71, habituation or removal or loss of these tactile and tactile like sensations as well as means to overcome habituation or dullness to stimulation 71. The devices to produce these sensations that can include but are not restricted to pressure or electromagnetic 102 hydraulic or mechanical, chemical or kinetic stimulation 71 or any kinesthetic or tactile and tactile-like sensations or stimulation 71 or production device, which can be felt or sensed and can include but is not restricted to the male, father, female mother, child, or infant, lover or intimate individual, family member or another living body both human and non-human. Kinesthetic or tactile and tactile-like sensations output devices can include but are not restricted to be utilized such that the kinesthetic or tactile and tactile-like sensations sensation can arise and be delivered from sites distant or adjacent to the breast 57 of lips or male or female organs and which can have the same or different kinesthetic or tactile and tactile-like sensations for different users and can consist of delivery 42 devices that can include but are not restricted to include kinesthetic or tactile and tactile-like sensations input or output from or to the mother and infant bond and suckling or can provide kinesthetic or tactile and tactile-like sensations other than the mother and infant bonding and suckling and that can include but is not restricted to stimulate lactation, suckling and bonding and pleasure or pleasurable events or experiences. The kinesthetic or tactile and tactile-like sensations can be acquired or released by a means to include thermal, chemical, electromagnetic, mechanical, visible 20, 43 light, UV 43, Infrared, electric, magnetic, kinetic, vibrational or ultrasound to distribute or release of disseminate or deliver said kinesthetic or tactile and tactile-like sensations sensation.

In one embodiment observed and subliminal signals 14 and sensations and reflexes and biological responses output devices can include but are not restricted to be delivered through any of the means described above. In one embodiment, the sensation or biological response can include but is not restricted to releasing hormones or peptides in the mother or child to include but not restricted to Oxytocin, Prolactin, Endorphins, Pheromones, FSH, L, and their likenesses or simulators and sex hormones to include but not restricted to Estrogen and Estrogen-like, Progesterone and Progesterone-like or Testosterone and Testosterone-like compounds as well as priming and facilitating muscle 65 and gland and breast 57 and digestive and eating functions and pleasures and in this embodiment substances 44, which can be natural or artificially manufactured can be delivered by any standard mean as well as the means discussed above and these can include but are not restricted to be in the form of a solid or liquid or gel or any combination and that can include but is not restricted to be delivered via nasal delivery 42 via a nasal cannula or a nasal plug or reservoir 43; or orally delivery 42 through a tube or pellet, reservoir 43 or granule or dropper or reservoir 43; or can be transcutaneously or subcutaneously delivered through a patch or dropper or cream, emollient or ointment which can be newly delivered or in a reservoir 43 and can be released as appropriately needed and signaled; or can be delivered through any orifice or meatus or can be delivered intravascularly to include but not restricted to intra-arterial and intravenous delivery 42. Observed and subliminal signals 14 and sensations and reflexes and biological responses output devices can include but are not restricted to be utilized such that the observed and subliminal signals 14 and sensations and reflexes and biological responses and sensation can arise and be delivered from any sites of the body or distant to the body and the substances 44 can include but is not restricted to being the form or simulating the form of a fragrance, perfume, essential oil, pheromone, hormone or chemical that can include but is not restricted to stimulate lactation, suckling and bonds and pleasure or pleasurable events or experiences. In one embodiment the breast 57 device can be associated with a reservoir 43 of scent or fragrance or smell that can be released at designated time to be promote a function to include but not restricted to stimulate lactation, suckling and bonding and pleasure or pleasurable events or experiences. The observed and subliminal signals 14 and sensations and reflexes and biological responses can be acquired or released by a means to include but not restricted to thermal, chemical, electromagnetic, mechanical, visible 20, 43 light, UV 43, Infrared, electric, magnetic, kinetic, vibrational or ultrasound to distribute or release of disseminate or deliver said observed and subliminal signals 14 and sensations and reflexes and biological responses.

Materials to include but not restricted to the skin 8 covering 36 and the mother's breast 57 and areola and nipple 58 and a child's binky or artificial nipple 58 can include but is not restricted to a covering 36 of the breast 57 or the lips and mouth 55 can be influenced to change shape 85, 86. Said materials can undergo a transformation and a change of shape 85, 86 that can create and alter the relationship between the skin 8 and the skin 8 covering 36 to include but not restricted to creating compression, pressure, stimulation 71, light touch, suction and vibration on the skin 8. This shape or state change can be triggered by energy 43 or substances 44 or forces to include but not restricted to but not restricted to thermal, chemical, electromagnetic, mechanical, visible 20, 43 light, UV 43, Infrared, electric, magnetic, kinetic, vibrational or ultrasound to alter the shape of the material as cited by this patent application and as discussed herein this patent application In another embodiment the suction and pump or the mechanisms or elements related to suction and pumping can include but are not restricted to being continuous or discontinuous, constant or non-constant, or alternating or non-alternating, or a periodicity of function and sensory 39, 66 and mechanical inputs and outputs determined from gathered data and information regarding functions to include but not restricted to lactating, suckling, collection and pleasure that can include but is not restricted to the data and information that can be gathered or modified or dispensed from sensor 39, monitors, and devices, and computers 18 regarding these functions and that can include but is not restricted to with both input and output data and information and functions. In one embodiment the pumping device can alter the suction or pressure or vacuum and partial-vacuum between the living being and the suction and pumping device and can create but is not restricted to create pumping or suction or pauses of suction and pumping or any combination of these. In one embodiment this can be used to collect more breast 57 milk. In another embodiment this can be used to feed the child or infant who is not getting adequate nourishment because of a poor suckling reflex, instinct or coordination. In another embodiment the breast 57 can be stimulated to experience more pleasure or to augment the pleasure or the bond of one or more than one living beings.

In one embodiment the suction and pumping mechanism can include but is not restricted to change the skin 8 or muscle 65 or nerves or other bodily functions and sensations to include but not restricted to stretch, stretch reflexes, neural reflexes neural signals 14, muscle 65 tone, proprioception, stereognosis, pain, pleasure, heat, cold, vibration or vibration-like or ultrasonic, thermal and temperature, pressure touch that can include but is not restricted to light touch and light pressure, tickling, tactile location, tactile discrimination, pressure, spatial location perception of size and shape, wetness and dryness, slipperiness, hardness and softness as well as the composite sensation referred to as feel and/or the lack or removal or loss of these tactile and tactile like sensations. And can include some examples to include but are not restricted to simulation of movement of the tongue 56, softness and pliability of the breast 57, the warmth and wetness and movement of the lips, simulation of suckling and impact and frictional contact.

In one embodiment the suction and pumping mechanism can include but is not restricted to simulate, periodicity, Movement of Tongue 56, proprioception and Position, Suction and position of Mother and Infant to promote lactation of suckling and facilitate the Let Down time, effectiveness, flow and volume of milk and nourishment and bonding and pleasure.

In one embodiment data and information profiles that can include but is not restricted to integrate or include the Mother to Baby, Baby to Mother and can incorporate the siblings, Father's or lovers or another living being or populations interaction.

In one embodiment the sensory 39, 66 and feedback 70 mechanism can include biological functions and data and information to include but not restricted to blood pressure, pulse, temperature respiration, and skin 8 conductivity, brain 69 activity to include but not restricted to brain 69 electrical signals 14, EEG 67 or EEG 67-like or MEG 68 or MEG 68-like devices (MEG 68 is Magnetoencephalogram). In another embodiment can measure peripheral nerve or muscle 65 signals 14 and function to include but not restricted to EMG, blood flow 104, chemical and neural detection. One embodiment can include but is not restricted to laser assessment of skin 8 and blood flow 104 and color 95.

In one embodiment the biological functions can be activated to include but not restricted to blood pressure, pulse, temperature respiration, and skin 8 conductivity, brain 69 activity to include but not restricted to brain 69 electrical signals 14, and magnetic devices. In another embodiment can activate peripheral nerve or muscle 65 and function to include but not restricted to muscle 65, blood flow 104, chemical reactions, sensory 39, 66 stimulation 71, and neural stimulation 71. One embodiment can include but is not restricted to laser, chemical or electromagnetic 102 or mechanical activation of the nerves and muscle 65 and skin 8 and mucosa.

Variant on the Breast 57 Stimulation 71 and Collection Device (BSCD)/Stimulation 71 Device (SD)

The breast 57 stimulation 71 and collection device 9 (BSCD) and modifications of the BSCD can also be used for pleasure and gratification that can include but is not restricted to sensual, sexual, and personal pleasure involving one or more living beings. All the elements of the Breast 57 and other devices described herein can be included in the Stimulation 71 Device (SD).

For this provisional the usage of the terms and functions and devices and components of the BSCD and SD and other devices can include but are not restricted to be used interchangeably or can be used as being different.

The SD can be utilized with the living body that can include usage by a male and a female and can include but is not restricted to being used on erogenous regions that can include but are not restricted to the breasts 57, nipple 58, female reproductive and pleasure regions and structures to include but not restricted to the vulva 11, vagina, labia, clitoris 1, clitoral engorgement regions; male reproductive and pleasure regions and structures to include but not restricted to the penis 35, scrotum and glans; the anus 4 and regions of the skin 8 that can include but is not restricted to measuring pleasure or biological function input or can receive biological pleasure or function output.

In one embodiment the SD can include but is not restricted to be used to improve biological function and or pleasure.

In one embodiment the SD can be used for the female and that can include but is not restricted to teach or improve or achieve orgasms that can include but is not restricted to different variations on orgasms to include clitoral, vaginal 3 and single and multiple orgasms, and ejaculatory orgasms, or lactate or derive greater sexual or sensual pleasure, or tolerate or enjoy anal 4 stimulation 71. In another embodiment the nerves and muscle 65 that can include but is not restricted to the regions of the vagina, urethra 2 and anus 4 can be and that can include but is not restricted to teach or improve or achieve contractions of muscle 65 or training 80, 81 of nerves and muscle 65, or coordination of these functions and structures to include but are not restricted to giving or receiving 16 greater pleasure, improving biological and pleasure responses, training 80, 81 the mind and body to work in harmony and effectiveness to achieve pleasure and satisfaction. In one embodiment the shape changes 85 and configurations 85 can include but are not restricted to Mechanical/Hydraulic/Kinetic shape changes 86, and shape changes from interaction of substances 87 or shape changes form interaction with energy 88 or any combination of these.

The methods and devices for SD are described herein and the same or similar or analogous sensory 39, 66 input and output and modification devices and computers 18 and output mechanisms and stimulators and sensory 39, 66 output devices can be used as are described both in the BCSD and the other devices herein as appropriate.

Another embodiments can include but is not restricted to using the SD to improve or strengthen pelvic floor 74 function after the delivery 42 of a child or with aging. Another embodiment can include but is not restricted to preventing urinary leakage.

Female Urinary Incontinence 83 and Prolapse 79 and Continence Assist Device and Female Erectile Function/Dysfunction Device/Orgasm (Female Assist Devices: FAD)

Figure 13A:
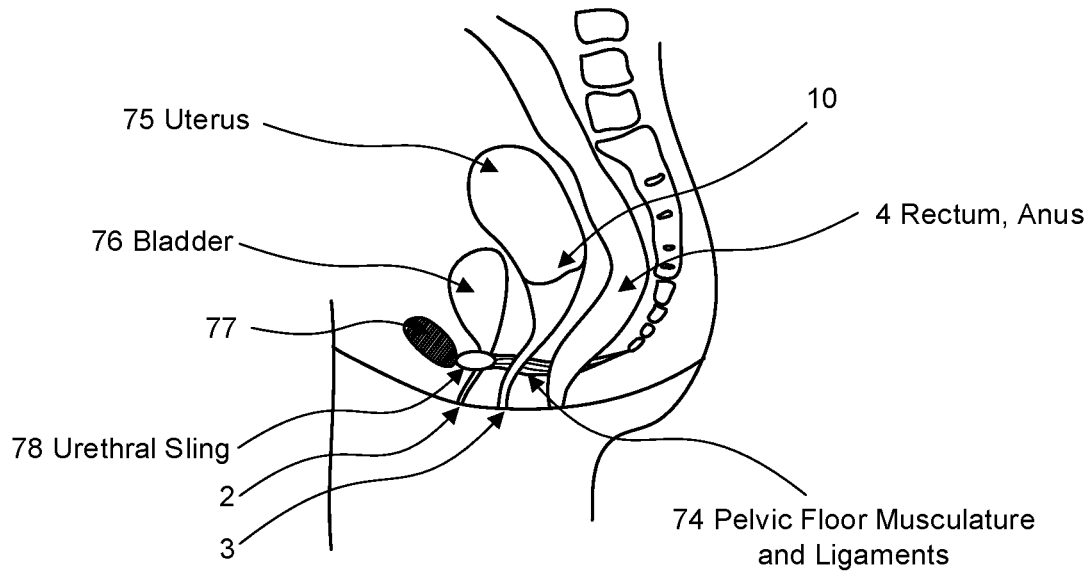
FIG. 13A is a sagittal rendering of a normal pelvic floor 74 and its related female anatomy.
Figure 13B:
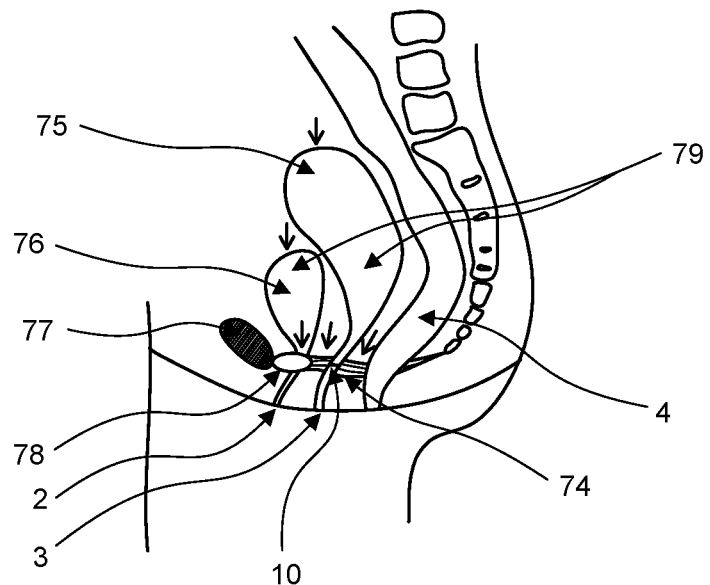
FIG. 13B is a sagittal rendering of an abnormal or incompetent pelvic floor 74 and its related female anatomy, which predisposes to urinary and vaginal 3 incontinence 83 and prolapse 79 and to prolapse 79.
Figure 14A:
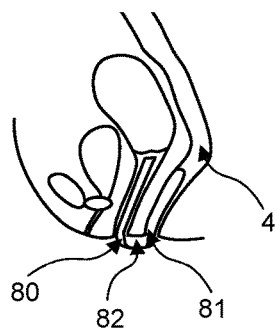
FIGS. 14A-F are sagittal renderings of the female pelvic floor 74 anatomy and devices to facilitate competence, treatment and training 80, 81 of the female pelvic floor 74 in response to urinary and vaginal 3 incontinence 83 and prolapse 79 and to prolapse 79, to improve bodily functions.
Figure 14B:
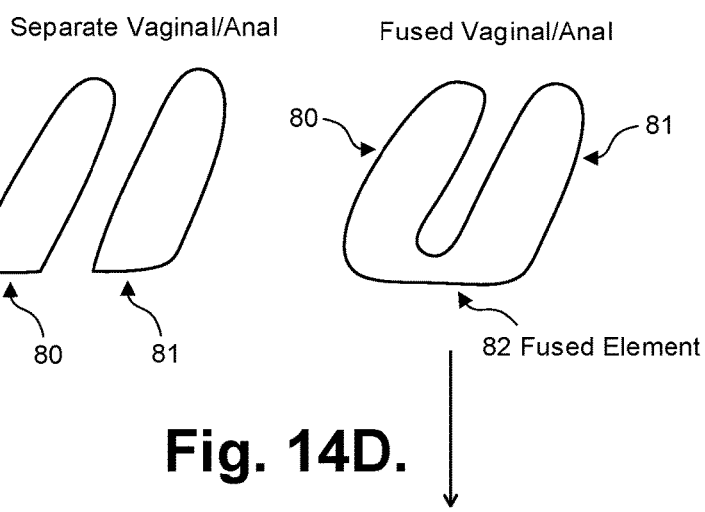
Figure 14C:
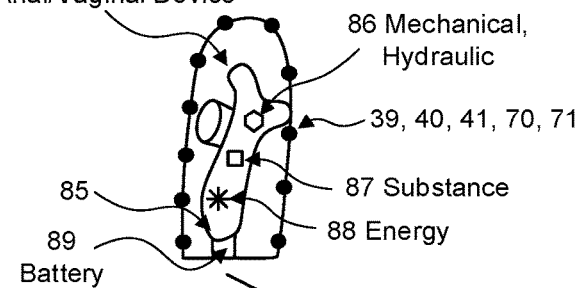
Figure 14D:
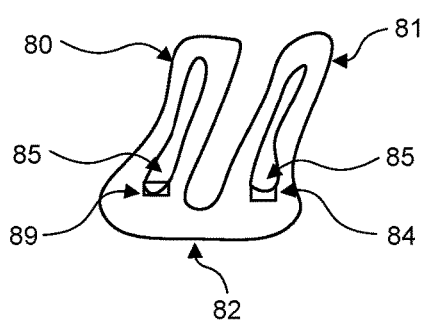
Figure 14E:
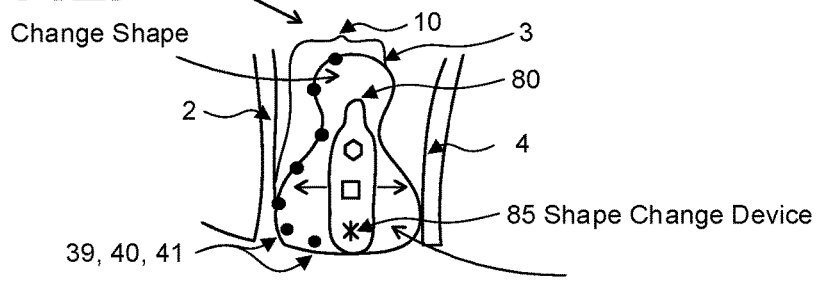
Figure 14F:
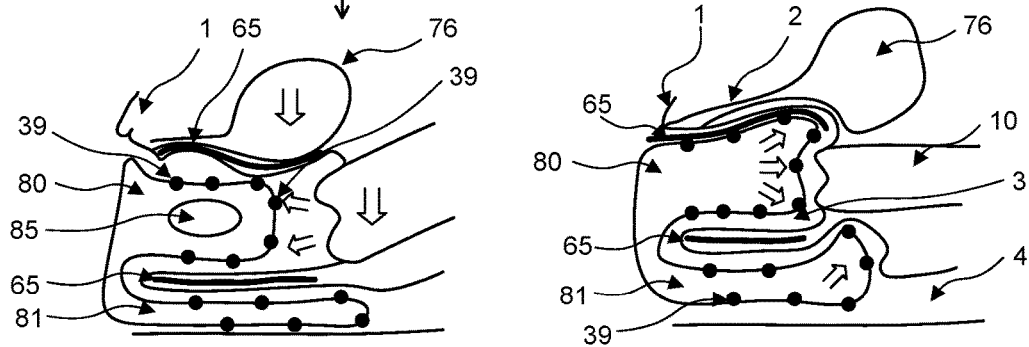

FIG. 13A is a sagittal rendering of a normal pelvic floor 74 and its related female anatomy. FIG. 13B is a sagittal rendering of an abnormal or incompetent pelvic floor 74 and its related female anatomy, which predisposes to urinary and vaginal 3 incontinence 83 and prolapse 79 and to prolapse 79.

FIGS. 14A-F are sagittal renderings of the female pelvic floor 74 anatomy and devices to facilitate competence, treatment and training 80, 81 of the female pelvic floor 74 in response to urinary and vaginal 3 incontinence 83 and prolapse 79 and to prolapse 79, to improve bodily functions.

Figure 15A:
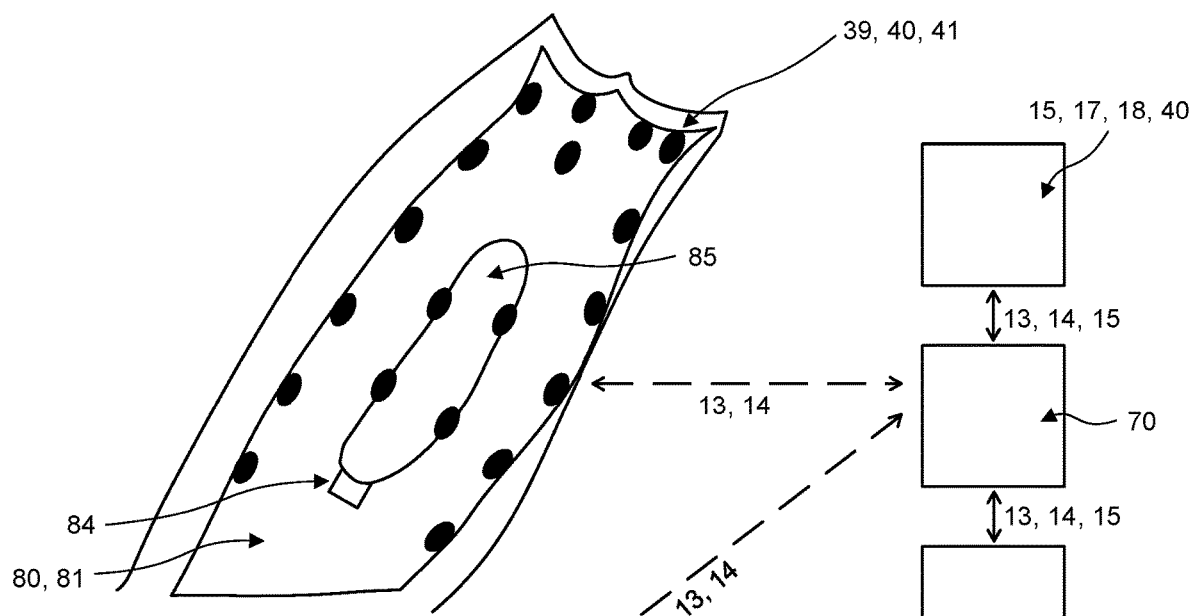
FIGS. 15A-B are sagittal renderings of female devices with associated computer 18 and sensor 39 and feedback 70 and stimulation 71 devices to improve and facilitate competence, treatment and training 80, 81 related to the female pelvis and genitourinary sexual, and, reproduction and alimentary bodily functions.
Figure 15B:
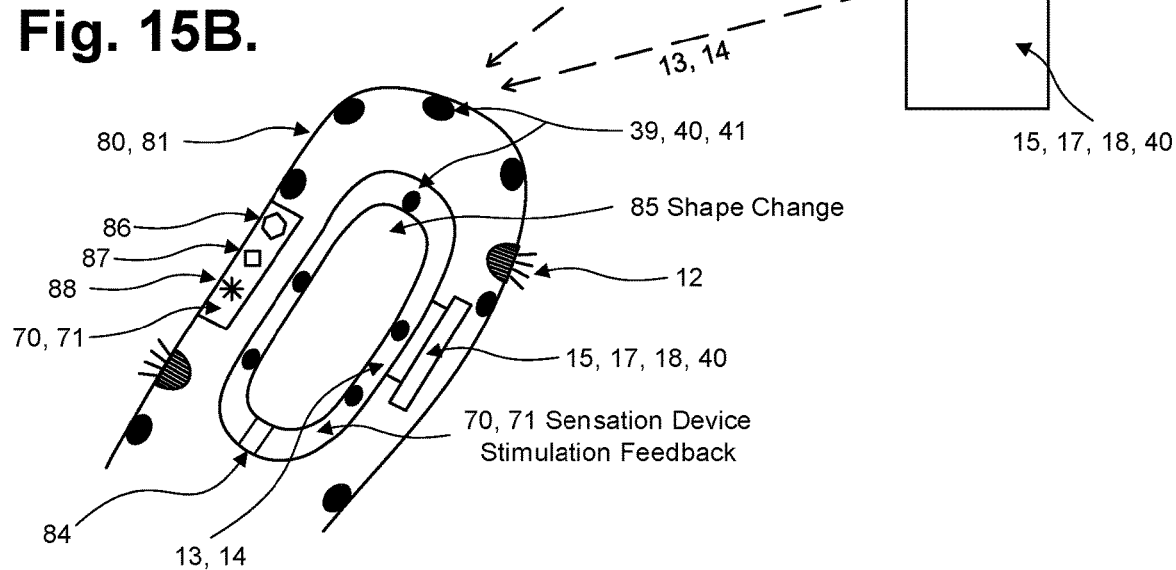

FIGS. 15A-B are sagittal renderings of female devices with associated computer 18 and sensors 39 39 and feedback 70 and stimulation 71 devices to improve and facilitate competence, treatment and training 80, 81 related to the female pelvis and genitourinary sexual, and, reproduction and alimentary bodily functions.

A vaginal 3 insert/device can be inserted into the vagina 3 or into the anus 4 or can be placed in or around or on the skin 8 or mucosa and can include but is not restricted to be composed of a material to include but not restricted to a gel, a soft silicone or plastic or cloth or rubber or glass or metal or fiber optic and said insert/devices can include but is not restricted to include sensor 39, input and output devices that can input and output and modify sensory 39, 66 and biological functions with the assistance of a computer 18 or mechanical device that can include but is not restricted to train and coordinate not just the vaginal 3 muscle 65 but also the periurethral 2 and urethral 2 and detrusor and perineal 25 and anal 4 muscle 65 and can receive feedback 70 on the function that can include but is not restricted to one or more than one of the muscle 65, muscle 65 groups or muscle 65 groupings. The feedback 70 input and output and modification device or sensor 39 can be mechanical but can also include but is not restricted to chemical or mechanical or hydraulic or vibratory or kinetic or electromagnetic 102 to include but not restricted to electrical, visible 20, 43 light, non-visible 43 light, UV 43 and Infrared energy 43 or thermal energy 43. In one embodiment the feedback 70 mechanism can act upon to include but is not restricted to include the vagina 3 and vaginal 3 insert or a covering 36 material and the clitoris 1 and the feedback 70 measurement can provide a signal 14 or a stimulation 71 to said structures and regions that can act upon or stimulate the regions to include but not restricted to changing shape, providing an electric current 100 to stimulate a muscle 65 contraction or nerve stimulation 71 or provide feedback 70 to the user, or provide a thermal response that can stimulate blood flow 104 or muscle 65 function and relaxation or contraction or the stimulus and response can be sent to and viewed on a computer 18 that can include but is not restricted to a computer, laptop, screen, handheld device, or watch-like or wearable 50 device. In one embodiment the feedback 70 input and output and modification device or sensor 39 can have a sensor 39 at the urethra 2 and can measure wetness and dryness and can teach the user which stimuli and biological functions to include but not restricted to muscle 65 contractions and nerve impulses can prevent or minimize or reduce urinary incontinence 83 and prolapse 79 and prolapse 79. Another embodiment can include but is not restricted to the combination of the users volitional and voluntary muscle 65 and neural and psychological actions coupled or used in concert with the devices feedback 70 and input and output stimuli to include but not restricted to working together with electrical stimulation 71 of the urinary specific muscle 65 to create continence. In another embodiment the device and the user can work together to create orgasms with a combination to include but not restricted to feedback 70 on a screen, stimulation 71 with chemical or mechanical or vibratory or kinetic or electromagnetic 102 to include but not restricted to electrical, visible 20, 43 light, non-visible 43 light, UV 43 and Infrared energy 43 or thermal energy 43 and the users own volitional efforts and this can include but is not restricted to the user activating a specific muscle 65 or neural group volitionally or via the computer 18 or any combination of these to learn biological function that can include but is not restricted to being continent of urine or stool 51 or having female erections or orgasms or variations on pleasure and orgasms.

In another embodiment a feedback 70 signal 14 is released that alters that primary properties of the vaginal 3 or anal 4 or vulva 11 region or clitoral covering 36 or insert to make it larger or smaller or activate a chemical, mechanical or thermal or electromagnetic 102 unit. Embodiments can include but are not restricted to the covering 36 or the insert responding to a chemical or specific pH or glucose or fructose or thermal or laser detected blood flow 104 signal 14 and then which acts upon a component of the insert or covering 36 or stimulatory device and that can include but is not restricted to be placing electromagnetic 102 energy 43 into a nano 63 particle, nano 63 composite material, or carbon fiber layers 98 or releasing a cooling agent or chemical that causes a gel to soften, seal 7 or stiffen of the feedback 70 device at a specific location of contact.

In another embodiment the vaginal 3 insert can have but is not restricted to be composed of one or more components or units that can include but is not restricted to a lever or out-pouching or contact point that can create resistance against the area or muscle 65 or region stimulated by a nerve that needs to be trained to pre-form a function to include but not restricted urinary and fecal incontinence 83 and prolapse 79, orgasms, vaginal 3 and pelvic floor 74 incompetence.

In one embodiment a sensor 39 is placed at the urethra 2 to detect urine or wetness such that the user can learn how to manage urinary incontinence 83 and prolapse 79 with a combination of a feedback 70 system that can include but is not restricted to be in combination with an activator 97 or output device or a mechanical device that can be used by the user or triggered by the computer 18 to improve biological function that can include but is not restricted to nerve damage training 80, 81 and repair, muscle 65 training 80, 81 and repair, muscle 65 accommodation to improve support or strength or coordination for a biological function such as but not restricted to urination which can include but is not restricted to being caused by damage or the loss of ligament and structures from to include but not restricted to surgery, childbirth, aging or trauma or cancer treatment. This embodiment can include a combination of input and output of the living being or user's own volition, choosing or effort; the computers 18 or sensory 39, 66 or mechanical device control of input and output devices and facilitators; or any combination of these including the user managing the computers 18 or sensory 39, 66 or mechanical device control of input and output devices. An analogous system can be used with appropriate sensor 39 and input and output and computer 18 and user control and effort for orgasms, vaginal 3 muscle 65 effort, fecal incontinence 83 and prolapse 79, and desired stimulations 71 and pleasures. In one embodiment the shape changes 85 and configurations 85 can include but are not restricted to Mechanical/Hydraulic/Kinetic shape changes 86, and shape changes from interaction of substances 87 or shape changes form interaction with energy 88 or any combination of these.

Male Urinary Incontinence 83 and Prolapse 79 and Continence Assist Device and Male Erectile Function/Dysfunction Device/Orgasm (Male Assist Devices: MAD)

In another embodiment, there can be a male urinary incontinence 83 and prolapse 79 and continence assist device and an erectile function/dysfunction device. In one embodiment of the male assist device (MAD) an anal 4 insert, perineal 25, penile 35 or skin 8 can include but is not restricted to be composed of a material to include but not restricted to a gel, a soft silicone or plastic or cloth or rubber or glass or metal or fiber optic material and said devices can include but is not restricted to include sensor 39, input and output devices that can input and output and modify sensory 39, 66 and biological functions with the assistance of a computer 18 or mechanical device that can include but is not restricted to train and coordinate not just the corpora cavernosum for erectile function and the prostate muscle 65 but also the periurethral 2 and urethral 2 and detrusor and perineal 25 and anal 4 muscle 65 and can receive feedback 70 on the function that can include but is not restricted to one or more than one of the muscle 65, muscle 65 groups or muscle 65 groupings. The feedback 70 input and output and modification device or sensor 39 can be mechanical but can also include but is not restricted to chemical or mechanical or vibratory or kinetic or electromagnetic 102 to include but not restricted to electrical, visible 20, 43 light, non-visible 43 light, UV 43 and Infrared energy 43 or thermal energy 43. In one embodiment the feedback 70 mechanism can act upon to include but is not restricted to include the MADs, inserts or a covering 36 material and the feedback 70 measurement can provide a signal 14 or a stimulation 71 to said structures and regions that can act upon or stimulate the regions to include but not restricted to changing shape, providing an electric current 100 to stimulate a muscle 65 contraction or nerve stimulation 71 or provide feedback 70 to the user, or provide a thermal response that can stimulate blood flow 104 or muscle 65 function or the stimulus and response can be sent to and viewed on a computer 18 that can include but is not restricted to a computer, laptop, screen, handheld device, or watch-like wearable 50 device. In one embodiment the feedback 70 input and output and modification device or sensor 39 can have a sensor 39 at the urethra 2 and can measure wetness and dryness and can teach the user which stimuli and biological functions to include but not restricted to muscle 65 contractions and nerve impulses can prevent or minimize or reduce urinary incontinence 83 and prolapse 79. Another embodiment can include but is not restricted to the combination of the users volitional and voluntary muscle 65 and neural and psychological actions coupled or used in concert with the devices feedback 70 and input and output stimuli to include but not restricted to working together with electrical stimulation 71 of the urinary specific muscle 65 to create continence or erection. In another embodiment the device and the user can work together to create orgasms with a combination to include but not restricted to feedback 70 on a screen, stimulation 71 with chemical or mechanical or vibratory or kinetic or electromagnetic 102 to include but not restricted to electrical, visible 20, 43 light, non-visible 43 light, UV 43 and Infrared energy 43 or thermal energy 43 and the users own volitional efforts and this can include but is not restricted to the user activating a specific muscle 65 or neural group volitionally or via the computer 18 or any combination of these to learn biological function that can include but is not restricted to being continent of urine or stool 51 or having erections or orgasms or variations on pleasure and orgasms.

Figure 16:
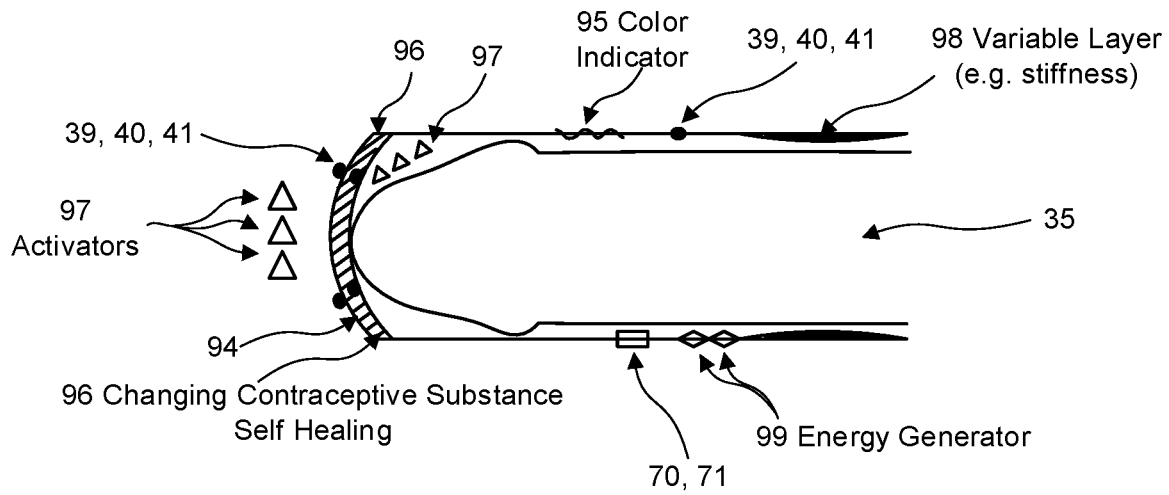
FIG. 16 is a sagittal rendering of the penis 35 and a covering 36 or condom with interactive devices and sensor 39 and indicators to alter the properties and environment of and about the covering 36 or condom.

FIG. 16 is a sagittal rendering of the penis 35 and a covering 36 or condom 36 with interactive devices and sensors 39 and indicators to alter the properties and environment of and about the covering 36 or condom 36. In another embodiment a feedback 70 signal 14 is released that alters that primary properties of the penile and anal 4 region covering 36 or insert to make it larger or smaller or activate a chemical, mechanical or thermal or electromagnetic 102 unit. Embodiments can include but are not restricted to the covering 36 or the insert responding to a chemical or specific pH or glucose or fructose or thermal or laser detected blood flow 104 signal 14 and then which acts upon a component of the insert or covering 36 or stimulatory device and that can include but is not restricted to be placing electromagnetic 102 energy 43 into a nano 63 particle, nano 63 composite material, or carbon fiber layers 98 or releasing a cooling agent or chemical that causes a gel to soften, seal 7 or stiffen of the feedback 70 device at a specific location of contact.

In another embodiment the MAD and anal 4 insert can have but is not restricted to be composed of one or more components or units that can include but is not restricted to a lever or out-pouching or contact point that can create resistance against the area or muscle 65 or region stimulated by a nerve that needs to be trained to pre-form a function to include but not restricted urinary and fecal incontinence 83 and prolapse 79, orgasms, vaginal 3 and pelvic floor 74 incompetence.

In one embodiment a sensor 39 is placed at the urethra 2 to detect urine or wetness such that the user can learn how to manage urinary incontinence 83 and prolapse 79 with a combination of a feedback 70 system that can include but is not restricted to be in combination with an activator 97 or output device or a mechanical device that can be used by the user or triggered by the computer 18 to improve biological function that can include but is not restricted to nerve damage training 80, 81 and repair, muscle 65 training 80, 81 and repair, muscle 65 accommodation to improve support or strength or coordination for a biological function such as but not restricted to urination which can include but is not restricted to being caused by damage or the loss of ligament and structures from to include but not restricted to surgery, aging or trauma or cancer treatment. This embodiment can include a combination of input and output of the living being or user's own volition, choosing or effort; the computers 18 or sensory 39, 66 or mechanical device control of input and output devices and facilitators; or any combination of these including the user managing the computers or sensory 39, 66 or mechanical device control of input and output devices. An analogous system can be used with appropriate sensor 39 and input and output and computer 18 and user control and effort for orgasms, prostate muscle 65 effort, fecal incontinence 83 and prolapse 79, and desired stimulations 71 and pleasures.

In another embodiment the MAD/FAD erectile component of the device can be used inside of the vagina 3 and erections and pleasure responses to include but not restricted to measure penile function, penile stiffness, orgasms and vaginal 3 function or response or can include but is not restricted to a vaginal 3 stimulation 71 or vaginal 3 function device to include but not restricted to vaginal 3 blood flow 104, vaginal 3 mucosal functions to include but not restricted to vaginal 3 swelling, secretions to include but not restricted to carbohydrate, fructose, glucose, sucrose, sugar, amino acid, peptide, protein, fat and lipid, urine, pH, and mechanical responses to include but not restricted to muscle 65 contractions and relaxations and orgasm facilitator, or assist device or sensor 39 and to include but not restricted to improve male and female reproductive and pleasure organ and erogenous zone and tissue responses, mucosal/clitoral/vaginal 3/vulva 11 and penile engorgement, erections and intercourse and fertility and contraception and pleasure of the partners to include males and females. In one embodiment the MAD can include but is not restricted to stimulate or excite or assist function through release of energy 43 that can include but is not restricted to energy 43 and power, force, impetus, control or momentum and which that can include but is not restricted to include electromagnetic/electrical/magnetic or thermal or hydraulic/kinetic/vibrational/mechanical or chemical energy 43 or radioactive and can be induced by to include but not restricted to macro, micro or nano 63 particle devices or any combination of these. In one embodiment the MAD device can include but is not restricted to include a sensor 39, which that can include but is not restricted to assess the state of male and female engorgement of tissue or blood flow 104 or secretions or pre-ejaculation bio-electrical activity, nerve activity, biologic chemical and metabolic state, pH, and hormones, or muscle 65 tonicity, relaxation and contraction.

In another embodiment the MAD, there can be a penile or male reproductive organ or perineal 25 or anal 4 device that can also be used as a contraception device that can include but is not restricted to contain a sensor 39 or a device to facilitate or increase or reduce function and can be associated with but is not restricted to a male and can include but is not restricted to condom a band or an insertion or membrane that can be used in the penile or anal 4 or a scrotal or perineal 25 region and can be used on or in the male or female living body and therefore can also include but not restricted to the female reproductive organs to include but not restricted to the vagina, clitoris 1, vulva 11, anal 4 or perineal 25 or breast 57 region.

In one embodiment, a sensor 39 on a band or membrane or condom or insertion can sense electrical-mechanical activity of the penis 35 to include but not restricted to muscle 65 contractions, nerve activity, galvanic skin 8 responses, blood flow 104, erectile tissue and mucosal engorgement and can warn the male prior to ejaculation with a sensory 39, 66 response to include but not restricted to a visual, olfactory, auditory, tactile, taste or any other sense of the living organism and can release or discharge or trigger an energy 43 or device or facilitator response to include but not restricted to in one embodiment the release and electrical response with an electrode 106 or electrode 106-like device that can strengthen the male ejaculatory response and tissues/nerves/muscle 65 to improve ejaculation to improve fertility or to create contraception or to prevent disease to include but not restricted to alter the male or female environment of the vagina 3 or fallopian tubes or male or female reproductive or sexual or sensual organs where material may to include but not restricted to intermingle or coexist and join or mix to include but not restricted to male or female bodily fluids or ejaculated or secretions or sperms or eggs or blood or semen or mucus or mucosa or body cells; and in another embodiment the release and electrical response with an electrode 106 or electrode 106-like device that can strengthen the female orgasmic tissues/nerves/muscle 65 to improve the female orgasmic or pleasure response; and in another embodiment the release and electrical response with an electrode 106 or electrode 106-like device that can stop the male ejaculatory response and tissues/nerves/muscle 65 to improve ejaculation to allow the male to have intercourse without ejaculation to facilitate contraception; and in another embodiment the release and electrical response with an electrode 106 or electrode 106-like device that can improve the responses and tissues/nerves/muscle 65 responsible for erections and that can include but is not restricted to increase blood flow 104 into the corpora/corpus cavernosum and reduce outflow from the corpora cavernosa and the corpora sinusoids and the arteries and nerves controlling erection to facilitate the erectile response; and in another response a thermal response either hot or cold can be used for the functions above; and in another embodiment an electromagnetic 102 pulse or energy 43 that can include but is not restricted to energy 43 and power, force, impetus, control or momentum and which that can include but is not restricted to include electromagnetic/electrical/magnetic or thermal or hydraulic/kinetic/vibrational/mechanical or chemical energy 43 or radioactive and can be induced by to include but not restricted to macro, micro or nano 63 particle devices or any combination of these and can release or message, signal, trigger or facilitate one of the responses cited by this patent application and as discussed herein this patent application and can utilize the patent applications cited by this patent application and as discussed herein this patent application. In one embodiment before, during or after ejaculation a UV 43 pulse can be released in the female reproductive system to include but not restricted to the vagina 3 or at the cervix 10 or the uterus 75 or fallopian tubes or near or adjacent to the ovaries and an energy 43 or medication can be released to include but not restricted to for exemplary purposes a UV 43 pulse can include but is not restricted to kill or destroy pathogens and infectious organisms or sperm or eggs/ova to prevent infection or impregnation/reproduction or a living being. In another embodiment of this invention the energy 43 or medication can be released to include but not restricted to for exemplary purposes a UV 43 releasing device can include but is not restricted to kill or destroy pathogens and infectious organisms or sperm or eggs/ova to prevent infection or impregnation/reproduction or a living being. The release or facilitation can include but is not restricted to be controlled by a sensor 39 or by a living being, or a computer 18 or a computer-assisted device or any combination of these.

In another embodiment an energy 43 or power or force that can include but is not restricted to energy 43 and power, force, impetus, control or momentum and which that can include but is not restricted to include electromagnetic/electrical/magnetic or thermal or hydraulic/kinetic/vibrational/mechanical or chemical energy 43 or radioactive and can be induced by to include but not restricted to macro, micro or nano 63 particle devices or any combination that can include but is not restricted to turn-on or turn-off/control, facilitate, message, signal, cause to function or trigger at least one of a device that can include but is not restricted to a device that is away from or on or inside or any combination of these related to a living being and said device can be released to trigger or facilitate one of the functions or responses or devices listed herein and within the patents and patent applications as cited by this patent application and as discussed herein this patent application and can utilize the patents and patent applications as cited by this patent application and as discussed herein this patent application. In another embodiment of this invention an energy 43 or medication can be released or triggered through at least one a devices to include but not restricted to a sensor 39 on a penile band or condom that detects the release of sperm that triggers a vaginal 3 or female reproductive tract UV 43 releasing device that can include but is not restricted to kill or destroy pathogens and infectious organisms or sperm or eggs/ova to prevent infection or impregnation/reproduction or a living being. The release that can include but is not restricted to be controlled by a sensor 39 or by a living being, a computer 18 or a computer-assisted device. In another embodiment, in a living being with erectile dysfunction a sensor 39 device can be implanted that can include but is not restricted to assess blood flow 104 or turgidity or tumescence of the corpora/corpus cavernosa/cavernosum of the male and the equivalent structure of the clitoral and female reproductive and pleasure tissue region and tumescent tissue and a second device can be used to stimulate the tissue/nerve/muscle 65 (voluntary and involuntary/smooth and striated) to increase blood flow 104 through energy 43 or medication release or a combination to include but not restricted to releasing Nitric Oxide (NO), stimulating Nitric Oxide NO receptors, relaxing smooth muscle 65 and tumescent tissue sinusoids, increasing blood flow 104, releasing and converting nitroglycerine and amyl nitrites which that can include but is not restricted to be topically or transcutaneously or orally administered and excited, reduced to or catalyzed into Nitric Oxide or to stimulate Nitric Oxide Nerve innervation or medications or arterial increase in flow to the general or specific target tissue 129, or venous decrease and exit of blood out of the tumescent tissue or the varicosities of the tumescent tissue mechanism and the energy 43 or medication activation mechanism can include bit is not restricted to energy 43 and power, force, impetus, control or momentum and which that can include but is not restricted to include electromagnetic/electrical/magnetic or thermal or hydraulic/kinetic/vibrational/mechanical or chemical energy 43 or radioactive and can be induced by to include but not restricted to macro, micro or nano 63 particle devices or any combination of these and can release or message, signal, trigger or facilitate one of the responses listed herein and within this patent application and within the patents and patent applications as cited by this patent application and as discussed herein this patent application and can utilize the patents and patent applications as cited by this patent and as discussed herein this patent. The release or facilitation can include but is not restricted to be controlled by a sensor 39 or by a living being, or a computer 18 or a computer-assisted device or any combination of these.

In another embodiment a female contraceptive device can include one or more than one of an energy 43 device that can include but is not restricted to being implanted in the female reproductive system to include but not restricted to the vagina 3 or at the cervix 10 or the uterus 75 or fallopian tubes or near or adjacent to the ovaries or the fallopian and uterine junction and an energy 43 or medication releasing device/mechanism that can include but is not restricted to the energy 43 or medication releasing/activation mechanism can include bit is not restricted to energy 43 and power, force, impetus, control or momentum and which that can include but is not restricted to include electromagnetic/electrical/magnetic or thermal or hydraulic/kinetic/vibrational/mechanical or chemical energy 43 or radioactive and can be induced by to include but not restricted to macro, micro or nano 63 particle devices or any combination of these and can release or message, signal, trigger or facilitate one of the responses listed herein and within this document and related pated applications cited herein. In one embodiment of a female contraceptive device a sensor 39 that detects hormones or peptides to include but not restricted to Luteinizing Hormone (LH), Follicle Stimulating Hormone (FSH), Oxytocin, Gonadotropin Hormones, Steroidal Hormones, Prolactin, Inhibin, Estrogen and Progesterone, Ovary Specific Hormones and Antigens, Antibodies and Immune compounds that can include but is not restricted to Atrial natriuretic peptide (ANP), ovary steroidogenic hormone and a tyrosine kinase receptor and/or can detect the ovum and when identified can be release a medication or an energy 43 source that can kill or destroy the egg/ovum or sperm. The release or facilitation can include but is not restricted to be controlled by a sensor 39 or by a living being, or a computer 18 or a computer-assisted device or any combination of these.

In one embodiment the shape changes 85 and configurations 85 can include but are not restricted to Mechanical/Hydraulic/Kinetic shape changes 86, and shape changes from interaction of substances 87 or shape changes form interaction with energy 88 or any combination of these.

Medications for killing ova or sperm and include standard medications currently known Nonoxynol-9 Octoxynol-9, lactic acid, Ella, RU-486, Progesterone blockers, and metals including silver and copper.

General Concepts

Elements and Elements of design or structures of devices and methods described herein when appropriate can be applied interchangeably to the Urine Sample for Diagnostic Urine Analysis and Culture using Sterile/Clean Urinary Collection Device (UCD 6) as well as a Menstrual 46 Collection device 9 (MCD) and a Fecal/Stool 51 Collection device 9 (FCD), Breast 57 Collection and Stimulation 71 Device (BCSD) and a Menstrual 46 flow Prevention Device (MFPD), Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and a some elements related to Contraception Device and when applicable can be applied to both the male and female versions of the devices One or more combinations of these described methods or devices can be used together or alone.

The UCD 6, MCD, MFPD, FCD, FAD, MAD and contraceptive devices can include but are not restricted to be used for short or acute use or intermediate or prolonged or chronic use which can include but is not restricted to temporal considerations that are based on standard temporal units or biologic considerations.

In one embodiment the shape changes 85 and configurations 85 can include but are not restricted to Mechanical/Hydraulic/Kinetic shape changes 86, and shape changes from interaction of substances 87 or shape changes form interaction with energy 88 or any combination of these.

The devices and methods described for the UCD 6 can be used for the UCD 6, MCD, MFPD, FCD, FAD, MAD, FCD and contraceptive device to include wherein the devices separate the urine from the vaginal 3 and anal 4 regions and their contaminants wherein the vagina 3 region can have contaminated that can include but are not restricted to contaminants to bacteria, yeast, menstrual 46 blood. In both the UCD 6, MCD, MFPD, FCD, FAD, MAD, FCD and contraceptive device the goal is to prevent mixing of the contaminants arising from the urethra 2 and or from the vagina 3 and uterus 75 and anus 4. In one embodiment wherein for the menstrual 46 collection device 9 (MCD) the goal is the egress and flow of menstrual 46 blood away from the living body and away from the urethra 2 and vulva 11 mucosa such that the menstrual 46 blood does not contaminate or intermix with to include but not restricted the urethra, anus 4, vulva 11 and mucosa of vulva 11 region and said contaminants to move away from the living body such that contaminants do not collect in, on or around the urethral 2 or vagina 3 or vulva 11, an anal 4 regions and that contaminants do not remain stationary and contaminants and secreted or excreted materials do not cause to include but not restricted to accumulate, in a manner that induces, infection, contamination, putrification, or toxicity to urethra, vulva 11, vagina, skin 8 or internal organs to include but not restricted to the bladder 76 and kidneys and fallopian tubes and uterus 75 and abdomen as well as the remainder of the living body.

These devices and the devices and methods can include but are not restricted to the UCD 6, Menstrual 46 Collection, Stool 51 or fecal collection devices 6 and methods and their components and methods that can include but is not restricted to tubing, pumps, containers and other components of these said devices and methods.

The reference to MCD, UCD 6 or Fecal Collector and its components can include either or both devices and methods as needed or indicated.

The devices and methods herein and one or more combinations of these described methods or devices can be used in a gravity environment or can be used in an increased or reduced or normal or partial gravity environment or in an increased or reduced or normal or partial pressure environment or in an increased or reduced or normal or partial force environment that can include but is not restricted to being the result of being within, in, under, above or on the water, within, in, under, above or on the land, within, in, under, above or on the sky or within, in, under, above or on the earth or within, on, under, above or in outer space or another planet or a non-earth environment.

For the devices and methods there can be one of more of these devices and of each of the components or regions for these devices or components that can be used in these various methods and devices.

Gel in this application can be used to include but not restricted to a gel, a gel-like material, and a gel-slurry and for this application can be used to include but not restricted to additional materials to include but not restricted to a soft silicon material, a soft skin 8-like synthetic material such as Cyberskin 8 (mixture of PVC and Silicon), soft rubbers, soft plastics, or latex or a material that can include but are not restricted to having properties between a solid and a liquid or sharing properties of both or either of a solid and or a liquid.

A 3-D scanner/printer 59 of any variety that creates physical objects can be used to create the devices described herein to include but not restricted to the Urine Sample for Diagnostic Urine Analysis and Culture using Sterile/Clean Urinary Collection Device (UCD 6) as well as a Menstrual 46 Collection device 9 (MCD) and a Fecal/Stool 51 Collection device 9 (FCD), Breast 57 Collection and Stimulation 71 Device 6 (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices and any of their component using the techniques discussed above and other know and to be developed techniques present in the art of 3-D scanning/printing.

The use of the terms medications and antibiotics and antifungals and antivirals can include but are not restricted to also include other agents that are used for killing infectious organisms or any organism that can include but is not restricted to being considered pathogenic organisms or can include but are restricted to normally non-pathogenic organisms that can become pathogenic under the correct circumstances to include but not restricted to opportunistic infections, immunosuppressed individuals being exposed, excessive exposure or overwhelming quantities of organisms or environmental conditions that can lead to infection and said infection can damage any portion of a living being or contaminate devices or implements or instruments or the food or the environment of any portion of a living being.

In one embodiment the flow of materials in a bidirectional manner that can include but is not restricted to having flow in more than one direction and can include but is not restricted to the MCD, the UCD 6 and the fecal collecting device and the application for this more than one direction or bidirectional flow can include but are not restricted to materials or medications or cleansing materials. In one embodiment materials can include solids and liquids and gases and gels and slurries that can include but is not restricted to the medications and materials for cleansing, and hydrogen peroxide, ozone, contraceptives, anti-infectious agents, laxatives, and other medications and cleansing agents and hydrating or skin 8 or mucosal or organ protective or killing agents or declogging agents.

In another embodiment the UCD 6, MCD, MFPD, FCD, FAD, MAD and contraceptive devices can include but are not restricted to use an energy 43 cited or discussed herein to sterilize or retard or clean or destroy or be a contraceptive or be a drying or desiccating agent. In another embodiment the UCD 6, MCD, MFPD, FCD, FAD, MAD and contraceptive devices can include but are not restricted to use a substance 44/chemical/treatment agent that is not an energy 43 to include but not restricted to a solid or gas or gel or liquid cited or discussed herein to sterilize or retard or clean or destroy or be a contraceptive or be a drying or desiccating agent and the energy 43 and substance 44 can be used alone or in combination In another embodiment the UCD 6, MCD, MFPD, FCD, FAD, MAD and contraceptive devices can include but are not restricted to use an energy 43 or substance 44 or a combination of these cited or discussed herein to seal 7 a breach, hole, crack, tear, opening or violation of the integrity of one of these devices and the energy 43 and substance 44 can be used alone or in combination. Embodiments of the UCD 6, MCD, MFPD, FCD, FAD, MAD and contraceptive devices can include sensor 39 that can include but is not restricted to detecting a breach to include but not restricted to a hole, crack, tear, opening or violation of the integrity of one of these devices and the detector/detection can be located on the inside or within or on the outside of the material composing the device and that can include but is not restricted to sense the breach in manners to include but not restricted to an opening in the material, a change in the environment to include but not restricted to a change in to include but not restricted to the percent or content or presence or absence or different kinds, or different than expected or standard materials/substances 44 of to include but not restricted to pH, fluids/liquid, gases, gels, solids and solid-like materials, of a biological structure to include but not restricted to biological and biochemical substances 44 such as but not restricted to carbohydrates, proteins, fats, nucleotides, urine, sperm, semen, vaginal 3 fluids, breast 57 milk, lactose/glucose/sucrose/fructose, feces 51, bacteria and other infections organisms, toxins and to include but not restricted to other materials cited or herein this patent application and to include but not restricted to energies cited or herein this patent application to include but not restricted to hydraulic, vibratory, ultrasonic, Brownian motion, motion, vacuum, suction, or electromagnetic 102 to include but not restricted to electrical, magnetic, visible 20, 43 light, non-visible 43 light, UV 43 and Infrared energy 43, radioactive; gravity or thermal and piezoelectric and nano 63, micro or macro particle energies and energy 43 sources. The detection/detector can include but not restricted to be a separate unit from the device or material or it can be an innate property of the material to detect and or transform itself in the presence of a change in environment.

In one embodiment the material and sensor 39 and seal 7 can include a condom that can include but is not restricted to detect changes in electrical potentials or signals 14, carbohydrates, proteins, fats, nucleotides, urine, sperm, semen, vaginal 3 fluids, breast 57 milk, lactose/glucose/sucrose/fructose, feces 51, bacteria and other infections organisms, toxins and in one embodiment the condom contains a gel that when in contact with vaginal 3 or semen or sperm materials swells up to seal 7 the breach.

In another embodiment to include but not restricted to a urine collection device 9 the material forming a component of the device can be self-seal 7 using one of the methods of sealing to include but not restricted to modifying a poly (ether ester) membrane with an amphiphilic polymer co-network in which the latter swells in water and the gel closes punctures, microencapsulated self-healing polymers, thermosetting polymers, fiber rein-forced composites, elastomers to include but not restricted to coatings, and self-healing adhesives to include but not restricted to submicron crack separation, dicyclopentadiene (DCPD) filled microcapsules, Grubbs' catalyst in graphite epoxy, encapsulated epoxy resin and a latent imidazole curing agent in the matrix material of a woven glass/epoxy. In an alternative approach, Pang and Bond [15, 16], Williams et al. [24], and Trask et al. [25]embed hollow glass fiber reinforcement into glass and carbon fiber-reinforced composites. These hollow glass fibers are used to deliver either pre-mixed two part epoxy healing agent, or uncured epoxy resin and curing agent in separate fibers to the fractured section of the sample. When the composite is damaged the hollow fibers rupture causing the healing agent to flow into the damage and, after the application of heat, heal the crack, polymeric membranes. Poly(dimethyl siloxane) (PDMS) to include but not restricted to PDMS layer 98 of a polyurethane/nylon/PDMS laminate using encapsulated PDMS resin and catalyst such that when the embedded resin and catalyst capsules ruptured, the two components come into contact and heal the puncture damage, preventing gas or fluids from leaking through the laminate, self-healing poly(ethylene-co-methacrylic acid) copolymer capable of thermally triggered molecular rearrangement, the self-healing functionality inherent isomers/ionomers/cross-linked ionic bonds, materials with two-step healing mechanism involving elastic recovery followed by inter-chain diffusion self-healing, woven glass fiber reinforced composite to include but not restricted to augmentation with an encapsulated healing agent, DCPD, and Grubbs' catalyst embedded in a polymer matrix composite to include but not restricted to varying concentrations and sizes of microcapsules, glass wax, paraffin and gum latex.

In another embodiment to include but not restricted to a self-sealing device or material, the material for the device to be constricted to can include but is not restricted to one or more layers 98. In one embodiment a layer 98 to include but not restricted to include an amphiphilic, an alliophillic, a xenophillic layer, a hydrophobic layer, a hydrophilic layer, a gel layer 98 or a layer 98 to include but not restricted to being able to undergo a phase change 94 94 from a solid to a gel or to being a gel that can become an expansile or tumescent gel or to become a more viscous material or develop from a liquid or the more liquid state of a gel to the more solid state or to a solid state; a layer 98 composed of encapsulated substances 44 where the capsule can be a gel, amphiphilic, a hydrophobic, a hydrophilic and also the encapsulated substance 44 can include but not restricted to an amphiphilic, an alliophillic, a xenophillic, a hydrophobic, a hydrophilic materials and composing or in conjunction, related, composed, adjacent, in or around these layers 98 or substances 44 or capsules can be a matrix that can be a gel, amphiphilic, an alliophillic, a xenophillic, a hydrophobic, a hydrophilic and other structures, to include but not restricted to layers 98, capsules substances 44 and matrices can be used alone or in combination and in one embodiment when combined in these two layers 98, capsules substances 44 and matrices.

In another embodiment the layers 98 or substances 44 or capsules or matrices can include but are not restricted to contain magnetic substances 44 that can include but is not restricted to ferrous and ferromagnetic and substances 44 attracted to magnetic fields 103 and substances 44 that contain, produce or have a magnet field 103 or quality.

In another embodiment one or more of the layers 98, capsules substances 44 and matrices can contain a substance 44 that can include but is not restricted to the property to tumesce, swell up, bloat up, tumefy and this property can cause the breach to be sealed.

In another embodiment self-sealing contraceptives can include but are not restricted to female diaphragms or condoms or condom-like devices, male condoms or condom like devices. Self-sealing materials can be used in the embodiments cited and within this patent application. One embodiment can include but not restricted to male and female to include but not restricted to contraceptive and urinary collection devices 6. One embodiment can include a female diaphragm the condom can be lined with a material to include but not restricted to a solid material that becomes a gel, a liquid that becomes a gel or a gel that becomes more turgid or tumescent and that swells up or tumesces or expands upon contact with materials to include but not restricted to biologic materials to include semen, sperm, and semen and sperm components; vaginal 3 fluid and vaginal 3 fluid, vaginal 3 mucosa, and vaginal 3 fluid and mucosal components, urine to include but not restricted to proteins, carbohydrates, fats and nucleotides and salts or minerals composing or found in these biologic tissues, fluids and materials or excreted or secreted by the biologic organism to include urea, uric acid, alkaline pH, neutral pH, or acid pH materials or fluids; or inorganic or organic materials to include but not restricted to vitamins, fructose, water or saline or gases or salts or minerals to include but not restricted to Sodium, Potassium, Chloride, Calcium or alkaline or acid materials.

In one embodiment the self-sealing device or material can be composed of one or more than one layer 98 that can include but is not restricted to being incorporated or integrated or have a layer 98 intercalated or inserted or placed within or on or onto or in or between the material or its layers 98 or similar or different layers 98 of material or the device such that the self-sealing layer 98 can include but is not restricted to tumesces or swell and in one embodiment the self-sealing layer 98 can contain or close or heal the breach in the material.

In another embodiment the activation of the self-sealing material can utilize energy 43 to activate an activated or a partially activated or a not-yet-activated sealing material in a manner that to include but not restricted to seal 7 or to more effectively seal 7 a breach in the material.

In one embodiment the self-sealing material can be activated in the presence of a full or partial breach or tear or in the absence of a breach or tear. When the self-sealing material is activated without a full or partial breach or tear or without a breach or tear this can be done to include but not restricted to reinforce region a region of the device or to respond to a change in the environment in which the self-sealing material resides or there can be a mechanical force to include but not restricted to a stretch or pressure upon the material and this can be done to include but not restricted to being a preventative measure to prevent a breach or tear or to trap a material outside of or inside of the devices environment or to prevent a material from entering or exiting from the environment of the device.

In one embodiment the device can include but not restricted to be a condom and the inner lining of the condom or a condom like device or a condom catheter or Female Urine and menstrual 46 collection device 9 can contain a material that expands and can be used to include but not restricted to seal 7 a breach and can include but not restricted to bodily fluids, excretion, secretions and evacuations and ejaculates to include but not restricted to sperm or semen or vaginal 3 fluid, urine or can be used with feces 51 and fecal collection devices.

Adsorbent and absorbent and hydroscopic and hydrophilic materials that can be used throughout this patent application can include but is not restricted to include but not restricted to hydrogels, water gel crystals, water gel polymers or hydrogel crystals or dehydrated gels, silica, colloids, cotton, paper, cellulose, salts to include but not restricted to sodium chloride, calcium chloride, potassium hydroxide, sodium hydroxide, deliquescent salts that can include but are not restricted calcium chloride, potassium hydroxide, sodium hydroxide, potassium carbonate, ferric ammonium citrate, ferric chloride; polymers to include but not restricted to Type-6 Nylon, nylon, polycarbonate, cellulose, ABS, polymethylmethacrylate, crystal water gel polymers, super hydrophilicity substances 44 to include but not restricted to titanium dioxide; hydrophilic materials to include but not restricted to alcohols and cyclodextrin.

In one embodiment the absorbent or adsorbent materials can be used to include but not restricted to one or more than one of the layers 98 of the self-sealing material within the device which can include but is not restricted to UCD 6, MCD, MFPD, FCD, FAD, MAD and contraceptive devices.

In one embodiment a change in the external or internal or both environments can trigger a response or the release or activation of a substance 44 to include but not restricted to convert an inactive to an active or activated substance 44 or sealing or sterilizing or cleaning or disinfecting or stiffening or expanding or lubricating or tumescing or hormone or contraceptive substance 44.

In one embodiment a condom can be the device and it can be composed of to include but not restricted to multiple layers 98 or an integrated layer 98 or matrix that can include but is not restricted to is composed of a hydrogel on or onto or in the male side or inside or in the substance 44 of the condom that when or if exposed to semen, or seminal fluid or their components or to vaginal 3 fluid or vaginal 3 mucosa or their components can activate the hydrogel and cause it to expand and can include but is not restricted to trap the semen or reinforce the strength of the condom or close a tear or breach in a condom.

In another embodiment a contraceptive diaphragm can contain a hygroscopic material that can include but is not restricted to trap semen or to reinforce the diaphragm or close a breach or tear in the diaphragm.

In another embodiment a condom catheter can be composed of a layer 98 that lies on the surface away from the male penis 35 or outer surface or integrated material in the design or construction that when exposed to urine can include but is not restricted to trap the urine or to reinforce the condom catheter or close a breach or tear in the condom catheter.

In another embodiment the layers 98 or matrix or sheets can be inseparable and can represent strata/stratum or regions of composition that partially or fully meld into one another and can be more of the predominating component of a given cross section of the material and in some embodiments layers 98 can be separated whereas in other embodiments the layers 98 are not separable but the layers 98 can include but is not restricted to predominated by one substance 44 or component within the material that forms the device.

In another embodiment the layer 98 can be a coating that can include but is not restricted to being bonded to the condom material.

In another embodiment a condom can be composed of an outer layer 98 that is the layer 98 on the female side of the condom/the side away from the penis 35 skin 8 that can contain but is not restricted to contain a lubricant that can include silicon or nano 63 particles with lubricants and oil-based lubricants that can include but is not restricted to be combined with nano 63 compounds based on tungsten and sulfur or selenium, dichalcogenides ($WS_2$ and $WSe_2$) and synthetic hydrocarbons and copper nano 63 particles and silica nano 63 particles. Surface modification of a layer 98 or membrane can include, but is not restricted to, nano 63 cellulose displays a high concentration of hydroxyl groups at the surface which can be reactive in part because of the hydrogen bonding, which strongly affects the reactivity of the surface hydroxyl groups. Impurities at the surface of nano 63 cellulose to include but not restricted to glycosidic and lignin fragments may alter the reproducibility and hydrogen bond effects. Cellulose nano 63 fibers can include changes in ionic behavior and can include, but is not restricted to, cationic cellulose increase the affinity for anions and anions affinity for cations. In one embodiment the ionic charge can but is not restricted to be utilized to alter the shape of the membrane or layer 98 or alter the shear and the viscosity of the fluid or gel, gas or solid exposed to the membrane and its charge, woven and non-woven polymer fibers that can include, but are not restricted, to para-aramid synthetic fibers, such as, but not restricted to, Kevlar and Kevlar-like or Twaron or Twaron-like materials and to include but not restricted to woven and non-woven polymer fibers that can include, but are not restricted to, para-aramid synthetic fibers, such as, but not restricted to, Kevlar and Kevlar-like or Twaron or Twaron-like materials. These polymer fibers traditionally are layered in sheets.

In one embodiment the lubricant can be liberated or released with to include but not restricted to progressive mechanical force to include but not restricted to friction, thermal energy 43 to include but not restricted to heat, or a chemical reaction to include but not restricted to reaction with the vaginal 3 fluid, a reaction to the pH of the vaginal 3 fluid, or the material can be time released to include but not restricted to the acidic environment of the vagina.

In another embodiment the outer layer 98 or portion of the condom can have an acidic or an alkaline layer 98 or coating to maintain an optimal vaginal 3 pH which can maintain vaginal 3 health and also act as a contraceptive and reduce stress on the vagina 3 and allow prolonged sexual intercourse.

In one embodiment a change in the external or internal or both environments can trigger a response or the release of energy 43 to include but not restricted to through a photochemical, photoelectric reaction or can activate a sensor 39 and an energy 43 producing device in a manner that is known or is cited or described herein this patent application.

In one embodiment the material integrated into the material of the device can cause the condom to become turgid and rigid which can assist with erectile function.

Embodiments of sealing materials can include but are not restricted to being within a part of the material or device and can include but is not restricted layers 98, integrated component, encapsulated substances 44 and matrices to include a solids or liquids or gases or gels.

In one embodiment the one of more layers 98 can be part of a device or layer 98 of a material or a wearable 50 and when that layer 98 is pierced or breached the layer 98 can be sealed.

In one embodiment to include but not restricted to include one possible design the self-sealing device can have multiple different layers 98 that when pierced that can include but is not restricted to swell to close the breach, can be attracted such as to include but not restricted to having magnetic particles come together through magnetic field 103 attraction, can close a weave that can include but not restricted to closing a molecular or a macro/micro/nano 63 level weave, and which can include closure of molecular bonds to include but not restricted to covalent bonds, and can include the attraction of positive and negative ions, and which can include covalent and hydrogen bonding, and which can include the movement of substances 44 to fill in the breach to include but not restricted to the shifting of hydrophilic and hydrophobic and mixed hydrophilic and hydrophobic compounds into the region of the breach to reseal 7 the breach and these can include but are not restricted to being encapsulated or non-encapsulated and in one embodiment there can be multiple moving layers 98, capsules substances 44 and matrices that can slide to fill in the breach and these layers 98, capsules substances 44 and matrices can be fully or partially bond to each other in any combination discussed above In these embodiments the layers 98, capsules substances 44 and matrices can be macro, micro or nano 63 or atomic or solid state size and can apply the concepts of the physics of these sized particles to include but not restricted to nano 63 technology and solid state technology or quantum mechanics or standard Newtonian physics and forces.

In another embodiment the trigger for the repair of the breach can include but is not restricted to the breach in manners to include but not restricted to an opening in the material, a change in the environment to include but not restricted to a change in to include but not restricted to the percent or content or presence or absence or different kinds, or different than expected or standard materials/substances 44 that usually reside in the environment/change in the environment temporally to include but not restricted to macro or micro or nano 63 environment to include but not restricted to pH, fluids/liquid, gases, gels, solids and solid-like materials, of a biological structure to include but not restricted to biological and biochemical substances 44 such as but not restricted to carbohydrates, proteins, fats, nucleotides, urine, sperm, semen, vaginal 3 fluids, breast 57 milk, lactose/glucose/sucrose/fructose, feces 51, bacteria and other infections organisms, toxins and to include but not restricted to other materials cited or herein this patent application and to include but not restricted to energies cited or herein this patent application to include but not restricted to hydraulic, vibratory, ultrasonic, Brownian motion, motion, vacuum, suction, or electromagnetic 102 to include but not restricted to electrical, magnetic, visible 20, 43 light, non-visible 43 light, UV 43 and Infrared energy 43, radioactive; gravity or thermal and piezoelectric and nano 63, micro or macro particle energies and energy 43 sources. The detection/detector can include but not restricted to be a separate unit from the device or material or it can be an innate property of the material to detect and or transform itself in the presence of a change in environment.

In another embodiment the particles of the material can be composed of repellent molecules such that when a breach occurs that said breach is filled in by the repellant nature that can reside in amphiphilic, an alliophillic, or a xenophillic compound.

Any combination of these methods, designs and material stated or cited herein can be used together.

One embodiment can include a condom that can include but is not restricted to be composed of layers 98, capsules substances 44 and matrices can be macro, micro or nano 63 or atomic or solid state size that when breached can be resealed have the amphiphilic, or alliophillic, material swell up or insinuate itself into the breach and seal 7 the condom. In one embodiment the trigger to seal 7 the breach can be a semen or seminal fluid or vaginal 3 fluids and in another embodiment a similar mechanism can be triggered by urine in a condom catheter.

In another embodiment the same techniques for cleansing and sterilization and disinfecting and sealing can be used to include but not restricted to the natural openings or junctions of transition points of the devices.

Sensor 39 and Input and Output Devices

In another embodiment the UCD 6, MCD, MFPD, FCD, FAD, MAD and contraceptive devices can include but are not restricted to contain but not restricted to sensor 39 and send and receive and recording devices that can access usage and function of the device to include but not restricted to movement, position, dynamics, and physical characteristics of the device and said function can be analyzed and monitored to provide feedback 70 and optimal utilization and functionality and wear-and-tear and time-to-replace and pleasure and pain and comfort and this information can be used to improve or optimize the function and minimize the dysfunction of the device in use, or optimize the users use of the device or give feedback 70 to include but not restricted to the manufacturer to include but not restricted to how to better manufacture or design or create the device; or the to the user to include but not restricted to better utilize the device or when to replace the device before it wears out or becomes dysfunctional or to insure that it remains in a range of optimal usage; or to have the device auto correct itself to provide optimal usage or normal range usage.

In one embodiment a junction of the device may be failing and the sensor 39 can inform the user that the junction is in an early stage of disrepair that can include but is not restricted to leaking or cracked or the pump is failing or the electrical system is failing. In another embodiment the sensor 39 information can be used for breast 57 pumping and can optimize the breast 57 experience and pump and position to include but not restricted to altimeters, levels, accelerometers, barometric pressure, temperature, hygrometers/wetness, pressure gauges in order to improve breast 57 milk flow, infant intake and sucking, mother letdown and breast 57 flow and nutrition.

In another embodiment a breast 57 device can be used for sensing pain and pleasure for personal or one or more than one physical pleasure or pain. In another embodiment a condom or a vaginal 3 covering 36 or condom or positioned sensor 39 can assess to include but are not restricted to assess, or monitor or ascertain to include but not restricted to partner pain and pleasure and satisfaction, and physiologic responses and reproducibility of a function that can be associated with acts that bring pain or pleasure to include but not restricted to intercourse, masturbation and self-pleasuring and defecating and urinating and breast 57 sucking and anal 4 sex and these functions can be assess these functions for present and past and future to include but not restricted to optimal and non-optimal, desired and undesired or und pleasure or pain responses so that these events can be reproduced or avoided as desired by the users.

In another embodiment the device can give feedback 70 to improve function to include but not restricted to erectile function, orgasms, sexual function, urinary function, decrease incontinence 83 and prolapse 79, improve and increase or initiate a urinary stream/micturition, improve bowel movements, defecation and fecal incontinence 83 and prolapse 79, improve breast 57 feeding/nursing and improve sexual performance and pleasure.

Sensor 39 Feedback 70 and Stimulation 71

In another embodiment, there can be sensor 39 and electrodes 106 can be placed to include but not restricted to into, on, within, adjacent, around or near the male and female sexual organs to include but not restricted to the vagina, clitoris 1, labia, uterus 75, cervix 10 and vulva 11, penis 35, scrotum, corpora cavernosa, corpus spongiosum, penile head and glans and breast 57, mouth 55, nose, eyes 23, nipple 58 and nipple 58-region, skin 8 and mucosa, erogenous zones and anus 4 and rectum 4 and bowel and bladder 76 and urethra 2 and their related structures to include but not restricted to skin 8 and mucosa, muscle 65, nerves, vessels to include arteries, veins and capillary networks and sinusoidal systems and sensor 39 can include but are not restricted to sensing physiologic function to include but not restricted to these organs and are capable of providing feedback 70 of the functioning of these organs to include but not restricted to their function to include but not restricted to wetness, chemical signals 14, pH, glucose, fructose, erectile function, orgasms, sexual function, urinary function, decrease incontinence 83 and prolapse 79, improve and increase or initiate a urinary stream/micturition, improve bowel movements/defecation, improve breast 57 feeding/nursing and improve sexual performance, sweat and wetness and dryness and pleasure and pain and pH, fluids/liquid, gases, gels, solids and solid-like materials, of a biological structure to include but not restricted to biological and biochemical substances 44 such as but not restricted to carbohydrates, proteins, fats, nucleotides, urine, sperm, semen, vaginal 3 fluids, sweat, wetness, breast 57 milk, lactose/glucose/sucrose/fructose, feces 51, bacteria and other infections organisms, toxins, muscle 65 contractions and tone and movement and electrical signal 14 or electrical potential, neural signals 14 and conduction velocities and electrical intensity, and to include but not restricted to other applications and materials cited within or herein this patent application.

In one embodiment the electrical and muscle 65 signal 14 can be measure by device that are similar to or can perform the functions of or similar to an electrode 106 used for to include but not restricted to these signals 14 can be assessed with methods and devices or devices similar to an electrode 106 capturing the electrical signal, In one embodiment, electrodes 106 can be placed near vital sensing and stimulatory sites of the living body to include but not restricted to the vagina, clitoris 1, labia, uterus 75, cervix 10 and vulva 11, penis 35, scrotum, corpora cavernosa, corpus spongiosum, penile head and glans and breast 57, mouth 55, nose, eyes 23, nipple 58 and nipple 58-region, skin 8, and mucosa, erogenous zones and anus 4 and rectum and bowel and bladder 76 and urethra 2 and their related structures to include but not restricted to skin 8 and mucosa, muscle 65, nerves, vessels to include arteries, veins and capillary networks and sinusoidal systems and these electrodes 106 can sense to include but not restricted to muscle 65 signals 14, contractions, electrical signals 14, galvanic signals 14, chemicals and chemical signals 14, blood flow 104, sweat and wetness and dryness and muscle 65 contractions and electrical signal, nerve innervation and electrical signals 14, and other bodily functions described and cited and discussed herein this patent application. These electrodes 106 can be used to include but not restricted to receive and sense signals 14 to include but not restricted to electrical, magnetic, photo or light, chemical, electromagnetic, kinetic, or mechanical, hydraulic, chemical, vibratory or Brownian or thermal and to include but not restricted to generate output or signals 14 to include electrical, magnetic, photo or light, chemical, electromagnetic, kinetic, or mechanical, hydraulic, vibratory or Brownian or thermal outputs. These outputs can be used to include but are not restricted to transmit a signal 14 to include but not restricted to stimulate or repress or activate or deactivate biological functions to include but not restricted to tissues to include but not restricted to skin 8, muscle 65, nerves, blood flow 104, endocrine or exocrine or chemical function or sinusoidal or ductal or urinary or bowel functions or any combination of these.

In one embodiment the electrodes 106 can be placed directly on the tissue to receive or to transmit a signal 14 or energy 43 to include but not restricted to detecting innervation or creating innervation or initiation to include but not restricted to a muscle 65 or nerve.

Electrodes 106 can be defined to include but not restricted to being receivers 40 or transmitters 40 of energy 43 to include but not restricted to include electrical, magnetic, photo or light, chemical, electromagnetic, kinetic, or mechanical, hydraulic, vibratory or Brownian or thermal or chemical substances 44 or energies or any combination of these. In another embodiment electrode 106 can be incorporated or place onto, in or any combination of these.

FIGS. 14A-F are sagittal renderings of the female pelvic floor 74 anatomy and devices to facilitate competence, treatment and training 80, 81 of the female pelvic floor 74 in response to urinary and vaginal 3 incontinence 83 and prolapse 79 and to prolapse 79, to improve bodily functions. In one embodiment the device can be used to treat, improve, facilitate urinary function to include but not restricted to treat incontinence 83 and prolapse 79 of urine. In one embodiment in the female an insert can be positioned in the vagina 3 or vaginal 3 region or anus 4 or anal 4 region and can include but not restricted to contain or have or incorporate a send and/or receive; or input and/or output units to include but not restricted to sensor 39, stimulators, electrodes 106, transmitters 40, or facilitators. In one embodiment the vaginal 3 insert can be positioned to include but not restricted to having the electrodes 106 positioned to innervate the urinary muscle 65 to include but not restricted to detrusor muscle 65, or to include but not restricted to a sphincter to include but not restricted to the external or internal urethral 2 sphincter, and pelvic floor 74 muscle 65 and nerves. These electrodes 106 can be used in conjunction with Kegel or pelvic floor 74 or sphincter exercises and the sensor 39 and transmitter electrodes 106 can be used to include but not restricted to monitor the effectiveness of the exercises and can be used to facilitate the exercises by discharging or receiving 16 to include but not restricted to and energy 43 or substance 44 that can include but is not restricted to an electric current 100 or thermal or electromagnetic 102 or photoelectric or visible 20, 43 light or UV 43 or Infrared or photoplethysmography or a chemical signal 14 or hormonal signal. In another embodiment, associated with the electrode 106 to include but not restricted to the sensor 39 or detector or transmitter or innervater, or monitor can be used to assess and improve to include but not restricted to the function or the control of micturition/urination and urinary incontinence 83 and prolapse 79, orgasms/sexual function, male and female erectile function/penile and clitoral and vaginal 3, defecation, suckling and rooting and breast 57 feeding.

In one embodiment the electrode 106/device to include but not restricted to the sensor 39 or detector or transmitter or innervating device, or monitor can send or receive a signal 14 from a computer 18 or computer-like device to include but not restricted to a hand-held device to include but not restricted to a cellphone 18 or screen that can be used to display 17 and give feedback 70 on the muscular or neural events and to include but not restricted to measure the user's ability to engage or initiate or facilitate or relax or contract a muscle 65 or assess coordination of the muscle 65 and the function being activated, relaxed or coordinated and in another embodiment the computer 18 or the user can vary the body efforts to alter the muscle 65 and neural function and in other embodiment the computer 18 or feedback 70 device can include but not restricted to initiate signals 14 or innervations or muscle 65 or nerve contracting or relaxing pulses to assist the user in the performance and coordination of these functional sphincter and pelvic floor 74 exercises and the combination of user volitional biologic efforts can be combined with computer 18 modeled or computer 18 generated feedback 70 and activation and relaxation to facilitate or achieve a more optimal biological functioning of the physiologic process being taught or practiced or generated. In another embodiment the optimization and facilitation of function and neural-muscular function can include but not restricted to muscular-neural feedback 70 and activation and relaxation of muscle 65 and nerves can be combined with mechanical feedback 70 to include but not restricted to pressure or compression or movement of to include but not restricted to the insert or device that can include but is not restricted to including the electrodes 106. This combination of electrical muscle 65 and nerve feedback 70 and stimulation 71 combined with the mechanical feedback 70 currently available can yield a more robust and effective training 80, 81 or facilitation of the desired or optimal physiologic outcome than the mechanical feedback 70 alone because the desired outcome can be mapped and the user and the trainer to include but not restricted to a human trainer or a computer 18 or device trainer or a combination of these can create corrections in the users efforts in a focused and tailored and non-random manner rather than the current 100 mechanical methodologies that utilize only random a gross or coarse experimentation to attempt to achieve a global rather than a specific or tailored outcome to include but not restricted to learn how to initiate or move or innervate a single muscle 65 or a specific set of muscle 65 rather than the current 100 broad approach of activating and relaxing multiple muscle 65 which can have unintended or undesired consequences or incompetent functional outcomes. The use of the individual muscle 65 or the designated muscle 65-nerve group initiation/function approach that is afforded by the above to include but not restricted to electrode 106 feedback 70, sensor 39, stimulation 71, initiation or relaxation, assist and training 80, 81 technique provides the advantage of modeling, precise training 80, 81 and multiple feedback 70 loops provides a more robust training 80, 81 for the desired functional improvement than the mechanical approach alone. The training 80, 81 device can have variable anatomic locations where both the electrical and mechanical responses and their input or output signals 14 can be evaluated or monitored or stimulated. In another embodiment the to include but not restricted to the input and output sensor 39 or stimulus can include but is not restricted to have a threshold or a sliding scale that can be utilized to include but not restricted to alter the input or output signal 14 or stimulus, to alter the training 80, 81 or exercise program, to gradually teach and identify more specific muscle 65 groups and these thresholds can be utilized to adjusted across the anatomy of the training 80, 81 device. In another embodiment the training 80, 81 device can have positive and negative feedback 70 to include but not restricted to pleasurable or painful stimulation 71 and the feedback 70 or stimulation 71 can include but is not restricted to electrical, magnetic, photo or light, chemical, electromagnetic, kinetic, or mechanical, hydraulic, chemical, vibratory or Brownian or thermal and to include but not restricted to generate output or signals 14 to include electrical, magnetic, photo or light, chemical, electromagnetic, kinetic, or mechanical, hydraulic, vibratory or Brownian or thermal outputs and these can be used to enhance or designate the site at which training 80, 81 or stimulation 71 for the user's or trainer's or computer's input or output can be directed or any combination of the above. The retraining/training 80, 81 device can also include mechanical devices that can include but is not restricted to alter shape focally or non-focally to include but not restricted to swell or expand or contract or take on a shape that can be a geometric or non-geometric shape that assists or trains or alters the physiologic function and the alteration of shape can be by magnetic or mechanical compression or expansion or electrical or other methods that can change the shape 85 of an object.

In one embodiment, a device which can include but is not restricted to an insert that can be inserted into the vagina 3 or anus 4, can contain to include but not restricted to electrodes 106, sensors 39, magnets 38 and measuring devices that can assess to include but not restricted to pressure, force, magnetic forces 38, transmitters and receivers 40, camera 12, fiber optics 13 and LPS 41 which can communicate with a computing device 18, computer 18, digital computing communication device or phone 18, and can include a display 17 and can anticipate and respond to body 8 movements to include female anatomy 11 including but not restricted to pelvic floor muscles and ligaments 74, muscles and muscle changes 65, Uterus 75, bladder 76, urethral sling 78, prolapsing anatomy 79 changes including prolapsing anatomy 79, 80, 81, to include but not restricted to into the vagina 3 or anal 4 or urethral 2 regions and for which to include but not restricted to the computing devices feedback 70 and response and stimulation 71, EMG, or magnetic forces 38, sensors and sensory changes 39, 66 can be perceived and which can be exerted by the anatomic changes to include but not restricted to prolapse and incontinence and sexual pleasure or sexual dysfunction and for which adaptive responses of the shape and size changing 85, and continuous or intermittent sensory stimulation 71 and feedback 70 can alter the device with adaptive responsive changes to the device 85 which can be generated by mechanical 86 or substance 87 or energy changing mechanisms 88 and which can be generated by to include but not restricted to a battery 84, energy 43 or a substance 44 or a wire 13 or fiber optic 13 energy 43 source or a generator 109, 110 including but not restricted to a standard or biogenerator that, can be exert forces or changes to include but not restricted to pressure, heat, light, electrical 43 or substance 44 discharge or delivery systems 42 can act to include but not restricted to neuro-muscle innervation or blood flow 104 or movement or repositioning of organs of the body to include but not restricted to train or retrain the body to improve or cure or correct or facilitate normal positioning or functional positioning or adequate or improved bodily and sexual functions. The training 80, 81 device can be also used to include but not restricted to an assist device that can include but is not restricted to being utilized, worn or present during the function that is being designated for improvement or monitoring.

In other embodiments of a training 80, 81 or an assist the elements and designs cited and described herein can apply and be used to include but not restricted to UCD 6, MCD, MFPD, FCD, FAD, MAD and contraceptive devices and to functions to include but not restricted to erectile function, orgasms, sexual function, urinary function, decrease incontinence 83 and prolapse 79, improve and increase or initiate a urinary stream/micturition, improve bowel movements, defecation and fecal incontinence 83 and prolapse 79, improve breast 57 feeding/nursing and improve sexual performance and pleasure. In these examples the specific and corollary muscle 65 and nerves and tissue that pertain to the given function would be the structures to be sensed or monitored or innervated or stimulated.

In one example of an alternative embodiment, fecal incontinence 83 and prolapse 79 can be reduced or trained to be eliminated using a an anal 4 probe that can assess and train to include but not restricted to the anal 4 sphincter including internal and external sphincters and rectal and pelvic sling muscle 65 and nerves.

In another embodiment, such as breast 57 feeding the method of training 80, 81 for the infant can utilize to include but not restricted to sensor 39 that assess sucking motions of an infant, breast 57 milk flow of the mother and can stimulate the cheek of the infant by utilizing a stimulus to augment or initiate the Rooting or Suckling reflex to include but not restricted to through mechanical scratching, vibration or thermal or electrical stimulation 71.

In another example of an alternative embodiment can include but is not restricted to erectile dysfunction in which the muscle 65 of the pelvic floor 74 can be innervated to include but not restricted to the muscle 65 attaching to the corpora cavernosa and these can be access to include but not restricted to around or adjacent or along the base of the penis 35 or the scrotum or through an insert placed into the anus 4 to reach otherwise inaccessible nerves and muscle 65.

Embodiments can include but are not restricted to placing the electrodes 106 or sensor 39 or devices in one or more than one location either superficial or deep or within or on or into to include but are not restricted to combinations of anatomic locations such as anal 4 and vaginal 3 vaults, penile region and anus 4, urethra 2 and vagina, urethra 2 and anus 4, lips and breast 57 and these can include but are not restricted to the same or differing living beings. The anal 4 and the vaginal 3 training 80, 81 and functional assist devices can separate or connected 82.

Environmental Challenges

In another embodiment, in an environment of altered gravity or pressure or vacuum, the ability of a substance 44 to behave as it does in full gravity is altered.

Energies and facilitators can be used to include but not restricted to vibrational, mechanical, ultrasound, electromagnetic, thermal, radiation, and electric and magnetic energies to compensate for some of the challenges of an altered environment. Some challenges of environmental changes include but not restricted to altered surface tension and adherence of materials to the tubing and the surfaces of the devices and components which include altered properties of to include but not restricted to altered behavior of solid, liquid, and gas, gel and slurry adhering or not flowing freely or not having properties or behavior that are normal for a full gravity environment.

Magnets and Magnetic Materials

In another embodiment a connection 82 between the penile covering 36 or the condom catheter can include no multiple or one magnet that can include but is not restricted to having the north and south poles of the magnet facing each other and adjacent to create a fixation or seal 7 or connection 82 that can be surrounded by to include but not restricted to a liquid or solid or gas or gel or gel or other form of slurry particles and these can include membranes or envelopes and said magnets 38 can also include interfaces with but not restricted to other non-magnets to include materials to include but not restricted to magnetic attractive materials, ferromagnetic metals, and ceramic and combinations of these materials and these magnets 38 and materials can be used in combination and can be other material embedded or impregnated into other materials that can include but are not restricted to be components of the Urine Sample for Diagnostic Urine Analysis and Culture using Sterile/Clean Urinary Collection Device (UCD 6) as well as a Menstrual 46 Collection Device (MCD) and a Fecal/Stool 51 Collection Device (FCD), Breast 57 Collection and Stimulation 71 Device (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices, or combinations of these.

Magnets 38 can be controlled in a manner to include causing the device to be more or less magnetic or not magnetic and the method of control can include but is not restricted to mechanical, electric, electromagnetic, magnetic, hydraulic, kinetic, ultrasound, pressure, air pockets and cavitation and thermal energy 43 methods.

Envelope

In one example the devices and components of the Urine Sample for Diagnostic Urine Analysis and Culture using Sterile/Clean Urinary Collection Device (UCD 6) as well as a Menstrual 46 Collection Device (MCD) and a Fecal/Stool 51 Collection Device (FCD), Breast 57 Collection and Stimulation 71 Device (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices can be constructed with to include but not restricted to a an envelope or membrane that can be the same or differ from the internal contents being enveloped and can include but is not restricted to a permeable or semi-permeable or non-permeable membrane and the membrane or envelope can include but is not restricted being internal, external or both or none or partial or fully enveloped or any combination and can include but is not restricted to examples of a silicon membrane for a gel-slurry internally, a gel that envelopes a plastic vaginal 3 insert, tubing that is lined lined-internally and externally with a magnetic material that can be activated to be magnetic or non-magnetic.

Corollary or Common Element of Design

In one example the devices and components of the Urine Sample for Diagnostic Urine Analysis and Culture using Sterile/Clean Urinary Collection Device (UCD 6) as well as a Menstrual 46 Collection Device (MCD) and a Fecal/Stool 51 Collection Device (FCD), Breast 57 Collection and Stimulation 71 Device (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices can be constructed with corollary or common or similar elements of design of the UCD 6 tubing and Collection container but with the objective that the goal be to remove menstrual 46 blood rather than urine. In MCD is composed of a vaginal 3 insert that can include materials that are solids, liquids or gases, gel or gel slurries or any combination of these and said materials can include but is not restricted to be covered or layered and laminated or enveloped fully, partially or not at all by a membrane. The vaginal 3 insert of the MCD can include but is not restricted to be conforming to the structures at or in or about the vagina 3 and cervix 10 and vulva 11.

Moldable and Elastic and Conforming

In another embodiment the Urine Sample for Diagnostic Urine Analysis and Culture using Sterile/Clean Urinary Collection Device (UCD 6) as well as a Menstrual 46 Collection Device (MCD) and a Fecal/Stool 51 Collection Device (FCD), Breast 57 Collection and Stimulation 71 Device (BCSD) and a Menstrual 46 flow Prevention Device (MFPD) Female Urinary Incontinence 83 and prolapse 79 And Continence Assist Device And Female Erectile Function/Dysfunction Device/Orgasm (Female Assist Devices: FAD); Male Urinary Incontinence 83 and prolapse 79 And Continence Assist Device And Erectile Function/Dysfunction Device/Orgasm (Male Assist Devices: MAD), and some elements related to Contraception Devices can be constructed to include is restricted to being moldable to the living body and methods for molding or contouring to the human body or the device can include but is not restricted to activating devices or methods that can include but is not restricted to thermal, hot or cold, electromagnetic, UV 43, Infrared, visible 20, 43 light, chemical, aqueous and non-aqueous chemicals, fat-like and oil, protein-like and amino acid and nucleotide, and carbohydrate, Kinetic, Ultrasound, pressure, chemical activators 97, nano 63 particle activators 97 and their effects and processes and reactions and any combination of these means methods or material.

In one embodiment the vaginal 3 insert can be hollow and can accept a fiber optic or light or electromagnetic 102 or energy 43 or electric or light both visible 20, 43 and invisible to the human eye and iris 23, 6423 that can react with the insert material to create a flexible 26 contouring material pattern that can include but is not restricted to contour to the human body to include is restricted to the vaginal 3 vault, vaginal 3 orifice or the vulva 11. In this embodiment the vaginal 3 insert can be transparent or opaque and when the energy 43 source including but not restricted to a UV 43 light source interacts with the vaginal 3 insert material that can include but is not restricted to a photosensitive gel that can include but is not restricted to containing silver or gold nano 63 particles, the said vaginal 3 insert material conforms to the topography of the vaginal 3 vault to create and airtight and watertight and blood tight seal.

In another embodiment the endpoint of the activation or molding process can result in a material to include but is not restricted to a foam or gel and envelope or gel or slurry or plastic that can be but is not restricted to be elastic or non-elastic, resilient or not resilient, fully partially or non-conforming to the device or its components and the living body or any combination of these and this process of activation can include but is not restricted to include it being performed once or multiple time or not at all and in a manner that can include but is not restricted to contour to the topography and contour of the device and the living body or both or one or none. In this embodiment the need to change topography can be caused by to include but not restricted to changes in body position, changes in biology, changes in environment, changes in gravity and pressure and vacuum and changes in body physiology to include but not restricted to swelling and resolution of swelling of the living body or the material used in the device and its components, menstruation, urination defecation, and other bodily functions or demands of the interaction between the living body and the device and its components in order to perform its functions and/or its need to be put into place or removed or altered from its place or position.

In another embodiment the device and its components can be created or activated to become and tacky elastic around inserted into become tacky or non-tacky.

Visualization

Embodiments can include but are not restricted to anatomic and non-anatomic oriented depictions, visualizations and optical 12 imaging.

Telemedicine

Telemedicine is becoming an increasingly important component of medical care and diagnosis and treatment.

In one embodiment the UCD 6 or Tubing or Collection container or other components of the devices can include but are not restricted to contain a region or chamber in the UCD 6, tubing or collection container that can include but is not restricted to containing growth/culture media to allow for analysis of the urine to determine whether there are any infectious agents to include but not restricted to the culture of bacteria, fungi, viruses, and other infectious organisms. The information from the culture can be but is not restricted to be analyzed by standard microbiology techniques or by computer 18 sensor 39, chips or digital or analog indicators or fiber optic or cameras 12 for visualization with or without special optics and lenses 24 24 and that information can be transmitted to include but is not restricted to a send and receive transmitter, that can include but is not restricted to fiber optics 13, RF, wires 13 or cables 13 or other standard transmitting 16 methods. The information that is transmitted can be analyzed by a computer 18 or computer-like device, which can include but is not restricted to a cellular phone 18 or a computer 18 and this can also be analyzed by a living being.

In one embodiment the UCD 6 or Tubing or Collection container or other components of the devices can include but are not restricted to contain a region or chamber in the UCD 6, tubing or collection container that can assess but is not restricted to the chemical, non-biologic or biologic parameters or qualities of the urine and can include but is not restricted to computer 18 sensor 39, chips or digital or analog indicators or fiber optic or cameras 12 for visualization with or without special optics and lenses 24 can be transmitted to include but is not restricted to a send and receive transmitter, that can include but is not restricted to fiber optics 13, RF, wires or cables 13 or other standard transmitting 16 methods. The information that is transmitted can be analyzed by a computer 18 or computer-like device, which can include but is not restricted to a hand-held device, cellular phone 18 or a computer 18 or computer-like or cellular-like device and this can also be analyzed by a living being for the use on a living being.

Replaceable

Components of the Devices within this patent application can be replaced and interchanged for newer components as needed.

Sealing Pad

In one embodiment the living body/skin 8 covering 36 pad can include but is not restricted to include being fully or partially between the skin 8 and the sealing pad, integrated into the sealing pad, or can lie away, outside, from or external to the skin 8 and the sealing pad or any combination of these.

Magnetic Materials and Magnets

Magnetic Materials and Magnets 38 can be attracting or repelling and can be activated by energy 43 to include but not restricted to electromagnetic 102 energy 43/electrical/magnetic/wavelength.

Skin 8 and Mucosa

For this provisional the terms skin 8, and mucosa can include but are not restricted to be used interchangeably.

Indicators

Indicators can be sensor 39 and sensor 39 can be indicators. Indicators can be used with all of the devices herein to alert the user to presence or absence of to include but not restricted to a material or a substance 44 to include but not restricted to a solid or liquid or gas or gel to include but not restricted to a quality or a change in quality to include but not restricted to a visual or color 95, thermal, hot or cold, tactile, wetness or dryness, vibration, olfactory, smell, auditory, sound or other sensory 39, 66 or combination of sensory 39, 66 inputs as well as but not restricted to biologic and organic and inorganic materials that are included and listed throughout this patent application. This indicator can have the ability to respond to and to alert the user or a living being or a computer 18 or a computer-assisted device or any combination of these devices herein this patent application to include but is not restricted to being an analog device to include but not restricted to a sensor 39 of quality or a change in quality to include but not restricted to a visual or color 95, thermal, hot or cold, tactile, wetness or dryness, vibration, olfactory, smell, auditory, sound or other sensory 39, 66 or combination of sensory 39, 66 inputs as well as but not restricted to biologic and organic and inorganic materials that are included and listed throughout this patent application to include but not restricted to indicators that can alert or combination of these; or a digital indicator that can be recognized or sensed by a living being or a computer 18 or a computer 18 assisted device or combination of these. Some examples can include but are not restricted to an indicator a wetness indicator near the urethral 2 meatus or opening that can include but is not restricted to an analog or digital signal; a sperm or sperm fragment indicator; a fructose or sugar or pH or vaginal 3 fluid specific material indicator inside of a condom that can be used for but not restricted to indicate that the condom has leaked and can include in one embodiment a change in color 95 of at least a portion of the condom and said indicator can be associated or separate or integrated into the condom; or an infectious disease or pathogen or chemical build up indicator that can include but is not restricted to being related to urine, fecal material blood, sperm, or vaginal 3 fluids, nasal and oral secretions or sweat or hormones or their fragments of components that can include but is not restricted to be detected on, or in or related to include but not restricted to a portion of the devices or of the male or female condom or contraceptive device or pleasure device or monitoring or diagnostic device which can be stand alone or integrated or any combination of these.

In one example the male or female condom or contraceptive device or pleasure device or monitoring or diagnostic device which can be stand alone or integrated or any combination of these and can include but is not restricted to an indicator or monitor or diagnostic device that can include but is not restricted to assess male and female reproductive elements or secretions or cells or tissue or fluids or materials to include but not restricted to organic or inorganic chemicals or molecules or their fragments or compounds or agents that can include but is not restricted to being related to urine, fecal material, blood, sperm, sexual and prostate secretions or vaginal 3 fluids, nasal and oral secretions or sweat or hormones or their biologic or chemical or molecular components or fragments to include but not restricted to male and female specific tissue and antigens and antibodies, to include but not restricted to vaginal 3 specific antigens, vaginal 3 or female reproductive system specific antibodies or antigens, or genetic material, vaginal 3 mucosal functions to include but not restricted to male or female hormones, or egg or ovarian or female reproductive tissue or fallopian or uterine or vaginal 3 secretions to include but not restricted to carbohydrate, fructose, glucose, sucrose, sugar, amino acid, peptide, protein, fat and lipid, urine, pH; and can include but is not restricted to male urine, fecal material, blood, sperm, or vaginal 3 fluids, nasal and oral secretions or sweat or hormones or their biologic or chemical or molecular components or fragments to include but not restricted to male and female specific tissue and antigens and antibodies, sperm, anti-sperm antibodies, sperm antigens or penile or prostate or urethral 2 or male reproductive system specific antibodies or antigens or hormone or antigens or antibodies or genetic materials related to reproduction and reproduction diseases to include but not restricted to carbohydrate, fructose, glucose, sucrose, sugar, amino acid, peptide, protein, fat and lipid, urine, pH and any combination of these male and female materials listed herein this patent application and can be indicated by a digital or analog signal 14 related to the female or male condom or indicator or sensor 39 or monitor device or any combination that can include but is not restricted to a color 95 or visual signal 14 or the an indicator of a sensor 39 that can communicate or send a signal 14 to a computer 18 or computer 18 assisted device to include but not restricted to a traditional or stand-alone devices, wearable 50 or handheld computing 18 or measuring device and the user and a living being or computer 18 or a computer-assisted device. In others embodiment these same elements described here can be used for other devices and embodiments herein as well as in cited by and herein this patent application It is recognized that the response to male or female tissue may be identified in the living being of the opposite gender and in one exemplary embodiment the female may produce antibodies to the male antigens and vice versa.

In one example the male or female condom or contraceptive device or pleasure device or monitoring or diagnostic device which can be stand alone or integrated or any combination of these and can include but is not restricted to an indicator or monitor or diagnostic device that can include but is not restricted to assess male and female infectious elements or tissue or fluids or materials to include but not restricted to organic or inorganic chemicals or molecules or their fragments or compounds or agents that can include but is not restricted to being related to include but not restricted to infectious agents and pathogens to include but not restricted to microbes, bacteria, bacteria-like, mycobacterial and mycobacterial-like, fungal and fungal-like, viral and viral-like, protozoa and protozoa-like, helminthes and helminthes-like, prions and prion-like, plasmid and plasmid-like, genetic replication material and genetic replication-like material and the list of these agents is too extensive to comprehensively or exhaustedly include but can include but is not restricted to Sexually Transmitted diseases to include but not restricted to HIV and AIDS, hepatitis, syphilis, chancroid, *trichomonas*, Human Papillomavirus (HPV), genital warts, herpes and all of the herpes strains, gonorrhea, *chlamydia*, bacterial vaginosis, pubic 'crab' lice, scabies, other causes of pelvic inflammatory diseases (PID), lymphogranuloma venereum (LGV), molluscum contagiosum, mucopurulent cervicitis (MPC). And can be measured alone or with to include but not restricted to uterine or vaginal 3 secretions to include but not restricted to carbohydrate, fructose, glucose, sucrose, sugar, amino acid, peptide, protein, fat and lipid, urine, pH; and can include but is not restricted to male urine, fecal material, blood, sperm, or vaginal 3 fluids, nasal and oral secretions or sweat or hormones or their biologic or chemical or molecular components or fragments to include but not restricted to male and female specific tissue and antigens and antibodies, sperm, anti-sperm antibodies, sperm antigens or penile or prostate or urethral 2 or male reproductive system specific antibodies or antigens or hormone or antigens or antibodies or genetic materials related to reproduction and reproduction diseases to include but not restricted to carbohydrate, fructose, glucose, sucrose, sugar, amino acid, peptide, protein, fat and lipid, urine, pH, enterotoxins, endotoxins, toxins and pathogens created by the infectious organism or the living being in response to the organism and any combination of these male and female materials listed herein this patent application can be indicated by a digital or analog signal 14 related to the female or male condom or indicator or sensor 39 or monitor device or any combination that can include but is not restricted to a color 95 or visual signal 14 or the an indicator of a sensor 39 that can communicate or send a signal 14 to a computer 18 or computer 18 assisted device to include but not restricted to a traditional or stand-alone devices, wearable 50 or handheld computing 18 or measuring device and the user and a living being or computer 18 or a computer-assisted device. In others embodiment these same elements described here can be used for other devices and embodiments herein as well as cited by and described herein this patent application.

It is recognized that the response to male or female tissue may be identified in the living being of the opposite gender and in one exemplary embodiment the female may produce antibodies to the male antigens and the male may produce antibodies to the female antigens Interrogated materials and substances 44 and matter can include the whole material or fragments of the materials and can include materials and substances 44 and matter listed herein this patent application and exemplary examples can include but are not restricted to genetic materials, cellular materials, pathogenic materials, reproductive materials, portions of proteins, nucleotides, carbohydrates, fats and other organic and inorganic materials and minerals and metals and compounds and pathogenic materials, poisons and toxins and can be used for the general uses herein this patent application to include but not restricted to biological functions to include but not restricted to bodily functions of reproduction, pleasure and pleasurable actions, intercourse, masturbation, sucking and suckling, nourishment, processes of eating, food and its intake and digestion, defecation, saliva production and salivary and saliva, mucus and mucous production, secretion, excretion, urination, continence of urine and feces 51 and to include but not restricted to the improvement and education of these said bodily functions.

In another embodiment the materials that can be interrogated that can include but is not restricted to organic and non-organic matter and can function to include but not restricted to bodily functions of reproduction, pleasure and pleasurable actions, intercourse, masturbation, sucking and suckling, nourishment, processes of eating, food and its intake and digestion, defecation, saliva production and salivary and saliva, mucus and mucous production, secretion, excretion, urination, continence of urine and feces 51 and to include but not restricted to the improvement and education and identification of normal and abnormal bodily functions and in one embodiment the identification can include but are not restricted to the identification and the detection and differentiation between one of at least a component of cancerous and non-cancerous structures to include but not restricted to non-cancerous and cancerous antibodies or antigens and their related compounds; to materials, compounds and components of living being to include but not restricted to one or any combination components that can include but are not restricted to one or more of a carbohydrate, sugar, carbohydrate fragment to include but not restricted to fructose, glucose/dextrose, sucrose, lactose, maltose and to an amino acid, peptide, peptide fragment, protein, protein fragment, and to a fat and lipid, and a lipid or fat fragment; and to genetic materials to include but not restricted to nucleotides, DNA and RNA, polymerases, proteases whole and their fragments of these structures, their structurally related reproducing materials and compounds; to cells and their cell components to include whole components and fragments and their antigens to include but not restricted to whole cells and cell membranes, mitochondria, nuclei and other cell components; to include but not restricted to blood and blood products to include but not restricted to red blood cells, white blood cells, lymphocytes, eosinophils, basophils, hematocrit, glucose, and other standard blood chemistries as well as toxic blood elements to include but not restricted to poisons, metals, lethal and normal doses of organic and inorganic materials and compounds to include but not restricted to medications, poisons, infectious agents, abnormal and normal living being cells and pathogens.

In one embodiment food or breast 57 milk or nourishment or digestibles or oral, nasal or anal or vaginal 3 intake or solids or fluids or drinks can be analyzed and that can include but are not restricted to organic and non-organic matter and can functions to include but not restricted to bodily functions of reproduction, pleasure and pleasurable actions, intercourse, masturbation, sucking and suckling, nourishment, processes of eating, food and its intake and digestion, defecation, saliva production and salivary and saliva, mucus and mucous production, secretion, excretion, urination, continence of urine and feces 51 and to include but not restricted to the improvement and education and identification of normal and abnormal bodily functions and in one embodiment the identification can include but are not restricted to the identification and the detection and differentiation between one of at least a component of cancerous and non-cancerous structures to include but not restricted to non-cancerous and cancerous antibodies or antigens and their related compounds; to materials, compounds and components of living being to include but not restricted to one or any combination components that can include but are not restricted to one or more of a carbohydrate, sugar, carbohydrate fragment to include but not restricted to fructose, glucose/dextrose, sucrose, lactose, maltose and to an amino acid, peptide, peptide fragment, protein, protein fragment, and to a fat and lipid, and a lipid or fat fragment; and to genetic materials to include but not restricted to nucleotides, DNA and RNA, polymerases, proteases whole and their fragments of these structures, their structurally related reproducing materials and compounds; to cells and their cell components to include whole components and fragments and their antigens to include but not restricted to whole cells and cell membranes, mitochondria, nuclei and other cell components; to include but not restricted to blood and blood products to include but not restricted to red blood cells, white blood cells, lymphocytes, eosinophils, basophils, hematocrit, glucose, and other standard blood chemistries as well as toxic blood elements to include but not restricted to poisons, metals, lethal and normal doses of organic and inorganic materials and compounds to include but not restricted to medications, poisons, infectious agents, abnormal and normal living being cells and pathogens.

A Living Being

A living being can include but is not restricted to human beings and non-human beings.

Urethra 2 and Vagina

Male and Female Urethra 2 and female vagina 3 can refer to but is not restricted to refer to the entire urethra 2 or vagina 3 structure or a portion of the urethra 2 or vagina 3 structure and can include but is not restricted to the meatus or opening, the orifice or opening or any component or combination of these structures or the entire penis 35 and reproductive system and the associated urinary systems.

Impact Device and Generators 99

Metals

The embodiments herein can utilize metals to include but not restricted to gold, silver, copper, zinc, and sulfur in the elemental state or as compounds and can be used in micro, macro or nano 63 particles such as but not restricted to gold and silver nano 63 particles which when exposed to electromagnetic 102 energy 43 such as but not restricted to Ultraviolet (UV 43), Infrared, and Visible 20, 43 light and can create a reaction that can include but is not restricted to a chemical, thermal, kinetic, electromagnetic, electrical, mechanical, mechanical-chemical biological energy 43 that can include but is not restricted to generate, store, power, transmit and receive and harness energy 43 that can include but is not restricted to an increase or decrease in energy 43 that can include but is not restricted to power or cause a device or sensor 39 or generator 99 or storage device to function.

Another embodiment can include but is not restricted to substances 44 such as Copper and Zinc and Silver and Gold that can create an antimicrobial environment that can kill or diminish harmful pathogens.

Tesla and Static Electric Activation

Figure 17:
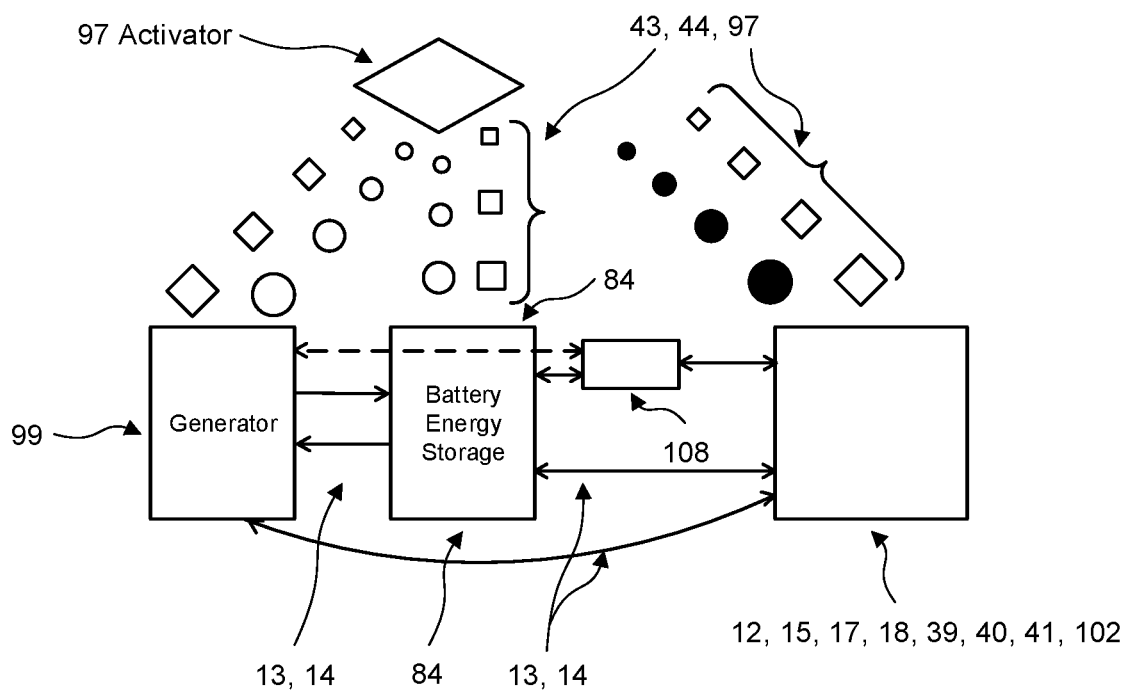
FIG. 17 is a schematic rendering of an activator 97 and its effect and communication with an LPS 41 and other interactive devices.

FIG. 17 is a schematic rendering of an activator 97 and its effect and communication with an LPS 41 and other interactive devices.

Figure 18:
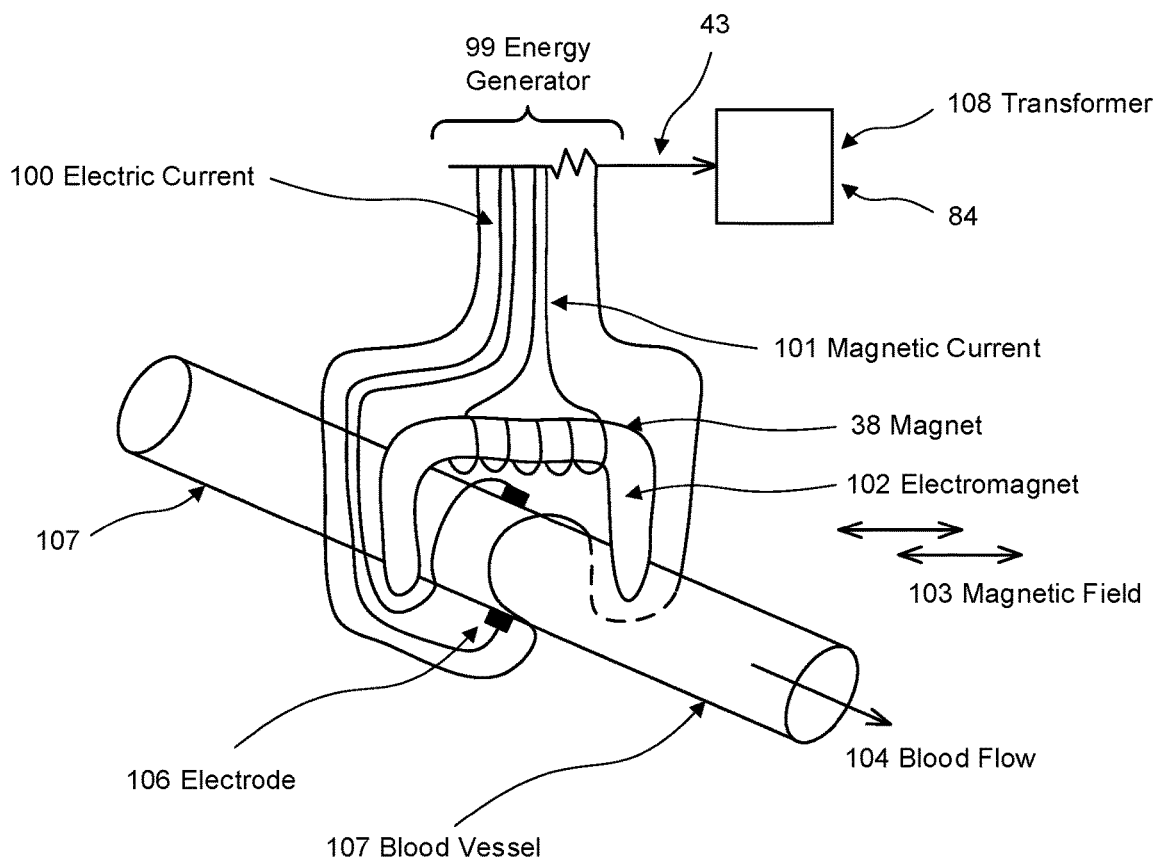
FIG. 18 is a schematic rendering of a micro-bioenergy 43 generator 99 related to blood flow 104.

FIG. 18 is a schematic rendering of a micro-bioenergy 43 generator 99 related to blood flow 104.

Figure 19:
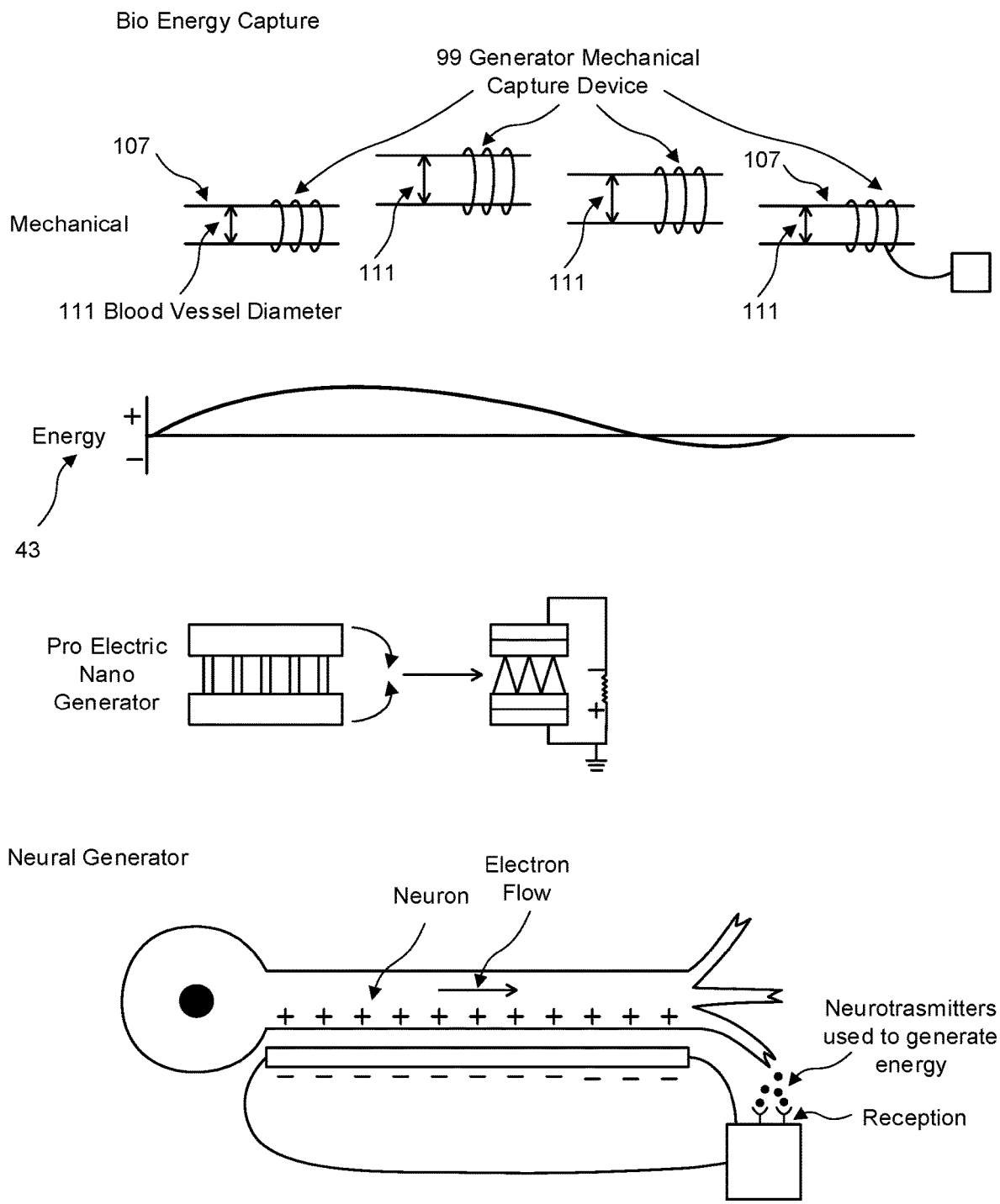
FIG. 19 is a schematic renderings of mechanical, piezoelectric and neuronal bioenergy 43 capture.

FIG. 19 is schematic renderings of mechanical, piezoelectric and neuronal bioenergy 43 capture.

In another embodiment, the activation or the causing to function, powering or initiating or the turning on of a device that can include but not restricted to an LPS 41, GPS, sensor 39 or treatment devices can to include but not restricted to power, energy 43, electromagnetic 102 energy 43, electric current 100, magnetic or electromagnetic 102 effects that can be generated by to include but not restricted a Tesla coils or Oudin coils that can include but are not restricted to one or more resonant transformer s 108 and their circuits, transformer s 108, AC main voltage, capacitors, primary windings, spark gap Tesla coil air-core double-tuned resonant transformer 108 capacitive electrodes 106 a torus, a corona discharge and streamer arcs, primary and secondary coils, oscillator transformer, radio-frequency transformer, resonant current 100, output circuits to include unipolar and bipolar and grounds and other components needed to produce these Tesla coils or Oudin coil, such that when a living being is in the presence of the said power or energy 43 produced by these coils the said devices which can include but are not restricted to include an antenna, the said device can capture the said energy 43. The embodiment will produce a voltage such that when the living being is exposed to the voltage the said voltage will be safe to the living being and in the preferred embodiment that voltage can include but is not restricted to low voltage, DC (Direct current 100) and AC (alternating current 100) electricity. Embodiments of delivery 42 of the Electrical charge can include known methods to include but not restricted to charges through the air, through one or more pads or electrodes 106 or devices associated with the living being and to include but not restricted to being place on or onto or in or into that living being.

Bio generators can include but are not restricted to mechanical generators, piezoelectric generators and neural generators and these can include but are not restricted to smaller than nano, nano, micro or macro generators Phase and Shape and Sealing Change Materials Devices can include but are not restricted to materials that can include but is not restricted to actively and passively have the ability to change Phase 94, 96 and Shape and Sealing and can include but are not restricted to use activators 97 and sensor 39 to assist with this process.

In another embodiment the materials or layers 98 to include but not restricted to the coverings 36, materials, layers 98, membranes, and frames can have its chemical property altered such that a thermal, chemical or kinetic or electromagnetic 102 energy 43 is released that alters that primary properties of that material. Embodiments can include but are not restricted to infusing electromagnetic 102 energy 43 into a nano 63 particle, nano 63 composite material, or carbon fiber layers 98 or releasing a heating or cooling agent or chemical that causes a layer to include but not restricted to a gel to stiffen at a specific site.

Activators 97

The materials or layers 98 to include but not restricted to the covering 36, materials, membranes, layers 98 and frames can incorporate activators 97. Activators 97 are devices that can include, but are not restricted to a mechanical or nano 63 machine or device or mechanism that can act mechanically on the layers 98 or materials of the layers 98 or the shape of the layers 98 or membranes or materials of said layer 98 and can include, but is not restricted to, vibration, heat, pulley, lever, or push or a pulling device or a motor. The activator 97 can also include but is not restricted to electromagnetic 102 forces or energy 43 that can include, but is not restricted to, magnets 38, nano 63 magnets, electrical charges that interact, visible 20, 43 light, infrared, ultraviolet lasers, nano 63 and chemical energy 43, and heat or cold 99 or transmitters or transmitters 40.

The activators 97 can be passively activated by the mechanical force generated by the sucking or suckling or friction or rubbing on the device or a layer 98 or a material that can include, but is not restricted to, the generation of pressure on a portion of the device or layer 98 or material. One embodiment can include, but is not restricted to, a softer layer 98 generating displacement on a sensor 39 that triggers the activation of a chemical reaction that heats another chemical in a layer 98 and causes that layer 98 to shift or stiffen or soften in one embodiment the laser can create heat and be directed into a gel causing the gel to soften. In another embodiment the mechanical force can trigger the sensor 39 to trigger an electromagnetic 102 energy 43 into a substance 44 to include but not restricted to a smart metal (Smart metal; Jun. 6, 2011, Helmholtz Association of German Research Centres) or a gel-metal slurry causing the material to harden. This process is virtually instantaneous and reversible. Another embodiment can include heating a colloidal substance 44 not dissimilar to the boiling of an egg that transforms a colloid to a solid but this is not reversible but with a colloid that can near instantaneously convert conform to the user's breast 57 or lips or mouth 55 and may not be reversible and thus would have a single user and may need to be altered over time and use and aging of the child or changes in the mother or user.

In another embodiment, the activator 97 is actively or preemptively activated. One embodiment can include a sensor 39 that lies on the surface of the device and in this embodiment the device can be a devise that provides pleasure. The sensor 39 sends a signal 14 to the activator 97 to which in turn can release an electromagnetic 102 signal 14 that causes a nano 63 particle material, nano 63 composite material, or carbon fiber material that can include, but is not restricted to, nano 63 cellulose that will stiffen. In other cases the sensor 39 can signal 14 for homogeneous or heterogeneous or softening or hardening of areas of the living body where there is contact and this hardening and softening can be dependent on the magnitude and direction of the force. One embodiment can include, but is not restricted to, creating a greater degree of stiffening directed toward the areas of maximal stimulation 71. In another embodiment the sensor 39 will direct where the maximum sensation will be generated and will stiffen that area maximally. In another embodiment a series of sensor 39 will communicate with each other and/or with the master sensor 39 and the area to be compressed or vibrated or warmed or mechanically altered will be predetermined by an algorithm that predicts the maximal desired function to include but not restricted to lactation, suckling, pleasure, suction, an airtight or watertight seal 7 or optimal or maximal flow.

Other elements of the device can include an embodiment that includes a gel-slurry that can serve as an interface. This gel slurry can be enclosed in envelopes or packets (referred to as envelopes) and the envelopes can be of variable size from a submicron size up to millimeters or larger than millimeters depending on the specific application. These envelopes when utilized together or separate can be all the same size or can be different sizes. The gel slurry can be within or form a layer 98 that can be composed of a Newtonian and Non-Newtonian fluids and gasses, gels and solids. The gel slurry and the enveloped gel slurry and the combination of these free and one or more enveloped gel-slurries can be used with Newtonian and Non-Newtonian fluids and gasses, gels and solids. The result of this may assist with the sealing properties.

Some sensor 39 and indicators can include but are not restricted to cameras 12, ultraviolet (UV 43), radio frequency (RF), infrared (IF), ultrasound (US), and global positioning system (GPS) device that can be incorporated into the Device. The sensor 39 and indicators can be used to adjust and can contain multiple openings or insinuations or valleys or cavities or outward bumps or outdents of the layers 98 by altering the layer 98 by mechanical or electromagnetic 102 alterations in the layer. One embodiment can include, but is not restricted to, the material of the layer 98 woven with a ferromagnetic substance 44 that when exposed to an electromagnetic 102 energy 43 alters the shape or strength or viscoelastic properties of the material or layer. In another embodiment an electromagnetic 102 energy 43 can include but not restricted to realign materials or layers 98 to include but not restricted to nano 63 particles, nano 63 composite materials, or carbon fiber particles of the material or layer.

Embodiments to alter the shape of the layers 98 or membranes of the layers 98 can include but are not restricted to nano 63 particles or nano 63 composite materials that can be impregnated with materials that are ferromagnetic or that create electromagnetic 102 response and can include but are not restricted to nano 63 cellulose which can readily be transformed into grafted magnetic nano 63 particles along the cellulose nano 63 fibers and can include performing this by impregnating the network with metal hydroxide/oxide precursors, which can form a magnetic cellulose foam which can form functional membranes that can be deformed into variable shapes and can include but are not restricted to adjustment in the size or shape or direction of openings or creation of insinuations or valleys or cavities or outward bumps or outdents of any given layer 98 or portion of the layer 98 or membrane.

Alterations and adjustments of layers 98 can be the entire layer 98 or a portion of the layer 98 which can include, but is not restricted to, one or more than one membrane or a component of a membrane. Surface modification of a layer 98 or membrane can include, but is not restricted to, nano 63 cellulose displays 17 a high concentration of hydroxyl groups at the surface which can be reactive in part because of the hydrogen bonding, which strongly affects the reactivity of the surface hydroxyl groups. Impurities at the surface of nano 63 cellulose to include but not restricted to glycosidic and lignin fragments may alter the reproducibility and hydrogen bond effects. Cellulose nano 63 fibers can include changes in ionic behavior and can include, but is not restricted to, cationic cellulose increase the affinity for anions and anions affinity for cations. In one embodiment the ionic charge can but is not restricted to be utilized to alter the shape of the membrane or layer 98 or alter the shear and the viscosity of the fluid or gel, gas or solid exposed to the membrane and its charge.

In another embodiment the layer 98 can have its chemical property altered such that a chemical or mechanical or vibratory or kinetic or electromagnetic 102 or thermal energy 43 is released that alters that primary properties of that layer. Embodiments can include but are not restricted to infusing a chemical or specific pH or glucose or fructose or lactose electromagnetic 102 energy 43 into a nano 63 particle, nano 63 composite material, or carbon fiber layers 98 or releasing a cooling agent or chemical that causes a gel to soften, seal 7 or stiffen at a specific location of contact.

The device can incorporate activators 97. Activators 97 are devices that can include, but are not restricted to, a mechanical or nano 63 machine or device or mechanism that can act mechanically on the layers 98 or materials of the layers 98 or the shape of the layers 98 or membranes or materials of said layer 98 and can include, but is not restricted to, vibration, heat, pulley, lever, or push or a pulling device or a motor. The activator 97 can also include but is not restricted to electromagnetic 102 forces or energy 43 that can include, but is not restricted to, magnets 38, nano 63 magnets 38, electrical charges that interact, visible 20, 43 light, infrared, ultraviolet lasers, nano 63 and chemical energy 43, and heat or cold generators 99 or transmitters or transmitters 40.

The activators 97 can be passively activated to include but are not restricted to a mechanical force or chemical reaction generated by contact with the device and a living being or a layer 98 or a material that can include, but is not restricted to, the generation of pressure on a portion of the device or layer 98 or material. One embodiment can include, but is not restricted to, a softer layer 98 generating displacement on a sensor 39 that triggers the activation of a material sensitive to but not restricted to a given chemical or pH or glucose or fructose or lactose in a layer 98 and causes that layer 98 to seal 7 or shift or stiffen or soften. In one embodiment an electromagnetic 102 energy 43 such as visible 20, 43 light or UV 43, or Infrared can create heat and be directed into a gel causing the gel to soften. In another embodiment the mechanical force can trigger the sensor 39 to trigger an electromagnetic 102 energy 43 into a substance 44 to include but not restricted to a smart metal (Smart metal; Jun. 6, 2011, Helmholtz Association of German Research Centres) or a smart metal slurry and a gel slurry causing the material to harden. This process is virtually instantaneous and reversible. Another embodiment can include heating a colloidal substance 44 not dissimilar to the boiling of an egg that transforms a colloid to a solid but this is not reversible but with a colloid that can near instantaneously convert but may or may not be reversible.

In another embodiment, the activator 97 is actively or preemptively activated. One embodiment can include a sensor 39 that lies on the surface of the device and in this embodiment the device detects the degree of contact or impact or sucking. The sensor 39 sends a signal 14 to the activator 97 to which in turn can release an electromagnetic 102 signal 14 that causes a nano particle material 63, nano composite material 63, or carbon fiber material that can include, but is not restricted to, nano cellulose 63 that will soften or stiffen prior to the event. In other cases the sensor 39 can signal 14 for homogeneous or heterogeneous or softening or hardening of the device at the specific areas of the living body where the device is in use and this hardening and softening can be dependent on the magnitude and direction of the force. One embodiment can include, but is not restricted to, creating a greater degree of stiffening directed toward vagina 3 or breast 57 or penis 35 or anus 4 or mouth 55. In another embodiment the sensor 39 will direct where the maximum force will be generated and will stiffen that area maximally. In another embodiment a series of sensor 39 will communicate with each other and/or with the master sensor 39 and the area to be stiffened or softened will be predetermined by an algorithm that is to include but not restricted to predicting maximal lactation flow, suckling or pleasure Other elements of the device can include an embodiment that includes a gel-slurry that can serve as an interface or impact absorber. This gel slurry can be enclosed in envelopes or packets (referred to as envelopes) and the envelopes can be of variable size from a submicron size up to millimeters or larger than millimeters depending on the specific application. These envelopes when utilized together or separate can be all the same size or can be different sizes. The gel slurry can be within or form a layer 98 that can be composed of a Newtonian and Non-Newtonian fluids and gasses, gels and solids. The gel slurry and the enveloped gel slurry and the combination of these free and one or more enveloped gel-slurries can be used with Newtonian and Non-Newtonian fluids and gasses, gels and solids. The result of this may assist with the increase, decrease, redirection or dispersion of contact Algorithms In one embodiment of the devices, algorithms can be created that can include but are not restricted to optimize the function that is being performed and can utilize input, modification and output of data and information to optimize a task or non-biological function or a biological function to include but not restricted to pleasure, lactation, suckling and collection and delivery 42 of biological and non-biological materials that can augment or assist or enhance or destroy or neutralize or act neutrally upon said functions for one or more living beings.

In one embodiment population data and information can be utilized to compare and contrast and augment the function of the devices and this can include but is not restricted to include early baselines when there is little or no data to assist the biologic function to include but not restricted to lactation, suckling, pleasure and collection.

Assessment and Stimulation 71 by Devices

Devices that can include but is not restricted to the sensory 39, 66 and feedback 70 mechanism can include biological functions and data and information to include but not restricted to blood pressure, pulse, temperature respiration, and skin 8 conductivity, brain 69 activity to include but not restricted to brain 69 electrical signals 14, EEG 67 or EEG 67-like or MEG 68 or MEG 68-like devices. In another embodiment can measure peripheral nerve or muscle 65 signals 14 and function to include but not restricted to EMG, blood flow 104, chemical, and neural detection and assessment. One embodiment can include but is not restricted to laser assessment of skin 8 and mucosa and blood flow 104 and color 95 and vital signs and chemical analysis.

Devices that can include but is not restricted to the biological functions can be activated to include but not restricted to blood pressure, pulse, temperature respiration, iris/muscle 65 and pupillary changes and skin 8 conductivity, brain 69 activity to include but not restricted to brain 69 electrical signals 14, and magnetic devices. In another embodiment can activate peripheral nerve or muscle 65 and function to include but not restricted to muscle 65, blood flow 104, chemical reactions, sensory 39, 66 stimulation 71, and neural stimulation 71. One embodiment can include but is not restricted to laser, chemical or electromagnetic 102 or mechanical activation of the nerves and muscle 65 and skin 8 and mucosa.

Energy 43, Power, Force

Energies that can be used can include herein in these embodiments and devices and the devices components and can include but are not restricted to measure, stimulate, activate, transmit, output, input, sense, modify, alter and react can include but are not restricted to chemical or biological or mechanical/kinetic to include but not restricted to hydraulic, vibratory, ultrasonic, Brownian motion, motion, vacuum, suction, or electromagnetic 102 to include but not restricted to electrical, magnetic, visible 20, 43 light, non-visible 43 light, UV 43 and Infrared energy 43, radioactive; gravity or thermal and piezoelectric and nano 63, micro or macro particle energies and energy 43 sources.

The terms energy 43 or power or force can be used interchangeably and can also include but are not restricted to drive or fuel that is stored or utilized or energy 43 to drive a function or device or machine.

Materials Compounds and Components of Living Being

Materials Compounds and Components of Living Being can include but is not restricted to male and female living-beings and materials that compose, function, assist or reside within or are on or are in or are a component of said living being to include but are not restricted to being secreted or excreted or ejaculated or excreted from the living being. Materials Compounds and Components of Living Being can include but are not restricted to being associated with reproduction, sexuality, and nourishment and evacuation. Materials Compounds and Components of Living Being can include but are not restricted to a portion or a complete material, compounds and components of said living being and can include but are not restricted to an organic or inorganic chemical or molecule or compound or agent, or metal or mineral to include but not restricted to the complete material or at least a portion component of said material that can include but is not restricted to being found or associated or related to secretions to include but not restricted to breast 57 milk and breast 57 and suckling; to evacuations to include but not restricted to feces 51, sputum, sloughed cells, nasal snot or any bodily discharges; to excretions to include but not restricted to or hormones or peptides or sweat, or sebum; to secretions ejaculations to include sperm and eggs or ovary and prostate and male and female reproduction fluids and ejaculate associated materials; to sloughing to include but not restricted to full or portions of cells or cell fragments; to body elements to include but not restricted, breast 57 milk blood, sperm, or vaginal 3 fluids, vaginal 3 or penile and prostate mucosal function materials or their biologic or chemical or molecular components; to immune and genetic materials to include but not restricted to antigens and antibodies and antigen and antibody related compounds which can include but are not restricted to female general and specific immune and genetic material to include but not restricted to vaginal 3, ovary, egg/ovum, and female cell or sloughed or ejaculated material and secretion and ejaculate and hormone and female reproduced materials and specific and general reproductive system antibodies or antigens and their compounds, which can include but are not restricted to male general and specific immune and genetic material to include but not restricted to penile, prostate, sperm, or sperm component or flagella, male cell, or sloughed or ejaculated material and secretion and production specific reproductive system antibodies or antigens and their compounds; to materials, compounds and components of living being to include but not restricted to one or any combination components that can include but are not restricted to one or more of a carbohydrate, sugar, carbohydrate fragment to include but not restricted to fructose, glucose/dextrose, sucrose, lactose, maltose and to an amino acid, peptide, peptide fragment, protein, protein fragment, and to a fat and lipid, and a lipid or fat fragment; and to genetic materials to include but not restricted to nucleotides, DNA and RNA, polymerases, proteases whole and their fragments of these structures, their structurally related reproducing materials and compounds; to cells and their cell components to include whole components and fragments and their antigens to include but not restricted to whole cells and cell membranes, mitochondria, nuclei and other cell components; to include but not restricted to blood and blood products to include but not restricted to red blood cells, white blood cells, lymphocytes, eosinophils, basophils, hematocrit, glucose, and other standard blood chemistries as well as toxic blood elements to include but not restricted to poisons, metals, lethal and normal doses of organic and inorganic materials and compounds to include medications; to include but not restricted to components of urine and feces 51 and sweat and nasal and other forms of mucus; to include but not restricted to food and food products and ingestibles or digestibles or excretables that can be assessed for composition including proteins and carbohydrates and fats and infectious organisms, and toxins to include but not restricted to enterotoxins, endotoxins and antigens for infectious organisms to include but not restricted to organisms causing food poisoning of infection *E. coli, Salmonella, Shigella, Clostridia, Listeria, Campylobacter*, Norovirus (Norwalk Virus), and other bacteria and viruses and virus and bacterial and fungal and mycobacteria like organisms; to include but not restricted to inorganic and organic compounds to include but not restricted to urea, creatinine, pH, glucose and other carbohydrates and sugars, cells, proteins and protein, peptides and related components and compounds, nucleotides and related components and compounds, fats and related components and compounds, bacteria, and other infectious or noxious organisms, homeostatic organisms, pathogens; to include but not restricted to p, metals, minerals, living body cells and cell fragments, infectious agents to include but not restricted to a virus, bacteria, fungus or other pathogens; to include but not restricted to a hormone, protease, neurotransmitter, chemical signaling agent, organic cell messengers to include but not restricted to medication and their native and breakdown compounds or male secretions or their fragments or components to include but not restricted to sperm, anti-sperm antibodies, sperm antigens or penile or male reproductive system specific antibodies or antigens related to reproduction and reproduction diseases and can be indicated by a digital or analog signal 14 related to the female or male condom that can include but is not restricted to a color 95 or visual signal 14 or the an indicator of a sensor 39 that can communicate or send a signal 14 to a computer 18 or computer 18 assisted device to include but not restricted to a traditional or stand-alone, wearable 50 or handheld computing 18 or measuring device.

Herein Inclusion

Herein shall include but is not restricted to the devices and methods and materials within this application as well as cited by and described herein this document.

Artificial and Natural

Devices can include but is not restricted to the materials and chemicals utilized can be artificial or naturally occurring.

Coupling Devices Herein with Local Positioning System/Signal 14 Devices (LPS 41)

The devices herein and cited within this patent application can be coupled to LPS 41 devices and sensor 39 and as well as cited by and described herein this patent application can be used in conjunction and Coupled with the devices described and discussed herein as well as cited by and described herein this patent application. Coupling mechanisms can include but are not restricted to optical 12, thermal, chemical, electromagnetic/electric/magnetic, and mechanical/kinetic/ultrasound couplers.

Human Mechanics Powering a Device

The devices discussed herein as well as cited by and described herein, including the Local Positioning System/Signal Devices 14, can include but is not restricted to utilize and obtain and store and harvest energy 43 or power from the environment or man-made devices or biologic kinetic or electrical-mechanical, or electromagnetic 102 and solar/magnetic/UV 43/Infrared/x-ray/radioactivity/visible 20, 43 light sources and mechanical or thermal or chemical energy 43 to include but not restricted to having said energy 43 or power derived from environment or standard energy 43 sources or devices or a living being to include but not restricted to batteries, generators 99, solar panels, biothermal, electricity as well as to include but not restricted to sources to include but not restricted to living being actions and functions to include but not restricted to muscle 65 contractions to include but not restricted to thermal, electrical, electromagnetic, magnetic, proton-spin and precession of biological molecules and atoms to include but not restricted to Magnetic Resonance, chemical, biochemical and kinetic/mechanical of which these can include but are not restricted to walking and running, respiration and chest movements, heartbeats, blood flowing 104 through a blood vessel 107, eye and iris 23, 6423 movements, jaw motion, human generated vibrations, joint motion, change in the center of gravity and changes in direction, acceleration and motion, voluntary and involuntary muscle 65 movement to include healthy and disease movements, tremors, spasms, twitches, muscle 65 and tendon and ligament stretching and contracting, weight bearing, fasciculations, oscillations, muscular contractions, voluntary and involuntary, anal contractions, vaginal 3 contractions, prostate contractions, and peristalsis to include but not restricted to digestive organs, the esophagus, the stomach, the small bowel, the large bowel/colon and the anus 4, and cilia motion to include but not restricted to the mucosa and nasal mucosa, penile and vaginal 3 motion and neural tissue including but not restricted to peripheral and central nerves, spinal nerves, the brain 69 and its components, nerves associated with muscle 65 and organs and cells of the living body. Embodiments for the capture or conversion of the kinetic or electrical power can include but are not restricted to piezoelectric wafers, piezoelectric devices and piezoelectric crystals. Piezoelectric and electro kinetic and triboelectric generators 99, virus-directed designs and block co-polymers and co-polymer self-generating assemblies, efficient energy 43 harvesting devices, devices that use the stress-composition coupling in electrochemically active materials, to include but not restricted to partially Li-alloyed Si or Ge, a coupling between mechanical stress and lithium ion thermodynamics and kinetics such as high-capacity anodes of lithium ion (Li+) batteries, which drives Li+ migration and generates electricity with prototype generators 99 demonstrating power density of 0.48 µW cm-2 at 0.3 Hz; galvanic generators 99 from skin 8 and sweat; capture and conversion of living body heat dissipation, joint rotation, enforcement of body weight, vertical displacement of mass centers, as well as elastic deformation of tissue and other attachments; neuroprosthetics to include but not restricted to items such as or similar to cochlear implant, functional retinal neuroprosthetics, robotic limb prosthetics, EEG 67 and scalp brain 69 signals 14, titanium implants, electrode 106 to nerve interfaces.

In another embodiment the device can include but is not restricted to utilize nano 63 particle technology that can include but is not restricted to nano 63 particles and nano 63 batteries and nano 63 tubes and nano 63 generators 99 and nano 63 supercapacitors and nano 63 catalysts that can include but are not restricted to zeolites, sulfur-TiO2 yolkshell nano 63 architecture with internal void space for long-cycle lithium-Sulphur batteries, silicon coated carbon nano 63 tubes for anodes for Lithium (LI)-batteries, silicon, silicon nano 63 particles for grapheme cages, a catalyst made from nitrogen-doped carbon nano 63 tubes, platinum as the catalyst, silicon nano 63 particles in the anode, carbon nano 63 tubes in 3-D structured electrodes 106, Nano 63 wire 13 to include but not restricted to being coated with gel, silicon nano 63 wire 13, aligned carbon nano 63 tubes on a substrate for use as an anode or cathode, graphene anodes, carbon nano 63 fibers encapsulating the sulfur, mesoporous carbon nano 63 particles with sulfur inside the nano 63 pores, cathode using carbon nano 63 tubes, cathodes made of nano 63 composition, organic or nano 63 or inorganic derived or constructed thermal cell and that can include but is not restricted to energy 43 release by nano 63 technology to include chemisorption, physisorption that can utilize to include but not restricted to organic and inorganic materials.

A battery 84 to include but not restricted to be small enough to be implanted in the eye and iris 23, 6423 or on the skin 8 and using electromagnetic 102 energy 43 to include but not restricted to solar, magnetic, UV 43, Infrared, x-ray, radioactivity, visible 20, 43 light sources and which that can include but is not restricted to be composed of a photosensitive or photoelectric crystal or nano 63 particle crystal.

One embodiment can include thermal cells composed of nano 63 tubes that can generate electricity to include the thermal source being the living beings thermal energy 43 that that can include but is not restricted to metabolic energy 43 that can be increased or decreased utilizing methods to include but not restricted to biological metabolic stimulants, external heating of the body including thermal blankets and Infrared or UV 43 or RF 43 energy 43 directed toward the thermal cell battery 84.

A battery 84 or energy 43 collector or energy 43 or electromagnetic 102 optical 12 signal 14 transmitter that that can include but is not restricted to a photoelectric cell, a Sodium Iodide (NAI) crystal or molecule, or a scintillator that can collect or convert one form of energy 43 into another form of energy 43 that can turn-on or operate or activate or control or maneuver or cause a device to function and said energy 43 can include but is not restricted to electromagnetic 102 energy 43 and to include but not restricted to ionizing radiation, radioactivity, gamma rays, beta ray particles, radiopharmaceuticals, radiotracers, Technetium 99m, Xenon 133, Iodine 123 and Iodine 131 and conversions of these energies can include but are not restricted to luminescence, fluorescence, and phosphorescence which can activate a photodiode, or a silicon photomultiplier or an energy 43 capture and conversion or transmission device which can then produce to include but is not restricted to photons or photo-electrons or electrons or electricity which can be transmitted and/or used to turn-on, activate or cause to function a device that can include but is not restricted to a sensor 39, a send and receive device that can include but is not restricted to an LPS 41 device, GPS device which can include but are not restricted to send and receive local positioning coordinates, sensory 39, 66 information gathered from the sensor 39, or activate one of the components of the devices cited by or herein this patent application.

In another embodiment, the energy 43 generation or storage or collection device 9 or production device or a battery 84 can be directly coupled to the to include but not restricted to the LPS 41 device, the sensor 39, or a send and receive device or transmitter or a mechanical or electrical device to include but not restricted to one of the devices or components of the devices cited by or herein this patent application.

In another embodiment blood flow 104 can be used to generate energy 43. In one embodiment the energy 43 can be generated, transformed and collected and stored or dispensed by capturing the kinetic energy 43 of the pulsations, vibrations and movements of said blood vessel 107 or adjacent tissue.

In one embodiment the vibration or movement that can include but is not restricted to the expansion and contraction of the brain 69 that occurs and is transmitted through the circulatory system to include but not restricted to blood vessels 107, the heart and the capillary system. The brain 69 expands and contracts with each pulsation and this kinetic and vibrational energy 43 can be captured to include but not restricted to using piezoelectric and nano 63 technology and mechanical and electrical and magnetic and electromechanical and electromagnetic 102 and chemical and kinetic or hydraulic systems that that can include but are not restricted to generate, transform, collect/store, dispense or transmit said energy 43 that can turn-on or operate or activate or control or maneuver or cause a device to function.

In another embodiment a living body can have the living being's tissue be thermally altered to include but not restricted to warmed or cooler or any combination of these, using electromagnetic 102 energy 43 to include UV 43, Infrared, visible 20, 43 light, or RF 43 which can include but is not restricted to be generated by an RF 43 generator 99 which can be targeted or non-targeted or an MRI machine and a thermal battery 84 to include but not restricted to a nano 63 thermal cell or membrane or battery 84 or Lithium or Cadmium or small micro, macro or nano 63 battery 84 can be used to be turned-on or operated or activated or controlled or maneuvered or caused to have a device function.

In another embodiment a living body can have the living being's tissue or the energy 43 generating or that can include but is not restricted to being vibrated by external or transcutaneous or percutaneous or internal mechanical vibrators or motors or Ultrasound or HIFU (High Frequency Ultrasound) or coolants or refrigerated caps worn over a portion of the living being or any combination and the thermally induced tissue which that can include but is not restricted to being warmed or cooled can include but is not restricted to being used for absorbing or sending 16 or inducing or generating or transforming or collecting/storing or dispensing or transmitting 16 said energy 43 that can turn-on or operate or activate or control or maneuver or can cause a device to function and said device can include but is not restricted to an LPS 41 device, one of the components or one of the devices herein this patent application or in as well as cited by and described herein this patent application.

In another embodiment the battery 84 or energy 43 collector or energy 43 membrane or cell can be coupled to or can be a part of the device or can be separate from the device or can be the same as or incorporated into the device.

In another embodiment an energy 43 collecting unit/device that can include but is not restricted to a macro, micro or nano 63 particle or biologic battery 84 or energy 43 collector or membrane or cell or a biologic collector or membrane can be coupled to or can be a part of the device or can be separate from the device or can be the same as or incorporated into the device one of the components or one of the said devices and said device can include but are not restricted to an LPS 41 device herein this patent application; and the said energy 43 collecting device can include but is not restricted to being used for absorbing or receiving 16 16 or inducing or generating or transforming or collecting/storing or dispensing or transmitting 16 said energy 43 that can turn-on or operate or activate or control or maneuver or can cause a device to function.

In another embodiment an energy 43 generating unit/device that can include but is not restricted to a macro, micro or nano 63 particle or biologic generators 99 can be coupled to or can be a part of a device or can be separate from a device or can be the same as or incorporated into a device that can include but are not restricted to an LPS 41 device, one of the components or one of the said devices herein this patent application or in as cited by and described herein this patent application and the energy 43 collecting unit/device can include but is not restricted to being used for absorbing or receiving 16 or inducing or generating or transforming or collecting/storing or dispensing or transmitting 16 said energy 43 that can turn-on or operate or activate or control or maneuver or can cause the said device to function.

In another embodiment the energy 43 and power, force, impetus, control or momentum for the function of the devices herein and as described herein and including as well as cited by and described herein this patent application can mean power and energy 43 that can be harnessed from human mechanical functions to include but not restricted to breathing and walking, the circulatory system to include but not restricted to heartbeats and the transmitted energy 43 and power of the pulse and vascular expansion and contraction, blood flow 104 and the electromagnetic 102 and hydraulic energy 43 and power from flowing blood and its components. In one embodiment the harnessing of energy 43 and power that can be biological-energy 43 and can include but is not restricted to the stretching, flexing, expansion and contraction, forces generated by or from to include but not restricted to muscle 65, bones, joints, ligaments, tendons, inspiration and expiration and respiration and movement of limbs and digits, orifices opening and closing and body parts movements and this biological-energy 43 can be harnessed or stored or produced or transmuted into to include but not restricted to electromagnetic/electric/magnetic or thermal or hydraulic/kinetic/vibrational/mechanical or chemical energy 43 and can utilize devices that can include but is not restricted to macro, micro or nano 63 particle scale and that can include but is not restricted to cause devices and sensor 39 to function and can include but are not restricted to devices herein including as well as cited by and described herein this patent application, machines and transmitters 40 and receivers and energy 43 emitters, and activators 97 and facilitators and triggers and controlling mechanisms, and reactions to include but not restricted to begin, stop, function, work or operate.

Bio-Generators 99 and Bio-Energy 43 Sources and Bio-Storage

Bio-generators 99 can include but are not restricted to devices that can harness, exploit, couple, yoke energy 43 or have the capacity to create or do work or perform a function using the potential and kinetic or active/activated energy 43 from produced or present in a biological living beings and that can include but are not restricted to chemical, electrical, mechanical, kinetic, magnetic or nuclear energies.

Bio-energy 43 sources can include but are not restricted to potential and kinetic or active/activated energy 43 from produced or present in a biological living beings and that can include but are not restricted to chemical, electrical, mechanical, kinetic, and magnetic or nuclear energies.

Bio-energy 43 Storage can include but are not restricted to any device capable of storing energy 43 or power or capacity to do work that can include but is not restricted to being able to accept, take-in, accumulate, store, and can have the capacity to release said energy 43 or power or capacity to do work can include but is not restricted to when being asked to release said energy 43.

The creation of bio-devices that can be used in smaller and more confined regions of the body and which can measure molecular and smaller compound and substance 44 characteristics requires the miniaturization of energy 43 sources and energy 43 generators 99 and energy 43 storage devices.

Bio-energy 43 sources can include but are not restricted to potential and kinetic or active/activated energy 43 from produced or present in a biological living beings and that can include but are not restricted to chemical, electrical, mechanical, kinetic, magnetic or nuclear energies.

The living being body is a constant source for usable bio-energy 43, which can be renewable or non-renewable. The harvesting of this bio-energy 43 can take the form of but is not restricted to inducing or producing or creating or harnessing or manufacturing or assisting in the manufacture of said energy 43 which that can include but is not restricted to a current 100 or flow or reaction or electromagnetic 102 wave or particle or light, or electromagnetic/electric/magnetic or thermal or hydraulic/kinetic/vibrational/mechanical or chemical energy 43 or radioactive form of energy 43 which can be used to perform a function that can include but is not restricted to macro, micro or nano 63 particle devices or any combination that can include but is not restricted to turn-on or turn-off/control, facilitate, message, signal, cause to function or trigger at least one of a device that can include but is not restricted to a device that is away from or on or inside or any combination of these related to a living being and said device can be released to trigger or facilitate one of the functions or responses or devices listed herein and within the patent applications as well as cited by and described herein this patent application and can utilize the patents as well as cited by and described herein this patent application.

Bio-energy 43 occurs in every realm and region of the living being and takes many forms. To date harvesting of this bio-energy 43 to operate and drive current 100 biotechnology has been limited. Currently, most medical and biology devices and applications have utilized external sources of energy 43 to measure biologic functions and drive biologic devices that include but are not restricted to diagnose, assess and treat the living being (e.g. Imaging—MRI and CT; Chemical analysis—laboratory blood sampling; Tumor assessment percutaneous needle biopsies) Also most bio-energy 43 is being created on a scale insufficient to activate and allow current 100 devices to function; or the bio-harnessing and bio-storage methods and bio-devices have not yet been invented, devised or created sufficient to operate most current 100 large size bio-devices. Raw materials now exist to create smaller scale bio-devices including but not restricted to the continuum of macro to micro to nano 63 to molecular/atomic level/substance 44/particle sized devices. Current 100 nano 63 and carbon and silicon materials exist today to replace larger copper wire 13 and magnets 38. And these smaller devices cannot only be placed into small or difficult portions of the body without interfering with body functions but also can be placed into devices and not interfere with the function of that device and these devices can include but are not restricted to be placed in devices used on or near the living being to include but not restricted to sensor 39 or facilitators or repair activation devices on condoms; or it can be used within the body in easy to reach regions that favor small devices to include but not restricted to percutaneous devices such as thermal or glucose or blood flow 104 sensor 39 that can be used to assess body function such as a living beings blood circulation and temperature when suffering a life threatening infection or heart condition or a separate application can include use as a gauge of male or female erectile function of their relevant tumescent tissue and the sensor 39 or monitor can include but is not restricted to be used to activate a device to increase erectile tissue nerve stimulation 71 or arterial blood flow 104 or relax smooth muscle 65 and engage and assist or facilitate the sinusoids responsible for the tumescence; or it can be used within areas of the body that are difficult to access such as the brain 69 that can include but is not restricted to a margin of resected tumor and normal brain 69 and the use of the LPS 41 device with a sensor 39 to assess markers of normal and abnormal/cancerous tissue to include but not restricted to antigens or antibodies or proteins peptides carbohydrates and lipids or nucleotides or organic and inorganic substances 44 or chemicals or fragments or portions or components of the markers and also including but not restricted to the environment and microenvironment of the abnormal and tumor and partially treated and normal tissue to include but not restricted to pH, glucose, oxygen and $CO_2$, Nitrogen and other gasses, extracellular matrices, cytokines, growth factors, mechanical cues, and vascular networks for nutrient and waste exchange, lactic acid, tumor markers, angiogenesis factors, RNA/DNA or their components. The application of these new materials should allow for the replacement of larger energy 43 generators 99 and batteries. By applying adaptations of physical principles and physics (e.g. Faraday's and Maxwell's Equations and Law's and Feynman's and Einstein's Papers) new designs of energy 43 generators 99 storage devices can be devised and invented and developed to be used to assess and diagnose and treat the living body. These new and smaller devices and the energy 43 storage units/devices can serve as a driving force to allow smaller bio-devices to be invented and created that can replace devices requiring large batteries and wire 13 that must course through the body. Many of the methods and devices distributed throughout and herein this patent application and within the patents and patent applications as well as cited by and described herein this patent application are examples of methods and devices and designs to include but are not restricted to utilize bio-energy 43.

In one embodiment, the size of the devices to include but not restricted to the energy 43 generators 99 and energy 43 storage units/devices and the facilitating devices and any of their components can include but are not restricted to any continuum of macro, micro, nano 63 or molecular/atomic sizes.

Faraday's law of induction is a basic law of electromagnetism and predicts how a magnetic field 103 interacts with an electric circuit to produce an electromotive force (EMF)—a phenomenon called electromagnetic 102 induction. It is the fundamental operating principle of transformers 108, inductors, and many types of electrical motors, generators 99 and solenoids. An electromagnetic 102 current 100 or field 103 applies Faraday's Law, the Maxwell-Faraday equation and Lorentz force laws to validate and define current 100 and energy 43 generated in a field 103 of moving electrons or charged or electromagnetic 102 particles: the motional EMF generated by a magnetic force on a moving wire, and the transformer 108 EMF generated by an electric force due to a changing magnetic field 103. Richard Feynman further defined the "flux rule" that the EMF in a circuit is equal to the rate of change of the magnetic flux through the circuit applies whether the flux changes because the field 103 changes or because the circuit moves (or both) . . . Einstein's reflection on this apparent dichotomy was one of the principal paths that led Einstein to develop special relativity.

These principles can be applied to many biologic systems. In one example flowing blood with Oxygen and other Gases as well as other blood substances 44 such as hemoglobin containing Iron, which has various ionic charges depending upon in the oxygenation of the blood, provide moving charged particles and these charged particles can be used to induce an electromagnetic 102 field 103. Also, there is an ion gap, the anion or cation gaps that get produced and can include but are not restricted to Sodium NA+ and Potassium K+ as well as other blood serum molecules and elements. In addition, the charged nature of blood can be influenced by pH or by contract agents to include but not restricted to agents with iodine, gadolinium, iron and iron oxide and iron platinum, magnesium, perfluorocarbons, proteins and paramagnetic and ionic compounds.

Energy 43 to include but not restricted to heat, kinetic/vibration/pulsations, movement, and electric and electrical charges and electromagnetic 102 energy 43, chemical energy 43 can be captured from but not restricted to flowing blood and lymphatics; the neuronal system and nerves and nerve signals 14 to include but not restricted to synapses and axons and nerve bodies and endings; brain 69 function and the energy 43 given off by the brain 69, muscle 65 and the musculoskeletal and movement systems, the sensory 39, 66 system, the gastrointestinal track and, the heart and circulatory system, the skin 8 and body covering 36 systems, the respiratory system and the O2 and CO2 exchange system, the genitourinary system and any other system of body function. In one embodiment these systems can exchange or have moving charged particles and the moving charged particles can induce an electromagnetic 102 force that can include but is not restricted to electricity or magnetism and the flowing blood can be used to create a generator 99. In one embodiment to include but not restricted to arterial blood, which is highly charged can generate an electromagnetic 102 field 103 and can include but is not restricted to this said flowing blood inducing by macro, micro or nano 63 particle generators 99 that can include but are not restricted to being composed and consisting of an magnet/electromagnet, a coil, and electrodes 106, as well as other components used for creating a generator 99 of input and output of an electromagnetic 102 generating system which can include but is not restricted to macro, micro or nano 63 particle wire 13 and that can include but is not restricted to induce a current 100 or flow or reaction or electromagnetic 102 wave or particle or light, or electromagnetic/electric/magnetic or thermal or hydraulic/kinetic/vibrational/mechanical or chemical energy 43 or radioactive. In another embodiment the functioning of the generator 99 can be facilitated or turned on or off or operated when the blood has a charge to include but not restricted to a charge below which the generator 99 does not function and a charge above which the generator 99 does operate and in one embodiment to include but not restricted to a system in which the charge of the blood can be augmented by to include but not restricted to a contrast agent, a change in pH or an agent that alters the ionic charge that can to include but not restricted to be dispensed or instilled, or delivered, distributed, conveyed, supplied—onto or into or within the circulatory or circulatory/blood system/stream on a temporal basis that can be continuous or discontinuous. In another embodiment the magnetic energy 43/field 103 can be externally aligned to the interrogated or utilized blood vessel 107 or blood vessels 107 and can serve as the magnet/electromagnet to include but not restricted to an MRI magnet or a standalone magnet or a peripheral magnet or mobile or non-mobile magnet that can include but is not restricted to be worn or not-worn and to include but not restricted to being within, on or outside of the living being in whom/which the energy 43 is being generated.

In another embodiment to include but not restricted to a send/transmit or receive or sensor 39 can include but not restricted to an Radiofrequency Localization (RFL) or Identification (ID) or Tagging (TAG) device and said device can include but is not restricted to an LPS 41 device to include but not restricted an LPS 41 or LPS 41-like or GPS and GPS-like device, a treatment or ablation device of living tissue of a living being, or any device within this patent application as well as cited by or herein this patent application. The embodiments described for powering, energizing, turning on and off and enervating, or accessing and processing an RFL, ID or TAG or LPS 41 can include and apply but are not restricted to the LPS 41 and LPS 41-like and GPS-like devices and are referred herein as RFL and Identification or Tagging. In one embodiment the LPS 41 and LPS 41-like devices can include but are not restricted to be to include but not restricted to activated and turned on and off and powered or do work or enervated or energized by the methods and devices that are used for and by Radiofrequency Localization (RFL) or Identification (ID) or Tagging (Tg) or LPS 41 devices or methods and such devices and methods include but are not restricted to the Radiofrequency Localization (RFL) or Identification (ID) or Tagging (Tg), or LPS 41 device or methods.

The Radiofrequency Localization (RFL) or Identification (ID) or Tagging (Tg) or LPS 41 device can be passive, active or battery 84-assisted passive. An active Radiofrequency Localization (RFL) or Identification or Tagging or LPS 41 device can include but is not restricted to be coupled, or associated or integrated with a battery 84 or energy 43 source and can periodically transmit its signal. A Radiofrequency Localization (RFL) or Identification or Tagging or LPS 41 device can include but is not restricted to a battery 84-assisted passive device that can include but is not restricted to having a small battery 84 on board which is activated when in the presence of an Radiofrequency Localization (RFL) or Identification or Tagging or LPS 41 device reader. A Radiofrequency Localization (RFL) or Identification or Tagging or LPS 41 device can include but is not restricted to a passive device can include but is not restricted to have no battery 84: instead, the Radiofrequency Localization (RFL) or Identification or Tagging or LPS 41 device uses the radio energy 43 transmitted by the user or Radiofrequency Localization (RFL) or Identification or Tagging or LPS 41 device reader and can include but is not restricted to be illuminated, irradiated, induced, interrogated, stimulated, prompted or provoked with a power level adequate for signal 14 transmission;

Radiofrequency Localization (RFL) or Identification or Tagging or LPS 41 devices that can include but is not restricted to read-only and have an assigned serial number that can include but is not restricted to being a code or a key or a unique identifier which can include but is not restricted to being interpreted or identified or deciphered, understood or translated by to include but not restricted to a computer 18 or monitor or database device.

Radiofrequency Localization (RFL) or Identification or Tagging or LPS 41 devices that can include but is not restricted to a read/write, where object-specific data can be written into the Radiofrequency Localization (RFL) or Identification or Tagging or LPS 41 devices by the system user computer 18 or monitor or database device, which can include but is not restricted to being interpreted or identified or deciphered, understood or translated by to include but not restricted to a computer 18 or monitor or database device.

In another embodiment Radiofrequency Localization (RFL) or Identification or Tagging or LPS 41 devices can include but is not restricted to programmable devices that can include but is not restricted to being write or read to include but not restricted to once or multiple times or un-programmed or blank Radiofrequency Localization (RFL) or Identification or Tagging or LPS 41 devices may be written with to include but not restricted to an electronic code or a key or a unique identifier by the to include but not restricted to the user computer 18 or monitor or database device.

In another embodiment Radiofrequency Localization (RFL) or Identification or Tagging or LPS 41 devices can include but is not restricted to contain at least one of integrated circuits for storing and processing information, modulating and demodulating a radio-frequency (RF) signal, collecting power or energy 43 to include but not restricted to DC power, AC power or an energy 43 source to include but not restricted to electromagnetic/electrical/magnetic or thermal or hydraulic/kinetic/vibrational/mechanical or chemical and/or biological energy 43 or radioactive energy 43 to include but not restricted to macro, micro or nano 63 particle devices or any combination of these that can power the device to include but not restricted to/from the incident reader signal, and other specialized functions; and an antenna for receiving 16 and transmitting 16 the signal. The Radiofrequency Localization (RFL) or Identification or Tagging or LPS 41 devices information can include but is not restricted to be stored in a memory device to include but not restricted to a non-volatile or static or unchanging or volatile or non-static or changing memory device.

The Radiofrequency Localization (RFL) or Identification or Tagging or LPS 41 devices can include but is not restricted to fixed or programmable logic for processing of the transmission or receiving 16 or sensor 39 data;

In another embodiment Radiofrequency Localization (RFL) or Identification or Tagging or LPS 41 devices can include but is not restricted to transmit an encoded radio signal 14 to interrogate the Radiofrequency Localization (RFL) or Identification or Tagging or LPS 41 devices to include but not restricted to their location or identification or tagging or sensor 39 information or any combination;

In another embodiment Radiofrequency Localization (RFL) or Identification or Tagging or LPS 41 devices can include but is not restricted to receive the message and then respond with its location or identification or tagging and sensory 39, 66 and other information. This can include but not restricted to their location or identification or tagging or sensor 39 information or any combination;

In another embodiment Radiofrequency Localization (RFL) or Identification or Tagging or LPS 41 devices can include but is not restricted to a unique serial number, location or identification or tagging or sensor 39 information or any combination and can include biological to include but not restricted to or non-biological information to include but not restricted to energies and information, chemicals and substances 44 to include but not restricted to thermal, hot or cold, electromagnetic, UV 43, Infrared, visible 20, 43 light, electrical, chemical, aqueous and non-aqueous chemicals, lipids and fat-like and oil, protein-like and amino acids, peptides and nucleotides, and carbohydrate, Kinetic, Ultrasound, pressure and their effects and processes and reactions energies or methods or materials and dates, time and temporal information, locations or other specific information. Since Radiofrequency Localization (RFL) or Identification or Tagging or LPS 41 devices have individual serial numbers, the RFID system design can discriminate among several Radiofrequency Localization (RFL) or Identification or Tagging or LPS 41 devices that might be within the range of the to include but not restricted to the RFID system and the sensor 39 system and read them to include but not restricted to sequentially, simultaneously or any combination of these;

In another embodiment Radiofrequency Localization (RFL) or Identification or Tagging or LPS 41 devices can include but is not restricted to the data can be interpreted or read by readers to include but not restricted to RFID systems that can be classified by the type of Radiofrequency Localization (RFL) or Identification or Tagging or LPS 41 devices and their readers/interpreters;

In one embodiment the Radiofrequency Localization (RFL) or Identification or Tagging or LPS 41 device can include but is not restricted to a passive reader which only receives radio signals 14 from active tags (battery 84 operated, transmit only). The reception range of such a system readerinterpreter can include but is not restricted from approximately 0-600 meters but can be lesser or greater as permitted by the specific device and application.

In another embodiment the Radiofrequency Localization (RFL) or Identification or Tagging or LPS 41 device can include but is not restricted to Active Reader with a Passive Radiofrequency Localization (RFL) or Identification or Tagging or LPS 41 device system that can include but is not restricted to have an active reader, that can include but is not restricted to transmits energy 43 that can include but is not restricted to interrogator signals 14 and energy 43 electromagnetic/electrical/magnetic or thermal or hydraulic/kinetic/vibrational/mechanical or chemical and/or biological energy 43 or radioactive and can be induced by to include but not restricted to macro, micro or nano 63 particle energies and also receives authentication or unique signals 14 from passive tags and Radiofrequency Localization (RFL) or Identification or Sensor 39 or Tagging or LPS 41 device In another embodiment the Radiofrequency Localization (RFL) or Identification or Tagging or LPS 41 device can include but is not restricted to an Active Reader Active Tag (ARAT) system uses active tags awoken with an interrogator signal 14 from the active reader. A variation of this system could also use a Battery 84-Assisted Passive (BAP) signal 14 or tag or LPS 41, which acts like a passive signal 14 or tag or LPS 41 but has a small battery 84 to power the signal 14 or tag or LPS 41 return reporting signal.

In another embodiment the Radiofrequency Localization (RFL) or Identification or Tagging or LPS 41 device can include but is not restricted to fixed readers can be set up to create a specific interrogation zone, which can be tightly controlled. This allows a highly defined reading area for when signal 14 or tag or LPS 41 go in and out of the interrogation zone. Mobile readers may be hand-held or mounted on carts or vehicles.

In another embodiment the Radiofrequency Localization (RFL) or Identification or Tagging or LPS 41 device can include but is not restricted to signaling between the reader and the tag or LPS 41 is done in several different compatible and incompatible ways, depending on the frequency band used by the tag or LPS 41. Tags or LPS 41 operating on LF and HF bands are, in terms of radio wavelength, very close to the reader antenna because they are only a small percentage of a wavelength away. Another embodiment can include but is not restricted to the near field 103 region, in which the signal 14 or tag or LPS 41 is closely coupled electrically with the transmitter in the reader. The signal 14 or tag or LPS 41 can modulate the field 103 produced by the reader by changing the electrical loading the signal 14 or tag or LPS 41 represents. By switching between lower and higher relative loads, the signal 14 or tag or LPS 41 produces a change that the reader can detect. In another embodiment at UHF and higher frequencies, the signal 14 or tag or LPS 41 is more than one radio wavelength away from the reader, requiring a different approach. The signal 14 or tag or LPS 41 can backscatter a signal. Another embodiment includes but is not restricted to active signal 14 or tag or LPS 41 that may contain functionally separated transmitters 40 and receivers 40, and the signal 14 or tag or LPS 41 need not respond on a frequency related to the reader's interrogation signal.

Another embodiment can include but is not restricted an Electronic Product Code (EPC), which is one common type of data stored in a signal 14 or tag or LPS 41. When written into the tag by an RFID printer 59, the tag can include but is not restricted to contain a 96-bit string of data and can include but are not restricted to have the first eight bits are a header which identifies the version of the protocol; the next 28 bits identify the organization that manages the data for this tag; the organization number is assigned by the EPC Global consortium; the next 24 bits are an object class, identifying the kind of product; and the last 36 bits are a unique serial number for a particular tag. These last two fields 103 are set by the organization that issued the tag. Rather like a URL, the total electronic product code number can be used as a key into a global database to uniquely identify a particular product.

Another embodiment can include but is not restricted to contain one tag that will respond to a signal 14 or tag or LPS 41 reader. One embodiment can include but is not restricted to devices to include but is not restricted to at least one individual sensor 39 or LPS 41 devices or any combination of these.

In another embodiment, detection can include but is not restricted to movement, change in orientation, location, collision, compression of devices, biologic and physiologic functions, is important to allow reading of data to include but not restricted to changes in temporal, spatial, physiologic, biologic and any combination of these and these can include but is not restricted to being on the atomic, molecular and single or multiple compound scales and can include but are not restricted to proteins/peptides/amino acids; carbohydrates; fats/fatty acids; nucleotides/pyrimidine/purine; biologic markers and biologically active or non-active expressed compounds and each groups structural components and derivatives and related compounds to include but not restricted to structures produced, expressed, created, formed to include but not restricted to malignant and benign structures to include but not restricted to cells, organelles, organs, tumors or components or any combinations of these in or by a living tissue, or organism.

Protocols embodiments can include but are not restricted to two different types of protocols to include but not restricted to a singular/singulation ID signal 14 or tag or LPS 41, a specific and defines/particular signal 14 or tag or LPS 41, which can include but is not restricted to allow data to be read in the midst of many other similar tags. Another embodiment can include but is not restricted to a slotted Aloha System, the reader broadcasts an initialization command and a parameter that the signal 14 or tag or LPS 41 individually use to pseudo-randomly delay their responses which can include but is not restricted to using an adaptive binary tree protocol, in which the reader sends an initialization symbol and then transmits one bit of ID, location or sensor 39 data at a time; only signal 14 or tag or LPS 41 with matching bits respond, and eventually only one signal 14 or tag or LPS 41 matches the complete the ID, location or sensor 39 string.

Another embodiment that can include but is not restricted to a binary tree method for identifying an RFID signal 14 or tag or LPS 41. Another embodiment can include but is not restricted to a bulk reading method, a strategy for interrogating multiple signal 14 or tag or LPS 41 at the same time. RFID readers and devices can be miniaturized to include but not restricted to sizes of millimeters and less than millimeters, including but not restricted to RFID chips of 0.05 mm×0.05 mm or smaller and can include but is not restricted to mu-chips using the silicon-on-insulator (SOI) process and these dust-sized chips can store 38-digit numbers using 128-bit Read Only Memory (ROM).

In an AC generator 99, as a metal coil passes through the magnetic field 103 in a generator 99, the electrical power produced constantly changes. At first, the generated electric current 100 moves in one direction (as from left to right). Then, when the coil reaches a position where it is parallel to the magnetic lines of force, no current 100 at all is produced. Later, as the coil continues to rotate, it cuts through magnetic lines of force in the opposite direction, and the electrical current 100 generated travels in the opposite direction (as from right to left).

One embodiment can include but is not restricted to an AC generator 99 that can include but is not restricted to be modified to produce direct current 100 (DC) electricity also, which can include but is not restricted to include a commutator, which can be a slip ring that has been cut in half, with both halves insulated from each other and the brushes attached to each half of the commutator are arranged so that at the moment the direction of the current 100 in the coil reverses, they slip from one half of the commutator to the other, such that the current 100 that flows into the external circuit, therefore, is always traveling in the same direction and the energy 43 can stored and or utilized as an energy 43 source to drive, activate or cause to function to include but not restricted to a device or a LPS 41 or sensor 39.

Another embodiment can include but is not restricted to magnetic flow meters or variations or derivatives of magnetic flow meters that can include but are not restricted to use a magnetic field 103 applied to the device, which results in a potential difference proportional to the flow velocity perpendicular to the flux lines and these potential difference are sensed by electrodes 106 aligned perpendicular to the flow and the applied magnetic field 103. The physical principle at work is Faraday's law of electromagnetic 102 induction. The magnetic flow meter requires a conducting fluid and a non-conducting pipe lining and the magnetic flow meters can have auxiliary transducers installed to clean the electrodes 106 in place. The applied magnetic field 103 is pulsed, which allows the flow meter to cancel out the effect of stray voltage in the piping system and can include but is not restricted to the energy 43 that would be utilized to assess flow can stored and or utilized as an energy 43 source to drive, activate or cause to function to include but not restricted to a device or a LPS 41 or sensor 39.

Figure 20:
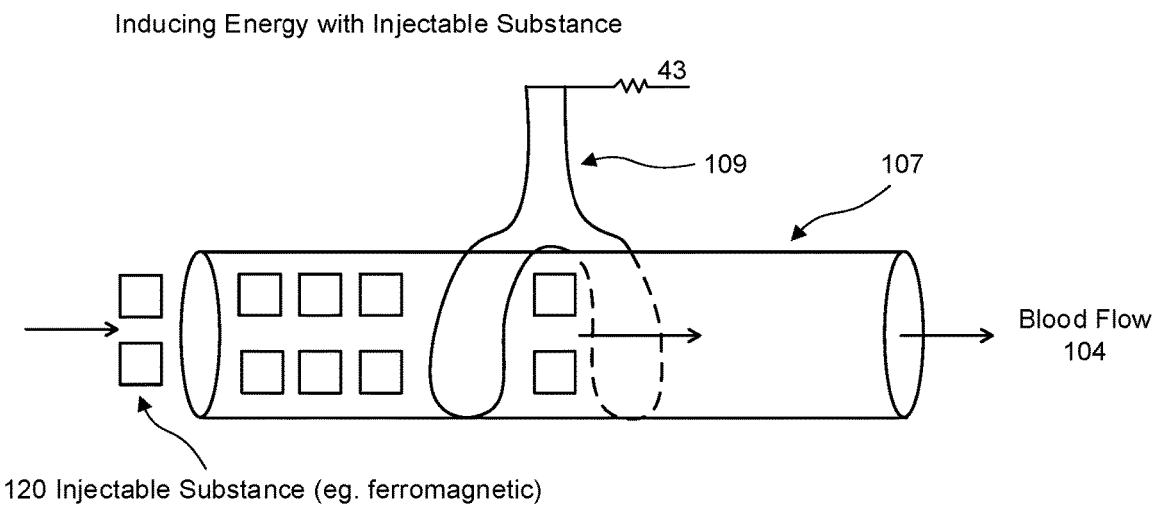
FIG. 20 is a schematic rendering of a micro-bioenergy 43 generator 99 related to blood flow 104 and the injection of a substances 44 such as magnetic and ferromagnetic substances 44 to induce the generation of energy 43.

FIG. 20 is a schematic rendering of a micro-bioenergy 43 generator 99 related to blood flow 104 and the injection of a substances 44, such as magnetic and ferromagnetic substances 44, to induce the generation of energy 43.

In another embodiment energy 43 can include but is not restricted to be stored or generated used to activate a device or sensor 39 with a non-contact electromagnetic 102 flow meter that can include but is not restricted to a system to include a Lorentz force flow meter (LFF) or a variant or derivative or combination of an LFF which can convert bulk Lorentz forces resulting from the interaction between a solids or gasses or liquids containing metallic or charged particles or compounds in motion and an applied magnetic field 103 and this can be performed to include but not restricted to contrast agents that can include to be composed of metallic components and can include but is not restricted to gadolinium, iodinated, barium, iron, manganese, perfluorocarbon and other metals an which can include but is not restricted to ionic and non-ionic agents and ferromagnetic and non-ferromagnetic substances 44 as well as to include but not restricted to solids liquids and gasses which can include carbon based and carbon dioxide and micro-bubbles and liposomal delivery 42 systems and any elements or compounds which are naturally occurring or which can be infused to augment energy 43 creation or storage or activation and which can generate forces that can generate and store and activate energy 43 using flow meter variants and derivatives and devices that can energize or a device or sensor 39.

In another embodiment a pulsatile flow generator 99 can include but is not restricted to harness and store energy 43 via the capture of forces to include but not restricted to motion/mechanical/contraction and expansions and compressions, that can include but is not restricted to rotary and linear forces to include capture by macro, micro and nano 63 devices to include but not restricted to mechanical, bladder 76, piezoelectric that can generate energy 43 to include but not restricted to being responsive to motion of the body to include but not restricted to vascular arterial and venous movements, flowing blood and cardiovascular motion, muscular movements to include but not restricted to smooth and striated muscle 65, voluntary and involuntary movements, and skin 8 movement, and bowel and other gastrointestinal movement activity and peristalsis, and bladder 76 and other genitourinary motion, and penile and vaginal 3 and other reproductive movements and brain 69 contraction and expansion and heart and cardiovascular motion and movements, as well as other bodily functions that create motion or movement either regular or non-regular or irregular in periodicity.

In another embodiment can include but is not restricted to a DC generator 99 that can include a generator 99 that can include but is not restricted to behave in accordance to Faraday's laws of electromagnetic 102 induction, whenever a conductor is placed in a varying magnetic field 103 or when a moving conductor is moved in a magnetic field 103, an electromotive force (EMF) gets induced in the conductor and that can include but is not restricted to create, generate and store energy 43 that can activate a device or sensor 39 and to include but not restricted to being responsive to motion of the body to include but not restricted to vascular arterial and venous movements, flowing blood, fluids and substances 44 that pass though or involve muscular movements that can induce EMF to include but not restricted to smooth and striated muscle 65, voluntary and involuntary movements, and skin 8 movement, and bowel and other gastrointestinal movement activity and peristalsis, and bladder 76 and other genitourinary motion, and penile and vaginal 3 and other reproductive movements and cardiovascular motion and respiratory contraction and expansion and movement of gases and brain 69 contraction and expansion and movements, as well as other bodily functions that create motion or movement either regular or non-regular or irregular in periodicity and that can include but is not restricted to interaction between a solids or gasses or liquids containing metallic or charged particles or compounds in motion and an applied magnetic field 103 and this can be performed to include but not restricted to contrast agents that can include to be composed of metallic components and can include but is not restricted to gadolinium, iodinated, barium, iron, manganese, perfluorocarbon and other metals an which can include but is not restricted to ionic and non-ionic agents and ferromagnetic and non-ferromagnetic substances 44 as well as to include but not restricted to solids liquids and gasses which can include carbon based and carbon dioxide and micro-bubbles and liposomal delivery 42 systems and any elements or compounds which are naturally occurring or which can be infused to augment energy 43 creation or storage or activation and which can generate forces that can generate and store and activate energy 43 using DC generator 99 variants and derivatives and devices that can energize or a device or sensor 39.

In one embodiment continuous flowing blood can be the primary source of energy 43 creation. Blood flow 104 is the continuous running of blood in the cardiovascular system and can be pulsating in the large arteries, diminishing in amplitude as it approaches the capillaries and none pulsating in the veins. Blood flow 104 can include but is not restricted to elements of laminar, concentric, telescoping and turbulent. The concept of electromagnetic 102 flow measurement was the successor of Fick's Principle and Fabre used these principles to measure blood flow 104 noninvasively with an electromagnetic 102 flow meter. The operation principle behind the electromagnetic 102 blood flow 104 meters is Faraday's law of electromagnetic 102 induction which states that if electrical current 100 carrying conductor moves at right angle through a magnetic field 103, an electromotive force is induced in the conductor. In the case of electromagnetic 102 blood flow 104 meters, while the blood flows between forces of magnetic field 103, which are provided by the electromagnetic 102 blood flow 104 meters, voltage is induced in the blood stream. The induced voltage is perpendicular to the magnetic field 103 and the direction of the flow of blood. Then the blood flow 104 transducer probes placed 90 degree to the direction of the blood flow 104 pick up this voltage. To date the goal has been to measure blood flow 104 but for the purposes of this invention the goal is to repurpose and reconfigure the flow meter to produce or store or generate energy 43 or any combination of these to activate or make work or drive a device or sensor 39, and which said energy 43 can include but is not restricted to being in the preferred embodiment electromagnetic-electrical-magnetic or other forms of energy 43 described herein. One embodiment can include but is not restricted to where the magnitude of voltage induced in the blood stream is proportional to the volume and velocity of the blood flow 104 and can be given by the following formula and where:

e=induced voltage, V
B=strength of the magnetic field 103, T
u=instantaneous velocity of blood, m/s
L=length between electrodes 106

In place of creating a flow determination a current 100 can be derived to power devices and sensor 39. Embodiments can include but is not restricted to DC and AC current 100 and the two most commonly used alternating electromagnetic 102 currents 100 can include but are not restricted sine wave and square wave electromagnetic 102 converted currents 100.

The sine wave electromagnetic 102 blood flow 104 generation can include but is not restricted to using wave alternating current 100 to generate the required magnetic field 103 and different compensation mechanisms can include but is not restricted to be used to modulate voltage and methods that include but are not restricted injecting equal magnitude voltage with reversed polarity and transformer 108 voltage or using a gated sine wave amplifier.

Another embodiment can include using more than one capacitor for varying voltage phase and combining these voltages such that the voltage can generated or utilized or stored and annealed or combined to result in a harmonic voltage. Another embodiment can include but is not restricted to utilizing each of the one or more than one capacitor's stored or accumulated different phase voltages, which may have similar or different phases of voltage and voltage direction which can be stored an used in harmony prior to being delivered to activate, generate, power or drive or make or cause the device or sensor 39 to function or work or operate or run or perform. Another embodiment can include but is not restricted to having one or more than one transformer s 108 use or coordinate or modulate the voltage or phase of the voltage or having the one. Another embodiment can include but is not restricted to having more devices or sensor 39 have the ability to use or coordinate or modulate the voltage or phase of the voltage or any combination of these devices or sensor 39 or methods.

One embodiment can include but is not restricted to having automatic quadrature suppression which adjusts the amount of supplied inverted signal 14 automatically based on the magnitude of the transformer 108 voltage and that can include but is not restricted to having the effect on the inverted signal 14 to cancel out the transformer 108 voltage so that the final read of the instrument is within the acceptable range Another embodiment can include quadrature-suppression electromagnetic 102 blood that detects the amplifier quadrature voltage and the quadrature generator 99 feeds back a voltage to balance out the probe-generated transformer 108 voltage Another embodiment can include but is not restricted to utilizing the square wave electromagnetic 102 blood flow 104 generator 99, the excitation is square wave alternating current 100, and the induced voltage is a square wave. One advantage of the square wave electromagnetic 102 blood flow 104 meter over the sine wave counterpart is the magnetization process. If the magnetization flux gets its maximum value, it doesn't need the application of any further potential difference (voltage) until the next transition occurs, which is not usual for sine wave excitation and in addition the width and duration of the transformer 108 voltage as the square wave electromagnetic 102 blood flow 104 generator 99 can include but is not restricted to the transformer 108 voltage appearing as a spike at the beginning of each transition for a short period of time which can be circumvented by using gated High amplitude voltage spikes can be a drawback causing amplifier overloading, which causes significant voltage change across the coupling and biasing capacitors. In turn this leads to a long time recovery and distortion but can be mitigated by storage of the charge or stepwise activation of the battery 84 or device or sensor 39.

One embodiment can include but is not restricted to probes or devices, which consist of electromagnetic 102 materials or non-electromagnetic 102 materials or fixed magnets 38 which can include but are not restricted to being with appropriate electric current 100 to produce the required magnetic field 103 and that can include but are not restricted to being composed of two point electrodes 106 which are made up of predominantly stainless steel or platinum. Which can include but are not restricted to be partially or fully encapsulated in a biologically inert material that can include but are not restricted to silicone, rubber, glass, a bio-inert gels and hydrophilic gels/hydrogels, bioglasses and polycrystalline ceramics, Titanium-Aluminum Vanadium Alloy, phosphoryl choline and derivatives, Polyethylene oxide polymers, silk and silk variants, diamond/ultranano 63 crystalline diamond, polyglycolic acid materials, calcium, potassium and other elements and compounds to include but not restricted to hydroxyappetite, uric acid as well as their derivatives as well as other inorganic minerals and metals that exist within the biologic organism to include but not restricted to include but not restricted to antigens or antibodies or proteins peptides carbohydrates and lipids or nucleotides or organic and inorganic substances 44 or chemicals or fragments or portions or components or materials used for or as prosthetic and organic materials that can include but are not restricted to cells or tissue or compounds or materials that are from that living being or from another living being to include but not restricted to grafts that can be Autologous, Isogeneic, Allogeneic, Xenogeneic in nature or any combination or these. These materials can be on the macro, micro or nano 63 or sub nano 63 particle level.

In one embodiment, the material chosen can include bio-similar or can be bio-dissimilar materials. Examples of embodiments of a bio-similar material can include but is not restricted to hydroxyapatite in teeth and bone or other parts of the body; glial and other neural cells in the brain 69 or neural cells; calcium or calcium deposits in the kidney or brain 69 or other parts of the body; lipids and fat within fat deposits or other parts of the body; collagen within the skin 8 or connective tissue or other parts of the body. Examples of embodiments of a bio-dissimilar material can include but is not restricted to hydroxyapatite or a hydroxyapatite lattice in breast 57 tissue/fat or in the skin 8 or brain 69 or other parts of the body; glial and other neural cells in muscle 65 or fat or connective tissue Examples of embodiments of a bio-similar material can include but is not restricted to hydroxyapatite in teeth and bone or other parts of the body; glial and other neural cells in the brain 69 or neural cells or other parts of the body; calcium or calcium deposits in the kidney or brain 69 or other parts of the body; lipids and fat within fat deposits or other parts of the body; collagen within the brain 69 or associated with neural tissue or other parts of the body; calcium or calcium deposits in the kidney or brain 69 or other parts of the body; lipids and fat within brain 69 or bone or solid and hollow viscous organisms or muscle 65 or hair or nails or other parts of the body; collagen within the skin 8 or connective tissue or other parts of the body. Each of these embodiments can include any combination of ectodermal, endodermal tissue and can occur in any combination of ectodermal, endodermal tissue.

One embodiment can include but is not restricted to alternating current 100 electromagnetic 102 blood flow 104 generators 99 with transducers, cuff type flow generators 99, with placement of the cuff in association with blood vessel 107 walls and blood vessel 107 wall conductivity the intracellular fluid. In one embodiment increasing the hematocrit, iron or ferromagnetic nature of the blood or fluid or flow in the vessel or hollow viscous structure or changing the flow rate changes the energy 43 generated In one embodiment blood flow 104 is one of the physiological parameters to generate, store, or create activating energy 43 and electromagnetic 102 energy 43. Generally, blood flow 104 rates range from 1 m/sec to 300 ml/sec in the venous and aortic structures and the frequency of aortic or venous blood flow 104 varies from up to extend up to 100 Hz. Electromagnetic 102 blood can measure a cardiac output of 4 l/min to 25 l/min with a frequency range of de to 20, 43 Hz. The frequency can also be as high as 60 Hz. Embodiment can include but are not restricted to band pass filters and a low pass filter which is a capacitor-resistor (RC) filter.

Other embodiments include but are not restricted to micro-power and micro micro-generators 99 and nano 63 generator 99 technologies that can include but is not restricted to Thermal Acoustic Piezo Energy 43 Conversion (TAPEC), which convert waste heat into acoustic resonance and then into electricity; Ultra-Wide-Bandwidth micro-scale piezoelectric energy 43 harvesting device by exploiting the nonlinear stiffness of a doubly clamped micro-electromechanical systems (MEMS) resonator; nano 63 meter-scale generators 99 which can include but are not restricted to arrays of vertically or horizontally or mixed aligned nano 63 wire 13 that move inside a "zigzag" plate electrode 106 that can include but is not restricted to zinc and zinc oxide and gold and silver platinum and other metals as well as inorganic and organic materials to include but not restricted to but not restricted to silicon and biologic materials, and that can include but is not restricted to nano 63 device which can have the capacity to generate energy 43 or power to be used to activate or power biomedical devices transmission that can include but is not restricted to data collection and transmission and control.

In another embodiment an electrode 106 can create direct current 100 or alternating current 100 created by movement to include but not restricted to flowing/pulsatile blood, a beating heart a peristalsing organ or bio-structure or electrical flow to include but not restricted to axonal or neural moving electrical flow and changing electrical charges.

In another embodiment the energy 43 produced by the living being can be harvested and amplified and stored to include but not restricted to the brain 69, which creates its own electrical energy 43 that can be captured by electrodes 106 or electrode 106-like devices/electrical energy 43 gathering devices and can include harvesting the energy 43 to include from the scalp and skull region, the Dura/Meninges region, the arachnoid/cerebral fluid spaces or from the brain 69 matter itself and can include electrodes 106 or electrode 106-like devices/electrical energy 43 gathering devices that can include but is not restricted to be placed onto, into, or within these structures/regions.

In one embodiment the electromagnetic 102 force/power can be amplified by infusing or injecting an inducing material into a blood vessel 107 or into a hollow viscous organ and said material can include but is not restricted to solids or gasses or liquids containing metallic or charged particles or compounds in motion and an applied magnetic field 103 and this can be performed to include but not restricted to contrast agents that can include to be composed of metallic components and can include but is not restricted to MR contrast agents, gadolinium, iodinated, barium, iron, manganese, perfluorocarbon and other metals and which can include but is not restricted to ionic and non-ionic agents and ferromagnetic and non-ferromagnetic substances 44 as well as to include but not restricted to solids liquids and gasses which can include carbon based and carbon dioxide and micro-bubbles and liposomal delivery 42 systems and any elements or compounds which are naturally occurring or which can be infused to augment energy 43 creation or storage or activation and which can generate forces that can generate and store and activate energy 43 using DC generators 99 variants and derivatives and AC generators 99 and generator 99 variants and devices that can energize or power a device or sensor 39.

One embodiment can include but is not restricted to an energy 43 threshold below, which the generator 99, battery 84, or energy 43 or power source is below the threshold to activate the device or sensor 39 such that the said device and sensor 39 are in the OFF or not yet activated state. When an inducing material is infused into a blood vessel 107 or a hollow viscous organ the energy 43 is above the energy 43 threshold to activate the device or sensor 39, or the generator 99, battery 84, or energy 43 or power source becomes or is above the energy 43 threshold to activate the device or sensor 39 such that the said device and sensor 39 are transformed or powered into an ON or activated state.

In another embodiment energy 43 can include but is not restricted to kinetic and mechanical and thermal electromagnetic, electrical, magnetic, or hydraulic/kinetic/vibrational/mechanical or chemical energy 43 or radioactive biological energy 43 and can include but is not restricted be to be used to generate, transform, power, collect and stored and dispensed energy 43 to power and activate a device and sensor 39 and can include but are not restricted to a form that is steady or consistent or changing or pulsatile or inconsistent and these naturally occurring bio-energy 43 forms can be enhanced or induced or activated or amplified by applying additional forms of energy 43 to the living being to include but not restricted to non-biologic and biologic induced kinetic and mechanical and thermal electromagnetic, electrical, magnetic, or hydraulic/kinetic/vibrational/ultrasonic/mechanical or chemical energy 43 or radioactive energy 43 and can include but is not restricted to electrical flow to include but not restricted to axonal or neural moving electrical flow and changing electrical charges.

Another embodiment can include electrodes 106 or energy 43 harvesters that can include but is not restricted to capturing and storing or transmitting 16 bursts of energy 43 or electrical or magnet currents 100 that are associated with electrical or magnetic fields 103 in living beings and that can include but is not restricted to being associated with brain 69 and neuron activity, sensory 39, 66 structures, blood vessels 107, the heart and cardiovascular system, muscle 65 and the musculoskeletal system, the lymphatic system, and structures that move or peristalsis, the respiration system, the digestive/gastrointestinal system and its accessory organs, hormonal systems, the genitourinary system, reproduction, and other biological functions. In another embodiment, blood intake of a region increases firing or neural activity and increases the energy 43 intake of the neurons, which can be captured. In another embodiment, the change in the magnetic properties when hemoglobin is deoxygenated and deoxygenated can be used to regulate energy 43 and influence thresholds to include but not restricted to powering and turning ON and OFF a device or sensor 39 or an energy 43 storage unit.

In another embodiment, the bio-generator 99, can include but is not restricted to being an exoskeleton that can include but is not restricted to an external stent or an external wire or mesh or network that can include but is not restricted to fully or partially surrounding a surrounding a biological structure and that can include but is not restricted to being macro or micro or nano 63 sized and can include but is not restricted to being magnetic or non-magnetic. In one embodiment the exoskeleton can include but is not restricted to being utilized as a component or an anchor 37 37 for a bio-generator 99, bio-storage unit, the bio-energy 43 capture device or for a device which can include but is not restricted to being a sensor 39 an LPS 41 device a locator or any of the devices described herein this patent application or in the cited patents and patent applications.

In another embodiment, the bio-generator 99, can include but is not restricted to being an exoskeleton that can include but is not restricted to an external stent or an external wire or mesh or network that can include but is not restricted to fully or partially surrounding a surrounding a biological structure and that can include but is not restricted to being macro or micro or nano 63 sized and can include but is not restricted to being magnetic or non-magnetic. In one embodiment the exoskeleton can include but is not restricted to being utilized as a component or an anchor 37 37 for a bio-generator 99, bio-storage unit, the bio-energy 43 capture device or for a device which can include but is not restricted to being a sensor 39 an LPS 41 device a locator or any of the devices described herein or in the cited patents. In one embodiment the exoskeleton can fully or partially surround a blood vascular, vessel, cardiac structure or a neural structure or a genitourinary, ureter, bladder 76; digestive, hollow viscous structure, esophagus, bowel, stomach; male and female reproductive parts, uterus 75, fallopian tube, penis 35 urethra 2 or other bodily structures.

In another embodiment, the bio-generator 99, can include but is not restricted to being an endoskeleton that can include but is not restricted to an internal stent or an internal wire or mesh or network that can include but is not restricted to fully or partially surrounding a surrounding a biological structure and that can include but is not restricted to being macro or micro or nano 63 sized and can include but is not restricted to being magnetic or non-magnetic. In one embodiment the endoskeleton can include but is not restricted to being utilized as a component or an anchor 37 37 for a bio-generator 99, bio-storage unit, the bio-energy 43 capture device or for a device which can include but is not restricted to being a sensor 39 an LPS 41 device a locator or any of the devices described herein the patents and patent applications or in the cited patents. In one embodiment the endoskeleton can fully or partially surround a blood vascular, vessel, cardiac structure or a neural structure or a genitourinary, ureter, bladder 76; digestive, hollow viscous structure, esophagus, bowel, stomach; male and female reproductive parts, uterus 75, fallopian tube, penis 35 urethra 2 or other bodily structures.

In another embodiment the exoskeleton or endoskeleton can include but is not restricted to being a component of the device or sensor 39 or energy 43 capturing or generating device or any device cited or described herein and can be preassembled and then place into the living being or can be partially assembled and then nano 63 particles can be placed in to the living being and can assemble in a configuration forming a functioning unit or device to include but not restricted to a device cited or described herein or a sensor 39 or generator 99 or energy 43 storage or capture device or an LPS 41 device.

In another embodiment the exoskeleton or endoskeleton can include but is not restricted to being a lattice or scaffolding or foundation or component and can fully or partially form or be a component of a device or sensor 39 or energy 43 capturing or generating device or any device cited or described herein and said lattice or scaffolding or foundation or component can be preassembled and then place into the living being or can be partially assembled and then nano 63 particles can be placed in to the living being and can assemble in a configuration forming a functioning unit or device to include but not restricted to the biological structures or a device cited or described herein or a sensor 39 or generator 99 or energy 43 storage or capture device or an LPS 41 device.

In one embodiment, the lattice or scaffolding or foundation or component and can fully or partially form or be a component of a device or sensor 39 or energy 43 capturing or generating device or any device cited or described herein and said lattice or scaffolding or foundation or component can be preassembled and then place into the living being or can be partially assembled and then nano 63 particles can be placed in to the living being and can assemble in a configuration forming a functioning unit or device to include but not restricted to a device cited or described herein or a sensor 39 or generator 99 or energy 43 storage or capture device or an LPS 41 device and can be placed within, on, in, or outside of a biological structure cited herein to include but not restricted to being associated with brain 69 and neuron structures and activity, sensory 39, 66 structures, blood vessels 107, the heart and cardiovascular system, muscle 65 and the musculoskeletal system, the lymphatic system, and structures that move or peristalsis, the respiration system, the digestive/gastrointestinal system and its accessory organs, hormonal systems, the genitourinary system, reproduction, and other biological functions.

In one embodiment the bio-generator 99 can include but is not restricted to an endovascular/endo-skeletal stent that can include but is not restricted to be coupled with an exo-vascular/exo-skeletal stent and said stents can include but is not restricted to being generators 99 with any combination of piezoelectric crystals/ceramics and electrodes 106 and magnets 38 and coils and nano 63, macro or micro sized devices can include but are not restricted to be designed to generate, capture and store energy 43 or power and these units can be coupled to other devices and sensor 39 as described and cited within this patent application.

Nano 63 technology can include but is not restricted to the manipulation of matter on an atomic or molecular or sub or supra-molecular level and can include but is not restricted to manipulating atoms and molecules for fabrication of nano 63, micro and macro-scale products A more generalized description of nano 63 technology was subsequently established by the National Nano 63 technology Initiative, which defines nano 63 technology as the manipulation of matter with at least one dimension sized from 1 to 100 nano 63 meters. This definition reflects the fact that quantum mechanical effects are important at this quantum-realm scale the lower limit is set by the size of atoms (hydrogen has the smallest atoms, which are approximately a quarter of a nm diameter) since nano 63 technology must build its devices from atoms and molecules. The upper limit is more or less arbitrary but is around the size below which phenomena not observed in larger structures start to become apparent and can be made use of in the nano 63 device. These new phenomena make nano 63 technology distinct from devices, which are merely miniaturized versions of an equivalent macroscopic device; such devices are on a larger scale and come under the description of micro-technology. Thus nano 63 scale devices differ from macro and micro sized devices even if their functions are similar in part because of the manner in which the devices are constricted and work to create that function differ.

In one embodiment, the catalytic, catabolic and anabolic activity of nano 63 materials can be used to include but not restricted to interact with biologic and biomaterials that can include but is not restricted to being native to or placed on or into or within the living being and its tissues, cells, structures and organisms and that can include but is not restricted to allowing biologic matter to couple communicate, transmit, interact, power, energize and function together with the nano 63 devices, generators 99, storage and energy 43 capture devices to perform their functions.

Nano 63 technology can include but are not restricted to nano 63 tubes, nano 63 particles and nano 63 wire 13 and nano 63 coils and nano 63 cubes and nano 63 tubes and nano 63 rods, nano 63 sensor 39, nano 63 chips, nano 63 materials with fast ion transport with nano 63 Ionics and nano 63 electronics, nano 63 pillars, nano 63 spheres and other nano 63 shapes, nano 63 cars, nano 63 lithography, magnetic nano 63 chains, nano 63 tweezers and include top-down approaches to include but not restricted to carbon and fullerenes, solid state silicone and magnetic and magnetoresistors/magneto-resistance, atomic layer 98 deposition (ALD), nano 63 electromechanical systems, single-molecule components in a nano 63 electronic, such as rotaxane, placing components with a desired functional outcome without regard to how they are assembled bionics and biomimicry, biomineralization, bionano 63 technology, nano 63 cellulose, and nano 63 robots, nano 63 surgical tools and nano 63 machines.

Nano 63 technology can include but is not restricted to even smaller sized devices/machines and sensor 39 to include but not restricted to picotechnology and femtotechnology and that can include but is not restricted to OD, 1D, 2D and 3D and 4D nano 63 materials. Curr excitation of the herein biological structures and the herein and cited devices and this can include but is not restricted to excitation by electrical charge, laser, thermal, kinetic, ultrasound, vibrational and chemical excitation and this can be captured with or without magnetic field 103, albeit usually small quantities of energy 43 and this energy 43 can be captured by the methods described herein.

In another embodiment the nano 63 materials or technology can include but are not restricted to metals to include but not restricted to gold, silver zinc, platinum that can be exposed to different energies.

Figure 21:
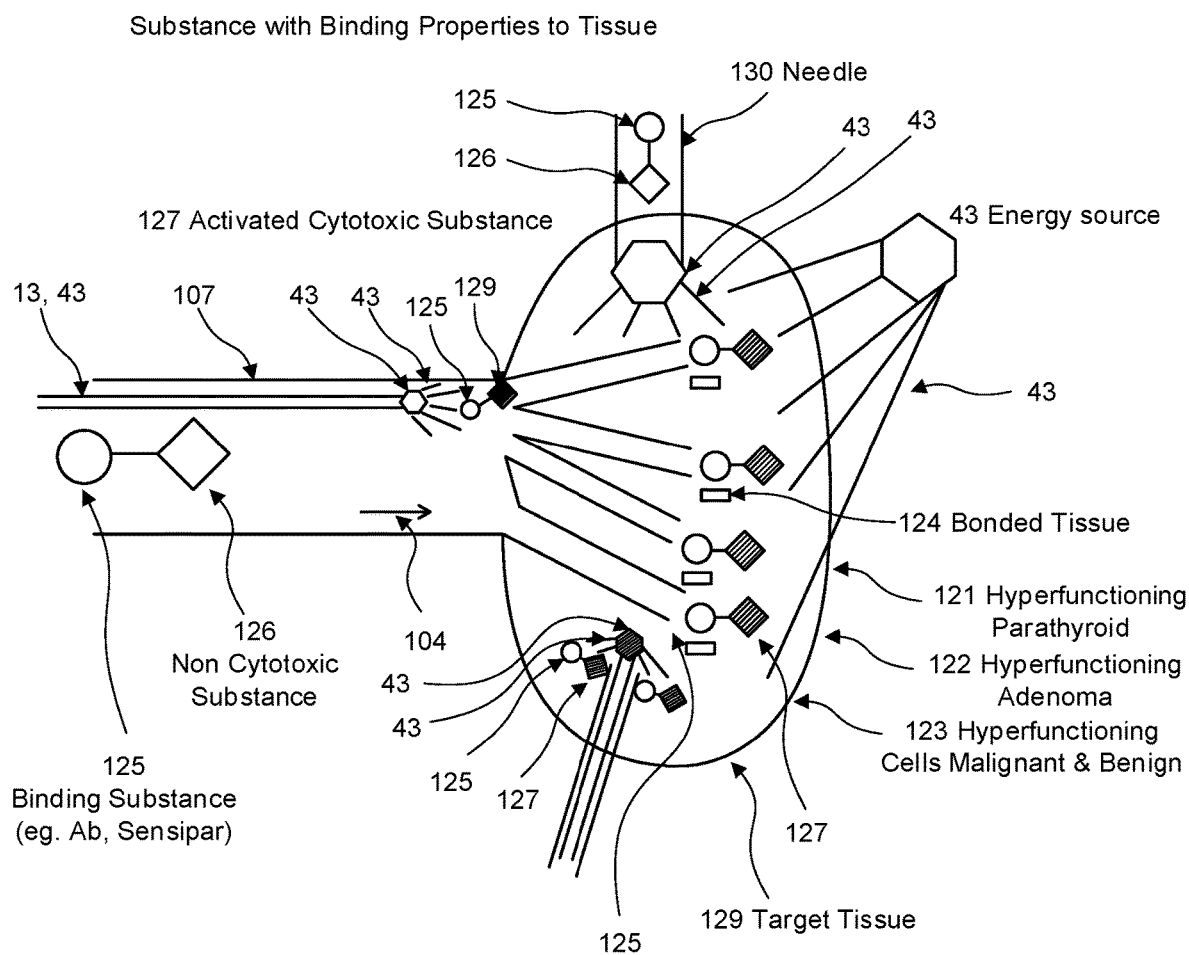
FIG. 21 is a sagittal rendering of a substance 44 that possesses binding properties to target tissue 129, which can convert from non-cytotoxic 126 to cytotoxic 127 with exposure to an energy 43 source.

FIG. 21 is a sagittal rendering of a substance 44 that possesses binding properties to target tissue 129, which can convert from non-cytotoxic 126 to cytotoxic 127 with exposure to an energy 43 source. In another embodiment the excitation of the nano 63 particle can include energy 43 to include the energies listed and cited herein this patent application. In one embodiment to include but not restricted to gold nano 63 particles can be the substance 44 to be activated to include but not restricted to it being a not-yet activated substance 44 or a partially activated or a fully activated substance 44 to maintain its activation can be activated by an energy 43 to include but not restricted to electromagnetic 102 energy 43 can be used to excite or activate the substance 44 can include but not restricted to infrared, UV 43 and visible 20, 43 light. In one embodiment the wavelength of the light can be utilized to modulate or control or excite the substance 44 to variable ranges of treatment or effect or degree to include but not restricted to activating the substance 44 to produce a thermal response that can include but is not restricted to heat, such that at one wavelength or frequency or amplitude of the electromagnetic 102 spectrum the substance 44 can have one effect and at another wavelength or frequency or amplitude the substance 44 can have another effect. In one exemplary scenario or embodiment the a gold nano 63 particle can be activated by infrared light or by UV 43 light or by a visible 20, 43 light spectrum color 95 such as red, orange, yellow, green, blue, indigo or violet, or white light or gold light or brown light or any intermediary color 95 and that can be achieved through a light source to include but not restricted to incandescent, led, laser, sunlight, fiber optic, photochemical, photoelectric light or any other light source known and these various light sources and wavelengths can be used to include but not restricted to being used once or more than once; being used as one or more than one wavelength; using one or more than one of the same or different light sources; can be used sequentially or simultaneously or as close to simultaneously as possible or any combination of these. One of the goals of the use of these various scenarios is to monitor and manipulate and control the light such that it provides to include but not restricted to controlled treatment and the optimal desired treatment and effect to the target tissue 129.

In one exemplary embodiment, gold on the macroscale do not interact with light whereas on the nano 63 scale and when not surrounded by water and not close to other particles it appears red, yet when near other particles appears blue, in this embodiment the an electromagnetic 102 energy 43 of varying wavelengths to include but not restricted to red and blue light can be used to include but not restricted to apply, excite, activate, be interrogated onto, shone onto, or irradiated onto these nano 63 particles which can be place onto the device to include but not restricted to the treatment delivery 42 device such that the distance between nano 63 particles and the presence and absence of water can be adjusted and can be used to control and monitor and excite the gold nano 63 particles with different wavelengths to generate different treatment substance 44 activation and treatment effects to include but not restricted to different thermal outputs that can include but is not restricted to be cytotoxic 127 to the target tissue 129 to include but not restricted to the parathyroid 121 tissue and gland and its function. In other embodiment other tissue types found in the living body tissues that can include but is not restricted to being cited or stated herein this patent application as well as other tissue found in the living body too numerous to list can be target tissues 129.

In another embodiment, the treatment substance 44 in the activated or the not yet-activated state can be to include but not restricted to coupled, bound 124, 125, attached, bonded, in association with an antibody (AB). In one embodiment a gold nano 63 particle can be to include but not restricted to coupled, bound 124, 125, attached, bonded, in association with an antibody (AB) that can include but is not restricted to a specific target tissue 129 to include but not restricted to a parathyroid 121 antibody. In other embodiment other tissue type Antibodies found in the living body tissues that can include but is not restricted to being cited or stated herein this patent application as well as other tissues found in the living body too numerous to list can be the target tissues 129 antibodies utilized and bond to the nano 63 particles of the treatment substance 44 in the activated or the not yet activated state. In one embodiment the target tissue 129 AB-nano 63 particle complexes can be injected into the body such that the target tissue 129 AB-nano 63 particle complexes become bound 124, 125 to the target tissue 129 or target organ and this allows for a tightly targeted treatment of the target tissue 129 because when the energy 43 is applied to the treatment substance 44 that can include but is not restricted to the activated and not yet activated treatment substance 44 the cytotoxic 127 ablative effect will be concentrated on the target tissue 129 where the AB-nano 63 particle complex is bound 124, 125. One embodiment can include but is not restricted to the target tissue 129 antibody (AB) being the parathyroid 121 tissue or gland or function or hormone and the nano 63 particle complex being a gold nano 63 particle and the PTH AB-gold Nano 63 particle complex can be injected into the body such that AB-gold Nano 63 particle complex becomes bound 124, 125 to the PTH target tissue 129 or target organ and this allows for a tightly targeted treatment of the PTH target tissue 129 because when the treatment energy 43 is applied to the treatment substance 44 that can include but is not restricted to the activated and not yet activated treatment substance 44 such that the cytotoxic 127 ablative effect will be concentrated on the PTH target tissue 129 where the AB-gold Nano 63 particle complex is bound 124, 125.

In another embodiment the AB and nano 63 particle treatment complex which can include but is not restricted to being fully or partially activated or not-yet activated and which can be delivered by the substance 44 treatment delivery 42 device to include but not restricted to embodiments as cited and as listed herein and that can include but is not restricted to percutaneous, transcutaneous surgically or intra-vascular and the energy 43 can be delivery 42 by the energy 43 treatment delivery 42 device that can excite or activate the AB and nano 63 particle treatment complex and which can be delivered by the energy 43 treatment delivery 42 device to include but not restricted to embodiments as cited and as listed herein and that can include but is not restricted to percutaneous, transcutaneous surgically or intra-vascular.

In another embodiment the treatment substance 44 can be attached to a second target substance 44 that can include but is not restricted to a mineral, salt, or molecule or biologic agent that has an affinity for the target tissue 129. In another embodiment the second target substance 44 and nano 63 particle treatment complex which can include but is not restricted to being fully or partially activated or not-yet activated and which can be delivered by the substance 44 treatment delivery 42 device to include but not restricted to embodiments as cited and as listed herein and that can include but is not restricted to percutaneous, transcutaneous surgically or intra-vascular and the energy 43 can be delivery 42 by the energy 43 treatment delivery 42 device that can excite or activate the second substance 44 and nano 63 particle treatment substance 44/complex and which can be delivered by the energy 43 treatment delivery 42 device to include but not restricted to embodiments as cited and as listed herein and that can include but is not restricted to percutaneous, transcutaneous surgically or intra-vascular. In one exemplary embodiment the second substance 44 can include but is not restricted to Calcium or Sensipar (cinacalcet) or other Parathyroid 121 avid molecules or minerals, which target the parathyroid 121 and that second substance 44 can be bound 124, 125 to a treatment substance 44 that can be not-yet activated and which can then be activated by an energy 43.

In another embodiment, ionizing radiation can be coupled to nano 63 particles and delivered to the target tissue 129 for direct treatment.

In one embodiment the radioactive material or isotope can be bound 124, 125 or associated to a gold nano 63 particle.

In another embodiment the radioactive material or isotope can be associated or bound 124, 125 with the Nano 63 particle or the Antibody or the second substance 44 discussed above or any combination of these. One exemplary embodiment can include a gold nano 63 particle associated with a parathyroid 121 AB and a radioactive isotope that has a short range and can be cytotoxic 127 and that can be placed into the parathyroid 121 and the isotope can include I-13; Gold-198 (198Au) iodine-125 (125I) and palladium-103 (103Pd), Cesium-131 (131Cs). In one embodiment the nano 63 particle can be gold and can include but is not restricted to Gold-198.

In another embodiment the radioactive material or isotope can be associated or bound 124, 125 with the Nano 63 particle or the Antibody or the second substance 44 discussed above or any combination of these and a cytotoxic 127 substance 44 to include but not restricted to alcohol, or sotrodecol.

In another embodiment the nano 63 particle can be a nano 63 technology to include but not restricted to nano 63 robot and nano 63 surgical tools that can include but is not restricted to destroy or kill or damage the target tissue 129 cells and can include but not restricted to be combined with other embodiments discussed herein or cited herein this application to include but not restricted to other devices or methods for cytotoxic 127 ablation, localization, monitoring or activation and retarding or deactivation of treatment.

In another embodiment the radioactive material or isotope can be associated or bound 124, 125 with the Nano 63 particle or the Antibody or the second substance 44 or a cytotoxic 127 substance 44 or an isotope or nano 63 technology or any combination of these or embodiment discussed above.

In embodiment throughout this application the any nano 63 particle or technology or substance 44 can include but is not restricted to a substances 44 cited by or listed herein to include but not restricted to embodiment as cited and as listed herein and that any nano 63 particle or technology or substance 44 can include but is not restricted to be delivered or excited or placed percutaneous, transcutaneous surgically or intra-vascular. Some embodiment of the nano 63 particles include but are not restricted to some of the more common forms to include but are not restricted to gold, carbon, graphite, graphene, silicon nano 63 particles and the nano 63 particles either cited or listed herein this application.

In one embodiment the substance 44 can include but not restricted to gold nano 63 particles that can be the substance 44 to be activated to include but not restricted to it being a not-yet activated substance 44 or a partially activated or a fully activated substance 44 to maintain its activation can be activated by energy 43.

In one embodiment the substance 44 can one or more form or type or species of substance 44 that can be utilized to modulate or control the degree or ranges of treatment or the effect of to include but not restricted to cytotoxic 127 ablation, sterilization and killing of tissue or organisms to include but not restricted to infectious organisms and the treatment substance 44 can include but not restricted to a not-yet activated or a fully or partially activated substance 44 and that can include but is not restricted to the treatment effect being to include but not restricted to producing a thermal response that can include but is not restricted to heat, such that with activation by an energy 43, the different specific substances 44 can different specific effects which differ with one substance 44 when compared to another substance 44 and the different substances 44 can also have different effects even when exposed to the same energy 43. In one embodiment a gold and a silicon nano 63 particle can be utilized together and can be excited by an energy 43 or excited by another substance 44 to include a nano 63 substance 44.

In another embodiment a substance 44 can be formulated with a similar nano 63 material but can and when it is formulated it can be formulated in a manner that it produces different responses to include but not restricted to responses to the same or to different forms of that same energy 43. In another embodiment a substance 44 can be formulated with similar nano 63 materials but can be formulated in a manner that it produces different responses even at different energies. In one exemplary scenario or embodiment the gold nano 63 particle Type 1 can be activated by one energy 43 and the nano 63 gold particle Type 2 can be activated by the same but the treatment or activations of Gold nano 63 particle exposed to the energy 43 can differ and in another embodiment the energy 43.

In another exemplary scenario or embodiment the gold nano 63 particle Type 1 when activated by the one energy 43 form yields a given treatment or activation effect.

In another exemplary scenario or embodiment the gold nano 63 particle Type 1 when activated by the two different energy 43 forms yields the same given treatment or activation effect.

In another exemplary scenario or embodiment the gold nano 63 particle Type 1 when activated by the two different energy 43 forms yields different treatment or activation effect.

In another exemplary scenario or embodiment the gold nano 63 particle Type 1 when activated by the two different energy 43 intensities or amplitudes yields different treatment or activation effects.

In another exemplary scenario or embodiment the gold nano 63 particle Type 1 and the gold nano 63 particle Type 2 can be activated by the same energy 43 form but they have different intensities of energy 43 yet they yield the same treatment or activation effects in one scenario and different energy 43 or treatment or activation effects in another scenario.

In another exemplary scenario or embodiment the gold nano 63 particle and the carbon nano 63 particle can be activated by the same energy 43 form yet they yield the same treatment or activation effect.

In another exemplary scenario or embodiment the gold nano 63 particle and the carbon nano 63 particle can be activated by the same energy 43 form yet they yield the different treatment or activation effects.

In another exemplary scenario or embodiment the gold nano 63 particle and the carbon nano 63 particle can be activated by the same energy 43 form but they have different intensities of energy 43 yet they yield the same treatment or activation effects in one scenario and different energy 43 or treatment or activation effects in another scenario.

In another exemplary scenario or embodiment the gold nano 63 particle Type 1 and the gold nano 63 particle Type 2 can be activated by the same energy 43 form yet they yield the same treatment or activation effect.

In another exemplary scenario or embodiment the gold nano 63 particle Type 1 and the gold nano 63 particle Type 2 can be activated by the same energy 43 form yet they yield the different treatment or activation effects.

In another exemplary scenario or embodiment the gold nano 63 particle Type 1 and the gold nano 63 particle Type 2 can be activated by the same energy 43 form but they have different intensities of energy 43 yet they yield the same treatment or activation effects in one scenario and different energy 43 or treatment or activation effects in another scenario.

In another exemplary scenario or embodiment the gold nano 63 particle and the carbon nano 63 particle can be activated by the same energy 43 form yet they yield the same treatment or activation effect.

In another exemplary scenario or embodiment the gold nano 63 particle and the carbon nano 63 particle can be activated by the same energy 43 form yet they yield the different treatment or activation effects.

In another exemplary scenario or embodiment the gold nano 63 particle and the carbon nano 63 particle can be activated by the same energy 43 form but they have different intensities of energy 43 yet they yield the same treatment or activation effects in one scenario and different energy 43 or treatment or activation effects in another scenario.

In another exemplary scenario or embodiment the gold nano 63 particle Type 1 and the gold nano 63 particle Type 2 can be activated by the different energy 43 forms yet they yield the same treatment or activation effect.

In another exemplary scenario or embodiment the gold nano 63 particle Type 1 and the gold nano 63 particle Type 2 can be activated by the different energy 43 forms and they yield the different treatment or activation effects.

In another exemplary scenario or embodiment the gold nano 63 particle Type 1 and the gold nano 63 particle Type 2 can be activated by the different energy 43 forms but they have different intensities of energy 43 yet they yield the same treatment or activation effects in one scenario and different energy 43 or treatment or activation effects in another scenario.

In exemplary and other embodiments the description of 2 or 3 or . . . and so on can signify a number or amount that is more than one.

In another exemplary scenario or embodiment the gold nano 63 particle and the carbon nano 63 particle can be activated by the different energy 43 forms yet they yield the same treatment or activation effect.

In another exemplary scenario or embodiment the gold nano 63 particle and the carbon nano 63 particle can be activated by the different energy 43 forms yet they yield the different treatment or activation effects.

In another exemplary scenario or embodiment the gold nano 63 particle and the carbon nano 63 particle can be activated by the different energy 43 forms but they have different intensities of energy 43 yet they yield the same treatment or activation effects in one scenario and different energy 43 or treatment or activation effects in another scenario.

Any combination of these and similar scenarios based on these concepts can be used and these are meant to be exemplary and not restrictive as to combinations.

In another exemplary scenario or embodiment the gold nano 63 particle Type 1 when activated by a red light yields one effect and when actives by infrared yields another effect. The purpose of this is to control to include but not restricted to control and monitor and adjust the intensity and the effectiveness of the treatment effect through to include but not restricted to varying the types of energy 43 utilized, varying the amounts or types of substance 44 utilized, and to vary the quantity or using one or more than one form of energy 43 or substance 44. By doing this precise treatment effects can be regulated to treat or cytotoxically ablate the target tissue 129 while preserving the non-target tissue 129 or to treat the hostile environment and preserve the non-hostile environment or treat the hyperfunctioning environment and preserve the normal functioning environment or to treat the abnormal tissue or environment and preserve the normal environment.

In exemplary and other embodiments the description of 2 or 3 or more than one can signify a number or amount that is more than one.

Energy 43 embodiments cited by and throughout this application can include but are not restricted to be applied to the devices, energy 43 units and energy 43 storage and energy 43 sources and energy 43 and methods cited by and throughout this application.

In one embodiment one or more than one energy 43 source can include but is not restricted to be utilized to activate or transmit or initiate or drive or power or excite a device or substance 44. Embodiments can include where one or more than one energy 43 form is can be used to activate or transmit or initiate or drive or power or excite a device or a substance 44 and can include but is not restricted to one or more form or similar or dissimilar infrared light or by UV 43 light or by a visible 20, 43 light spectrum color 95 such as red, orange, yellow, green, blue, indigo or violet, or white light or gold light or brown light or any intermediary color 95 and that can be achieved through a light source to include but not restricted to incandescent, led, laser, semiconductor lasers, quantum wells, plasmonics, photoacoustics, sunlight, fiber optic, photochemical, photoelectric, light, photoelectric, or any other light source known and these various light sources and wavelengths can be used to include but not restricted to being used once or more than once; being used as one or more than one wavelength; using one or more than one of the same or different light sources; can be used sequentially or simultaneously or as close to simultaneously as possible or any combination of these. One of the goals of the use of these various scenarios is to monitor and manipulate and control the light such that it provides to include but not restricted to controlled treatment and the optimal desired treatment and effect to the target tissue 129 to include but not restricted to cytotoxic 127 ablation, partial or full, to the of the tissue or gland or function.

Embodiments can include and are not restricted to having multiple substances 44, multiple energies and can undergo multiple excitations in a manner that can include but is not restricted to optimize treatment and the function and the effect that is so desired.

LPS 41 Devices

In one embodiment an LPS 41 device that can have a send and receive component and can communicate with a computer 18 or computer-like device can include but is not restricted to be placed into or on or within or around structures to include artificial, partially or fully man-made or organic or user's body tissues. In one embodiment the LPS 41 device, which can include but is not restricted to include a sensor 39 or a treatment device or treatment substance 44 or element or an energy 43 storage or generating device can include but is not restricted to being used within the artificial or partially or fully man-made or man-altered device or biologic structures or a hybrid or combination of these to include but not restricted to a prosthesis, a pump, a substitute nerve or muscle 65 or bone or component of the brain 69 or sensory 39, 66 system (sight, hearing, smell, taste, various iterations and forms of touch or immune system or circulatory system, heart, artery, vein or capillary, or urological system, kidney, bladder 76, ureter or urethra, or a reproductive system or penile or vaginal 3 or ovary or fallopian tube or semen producing structures, or other reproductive components, locomotion and mobility organs to include but not restricted to muscle 65 and bones and nerves, gastrointestinal structures to include but not restricted to the esophagus, stomach bowel, intestine, teeth oral mucosa; the skin 8 and mucosa as well as other bodily functions.

One embodiment can be a an LPS 41 device which can include sensor 39 or send and receive transmitters 40 which can include but not restricted to be transmitted to a computer 18 or computer-like device and can include sensor 39 that can but is not restricted to triangulate a distance between the LPS 41 devices and one or more than one LPS 41 devices that can be located in a prosthesis that can include but is not restricted to be fully or partially artificial or machine or man-made or altered or can be a grafted bone to include but not restricted to cadaveric, allograft, autograft or a xenograft and in addition these said LPS 41 devices can also be located within the tissue to include but not restricted to the bone of the user within or into whom the prosthesis is placed and these LPS 41 devices can be in a stable position. The LPS 41 devices can be to include but not restricted to triangulate with each other. If prosthesis is suspected of being loose then the distances immediately after surgery and a time after surgery can have the triangulated distances compared. If there is a change in distance or orientation then this most likely represents a loosening or a shift in the position of the prosthesis relative to the bone.

In another embodiment one or more than one LPS 41 device can be in more than one prosthesis and the relationship of the prosthesis and the movement of the prosthesis can be monitored.

In another embodiment one or more than one LPS 41 device can be placed within more than one region of living tissue and the relationship of the living tissue regions relative to each other can be compared this can include but is not restricted to distance between LPS 41 devices or in another embodiment the sensor 39 can measure a biological or chemical value to include but not restricted to glucose of pH or a protein or carbohydrate or fat or nucleotide or marker to include but not restricted to a tumor or hormone marker and a biological functional environment map can be constructed and this can be used to assess the environment of the tissue and can include but not restricted to assist with assessment of benign tissue and malignant tissue and hormonal hyper and normal functioning tissue to include but not restricted to assessment of the effectiveness of a treatment or the presence or recurrence of a tumor or the distinction between normal and pathologic tissue.

In another embodiment one or more than one LPS 41 device can be placed in the living being and can be placed within a wearable 50 and the relationship of these can be used to assess how the wearable 50 interacts with the living being.

In another embodiment the LPS 41 which is coupled to one or more than one sensor 39 can assess biological function in the region of the sensor 39.

In another embodiment the LPS 41 which is coupled to one or more than one sensor 39 can assess Treatment of Hyperfunctioning Tissue/Glands including Parathyroid 121 and other Hyperfunctioning Adenomas 122 and Benign and Malignant Hyperfunctioning Tissue/Tumors Prior patents as cited by or herein this patent application the embodiments of treatment for parathyroid 121 hyperfunctioning tissue and glands utilizing substances 44 and energy 43 that when in the not yet activated are non-cytotoxic 126 to living tissue. And when combined the substance 44 can be activated by the energy 43 or the energy 43 can be activated by the substance 44 and then the product of these combinations can become cytotoxic 127 to the tightly targeted tissue. Embodiments of target tissue 129 can include but are not restricted to parathyroid 121 tissue/glands, adenomatous 122 tissue, hyperfunctioning tissue, and benign and malignant and cancerous tissue and normal and abnormal tissue or cells or fluid or organs, or components of the living body and can include but is not restricted to the parathyroid 121.

Embodiments of treatment substance 44 delivery 42 devices of not yet activated substances 44 that can be transformed to activated substance 44 can include but are not restricted to treatment devices for delivering the treatment substance 44 to the tissue and can include but are not restricted to structural devices to include but not restricted to hollow or solid needles, probes, endoscopes, stylets, wire 13 or a pointed or blunt instruments or fiber optics 13 or endoscopes that can include but are not restricted to being flexible 26, semi-rigid or rigid and that can include but is not restricted to being capable of passing through a hollow needle, conduit 5 or catheter and that in another embodiment can include but is not restricted to being utilized alone and without a hollow needle, conduit 5 or catheter.

Embodiments of the treatment substance 44 delivery 42 devices of not yet activated substances 44 that can be transformed to activated substance 44 can include but are not restricted to placing particles to include but not restricted to into, in, within, on or near to include but not restricted to target tissue 129 to include but not restricted to the cells, fluids, tissues or organs or glands to be treated by these said substances 44 to include but not restricted to passing through the said delivery 42 device; or being permanently affixed to the said delivery 42 device; or coating the said delivery 42 device; or being not permanently affixed or coated to the said delivery 42 device and being released or delivered to the target tissue 129; or the said treatment delivery 42 device being composed fully or partially of said substance 44; or any combination of these. In another embodiment to include but not restricted to there being one or more treatment delivery 42 devices and systems that can be used alone or in combination and can include but is not restricted to the parathyroid 121.

The treatment delivery 42 devices can include but are not restricted to composed of one or more than one component. In another embodiment there can be a component of the delivery 42 device that can include but is not restricted to being detachable. In another embodiment the components can be made of one or multiple combinations of materials, which can include but are not restricted to one or more fully or partially detachable components or filaments or coils or geometric shapes or hook-like elements and the said treatment device being composed of the said treatment substance 44 can have the various components to include but not restricted to the detachable component being made fully or partially of the said treatment substance 44. Embodiments can include treatment devices or their components that can include but are not restricted to being left within the living being or their cells, fluids, tissues, organs, glands or substance 44 of the living being and the targeted or non-targeted tissue and can include but is not restricted to the parathyroid 121.

Another embodiment includes but is not restricted to a coating of the treatment delivery 42 device to include but not restricted to include the said treatment substance 44 that can include but is not restricted to being fully or partially removable and can include but is not restricted to be left fully or partially within the within the living being or their cells, fluids, tissues, organs, glands or substance 44 of the living being and to include but not restricted to the targeted or non-targeted tissue and can include but is not restricted to the parathyroid 121.

Another embodiment includes but is not restricted to having the treatment substance 44 delivered fully or partially through a passage or hollow within the conduit 5 or catheter treatment deliver delivery 42 device.

In another embodiment the substance 44 delivered can include but is not restricted to a treatment or a non-treatment substance 44 or any combination of these.

In another embodiment any combination of these treatment devices or substances 44 can be used fully or partially in the combinations described and cited herein.

Another embodiment can include the energy 43 treatment delivery 42 device that can include but are not restricted to hollow or solid needles, probes, endoscopes, stylets, wire 13 or a pointed or blunt instruments or fiber optics 13 or endoscopes that can include but are not restricted to being flexible 26, semi-rigid or rigid and that can include but is not restricted to being capable of passing through a hollow needle, conduit 5 or catheter and that in another embodiment can include but is not restricted to being utilized alone and without a hollow needle, conduit 5 or catheter and the solid and hollow devices/instruments can be used to include but not restricted to in combination, in tandem, together and that can include but are not restricted to being solid or hollow components and can include one or more than one/multiple forms and can include but are not restricted to be partially or fully composed of these designs or architectures/manners and that can include but are not restricted to in all combinations of these cited or described herein.

Another embodiment can include but is not restricted to a delivery 42 device that can include but is not restricted to a substance 44 or energy 43 that can partially or fully deactivate, slow or reverse or stop or prevent the continuation of the treatment substance 44 or treatment process.

In another embodiment can include but is not restricted to a substance 44 delivery 42 device that can include but is not restricted to a substance 44 that partially or fully deactivates or prevents or insulates or protects or reverses or retards or stop the effects of the treatment substance 44 or process that can include but is not restricted to occurring before, during or after activation and treatment has begun and that can include but is not restricted to any combination of these.

In another embodiment can include but is not restricted to an energy 43 delivery 42 device that can include but is not restricted to an energy 43 that partially or fully deactivates or prevents or insulates or protects or reverses or retards or stops the effects of the treatment substance 44 or process that can include but is not restricted to occurring before, during or after activation and treatment has begun and that can include but is not restricted to any combination of these.

Another embodiment can include a conduit 5 that provides and allows for the passage of to include but not restricted to one or more than one of the treatment device(s) or the energy 43 device(s) that can include but is not restricted to facilitate or promote or initiate or activate or that can also include but is not restricted one or more devices to insulate or protect or prevent or retard or stop or deactivate the treatment process or any combination of these.

Another embodiment can include a probe that has or combine on or more than one device to include but not restricted to one or more than one of the treatment device(s) or the energy 43 device(s) that can include but is not restricted to facilitate or promote or initiate or activate or that can also include but is not restricted one or more device(s) to prevent or insulate or protect or retard or stop or deactivate the treatment process or any combination of these.

In one of the preferred embodiments one or more than one treatment substance 44 devices can be inserted into the parathyroid 121 gland and said probe can include but is not restricted to be composed of a treatment delivery 42 substance 44 the is not yet activated. A second device or instrument can be inserted that can include but is not restricted to an energy 43 delivery 42 device that is a non-cytotoxic 126 energy 43 without the not yet activated treatment delivery 42 substance 44. In one embodiment the one or more than one treatment substance 44 devices can be partially or fully composed of or can release the not yet activated substance 44 treatment delivery 42 substance 44 and the portion of the treatment substance 44 device that partially or fully contains the treatment substance 44 can be inserted or placed into or near or on or onto a parathyroid 121 gland/tissue that can include but is not restricted to a parathyroid 121 tissue/gland that is hyperfunctioning. Also in this embodiment, a treatment energy 43 device can include but is not restricted to be inserted or placed adjacent or into or near or on or onto the target tissue 129 to include but not restricted to parathyroid 121 gland/tissue and/or the treatment energy 43 device can include but is not restricted to be inserted or placed adjacent or into or near or on or onto the treatment substance 44 device or treatment substance 44 such that the treatment substance 44 can be activated by the treatment energy 43 and cytotoxically ablate the target tissue 129 to include but not restricted to the parathyroid 121 tissue to include but not restricted to the hyperfunctioning parathyroid 121 tissue. And in this embodiment the treatment energy 43 and substance 44 and their respective devices when properly utilized can cytotoxically ablate the abnormal target tissue 129 and return the target tissue 129 to a state to include but not restricted to normal functioning or normal cellularity or to a benign state or eradicate abnormal functioning or abnormal cellularity or to the non-benign state of the tissue organ or gland.

In another embodiment the substance(s) 44 or energy(ies) 43 or their respective device(s) that can include but are not restricted to having the ability to prevent or insulate or protect or retard or stop or deactivate the treatment process can also be inserted or placed adjacent or into or near or on or onto each other or can include but are not restricted to be inserted or placed adjacent or into or near or on or onto the target tissue 129 to include but not restricted to parathyroid 121 gland/tissue and/or the treatment energy 43 or substance 44 or their respective devices and can include but are not restricted to be inserted or placed adjacent or into or near or on or onto the treatment substance 44 or energy 43 or their respective devices such that the treatment substance 44 process can be initiated and activated and/or deactivated or retarded or stopped by the treatment substance 44 and energy 43 and the treatment process to include but not restricted to controlled cytotoxic 127 ablation of the target tissue 129 to include but not restricted to the parathyroid 121 tissue to include but not restricted to the hyperfunctioning parathyroid 121 tissue. And in this embodiment the treatment energy 43 and substance 44 and their respective devices and processes and/or the prevention or insulation or protection or retardation or stop/cessation or deactivation substance(s) 44 or energy(ies) 43 or their respective devices or processes or any combination of these when properly utilized can tightly targeted cytotoxically ablate the abnormal target tissue 129 and return the target tissue 129 to a state to include but not restricted to normal functioning or normal cellularity or to a benign state or eradicate abnormal functioning or abnormal cellularity or to the non-benign state of the tissue organ or gland and that can include but is not restricted to preserve normal functioning or normal cellularity or to a benign tissue and protect or prevent significant functional damage to local tissue to include but not restricted to tissue near the target tissue 129 to include but not restricted to the parathyroid 121 gland/tissue.

In one embodiment the treatment substance 44 can be activated by the energy 43 and the treatment substance 44 is not released from the substance 44 delivery 42 device but is activated on or in or upon or within or as a component or the treatment delivery 42 device In another embodiment the treatment substance 44 can be activated by the energy 43 and the treatment substance 44 can be released from substance 44 delivery 42 device. The substance 44 delivery 42 device can be partially or fully composed of the treatment substance 44.

In another embodiment the substance 44 delivery 42 device can include but is not restricted to being fully or partially composed of a filament or probe or needle or catheter or conduit 5 or coil or coating or devices described or cited herein that can include but are not restricted to where the treatment substance 44 cannot be released or can be partially or can be fully released from the substance 44 delivery 42 device.

In another embodiment the substance 44 delivery 42 device can include but is not restricted to being fully or partially composed of a filament or probe or needle or catheter or conduit 5 or coil or coating or devices described or cited herein that can include but is not restricted to where these said devices can be fully or partially separated or removed or detached from one or more than one component of the substance 44 delivery 42 device.

In another embodiment the treatment substance 44 that is released can be released to include but not restricted to by an energy 43 or mechanism to include but not restricted to energy 43 and power, force, impetus, control or momentum and which can include but is not restricted to include electromagnetic/electrical/magnetic or thermal or hydraulic/kinetic/vibrational/mechanical or chemical energy 43 or radioactive energy 43 and can be induced by to include but not restricted to macro, micro or nano 63 particle devices or any combination.

In another embodiment the energy 43 treatment device can be coupled with the substance 44 delivery 42 device and can include but not restricted to being architecturally one or more than device.

One embodiment can include but is not restricted to having energy 43 be used to release the treatment substance 44 from the treatment substance 44 device and that said energy 43 can be include but is not restricted to an energy 43, power, force, impetus, control or movement, resistance, friction or momentum and which that can include but is not restricted to include electromagnetic/electrical/magnetic or thermal/hot/cold or hydraulic/kinetic/vibrational/mechanical or chemical energy 43 or radioactive and can be used to release the treatment substance 44 to include but not restricted to by macro, micro or nano 63 particle devices or any combination.

In the embodiments above and herein and cited herein the treatment substance 44 can partially or fully remain a component of the substance 44 delivery 42 device.

In the embodiments above and herein and cited herein the treatment substance 44 can partially or fully remain a component of the substance 44 delivery 42 device can also be coupled with the energy 43 delivery 42 device that can include but not restricted to being architecturally one or more than device.

In the embodiments above and herein and cited herein the treatment substance 44 can partially or fully remain a component of the substance 44 delivery 42 device can also be coupled with the energy 43 delivery 42 device that can include but not restricted to being architecturally one or more than device and can have no removable components.

In another embodiment, the treatment substance 44 can include but is not restricted to a substance 44 that can include but is not restricted to having the ability to be activated and not-yet activated and inactivated and activation can result in to include but not restricted to cytotoxically ablate target tissue 129 and in another embodiment the treatment substance 44 can use the same devices and methods herein for delivery 42 of a substance 44 that partially or fully deactivates or prevents or insulates or protects or reverses or retards or stop the effects of the treatment substance 44 or process that can include but is not restricted to occurring before, during or after activation and treatment has begun and that can include but is not restricted to any combination of these.

In another embodiment the treatment substance 44 can include but not restricted to being thermally/melted/frozen/heated/cooled in a manner such that the substance 44 is released from the substance 44 delivery 42 device, or any combination of these.

In another embodiment the treatment substance 44 can include but not restricted to being mechanically released from the substance 44 delivery 42 device to include but not restricted to being released by friction or a screw-like mechanism, or tapping, scraping, rubbing, Brownian motion or movement, Ultrasound, acoustic or other mechanical or friction related movements or any combination of these.

In another embodiment the treatment substance 44 can include but not restricted to being electromagnetically released from the substance 44 delivery 42 device to include but not restricted to being released by an electrical current 100, a magnetic current 100 101, magnetic field 103 or a an electromagnetic 102 wavelength or energy 43 to include but not restricted to any portion of the visible 20, 43 light spectrum or any portion of the non-visible 43 light/electromagnetic 102 spectrum to include but not restricted to X-ray, radioactive, UV 43, infra-red or any other portion of the electromagnetic 102 spectrum and can include one or more of these component/portions and any combination of these.

In another embodiment the treatment substance 44 can include but not restricted to being chemically released from the substance 44 delivery 42 device to include but not restricted to being released by exothermic or endothermic reactions, elementary or dissociation or trans-cis-isomeric reactions, polymerization, hydrogen-oxygen, equilibrium, and can include but is not restricted to catalytic or reactant reaction to include but not restricted to reactant, surface area, activation energy 43, pressure, hydraulic, thermal reactions and that can include but is not restricted to synthesis, decomposition, single replacement and double replacement reactions, oxidation and reduction (Redox) reactions, covalent and non-covalent bonding, ligands, complexes/complexation, acid-base reactions, solid-state reactions, precipitation reactions, photochemical/photoelectric/bioluminescent reactions, catalysis, and catabolic and anabolic reactions, organic reaction, substitution reactions, electrophilic substitution, addition and elimination reactions, addition and subtraction of bonds, rearrangement reactions, biochemical reactions, enzymatic reactions, base-pair reactions such as but not restricted to nucleotide, DNA, RNA, protein, lipid and carbohydrate biochemical reactions, thermite reactions, fluorescent reactions and photosynthesis and photo-reactive reactions and the substrates or substances 44 can include but are not restricted to organic materials to include but not restricted to nucleotide, DNA, RNA, protein, lipid and carbohydrate, glucose and carbon based materials and their compounds or combinations and inorganic materials to include but not restricted to periodic elements gems, minerals to include but not restricted to metals to include but not restricted to gold silver, zinc, lithium, cadmium, and gasses to include but not restricted to oxygen, hydrogen, nitrogen, carbon dioxide and other oxide combinations, halogens and halides and can include one or more of these reactions and any combination of these and other materials known but too numerous to list.

In another embodiment the treatment substance 44 can include but not restricted to being energetically released from the substance 44 delivery 42 device to include but not restricted to being released by any other form of energy 43 to include but not restricted to potential energies such as chemical, nuclear, gravitational and mechanical/elastic energies and kinetic energies to include but not restricted to vibrational, thermal/temperature, sound/acoustic/vibrational, electric/electromagnetic/electromechanical/and magnetic energies and motion and can include one or more of these component/portions and any combination of these.

In another embodiment the treatment substance 44 can include but not restricted to being released from the substance 44 and/or the energy 43 delivery 42 device or any combination of these which can include but is not restricted to the substance 44 and or the energy 43 delivery 42 devices being combined, coupled or constructed as a single or a multiple/a more than one treatment or substance 44 delivery 42 device unit(s) and can include one or more of these component/portions and any combination of these.

In one embodiment the delivery 42 of the substance 44 can be released or controlled the delivery 42 by the energy 43 device.

In another embodiment the delivery 42 of the energy 43 can be released or controlled the delivery 42 by the treatment substance 44 device.

In another embodiment the delivery 42 of the treatment substance 44 can be released or controlled by applying an energy 43 to the substance 44 delivery 42 device. Embodiments can include but are not restricted to the substance 44 delivery 42 device be composed in a manner that can include but is not restricted to the delivery 42 device containing or being composed partially or fully of an energy 43 component that can include but is not restricted to being capable of thermal/hot or cold, chemical, kinetic/Brownian/vibrational/mechanical, magnetic, chemical reactions, electromagnetic/visible 20, 43 and non-visible 43 light and spectral wavelengths that include but are not restricted to UV 43, Infrared, x-ray, radioactive energy 43/wavelengths/spectrum, or chemical energy 43 and the design of the component of the substance 44 delivery 42 device that delivers this controlling or releasing energy 43 can include but is not restricted to an architecture that fully or partially is solid core, interrupted core, and that includes but is not restricted to coat, lie at the inner central core or away from the to the inner central core, be circumferential or an integrated design that integrates, binds, insinuates, interlaces, intermingles, assimilates, incorporates or amalgamates itself into the components of the substance 44 delivery 42 device.

Figure 22:
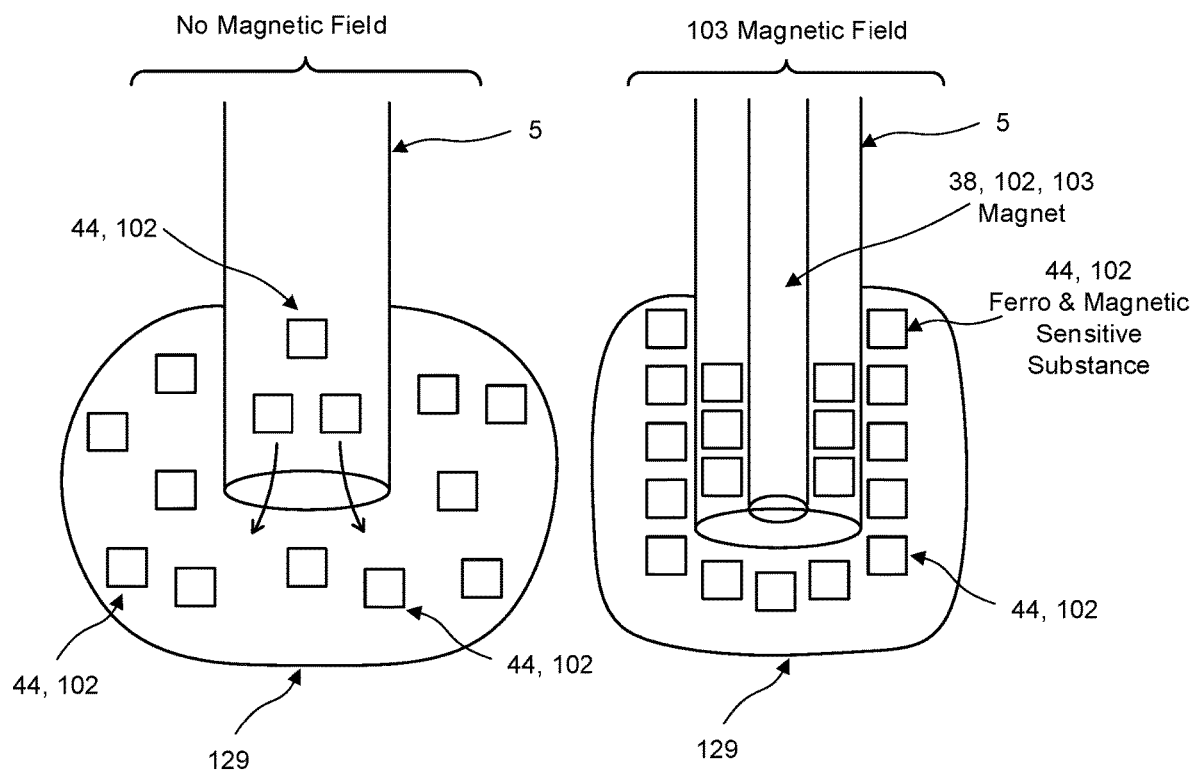
FIG. 22 is a sagittal rendering of a substance 44 that possesses properties such as ferromagnetic or magnetic properties that can return to a magnetic source device after a magnetic field 103 is generated.

FIG. 22 is a sagittal rendering of a substance 44 that possesses properties such as ferromagnetic or magnetic properties that can return to a magnetic source device after a magnetic field 103 is generated.

In one embodiment the treatment substance 44 device can include a ferromagnetic component that can be fully or partially bound 124, 125 to the substance 44 delivery 42 device when the substance 44 delivery 42 device is magnetized and can be released or bound 124, 125/attached or re-bound 124, 125/re-attached to the substance 44 delivery 42 device when the magnetic field 103 is turned on and turned off.

In one embodiment the treatment substance 44 device can include a thermal conducting component that can be fully or partially integrated into the substance 44 delivery 42 device when the substance 44 delivery 42 device is thermally altered by heating or cooling and can be released or bound 124, 125/attached or re-bound 124, 125/re-attached to the substance 44 delivery 42 device when the thermal energy 43 is turned on and turned off.

In one embodiment the treatment substance 44 device can include a an electromagnetic 102 component that can be fully or partially integrated into the treatment substance 44 delivery 42 device that can include but is not restricted to being a fiber optic, photo-conducting or reflecting material, or mineral or gem or metal that when the substance 44 delivery 42 device is illuminated or energized by the electromagnetic 102 visible 20, 43 or non-visible 43 components of the electromagnetic 102 spectrum can cause the treatment substance 44 to be released or bound 124, 125/attached or re-bound 124, 125/re-attached to the substance 44 delivery 42 device when the electromagnetic 102 energy 43 is turned on and turned off and some examples can include one or multiple wavelengths of visible 20, 43 or non-visible 43 light that can include but is not restricted to UV 43, Infrared, X-ray or other portions of the electromagnetic 102 spectrum.

As stated previously the treatment substance 44 or substance 44 can refer to and can include but is not restricted to the not yet activated cytotoxic 127 treatment substance 44, the activated cytotoxic 127 treatment substance 44, the insulating or deactivating or inactivating or retarding or stopping or limiting/delimiting substance 44 discussed and cited previously herein this application.

In another embodiment there can be differing energies that can perform different functions and that can include but are not restricted to one energy 43 or method releasing one or more than one of the not yet activated cytotoxic 127 treatment substance 44, the activated cytotoxic 127 treatment substance 44, the insulating or deactivating or inactivating or retarding or stopping or limiting/delimiting substance 44 and another energy 43 or method releasing one or more than one of the not yet activated cytotoxic 127 treatment substance 44, the activated cytotoxic 127 treatment substance 44, the insulating or deactivating or inactivating or retarding or stopping or limiting/delimiting substance 44.

In one embodiment a magnetic field 103 can hold the not yet activated cytotoxic 127 substance 44/material to the treatment substance 44 delivery 42 device and when an activation energy 43 is applied to the not yet activated cytotoxic 127 substance 44/material and activates and converts the not yet activated cytotoxic 127 substance 44/material into an activated cytotoxic 127 substance 44/material the magnetic field 103 can be turned off or discontinued and the activated cytotoxic 127 substance 44/material released and to partially or fully recapture/reacquire/rebind the activated cytotoxic 127 substance 44/material to the treatment substance 44 device the magnetic field 103 can be turned on or continued. In other embodiments, to accomplish equivalent or similar binding/holding and releasing effects or tasks, the magnetic field 103 can be replaced with other energies that can include but are not restricted to being thermal/hot or cold, chemical, kinetic/Brownian/vibrational/mechanical/ultrasound, photo-acoustic, magnetic, chemical reactions, electromagnetic/visible 20, 43 and non-visible 43 light and spectral wavelengths that include but are not restricted to UV 43, Infrared, x-ray, radioactive energy 43/wavelengths/spectrum, or chemical energy 43.

All of these embodiments can be used as one or more than one embodiment or in combination and can be used with as stated previously the treatment substance 44 or substance 44 can refer to and can include but is not restricted to the not yet activated cytotoxic 127 treatment substance 44, the activated cytotoxic 127 treatment substance 44, the insulating or deactivating or inactivating or retarding or stopping or limiting/delimiting substance 44 discussed and cited previously herein this application.

In another embodiment the treatment substance 44 or substance 44 can be delivered through a conduit 5 and at the same or differing times/temporal periods the treatment substance 44 or substance 44 can include but is not restricted to the not yet activated cytotoxic 127 treatment substance 44, the activated cytotoxic 127 treatment substance 44, the insulating or deactivating or inactivating or retarding or stopping or limiting/delimiting substance 44 and these can be used in combination with the binding and unbinding and the activating and inactivating and deactivating substance 44.

In another embodiment, the not yet activated cytotoxic 127 treatment substance 44 can bound 124, 125 to a treatment substance 44 delivery 42 device and can pass through a conduit 5 and can include but is not restricted to be to include but not restricted to placed or instilled or delivered to include but not restricted to in or on or around or into or within the target organ to include but not restricted to the parathyroid 121 or a hyperfunctioning adenoma 122 or hyperfunctioning tissue or other benign or malignant hyperfunctioning tissue 123 and the not yet activated cytotoxic 127 treatment substance 44 can be activated by an energy 43 treatment device to include but not restricted to one or more than one wavelength of the visible 20, 43 light or the non-visible wavelength of the electromagnetic 102 energy 43 spectrum and can be delivered to include but not restricted to through a conduit 5 and a second energy 43 form can augment or deactivate or inactivate or retard or stop the treatment by an energy 43 to include but not restricted to one or more than one wavelength of the visible 20, 43 light or the non-visible wavelength of the electromagnetic 102 energy 43 spectrum.

In another embodiment, the not yet activated cytotoxic 127 treatment substance 44 can bound 124, 125 to a treatment substance 44 delivery 42 device and can pass through a conduit 5 and can include but is not restricted to be to include but not restricted to placed or instilled or delivered to include but not restricted to in or on or around or into or within the target organ to include but not restricted to the parathyroid 121 or an adenoma 122 or hyperfunctioning tissue or other benign or malignant hyperfunctioning tissue 123 and the not yet activated cytotoxic 127 treatment substance 44 can be activated by an energy 43 treatment device to include but not restricted to one or more than one wavelength of the visible 20, 43 light or the non-visible wavelength of the electromagnetic 102 energy 43 spectrum and can be delivered to include but not restricted to through a conduit 5 and also a chemical substance 44 can be delivered to include but not restricted to through a conduit 5 that can include but is not restricted to augment or deactivate or inactivate or retard or stop the treatment process.

In another set of embodiments the embodiments discussed above in the Treatment of Parathyroid 121 Tissue/Glands and other Hyper-functioning Tissue/Adenoma 122 and Tumors the designs and methods revealed herein as applied to the substance 44 delivery 42 device can be applied in a similar or equivalent or in a corollary manner as well to the energy 43 delivery 42 device or any combination of these.

In another embodiment the treatment substance 44 delivery 42 and the energy 43 delivery 42 device or any combination of these can be designed with an architecture where a component device is fully or partially insulated or composed of a material that does not transmit or propagate an energy 43 that is delivered or that is produced as a result of the functions or the treatment caused or initiated or produced or delivered by the treatment substance 44 delivery 42 and the energy 43 delivery 42 devices or any combination of these. In one embodiment the treatment device (substance 44 or energy 43 or any combination of these) can be composed fully or partially of a material that can include but is not restricted to not propagate cytotoxic 127 energy 43 to include electromagnetic/electrical/magnetic or thermal/hot/cold or hydraulic/kinetic/vibrational/mechanical or chemical energy 43 or radioactive and can be used to release the treatment substance 44 to include but not restricted to by macro, micro or nano 63 particle devices or any combination.

In one embodiment the treatment devices can include but are not restricted to having the distal tip aspect of the device produce the cytotoxic 127 ablative treatment effect but a component of the device referred to as the non-treatment component is not capable of producing the cytotoxic 127 ablative treatment effect and that said component can include but is not restricted to a location that is proximal to the distal treatment component to include but not restricted to the distal aspect or the tip of the device and the said non-treatment component does not propagate or transfer or conduct the treatment effect or energy 43 or activated substance 44 or its cytotoxic 127 ablative or functional treatment effect or energy 43 in a manner that is proximal to the distal treatment component. In other embodiments the treatment component can include but is not restricted to a location at a site that is not the distal tip. In another embodiments the treatment component can be a combination or mixture of the distal and the not distal components and can be at one or more than one location.

In another embodiment, non-treatment components can include but are not restricted to components that include but are not restricted to non-conductive or non-propagating or non-transferring or non-transfusing or non-delivering or non-conveying of energies to include but not restricted to thermal/hot or cold, chemical, kinetic/Brownian/vibrational/mechanical/ultrasound, photo-acoustic, magnetic, chemical reactions, electromagnetic/visible 20, 43 and non-visible 43 light and spectral wavelengths that include but are not restricted to IV 43, Infrared, x-ray, radioactive energy 43/wavelengths/spectrum, or chemical energy 43 of their treatment effects or substances 44 and their treatment effects.

Embodiments of components of the energy 43 or substance 44 delivery 42 devices can include but are not restricted to non-conductive or non-propagating or non-transferring or non-transfusing or non-delivering or non-conveying or insulating of energies or substances 44 and their treatment effects and can include but are not restricted to argon, beryllium, bismuth, brick, cork, glycol, gold, granite, Helium, lead, nitrogen, paper, wood, perlite, polymers, tin, zinc, titanium, poor thermal conductors to include but not restricted to carbon-based, and carbon-fiber based materials, graphite and graphene and exfoliated graphite (nano 63 particles), epoxy ad epoxy-graphite, composite phase change 94,96 and phase change 94,96 materials, paraffin, precious biological materials, plastics, aluminum, fiberglass, glass and foam glass, silica, polyurethane, polystyrene, and fiber optic materials, and foams and fluids and semiprecious and non-precious gems and minerals and stone to include but not restricted to diamonds, rubies, sapphires, marble, quartz, and other gems and stones and minerals and elements of the periodic tables and solids and gels and liquids and air/gases and translucent, transparent and opaque materials or any combination of these and these can be macro, micro or nano 63 materials and can include but are not restricted to other structures cited or described herein.

Nano 63 Technology

Embodiments cited and herein this application can use technology to include but not restricted to nano 63 technology substances 44 that can include but is not restricted to nano 63 tubes, nano 63 particles and nano 63 rods, nano 63 sensor 39, nano 63 chips, nano 63 materials with fast ion transport with nano 63 Ionics and nano 63 electronics, nano 63 pillars, nano 63 spheres and other nano 63 shapes, nano 63 cars, nano 63 lithography, magnetic nano 63 chains and include top-down approaches to include but not restricted to carbon and fullerenes, solid state silicone and magnetic and magnetoresistors/magneto-resistance, atomic layer 98 deposition (ALD), nano 63 electromechanical systems, single-molecule components in a nano 63 electronic, such as rotaxane, placing components with a desired functional outcome without regard to how they are assembled bionics and biomimicry, biomineralization, bionano 63 technology, nano 63 cellulose, and nano 63 robots, nano 63 surgical tools. Nano 63 technologies and nano 63 sensor 39 and nano 63 devices and macro and micro particles and devices and in this application can also be used to described t include but are not restricted to particles smaller than nano 63 particles to include but not restricted to quantum dots and solid state and atomic self-assembling particles and devices and hydrophobic and hydrophilic and combined hydrophobic and hydrophilic to include but not restricted to Janus 4 particles, and plasma materials to include but not restricted to thermal plasmas, and sol (solid)-gels and gas-gels and liquid-gels and affinity bates and analytes including organic and non-organic and solids and liquids and gels and gases and combinations of these and they can be constructed to include but not restricted to gas condensation, attrition, chemical precipitation, pyrolysis and hydrothermal synthesis, ball mill, exploding wire techniques, induction plasma technology, inert-gas condensation, radiolysis and other technologies.

In one embodiment the treatment delivery 42 device and the energy 43 treatment delivery 42 device can include but is not restricted to being composed of or coated with a not yet activated substance 44 that can be activated and that can include but is not restricted to nano 63 technology substances 44 that can include but is not restricted to nano 63 tubes, nano 63 particles and nano 63 rods, nano 63 sensor 39, nano 63 chips, nano 63 materials with fast ion transport with nano 63 Ionics and nano 63 electronics, nano 63 pillars, nano 63 spheres and other nano 63 shapes, nano 63 cars, nano 63 lithography, magnetic nano 63 chains and include top-down approaches to include but not restricted to carbon and fullerenes, solid state silicone and magnetic and magnetoresistors/magneto-resistance, atomic layer 98 deposition (ALD), nano 63 electromechanical systems, single-molecule components in a nano 63 electronic, such as rotaxane, placing components with a desired functional outcome without regard to how they are assembled bionics and biomimicry, biomineralization, bionano 63 technology, nano 63 cellulose, and nano 63 robots, nano 63 surgical tools. Nano 63 technologies and nano 63 sensor 39 and nano 63 devices and macro and micro and particles smaller than nano 63 particles to include but not restricted to quantum dots and solid state and atomic self-assembling particles and devices and hydrophobic and hydrophilic and combined hydrophobic and hydrophilic to include but not restricted to Janus 4 particles, and plasma materials to include but not restricted to thermal plasmas, and sol (solid)-gels and gas-gels and liquid-gels and affinity bates and analytes including organic and non-organic and solids and liquids and gels and gases and combinations of these and they can be constructed to include but not restricted to gas condensation, attrition, chemical precipitation, pyrolysis and hydrothermal synthesis, ball mill, exploding wire techniques, induction plasma technology, inert-gas condensation, radiolysis and other technologies.

In another embodiment nano 63 technology discussed as cited and herein can be applied to the energy 43 treatment device and can include but is not restricted to not yet activated energy 43 sources and can include but is not restricted to containing or being composed partially or fully of an energy 43 component that can include but is not restricted to being capable of thermal/hot or cold, chemical, kinetic/Brownian/vibrational/mechanical, magnetic, chemical reactions, electromagnetic/visible 20, 43 and non-visible 43 light and spectral wavelengths that include but are not restricted to UV 43, Infrared, x-ray, radioactive energy 43/wavelengths/spectrum, or chemical energy 43 and can include but not restricted to any combination or energies and substances 44 and transformations such as transforming a substance 44 to an energy 43 to include but not restricted to include the absorption and release of energy 43 to include but not restricted to UV 43, Infrared or the visible 20, 43 spectrum of light and can include but are not restricted to photoexcitations, reactions such as but not restricted to being governed by the Grotthuss-Draper and Stark-Einstein Laws and quantum and photochemical, photoelectric reactions, fluorescence, phosphorescence, mercury-vapor lamps, photosynthesis, bioluminescence that can include but is not restricted to photo initiators, photo degradation, photodynamic therapy, photo resistors, biological retina vision receptors technology such as rhodopsin reactions, toray photochemical, photoelectric production of caprolactame, photo chemical production of artemisinin by anti-malarial drugs and photo alkylation, organic photochemistry to include but not restricted to organic reactions to include but not restricted to electro cyclic, radical, photo isomeration and Norrish reactions, alkene reactions to include but not restricted to cis-trans isomeration, DNA, thymine dimer ergosterol and retinal, Vitamin D, chlorine and toluene reactions, Mercaptans reactions produced from hydrogen sulfide and olefins; as well as to include but not restricted to inorganic or organometallic photochemistry to include but not restricted to metal carbonyls, UV 43 molybdenum hex carbonyl reactions and iron Penta carbonyl reactions and alpha santonin reactions and Diels-Alder reactions, photoelectric effect, photo molecules and photosynthesis and photochemical, photoelectric logic gates.

Detachable and Disuniting Devises

In one embodiment the treatment substance 44 and/or the energy 43 delivery 42 device can have one or more than one detachable or disuniting component(s) and the detachable or disuniting component can be constructed of substances 44 or materials or devices to include but not restricted to treatment substance 44(s) or treatment energy 43 (s), or the treatment substance 44 device or the treatment energy 43 device or an anchoring device that holds any combination of these in place to include but not restricted to the target tissue 129 to include but not restricted to the parathyroid 121 or adenoma 122 or hyperfunctioning tissue or benign or malignant hyperfunctioning tissue 123.

In one embodiment the treatment substance 44 and/or the energy 43 delivery 42 device can have one or more than one detachable or disuniting component(s) and the detachable or disuniting component can be constructed of substances 44 or materials or devices to include but not restricted to it not being a treatment substance 44(s) or treatment energy 43 (s), or a treatment substance 44 device or a treatment energy 43 device or an anchoring device that holds any combination of these in place to include but not restricted to the target tissue 129 to include but not restricted to the parathyroid 121 or adenoma 122 or hyperfunctioning tissue or benign or malignant hyperfunctioning tissue 123.

In another embodiment the materials that are conducting and non-conducting can include but are not restricted to one or more regions that can be interlaced or entwined or combined.

In another embodiment the energy 43 or the substance 44 delivery 42 devices can be composed and designed in a manner to include but not restricted to incorporating one or more than on gap or conduction barrier or insulated/non-conducting region/material that are designed to include but not restricted to reduce, restrict or prevent the conduction or the transfer of energy 43 or the transfer of the treatment effect to include but not restricted to beyond the precise site of the tightly targeted treatment or to an appropriate or designated distance to include but not restricted to a distance that cytotoxically ablates or treats the targeted tissue but does not treat a region beyond the designated targeted tissue to be treated and this gap or conduction barrier or insulated/non-conducting region/material can include a gas or liquid or gel or a solid that poorly conducts the energy 43 or substance 44 treatment effect and some embodiments can include but are not restricted to an air/gaseous gap or a carbon fiber or glass or mineral or stone region to prevent thermal conduction to regions distal to the targeted region of tissue or to the treator/the individual utilizing the treatment device to treat the patient; or an opaque or translucent region to prevent the egress of light or electromagnetic 102 energy 43 to prevent the unwanted electromagnetic 102 energy 43 of non-targeted tissue or to the caregiver/treator/the individual providing/utilizing the treatment device to treat the patient.

In another embodiment anchors related to the device can include barbs, hooks, threaded screw-like devices, pincers, sharp probes, needles, stylets and catheters.

In one embodiment there can be an introducer that that can include but is not restricted to utilized magnetic field 103/energy 43 to fasten the treatment devices to the target tissue 129 or organs or skin 8 or body parts.

In another embodiment the treatment devices can be attached or fastened or fixed to each other using a magnetic field 103/energy 43.

In another embodiment the detaching/disuniting component/filament can be held together by means to include but not restricted to magnetic fields 103 in which the magnetic field 103 can be turned on and off to attach and detach the detaching/disuniting component.

In another embodiment a section of the treatment device can include but is not restricted to a detachable junction between one or more than one section(s) to be delivered and the one or more than one section(s) that is not to be delivered and that said junction can a region of the said device that when exposed to an energy 43 causes one or more sections of the device to detach or disunite and the energy 43 can include but is not restricted to electromagnetic/electrical/magnetic or thermal/hot/cold or hydraulic/kinetic/vibrational/mechanical or chemical energy 43 or radioactive energy 43. In one embodiment the one or more junction(s) can act in a manner similar to a fuse that can include but is not restricted to when an electric current 100 is run through that section the delivered component is disunited treatment component fully or partially separates from the non-treatment component.

In another embodiment, the one or more junction(s) can melt at a different thermal point/temperature than other components of the delivery 42 devices and a component to include but not restricted to a coil, a screw-like device, a filament that can be straight or curved or a geometric shape to include but not restricted to a rectangle or triangle or a multisided-geometric shape 2-d or 3-D shape such as a polyhedral or sphere shape and which can be a combination of these and which can be one or more than one of these shapes and shapes can have one or more than one identical/similar sizes or shapes and/or one or more different sizes or shapes.

Figure 23A:
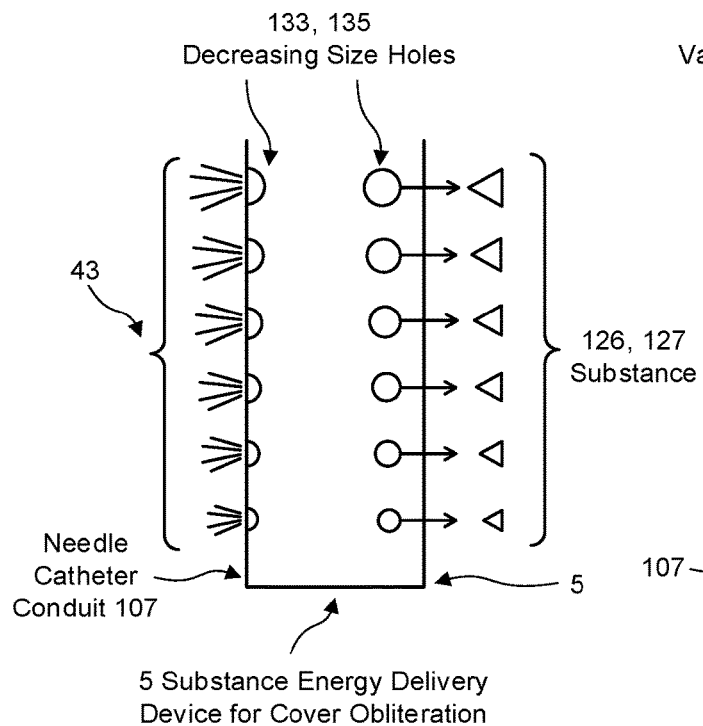
FIGS. 23A-B are renderings of a conduit 5 with holes 133 of variable and graduating size.
Figure 23B:
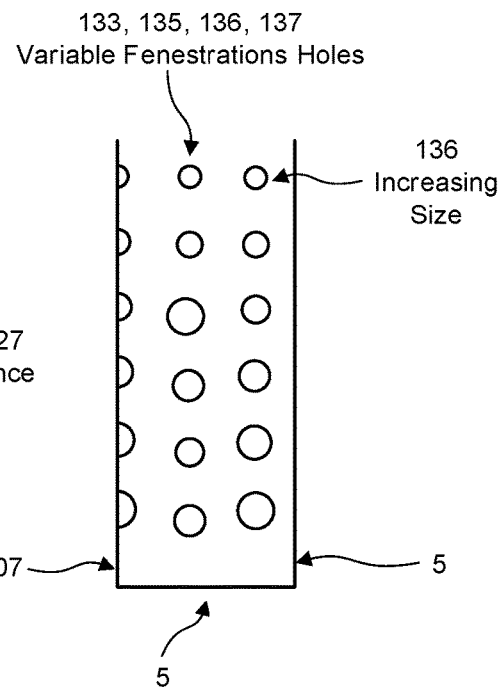
Figure 23B:
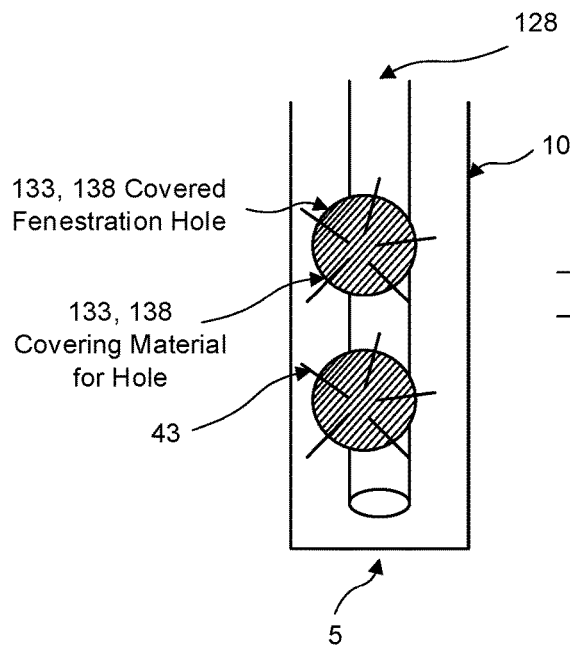
Figure 23B:
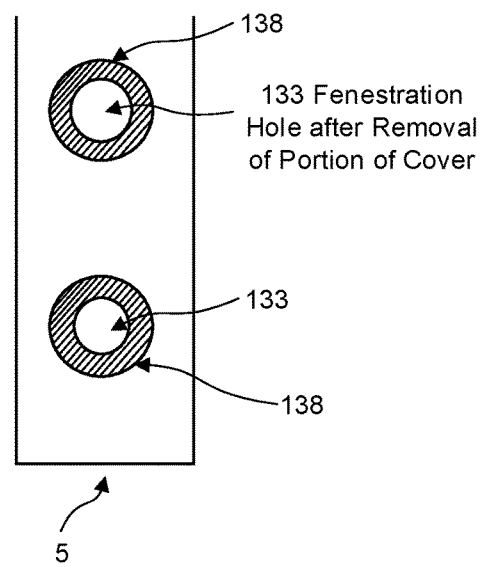

FIGS. 23A-B are renderings of a conduit 5 with holes 133 of variable and graduating size. In another embodiment of a treatment substance 44 and an energy 43 delivery 42 device, the device can include but is not restricted to have a hollow, an empty core, a cavity, a pit or a recess and that can include but is not restricted to having outer walls that surround the hollow fully or partially on/around its sides or circumference or surfaces and the ends can be absent and have no openings and the hollow can be fully covered/enclosed or it can have one or more than one opening. In one embodiment of this design, the hollow can be fully enclosed and none, none or one or more than one of the treatment substance 44(s) and none, or one or more than one of the activating energy 43 (*s*) or energy 43 device(s) or any combination of these can be located within the hollow. In one of these embodiments both the energy 43 or energy 43 devices or the treatment substance 44 or treatment substance 44 device(s) that can be not yet activated or can be in the activated state can reside within the hollow of the conduit 5 or the delivery 42 device and the outer shell of these and in this embodiment the treatment activation can include but not restricted to occur within the hollow or confines of the conduit 5 or delivery 42 device. In a similar embodiment, the outer covering 36/coating/enclosure surrounding the hollow/cavity can have one or more than one opening/133 or fenestration 133 133 and can occur on the ends or on the side/covering 36 and these can be similar or variable in size and can include smaller to larger 136 or larger to smaller 135 proximal to distal or any combination of these and these opening or holes 133 or fenestrations 133 can be opaque or translucent or transparent and can be a window in the delivery 42 device covering 36 that can include but is not restricted to being solid, or liquid or gel or gas and an example of this embodiment can include a solid transparent window that allows to include but not restricted to electromagnetic 102 energy 43 such as visible 20 light or UV 43 or Infrared to pass through the window and treat the target tissue 129 and in one embodiment this can be constructed to include but not restricted to where no treatment substance 44 can egress out of the hollow or out of the openings or holes 133 or fenestrations 133. And in another embodiment the openings or holes 133 or fenestrations 133 can be devoid of material and can be a true opening and in one embodiment can include is not restricted to allowing treatment substance 44 or other materials to include but not restricted to protective or inhibiting/retarding or treatment slowing materials and energy 43 to pass out of the openings or holes 133 or fenestrations 133 and into the targeted tissue. In another embodiment the treatment energy 43 can arise transcutaneously or cutaneously or percutaneously or surgical approaches and can include but is not restricted to being used without or in combination with the hollow delivery 42 devices.

FIGS. 24A1-A2 are renderings of a conduit 5 with holes 133 with a cover over the holes 133, which when the covers are exposed to a substance 44 or an energy 43 change in size. In another embodiment the covering 138 of the holes or fenestrations 140 can be to include dissolved or melted or disintegrated or creating a hole 140 or fenestration 140 that can be enlarged when at least one substance 44 or energy 43 or combination of these is placed in contact with said covering 138 or hole 140.

In another embodiment the covering 138 of the holes or fenestrations 140 can have no complete covering 138 but when at least one substance 44 or energy 43 or combination of these is placed in contact with said covering 138 or hole 140, said hole 140 or covering 138 diminishes in size.

In another embodiment the conduit 5 or the delivery 42 devices can be constructed and designed to include but not restricted to allowing less treatment effect to include but not restricted to allowing less light transmission (more opaque) or less heat conducting materials away from the target tissue 129 than at the target tissue 129 and in another embodiment the delivery 42 devices can have a coating such that can include but is not restricted to being constructed to include a coating of the conduit 5 or delivery 42 device that insulates the delivery 42 devices but not restricted to allowing less treatment effect to include but not restricted to allowing less light transmission (more opaque) or less heat conducting materials away from the target tissue 129 than at the target tissue 129

In another embodiment the conduit 5 or the delivery 42 devices can be constructed and designed to include but not restricted to allowing more treatment effect at the target tissue 129 to include but not restricted to allowing more light transmission (more opaque) or more heat conducting materials at the target tissue 129 than away from the target tissue 129 and in another embodiment the conduit 5 and delivery 42 devices can have a coating such that can include but is not restricted to being constructed to include a coating of the conduit 5 or delivery 42 device that allows the conduit 5 and the delivery 42 devices to but not restricted to allowing more treatment effect at the target tissue 129 to include but not restricted to allowing more light transmission (more opaque) or more heat conducting materials at the target tissue 129 than away from the target tissue 129.

In another embodiment the conduit 5 or the delivery 42 devices can be constructed and designed to include but not restricted to having the treatment energy 43 emitters or the treatment substance 44 to include but not restricted to both the activated and the not yet-activated substance 44 to include but not restricted to being distributed as a component of the conduit 5 or the treatment devices or their coating such that the treatment effect is proportional and related to the variable or fixed distribution of the said treatment energy 43 or substance 44 distribution which can be concentrated or not concentrated to include but not restricted to the target tissue 129 location.

Other embodiments can include any combination of the above and can include a combination in which the covering 138 to include but not restricted to the fenestration 133 can be to include but not restricted to be removed, dissolved, melted or changed in size or in its ability to include but not restricted to transmit or allow energy 43 or a substance 44 to pass through the said covering 36.

Combined Computer 18 and Mechanical and Living-Being Control

Devices can include but is not restricted to include a combination of input and output of the living being or user's own volition, devices to include but not restricted to mechanical, vibrational and ultrasound, electromagnetic, electric, visible 20, 43 and non-visible 43 wavelengths, thermal and chemical piezoelectric and nano 63 particle and nano 63 tube devices controlled through the users volition or through a computer 18 or a device modulation or assisting the user/living-being and of the choosing or effort of the user/living-being and the computer 18 or a combination of these; the computers 18 or sensory 39, 66 or mechanical device control of input and output devices and activators 97 or facilitators; or any combination of these including the user's, the computer's or the sensory 39, 66 or mechanical device's control of input and output devices management or any combination of these. An analogous system can be used with appropriate sensor 39 and input and output and computer 18 and user control and effort for orgasms, vaginal 3 muscle 65 effort, urinary incontinence 83 and prolapse 79, fecal incontinence 83 and prolapse 79, erectile function and dysfunction in the male or female and/or a desired stimulation 71 or pleasures or any combination of these. The use of the devices describe herein and the application to the living being can be coordinated to optimize function and use one or more devices with one of more living beings.

Many of the elements that are desired for the embodiments listed herein are discussed in U.S. Provisional Patent application, entitled "Female Urine Collection Device," Ser.

No. 62/435,016, filed Dec. 15, 2016; U.S. Patent application, entitled "Gel-Based Seals And Fixation Devices And Associated System And Methods," Ser. No. 14/663,348, filed Mar. 19, 2015, U.S. Pat. No. 9,820,798, issued Nov. 21, 2017; U.S. Pat. No. 9,931,071, issued Apr. 3, 2018; and U.S. Pat. No. 9,521,966, entitled "Localization Of The Parathyroid 121," issued Dec. 20, 2016, the disclosures of which are incorporated herein by reference and cited supra.

While the invention has been particularly shown and described as referenced to the embodiments thereof, those skilled in the art will understand that the foregoing and other changes in form and detail may be made therein without departing from the spirit and scope.

The invention claimed is:

1. A vaginal device, comprising:
    a conformable vaginal insert shaped for insertion into a vaginal cavity of a female human;
    a contact point configured to change a shape of the conformable vaginal insert;
    a sensor configured to measure and relay measured characteristics of the vaginal cavity and the surrounding structures of the vaginal cavity and the supportive structures of the vaginal cavity, wherein
        the measured characteristics are acquired on at least one of a one-time basis and a multiple-time basis comprising one of a non-continuous period, a continuous period, and an intermittent temporal period; and
    a processor configured to:
        control the contact point to shape the conformable vaginal insert;
        generate information on the vaginal cavity and the surrounding structures of the vaginal cavity and the supportive structures of the vaginal cavity comprising at least one of a vaginal cavity profile and a vaginal cavity device profile as generated by the processor from at least of one of the measured characteristics, a computer modeling process, a physiologic characteristic, a biologic characteristic, a mechanical characteristic, an optimization process, an activation process, a relaxation process, a neuromuscular function feedback, a physiologic feedback, a mechanical feedback and a biological feedback characteristic;
        store the measured characteristics and the information; and
        based on the stored measured characteristics and the stored information, automatically modify the shape of the conformable vaginal insert to change the characteristics of the vaginal cavity and the surrounding structures of the vaginal cavity and the supportive structures of the vaginal cavity to provide treatment, wherein
            the processor can modify the shape of the conformable vaginal insert on at least one of a one-time basis and a multiple-time basis comprising one of a non-continuous period, a continuous period, and an intermittent temporal period.

2. A vaginal device in accordance with claim 1, further comprising:
    a delivery device configured to perform interfacing with the walls of the vaginal cavity under control of the processor.

3. A vaginal device in accordance with claim 2, wherein the delivery device is provided relative to a surface of the conformable vaginal insert that faces one of the walls of the vaginal cavity.

4. A vaginal device in accordance with claim 2, wherein interfacing with the walls of the vaginal cavity comprises one or more of mechanical interaction, electrical interaction, chemical interaction, kinetic interaction, Brownian motion, mechanical and thermal interaction, pressure, hot, cold, electromagnetic interaction, electrical interaction, magnetic interaction, electromechanical interaction, hydraulic interaction, vibrational interaction, acoustic interaction, ultrasonic interaction, chemical energy interaction, interaction with biological forces, interaction with energy, biological chemical interactions, hormonal and neurotransmitter interactions, interaction with gravitational force, interaction with position, interaction with pressure, interaction with biological sensations, pain interaction, pleasure interaction, interaction with visible light, interaction with non-visible light, interaction with infrared energy, interaction with ultraviolet energy, interaction with radioactive energy, and triggering a state change.

5. A vaginal device in accordance with claim 4, wherein the chemical interaction comprises one or more of outputting into the vaginal cavity a liquid, solid, gas, gel, gel slurry, nitric oxide, a biological chemical, and at least one of a fully formed and a precursor of, a hormone, peptide, and neuromuscular transmitter.

6. A vaginal device in accordance with claim 1, the information further comprising at least one of:
    a definition of a target shape of the conformable vaginal insert configured to address a homeostatic biological female function; and
    a definition of a target shape of the conformable vaginal insert configured to address a rehabilitate medical target female condition.

7. A vaginal device in accordance with claim 1, wherein the information is tailored to the female human and to a specific disease state or dysfunction affecting the female human.

8. A vaginal device in accordance with claim 1, further comprising:
    a guidance system operatively coupled to the the processor configured to modify the information as a further function of a user input provided through the guidance system, wherein the user input can be derived from at least one of:
        one of a user awareness sensation received by the processor as feedback through the guidance system;
        an internal sensor which is a component of the conformable vaginal insert; and
        an external sensor which is not a component of the conformable vaginal insert.

9. A vaginal device in accordance with claim 1, the conformable vaginal insert further comprising one or more of:
    a structure defining a plurality of chambers;
    a structure comprising of one or more of a solid, gas, gel, and gel slurry; and
    a structure comprising one or more of macro, micro, and nano structures and devices.

10. A vaginal device in accordance with claim 1, further comprising at least one of:
    a transceiver through which signals can be wirelessly relayed between the sensor and the processor;
    a transceiver through which signals can be wirelessly relayed between the contact point and the processor;
    a wired connection over which signals can be hardwire relayed between the sensor and the processor; and
    a wired connection over which signals can be hardwire relayed between the contact point and the processor.

11. A vaginal device in accordance with claim 1, wherein the measured characteristics comprise one or more of position, shape, size, pressure, physical contact, movement, temperature, vibration, and tumescence, blood chemistry, blood flow, neural sensations, taste, odor, sound, visual characteristics, color, tactile, kinesthetic, moisture, hardness and softness, durometers, elasticity, resiliency, chemical, hormonal, transitions of states, static phases, changing phases, pulsatile phases, intermittent phases, continuous phases, sucking, pumping, throbbing, physical sensations, proprioception, stereognosis, special relationships, slipperiness, contraction, relaxation, change in length, pulse, blood pressure, electro-conductivity, physiology, biology functions and measurements, bio-structure measurements, physical measurements, biologic function measurements, physiologic measurements and associated, initial, static and change of state in bio-structure measurements, biology measurements, physical measurements, and a physiologic measurements of a body.

12. A vaginal device in accordance with claim 1, the sensor configured to sense one or more of position, shape, pressure, physical contact, movement, temperature, thermal, vibration, and tumescence, blood flow, neural sensations, taste, odor, sound, visual characteristics, color, tactile, kinesthetic, moisture, hardness and softness, durometers, elasticity, resiliency, chemical, hormonal, transitions of states, static phases, changing phases, pulsatile phases, intermittent phases, continuous phases, sucking, pumping, throbbing, physical sensations, pain, pleasure, proprioception, stereognosis, special relationships, slipperiness, contraction, relaxation, change in length, pulse, blood pressure, electro conductivity, change of state, and physiology, biology functions and measurements, bio-structure measurements, physical measurements, biologic function measurements, physiologic measurements and associated, initial, static and change of state in bio-structure measurements, biology measurements, physical measurements, and a physiologic senses of a body.

13. A vaginal device in accordance with claim 1, further comprising:
   a memory operatively coupled to the processor and within which programmable algorithmic instructions that are performable by the processor are stored.

14. A vaginal device in accordance with claim 13, the programmable algorithmic instructions comprising at least one of:
   generating a description of at least one of a physical and a physiologic aspect of the vaginal cavity;
   generating a description of a physical aspect of the conformable vaginal insert; and
   generating a description of at least one of a physical and a physiologic aspect of the vaginal cavity and the relationship of the vaginal cavity to a physical aspect of the conformable vaginal insert.

15. A vaginal device in accordance with claim 13, the programmable algorithmic instructions comprising:
   evaluating a medical condition relating to one or more of urination, defecation, prolapse, sexual function, and physiology of a body.

16. A vaginal device in accordance with claim 13, the programmable algorithmic instructions comprising:
   describing physical structure of one or more of the walls of the vaginal cavity, an urethra, a bladder, an uterus, a rectum, and an anus.

17. A vaginal device in accordance with claim 13, the programmable algorithmic instructions comprising at least one of:
   facilitating rehabilitation of structure of the vaginal cavity;
   addressing urinary incontinence of the female human;
   addressing prolapse of structure of the vaginal cavity;
   mapping the vaginal cavity;
   stimulating the vaginal cavity and local region; and
   measuring and arousing pleasure.

18. A vaginal device in accordance with claim 1, further comprising at least one of an additional conformable vaginal insert and an attachment to the conformable vaginal insert, the additional conformable vaginal insert and the attachment to the conformable vaginal insert comprising at least one of characteristics similar to the conformable vaginal insert and characteristics dissimilar to the conformable vaginal insert, the additional conformable vaginal insert and the attachment to the conformable vaginal insert comprising at least one of:
   an anal insert shaped for insertion into the anus and the rectal cavity of the female human;
   an additional structure shaped to conform to an external female genitalia of the female human; and
   an additional conformable insert provides placement and support to the conformable vaginal insert.

19. A vaginal device in accordance with claim 18, further comprising:
   an additional sensor configured to measure and relay signals reflecting additional measured characteristics of at least one of an external female genitalia, female supportive structures, female pleasure structures, perineum, anus, and rectal cavity while the conformable vaginal insert is in a target shape; and
   the processor further configured to:
      modify the stored information as a further function of the additional measured characteristics as reflected by the female physiology.

20. A vaginal device in accordance with claim 1, further comprising a power source comprising at least one of:
   a battery power source;
   a wired power source;
   a solar power source;
   a wireless power source;
   a magnetic power source;
   an electromagnetic power source; and
   a kinetic power source.

* * * * *